United States Patent
Vankayalapati et al.

(10) Patent No.: US 9,834,551 B2
(45) Date of Patent: Dec. 5, 2017

(54) SUBSTITUTED PYRROLO[2,3-B]PYRAZINES AND SUBSTITUTED PYRAZOLO[3,4-B]PYRIDINES AS ITK AND JAK KINASE INHIBITORS

(71) Applicant: Arrien Pharmaceuticals LLC, Salt Lake City, UT (US)

(72) Inventors: Hariprasad Vankayalapati, Draper, UT (US); Venkatakrishnareddy Yerramreddy, Hyderabad (IN); Paramareddy Gangireddy, Hyderabad (IN); Rajendra P. Appalaneni, Saddle River, NJ (US)

(73) Assignee: ARRIEN PHARMACEUTICALS LLC, Salt Lake City, UT (US)

( * ) Notice: Subject to any disclaimer, the term of this patent is extended or adjusted under 35 U.S.C. 154(b) by 73 days.

(21) Appl. No.: 14/924,427

(22) Filed: Oct. 27, 2015

(65) Prior Publication Data
US 2016/0046627 A1    Feb. 18, 2016

Related U.S. Application Data

(62) Division of application No. 14/254,398, filed on Apr. 16, 2014, now Pat. No. 9,206,188.

(60) Provisional application No. 61/813,225, filed on Apr. 18, 2013.

(51) Int. Cl.
*C07D 487/04* (2006.01)
*C07D 471/04* (2006.01)

(52) U.S. Cl.
CPC ......... *C07D 471/04* (2013.01); *C07D 487/04* (2013.01)

(58) Field of Classification Search
CPC .................... C07D 471/04; C07D 487/04
USPC .......................... 544/350; 546/119
See application file for complete search history.

(56) References Cited

U.S. PATENT DOCUMENTS

| | | | |
|---|---|---|---|
| 7,291,630 B2 | 11/2007 | Graczyk | |
| 7,348,432 B2 | 3/2008 | Jiang | |
| 7,361,763 B2 | 4/2008 | Arnold | |
| 7,432,375 B2 | 10/2008 | Graczyk | |
| 7,446,199 B2 | 11/2008 | Aronov | |
| 7,534,800 B2 | 5/2009 | Graczyk | |
| 7,829,558 B2 | 11/2010 | Arnold | |
| 7,906,648 B2 | 3/2011 | Arnold et al. | |
| 8,012,974 B2 | 9/2011 | Bamberg | |
| 8,110,576 B2 * | 2/2012 | Ibrahim ............... | C07D 487/04 514/249 |
| 8,143,271 B2 | 3/2012 | Ibrahim | |
| 8,987,454 B2 | 3/2015 | Salituro | |
| 9,260,426 B2 | 2/2016 | Vankayalapati | |
| 2005/0137201 A1 | 6/2005 | Aronov | |
| 2005/0272761 A1 | 12/2005 | Graczyk | |
| 2006/0030583 A1 | 2/2006 | Arnold | |
| 2006/0035898 A1 | 2/2006 | Arnold | |
| 2006/0111390 A1 | 5/2006 | Graczyk | |
| 2006/0111391 A1 | 5/2006 | Jiang | |
| 2006/0270646 A1 | 11/2006 | Graczyk | |
| 2009/0203687 A1 | 8/2009 | Arnold | |
| 2012/0022098 A1 | 1/2012 | Ibrahim | |
| 2012/0053177 A1 | 3/2012 | Ibrahim et al. | |
| 2012/0238588 A1 | 9/2012 | Frazee | |
| 2014/0249138 A1 | 9/2014 | Salituro | |
| 2014/0256704 A1 | 9/2014 | Vankayalapati | |
| 2015/0152103 A1 | 6/2015 | Salituro | |

FOREIGN PATENT DOCUMENTS

| | | |
|---|---|---|
| JP | 2005534618 A | 11/2005 |
| JP | 2005534619 A | 11/2005 |
| JP | 2007504252 A | 3/2007 |
| JP | 2007238612 A | 9/2007 |
| JP | 2007531760 A | 11/2007 |

(Continued)

OTHER PUBLICATIONS

CAS Registry Database, RN: 889447-14-7, entered STN: Jun. 26, 2006, accessed on Feb. 26, 2016.*
Notification of Refusal for corresponding JP Application No. 2016-509089, 10 pages, dated Dec. 13, 2016.
Mui Cheung, et al., "Synthesis of 5-Substituted 7-Azaoxindoles Via Palladium-Catalyzed Reactions", Heterocycles vol. 55, No. 8, 10 pages No. 1583-1590, 2001.
International Search Report and Written Opinion for corresponding PCT /US2014/34441, dated Jan. 27, 2015.
Cha, etal. 'Discovery of a Novel Her-1/Her-2 Dual Tyrosine Kinase Inhibitor for the Treatment of Her-1 Selective Inhibitor-Resistant Non-small Cell Lung Cancer'. Journal of Medicinal Chemistry, 2009, vol. 52, pp. 6880-6888.

(Continued)

*Primary Examiner* — Douglas M Willis
(74) *Attorney, Agent, or Firm* — Timothy X. Gibson, Esq.; Gibson & Dernier LLP

(57) ABSTRACT

The present invention relates to compounds described by Formula I:

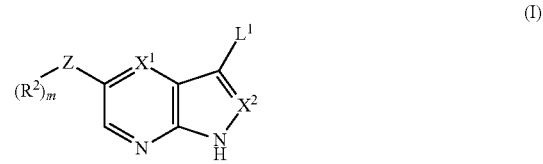

salts thereof, their synthesis, and their use as ITK and JAK3 inhibitors including such compounds and methods of using said compounds in the treatment of various diseases and or disorders such disease associated with abnormal cell growth such as autoimmune, inflammation, rheumatoid arthritis, systemic lupus erythematosus, atherosclerosis, ulcerative colitis, psoriatic arthritis, psoriasis, Crohn's, metabolic and cancer diseases. The present invention also provides pharmaceutically acceptable compositions comprising the compounds of the invention and methods of using the compositions and processes for preparing the compounds of the invention.

20 Claims, No Drawings

(56) References Cited

FOREIGN PATENT DOCUMENTS

| JP | 2008508303 A | 3/2008 |
|---|---|---|
| JP | 2008508304 A | 3/2008 |
| JP | 2008518010 A | 5/2008 |
| JP | 2008523085 A | 7/2008 |
| JP | 2008546797 A | 12/2008 |
| JP | 2016504316 A | 2/2016 |
| WO | 03082868 A1 | 10/2003 |
| WO | 03082869 A1 | 10/2003 |
| WO | 2005028475 A2 | 3/2005 |
| WO | 2005095400 A1 | 10/2005 |
| WO | 2006015124 A2 | 2/2006 |
| WO | 2006063167 A1 | 6/2006 |
| WO | 2008079903 A1 | 7/2008 |
| WO | 2010049173 A1 | 5/2010 |
| WO | 2012135631 A1 | 10/2012 |
| WO | 2013052355 A1 | 4/2013 |
| WO | 2014081732 A1 | 5/2014 |

OTHER PUBLICATIONS

Corrected International Search Report and Written Opinion for corresponding PCT /US2014/34441, dated Apr. 28, 2015.
Office Action for related U.S. Appl. No. 14/254,398, dated Jan. 30, 2015.
Office Action for related U.S. Appl. No. 14/254,398, dated Apr. 28, 2015.
European Search Report for corresponding EP Application No. 14784823.8, 16 pages, dated Oct. 14, 2016.
Notification of Refusal for corresponding JP Application No. 2016-509089, 8 pages, dated Jun. 27, 2017.

\* cited by examiner

SUBSTITUTED PYRROLO[2,3-B]PYRAZINES AND SUBSTITUTED PYRAZOLO[3,4-B]PYRIDINES AS ITK AND JAK KINASE INHIBITORS

CROSS-REFERENCE TO RELATED APPLICATIONS

This application is a divisional application of U.S. patent application Ser. No. 14/254,398 filed Apr. 16, 2014, the entirety of which is incorporated by reference herein, and claims the benefit of U.S. Provisional Patent Application No. 61/813,225 filed Apr. 18, 2013.

FIELD OF INVENTION

The present invention is directed to compounds, their synthesis, and their use as modulators or inhibitors of the IL-2 inducible T-cell kinase ("ITK"), which belongs to the TEC family of non-receptor tyrosine kinases essential for T cell activation. The present invention is also directed to compounds, their synthesis, and their use as modulators or inhibitors of the Janus Kinase 3 ("JAK3"), which is one of the Janus Kinases ("JAKs"): JAK1, JAK2, JAK3 and TYK2. JAKs are signal transducers and activators of transcription ("STAT") family of transcription factors that play key roles in cytokine-induced signal transduction leading to IL-2, IL-4, IL-7, IL-9 and IL-15 release. In particular, the present invention is directed to 3,5-(un)substituted-1H-pyrrolo[2,3-b]pyridine, 1H-pyrazolo[3,4-b]pyridine and 5H-pyrrolo[2,3-b]pyrazine compounds that are dual ITK and JAK3 kinase inhibitors.

ITK plays a central role in signaling through antigen-receptors; TCR and collectively with co-stimulation of CD4 and CD28, the TCR will trigger a cascade of signal transduction events. Tec kinase family of kinases includes; ITK, TEC, BMX, BTK, TXK/RLK. ITK is highly expressed in inflammatory T-cells, NK and mast cells and communicate signals to downstream effectors, including PLC-γ. TEC family of kinases play prominent role in T-cell proliferation and the release of cytokines such as IL-2, IL-4, IL-5, IL-10 and IL-13 and IFN-γ.

Janus Kinases ("JAKs") JAK1, JAK2, JAK3 and TYK2 are tyrosine kinases associated to common chain signaling to intracellular effector pathways and are signal transducer and activator of transcription (STAT) family of transcription factors. The cytokine receptor binding stimulates the recruitment of JAKs, which is autophosphorylated. JAKs then phosphorylate the receptor, and a STAT protein binds to the phosphorylated receptors (SRC homology 2 (SH) domain) leading to the phosphorylation of STATs by JAKs. Phosphorylated STAT proteins in turn dimerize and then translocate to the nucleus in order to regulate gene expression.

Blocking and or targeting of the JAK-STAT pathway have been shown to be efficacious in clinical trials, with the successful use of JAK kinase inhibitors, for treating of patients with rheumatoid arthritis ("RA"). Non-selective JAK inhibitors or lack of JAK3 selective inhibitors has delayed the role of JAK3 in autoimmune disorders. A selective JAK3 inhibitor has the potential benefit of relieving adverse effects of JAK1 and JAK2 inhibition such as hematopoiesis and dyslipidemia. Thus, there is a great need for such selective JAK3 inhibitors. A new strategy led to potent, selective JAK3 inhibitors by the application of FFDD™ based design of covalent/irreversible, reversible compounds targeting a cysteine residue in the active site of JAK3 and provided the blockade of IL-2 and IL-4 cytokine signaling cascade as well.

The compounds of the present invention are covalent/irreversible and reversible inhibitors useful for modulating (e g inhibiting) ITK and JAK3 activity for treating diseases or conditions mediated by ITK and JAK3 such as, for example, disease states associated with abnormal cell growth such as autoimmune, inflammation, rheumatoid arthritis and cancer diseases. The present invention also provides pharmaceutically acceptable compositions comprising the compounds of the invention and methods of using the compositions in the treatment of various autoimmune, inflammatory, metabolic and cancer disorders. The invention also provides processes for preparing the compounds of the invention.

BACKGROUND OF THE INVENTION

Non-receptor tyrosine kinase ITK and Janus kinases (JAKs) are key regulators of cytokine pathways and are important targets of therapeutic value in both inflammatory/RA and Cancer/Myeloproliferative diseases. Selective small-molecule inhibitors of both ITK and JAK3 is a challenging due to the highly conserved ATP binding pocket within the TEC-kinase family; ITK, TEC, BMX, BTK and TXK/RLK and Janus family members; JAK1, JAK2, JAK3 and TYK2. Three variable amino acids within the ATP binding pocket was utilized and rationally designed by employing proprietary FFDD™ (Fragment Field Drug Design) technology to achieve selectivity even at high concentration of ATP among TEC and JAKs. This methodology assisted in fragments, scaffolds to lead compounds, and subsequent screening and SAR efforts; we have discovered the present first-in-class 3,5-(un)substituted-1H-pyrrolo[2,3-b]pyridine,1H-pyrazolo[3,4-b]pyridine and 5H-pyrrolo[2,3-b]pyrazine dual ITK and JAK3 inhibitors claimed here, useful for treating multiple disease indications, including autoimmune diseases; more specifically rheumatoid arthritis and other disease indications such as inflammatory, hyperproliferative, or immunologically-mediated diseases. The present invention encompassing administering to a human patient a compound of the present invention. The compounds may be in a composition as a single dosage form or as part of a multiple dosage forms.

The present invention includes the use of the compounds herein to treat rheumatoid arthritis, psoriasis, lupus erythematosus, systemic lupus erythematosus, artherosclerosis, idiopathic thrombocytopenia purpura, restenosis, angioplasty, tumours, artherosclerosis, systemic lupus erythematosus, chronic allograft rejection and acute allograft rejection (including from transplantation of heart, liver, kidney, lung, bone marrow, skin and cornea), chronic graft versus host diseases, asthma, allergic acute rhinitis, psoriatic arthritis, systemic sclerosis, atopical dermatitis, erythemas, Alopecia, multiple sclerosis, artherosclerosis and plethora of diseases including immunodeficiencies, myeloproliferative disorders and cancer (acute leukemia, gain of function mutations associated with inherited polycythaemia) diseases in human patients.

International patent publication WO 2013024282 describes TBK1 and IKK epsilon kinase inhibitors for the treatment of cancer. U.S. Pat. Nos. 7,709,645, 7,361,763, 7,361,764, and 7,906,648 describe Preparation of pyrrolo[2,3-b]pyridine derivatives as kinase modulators.

These compounds are known in the chemical database:

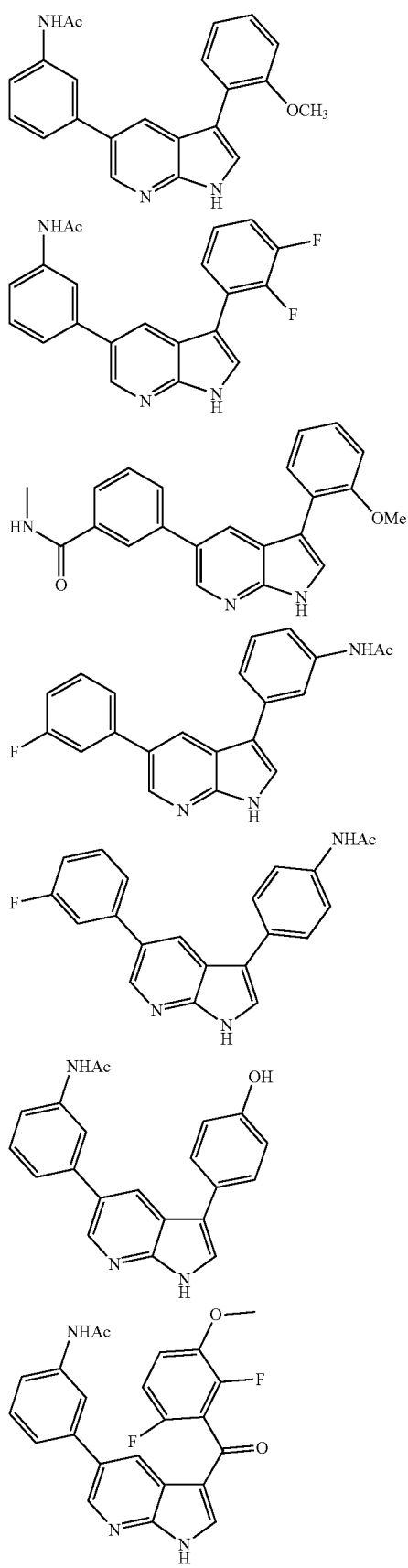

SUMMARY OF THE INVENTION

The present invention concerns compounds active on protein kinases, specifically ITK and JAK3, including mutations of these kinases and their use in treating disease and conditions associated with regulations of the activity of these kinases. More specifically the invention concerns compounds of Formula I as described below. Thus the invention provides use of novel compounds for therapeutic methods involving inhibition and/or modulation of protein kinases ITK and JAK3.

Compounds of the present invention are described by the Formula I,

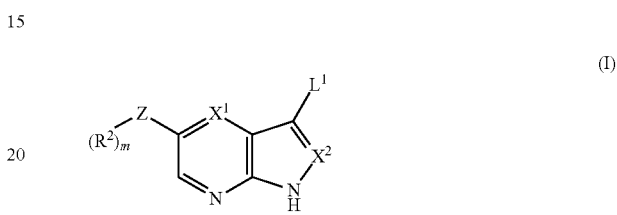

to pharmaceutically acceptable compositions or salts thereof, their synthesis and their use as ITK and JAK3 inhibitors including such compounds and methods of their use in the treatment of various diseases and disorders such as autoimmune diseases.

The present invention relates to compounds according to Formula I and its sub-genus Formulas IA, IB and IC below and pharmaceutically acceptable compositions and salts thereof, their synthesis and their use as ITK and JAK3 inhibitors including such compounds and methods of their use in the treatment of various diseases and disorders such as rheumatoid arthritis, psoriasis, inflammation, hyperproliferative diseases, or immunologically-mediated diseases and encompasses administering such compounds to a human disease patient.

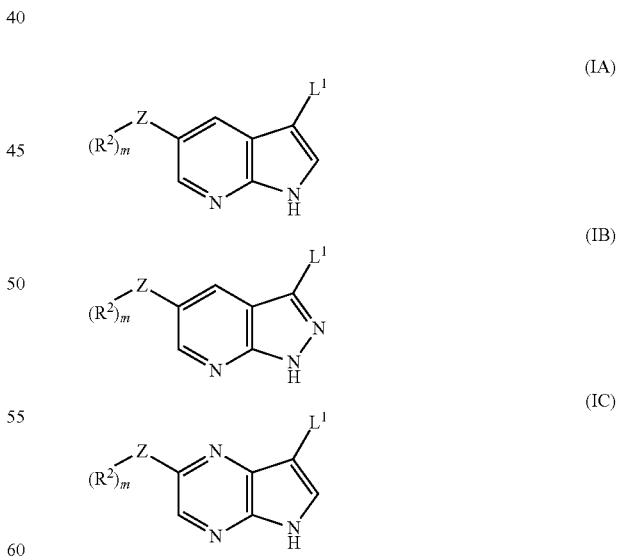

DETAILED DESCRIPTION OF THE INVENTION

Compounds of the present invention are described by Formula I:

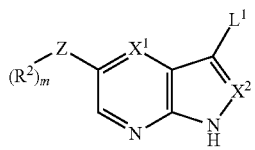
(I)

or a pharmaceutically acceptable salt thereof, wherein:
one of $X^1$ and $X^2$ is N, the other is CH; or both $X^1$ and $X^2$ is CH; or, $L^1$ is H, $X^1$ is CH, and $X^2$ is >C=O;
$L^1$ is H, halo, $C_{1-4}$alkyl, —NH—S(O)$_2$($C_{1-4}$alkyl),

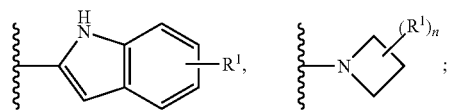

or phenyl optionally substituted with 1-3 substituents, each substituent independently selected from halo, $C_{1-4}$alkyl, $C_{1-4}$alkoxy, —CO—O—$C_{1-4}$alkyl, —CO—N($C_{1-4}$alkyl)($C_{1-4}$alkyl),

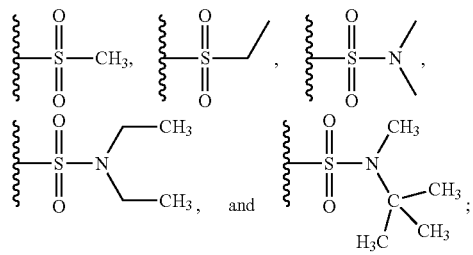

$R^1$ is each independently H, halo, $C_{1-4}$alkyl, or $C_{1-4}$alkoxy;
Z is

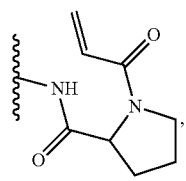 [SMILES: *NC(=O)C1CCCN1C(=O)C=C]

or Z is

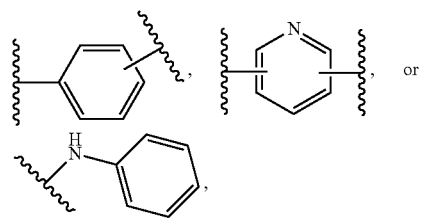

optionally substituted with 1-3 independent halo or $C_{1-4}$alkyl substituents;
$R^2$ is each independently H, halo, $C_{1-4}$alkyl, cyano-$C_{1-4}$alkyl,

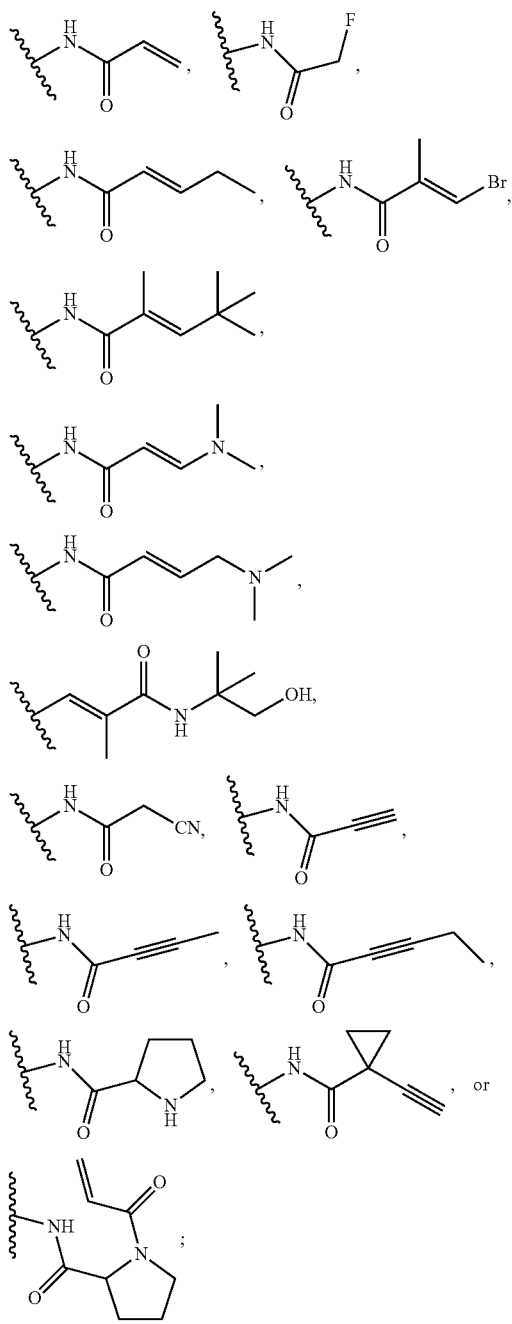

m is 0, 1, 2 or 3; and
n is 0, 1, or 2; provided that the compound is not

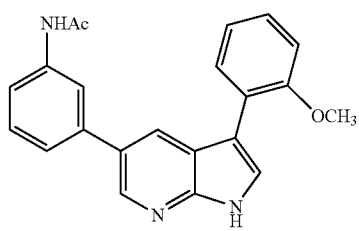

-continued

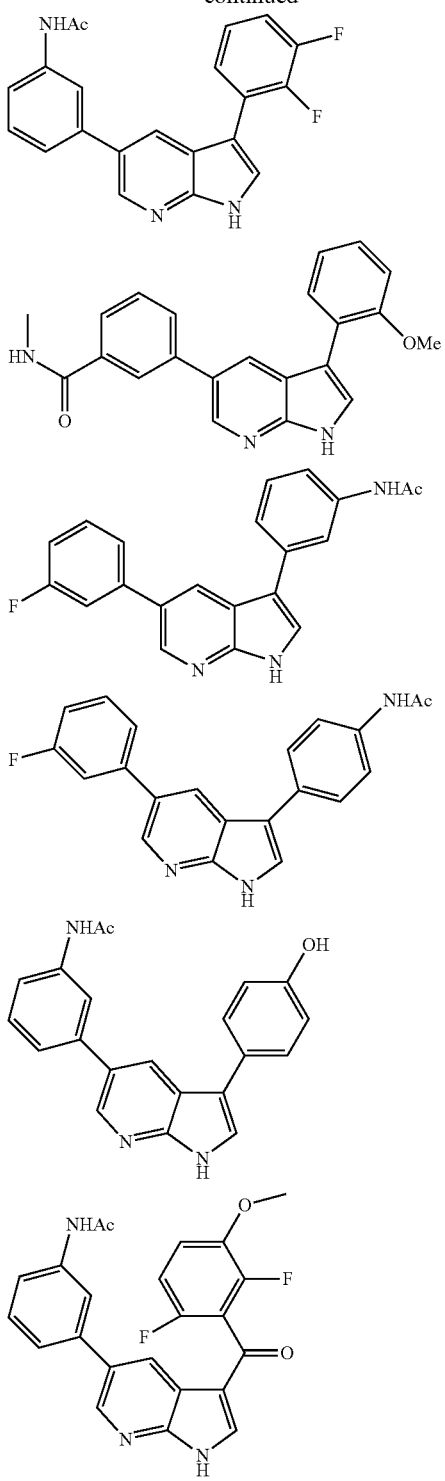

In an aspect of the invention, compounds of the present invention are described by Formula (I) and pharmaceutically acceptable salts thereof, wherein $X^1$ is N, $X^2$ is CH, and the other variables are as defined above for Formula (I).

In an embodiment of the aspect of the invention, compounds of the present invention are described by Formula (I) and pharmaceutically acceptable salts thereof, wherein $X^1$ is N, $X^2$ is CH, $L^1$ is

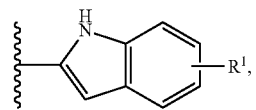

and the other variables are as defined above for Formula (I).).

In another embodiment of the aspect of the invention, compounds of the present invention are described by Formula (I) and pharmaceutically acceptable salts thereof, wherein $X^1$ is N, $X^2$ is CH, $L^1$ is

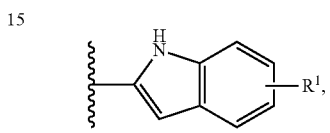

Z is phenyl, and the other variables are as defined above for Formula (I).

In still another embodiment of the aspect of the invention, compounds of the present invention are described by Formula (I) and pharmaceutically acceptable salts thereof, wherein $X^1$ is N, $X^2$ is CH, $L^1$ is phenyl optionally substituted with 1-3 substituents, each substituent independently selected from halo, $C_{1-4}$alkyl, $C_{1-4}$alkoxy, —CO—O—$C_{1-4}$alkyl, —CO—N($C_{1-4}$alkyl)($C_{1-4}$alkyl),

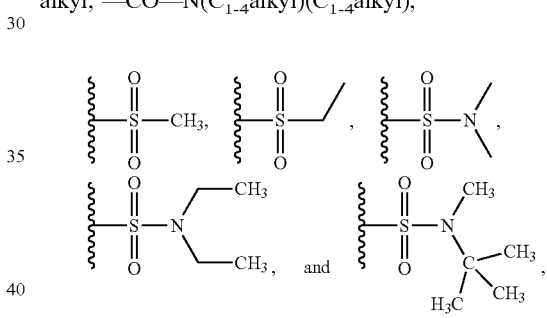

and the other variables are as defined above for Formula (I).

In another embodiment of the aspect of the invention, compounds of the present invention are described by Formula (I) and pharmaceutically acceptable salts thereof, wherein $X^1$ is N, $X^2$ is CH, $L^1$ is phenyl optionally substituted with 1-3 substituents, each substituent independently selected from halo, $C_{1-4}$alkyl, $C_{1-4}$alkoxy, —CO—O—$C_{1-4}$alkyl, —CO—N($C_{1-4}$alkyl)($C_{1-4}$alkyl),

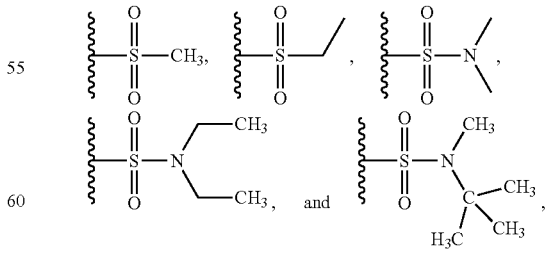

Z is phenyl, and the other variables are as defined above for Formula (I).

In yet another embodiment of the aspect of the invention, compounds of the present invention are described by Formula (I) and pharmaceutically acceptable salts thereof, wherein $X^1$ is N, $X^2$ is CH, $L^1$ is H, Z is phenyl, and the other variables are as defined above for Formula (I).

Compounds of the present invention include:

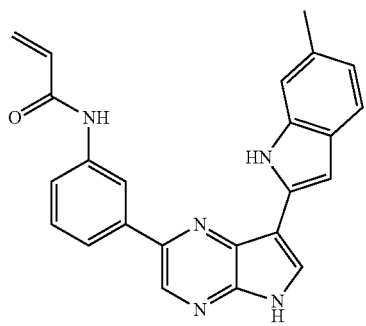

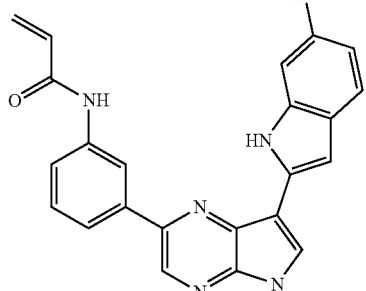

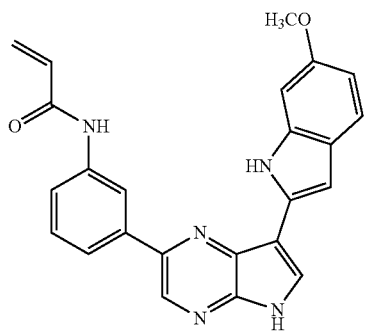

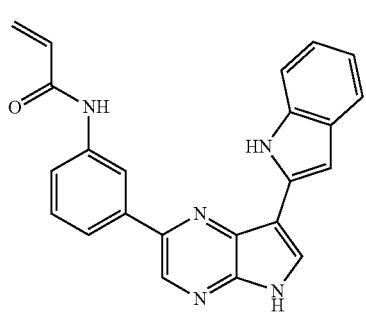

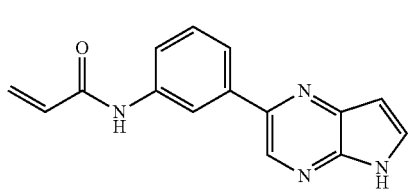

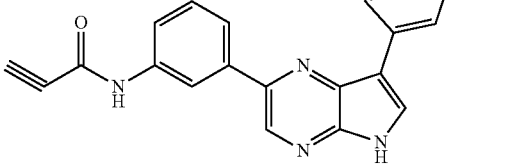

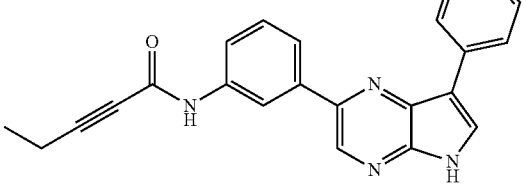

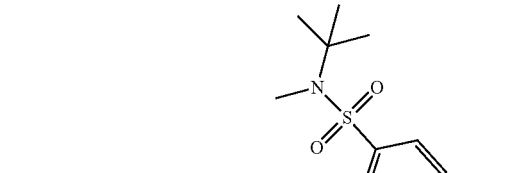

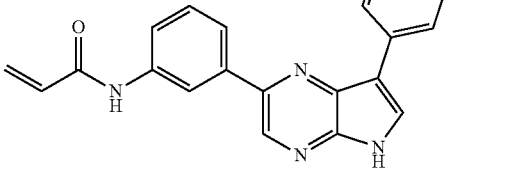

In another aspect of the invention, compounds of the present invention are described by Formula (I) and pharmaceutically acceptable salts thereof, wherein $X^1$ is CH, $X^2$ is N, and the other variables are as defined above for Formula (I).

In an embodiment of this aspect of the invention, compounds of the present invention are described by Formula (I) and pharmaceutically acceptable salts thereof, wherein $X^1$ is CH, $X^2$ is N, Z is phenyl, and the other variables are as defined above for Formula (I).

In still another embodiment of this aspect of the invention, compounds of the present invention are described by Formula (I) and pharmaceutically acceptable salts thereof, wherein $X^1$ is CH, $X^2$ is N, Z is phenyl, $L^1$ is $C_{1-4}$alkyl, and the other variables are as defined above for Formula (I).

Compounds of the present invention include:

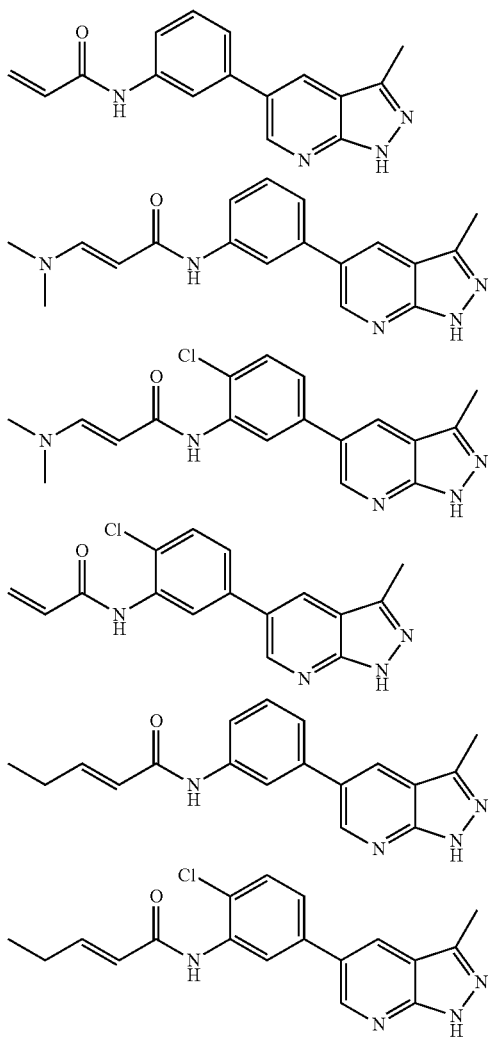

In still another aspect of the invention, compounds of the present invention are described by Formula (I) and pharmaceutically acceptable salts thereof, wherein $X^1$ is CH, $X^2$ is CH, and the other variables are as defined above for Formula (I).

In an embodiment of this aspect of the invention, compounds of the present invention are described by Formula (I) and pharmaceutically acceptable salts thereof, wherein $X^1$ is CH, $X^2$ is CH, Z is phenyl, and the other variables are as defined above for Formula (I).

In another embodiment of this aspect of the invention, compounds of the present invention are described by Formula (I) and pharmaceutically acceptable salts thereof, wherein $X^1$ is CH, $X^2$ is CH, Z is phenyl, $L^1$ is H, and the other variables are as defined above for Formula (I).

In yet another embodiment of this aspect of the invention, compounds of the present invention are described by Formula (I) and pharmaceutically acceptable salts thereof, wherein $X^1$ is CH, $X^2$ is CH, Z is phenyl, $L^1$ is halo, and the other variables are as defined above for Formula (I).

In another embodiment of this aspect of the invention, compounds of the present invention are described by Formula (I) and pharmaceutically acceptable salts thereof, wherein $X^1$ is CH, $X^2$ is CH, Z is phenyl, $L^1$ is $C_{1-4}$alkyl, and the other variables are as defined above for Formula (I).

In still another embodiment of this aspect of the invention, compounds of the present invention are described by Formula (I) and pharmaceutically acceptable salts thereof, wherein $X^1$ is CH, $X^2$ is CH, Z is phenyl, $L^1$ is —NH—S(O)$_2$($C_{1-4}$alkyl), and the other variables are as defined above for Formula (I).

In an embodiment of this aspect of the invention, compounds of the present invention are described by Formula (I) and pharmaceutically acceptable salts thereof, wherein $X^1$ is CH, $X^2$ is CH, Z is phenyl, $L^1$ is

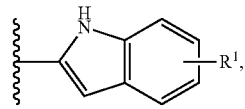

and the other variables are as defined above for Formula (I).

In another embodiment of this aspect of the invention, compounds of the present invention are described by Formula (I) and pharmaceutically acceptable salts thereof, wherein $X^1$ is CH, $X^2$ is CH, Z is phenyl, $L^1$ is

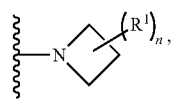

and the other variables are as defined above for Formula (I).

In yet still another embodiment of this aspect of the invention, compounds of the present invention are described by Formula (I) and pharmaceutically acceptable salts thereof, wherein $X^1$ is CH, $X^2$ is CH, Z is phenyl, $L^1$ is optionally substituted phenyl, and the other variables are as defined above for Formula (I).

In yet another embodiment of this aspect of the invention, compounds of the present invention are described by Formula (I) and pharmaceutically acceptable salts thereof, wherein $X^1$ is CH, $X^2$ is CH, Z is

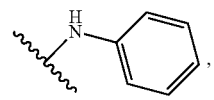

and the other variables are as defined above for Formula (I).

In another embodiment of this aspect of the invention, compounds of the present invention are described by Formula (I) and pharmaceutically acceptable salts thereof, wherein $X^1$ is CH, $X^2$ is CH, Z is

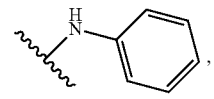 [SMILES: *Nc1ccccc1]

$L^1$ is H, and the other variables are as defined above for Formula (I).

In still another embodiment of this aspect of the invention, compounds of the present invention are described by Formula (I) and pharmaceutically acceptable salts thereof, wherein $X^1$ is CH, $X^2$ is CH, Z is

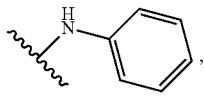

$L^1$ is $C_{1-4}$alkyl, and the other variables are as defined above for Formula (I).

In yet another embodiment of this aspect of the invention, compounds of the present invention are described by Formula (I) and pharmaceutically acceptable salts thereof, wherein $X^1$ is CH, $X^2$ is CH, Z is pyridyl, and the other variables are as defined above for Formula (I).

In another embodiment of this aspect of the invention, compounds of the present invention are described by Formula (I) and pharmaceutically acceptable salts thereof, wherein $X^1$ is CH, $X^2$ is CH, Z is pyridyl, $L^1$ is H, and the other variables are as defined above for Formula (I).

In still another embodiment of this aspect of the invention, compounds of the present invention are described by Formula (I) and pharmaceutically acceptable salts thereof, wherein $X^1$ is CH, $X^2$ is CH, Z is pyridyl, $L^1$ is $C_{1-4}$alkyl, and the other variables are as defined above for Formula (I).

In another embodiment of this aspect of the invention, compounds of the present invention are described by Formula (I) and pharmaceutically acceptable salts thereof, wherein $X^1$ is CH, $X^2$ is CH, Z is pyridyl, $L^1$ is optionally substituted phenyl, and the other variables are as defined above for Formula (I).

In an embodiment of this aspect of the invention, compounds of the present invention are described by Formula (I) and pharmaceutically acceptable salts thereof, wherein $X^1$ is CH, $X^2$ is CH, Z is

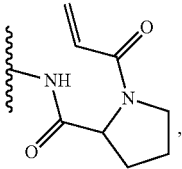 [SMILES: *NC(=O)C1CCCN1C(=O)C=C]

and the other variables are as defined above for Formula (I).

In yet another embodiment of this aspect of the invention, compounds of the present invention are described by Formula (I) and pharmaceutically acceptable salts thereof, wherein $X^1$ is CH, $X^2$ is CH, Z is

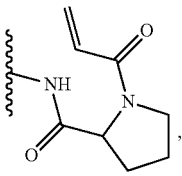 [SMILES: *NC(=O)C1CCCN1C(=O)C=C]

$L^1$ is H, and the other variables are as defined above for Formula (I).

In yet still another embodiment of this aspect of the invention, compounds of the present invention are described by Formula (I) and pharmaceutically acceptable salts thereof, wherein $X^1$ is CH, $X^2$ is CH, Z is $L^1$ is $C_{1-4}$alkyl, and the other variables are as defined above for Formula (I).

Compounds of the present invention include:

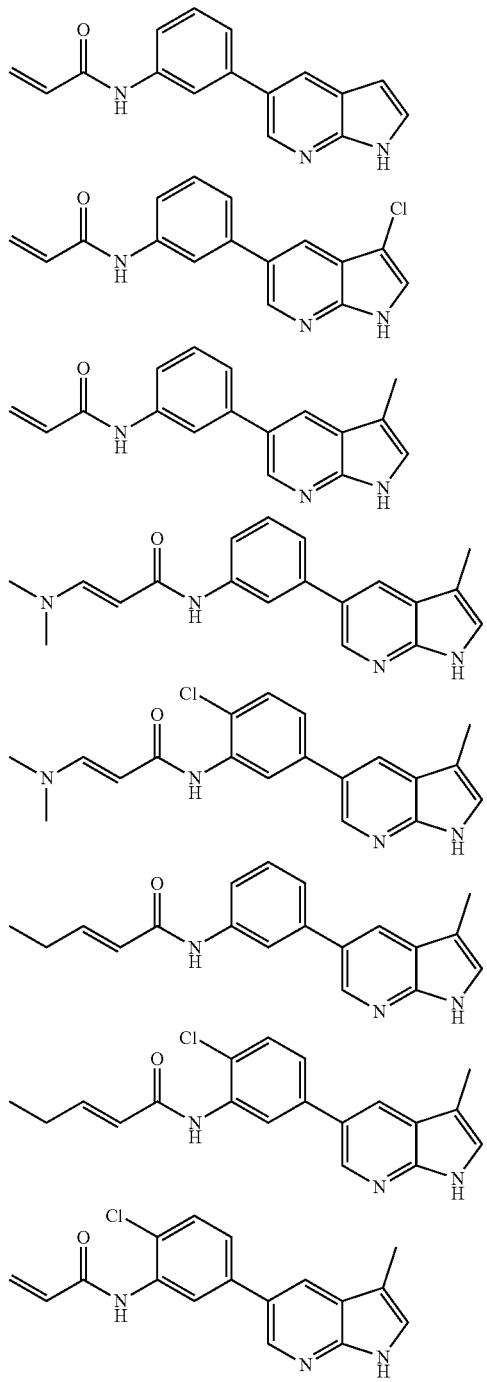

-continued
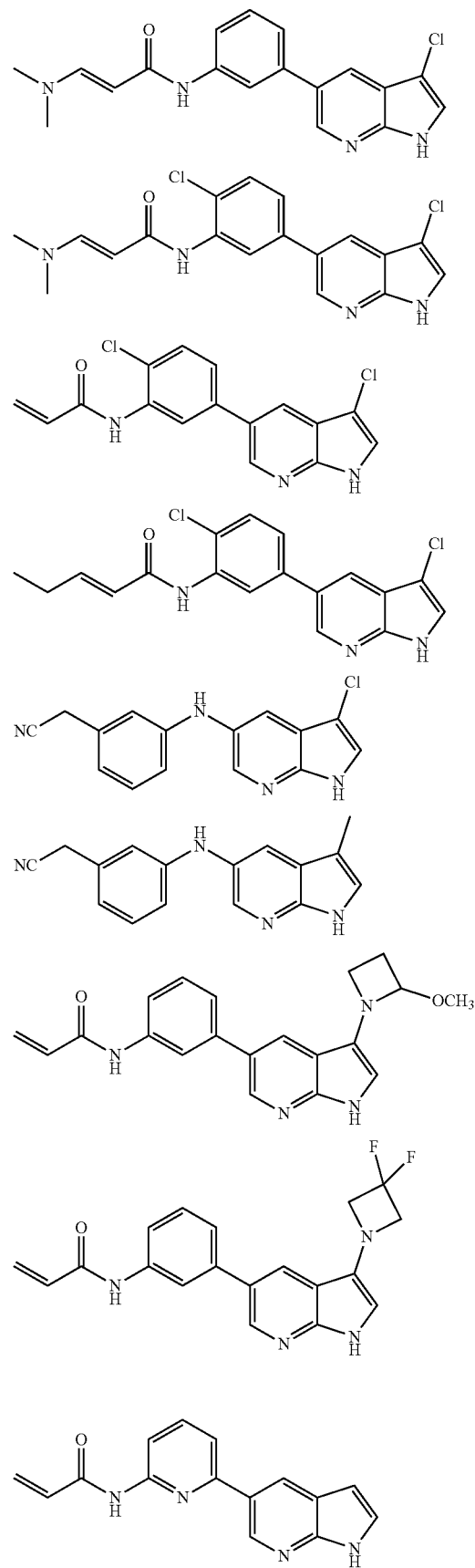
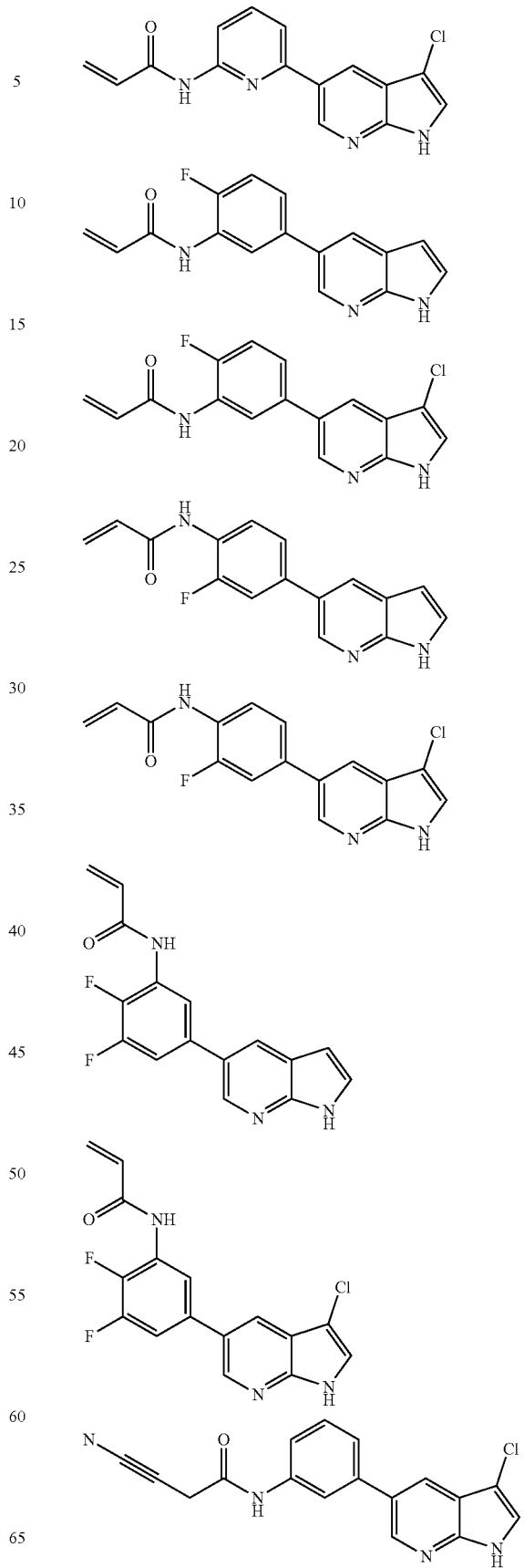

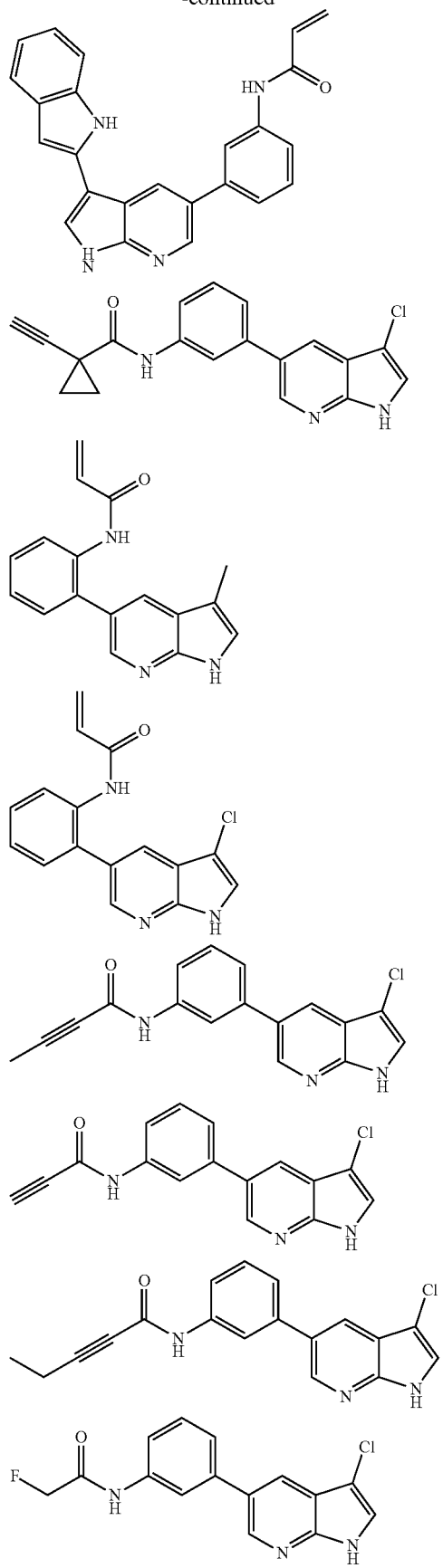
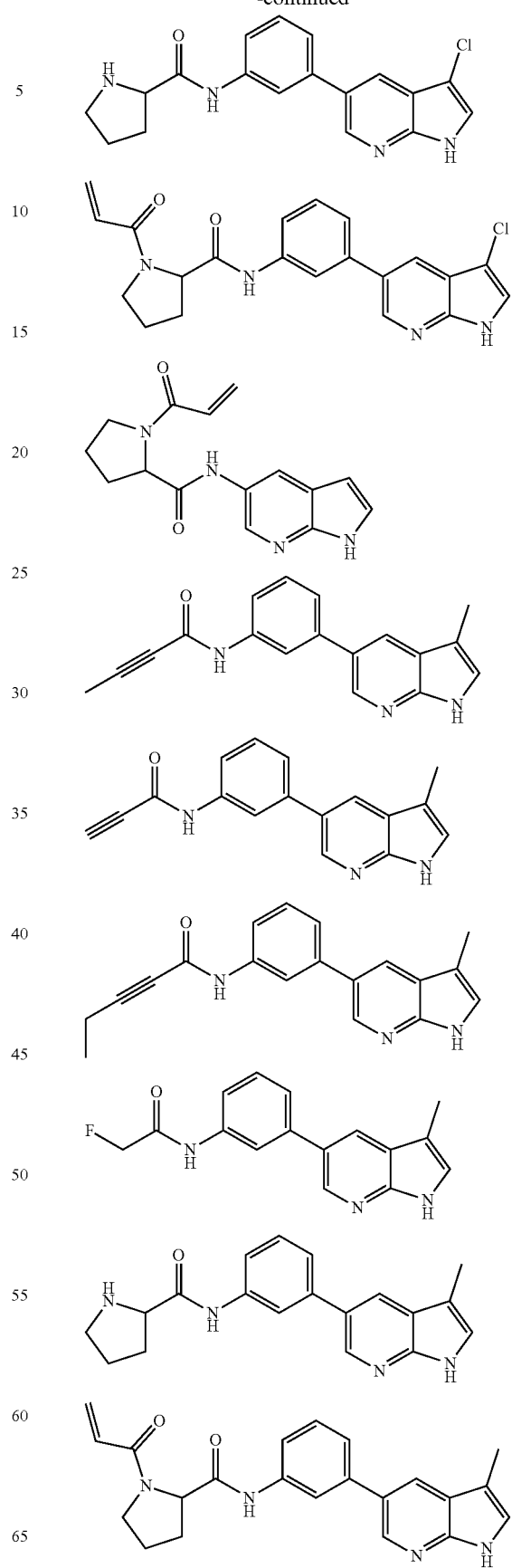

19
-continued
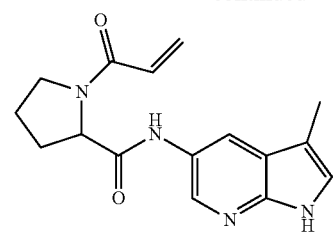
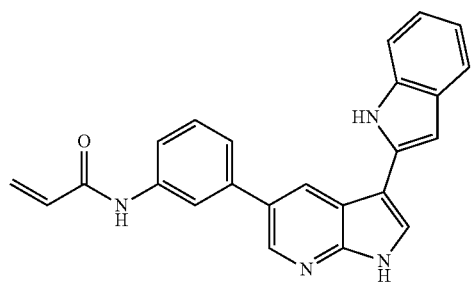
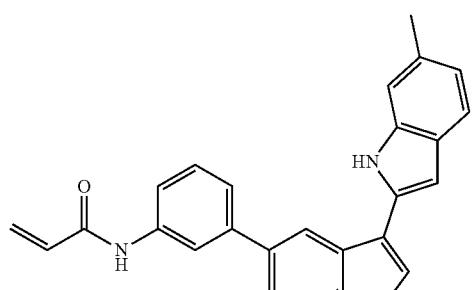
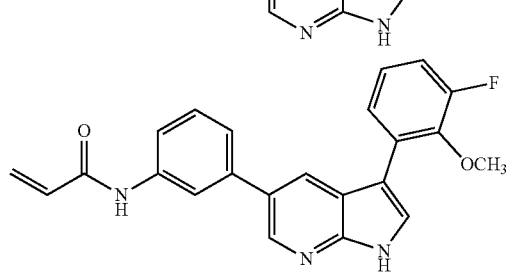
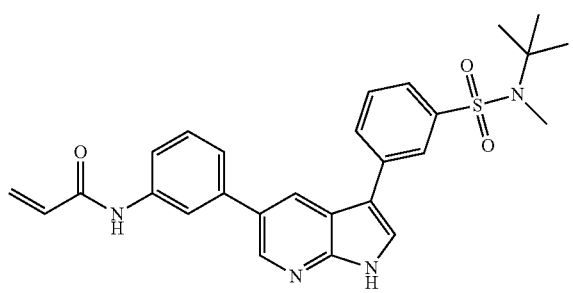
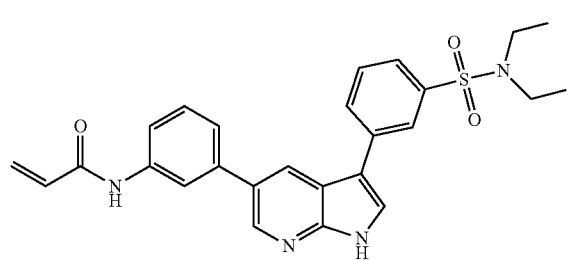
20
-continued
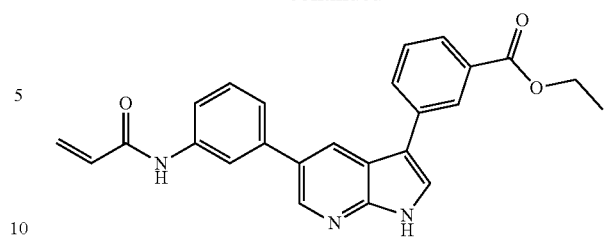
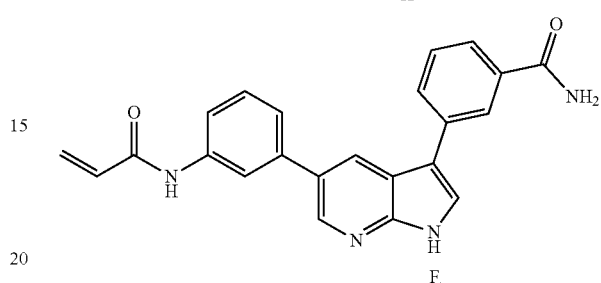
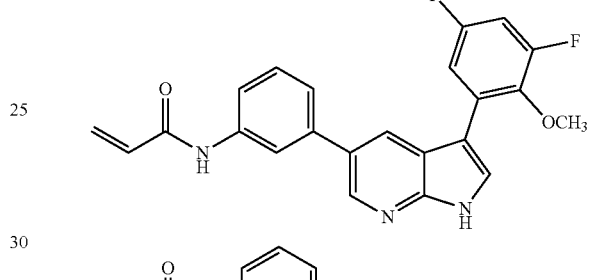
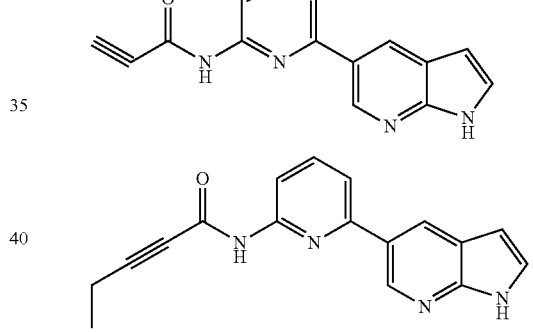
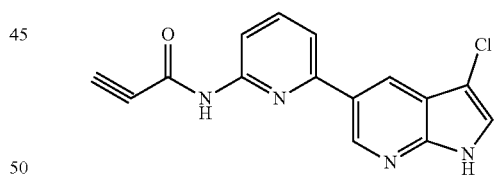
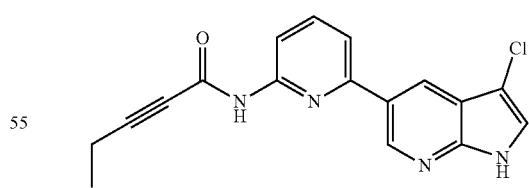
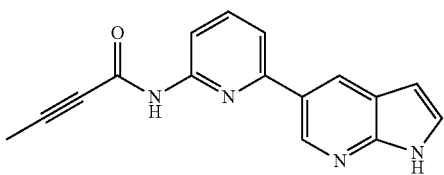

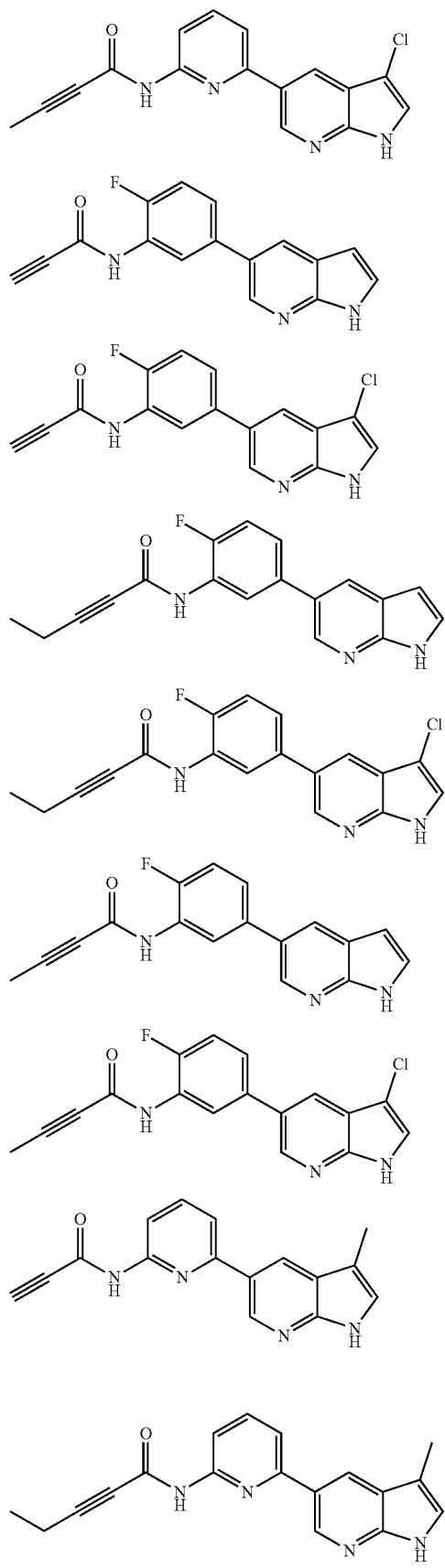
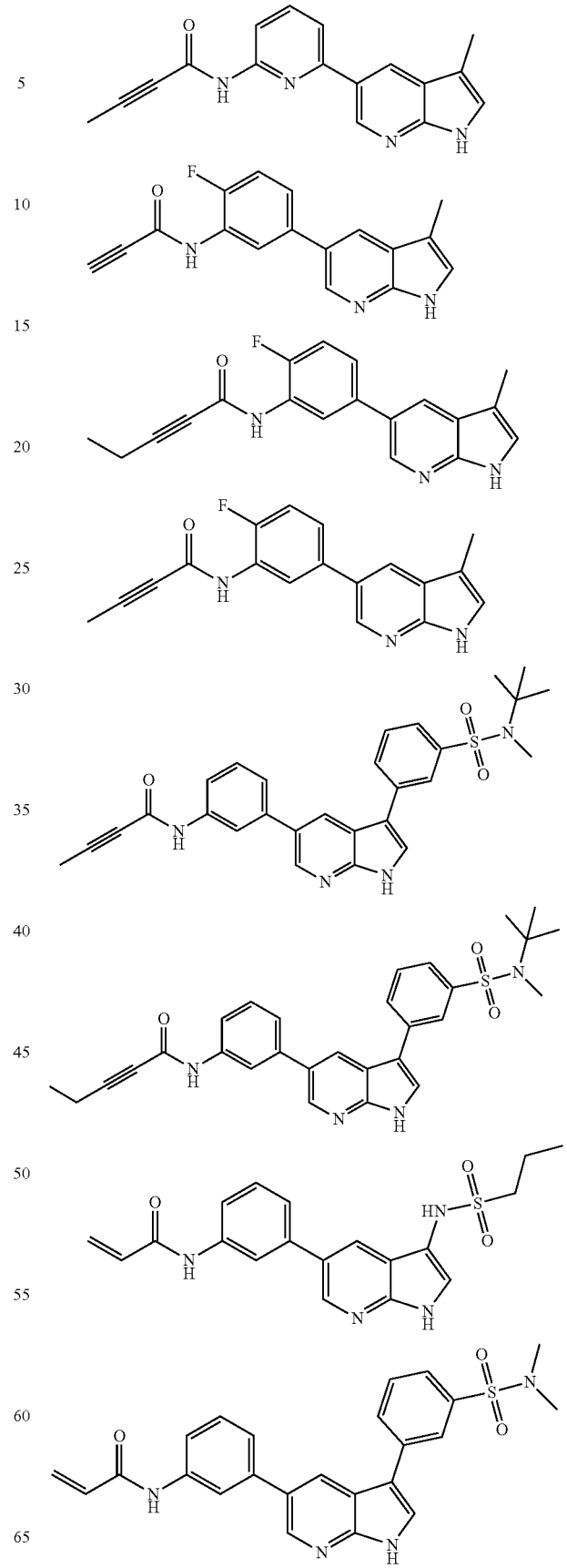

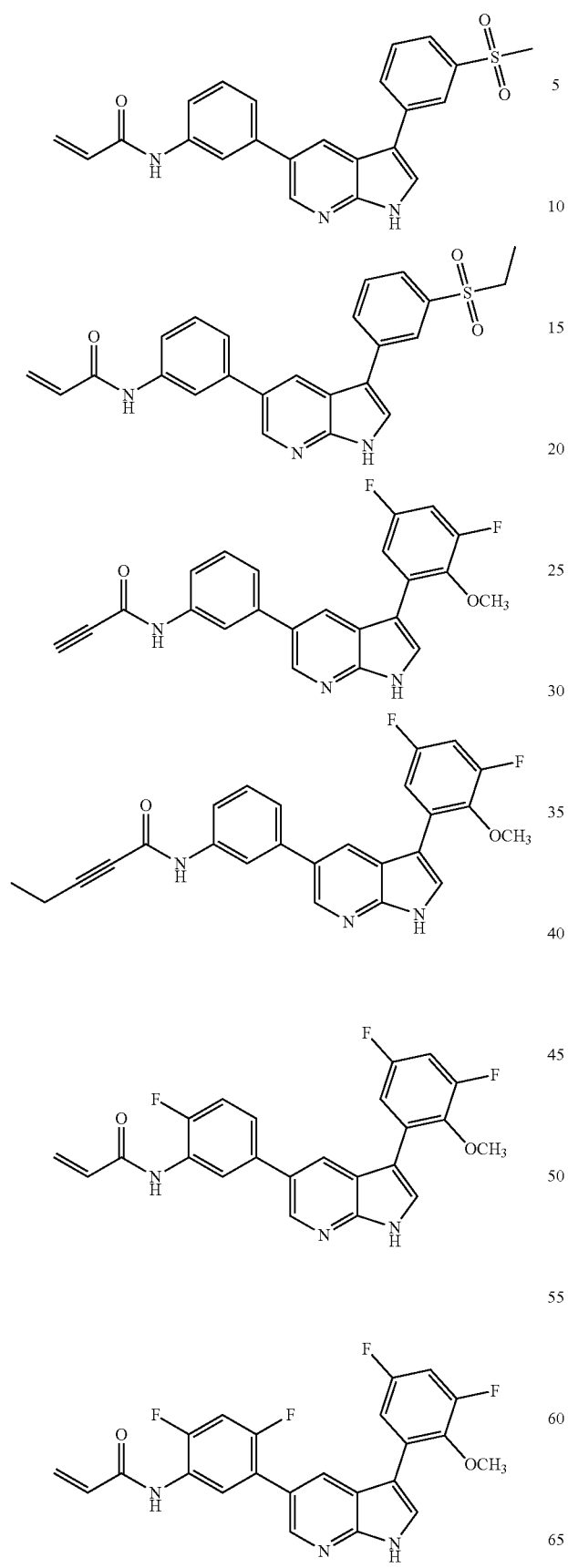
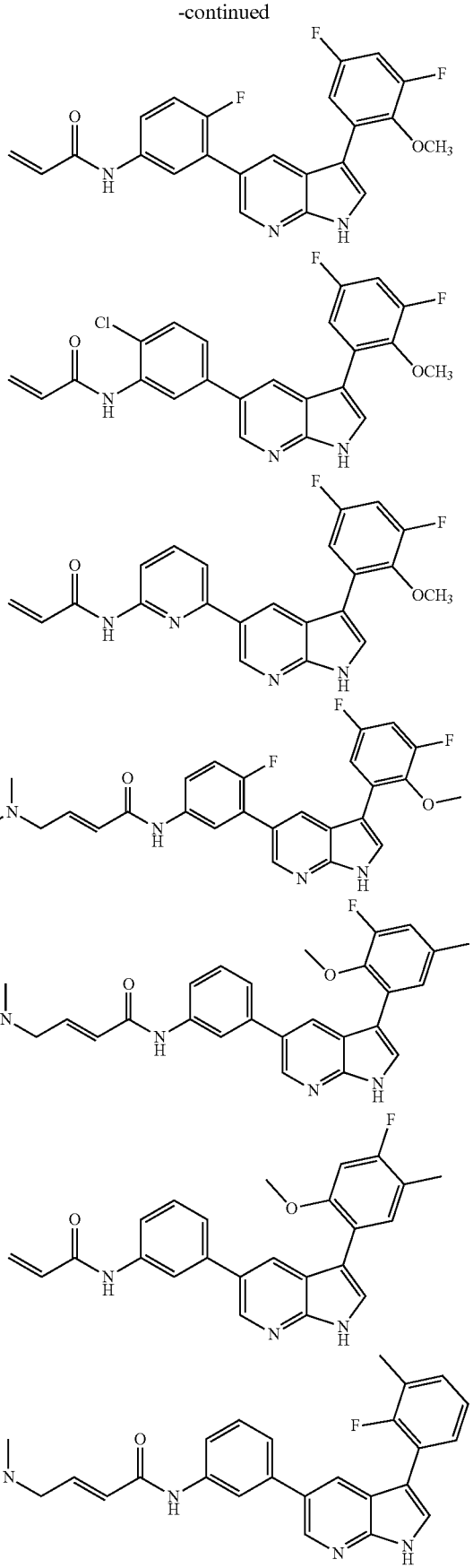

-continued
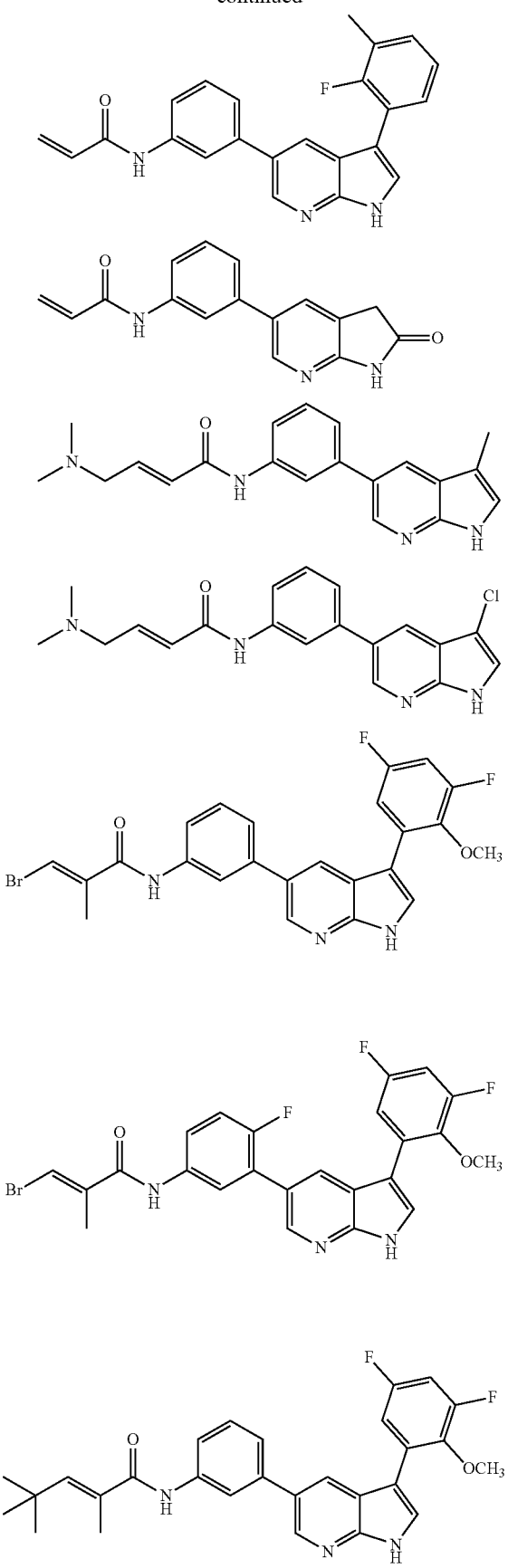
-continued
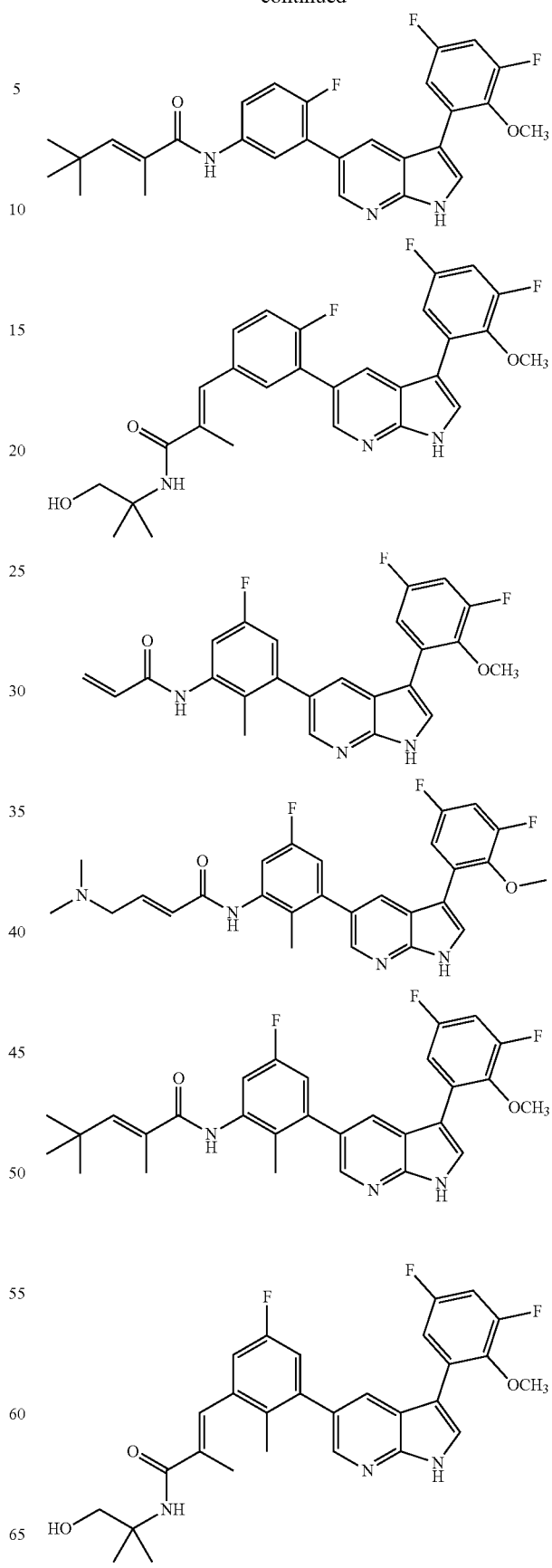

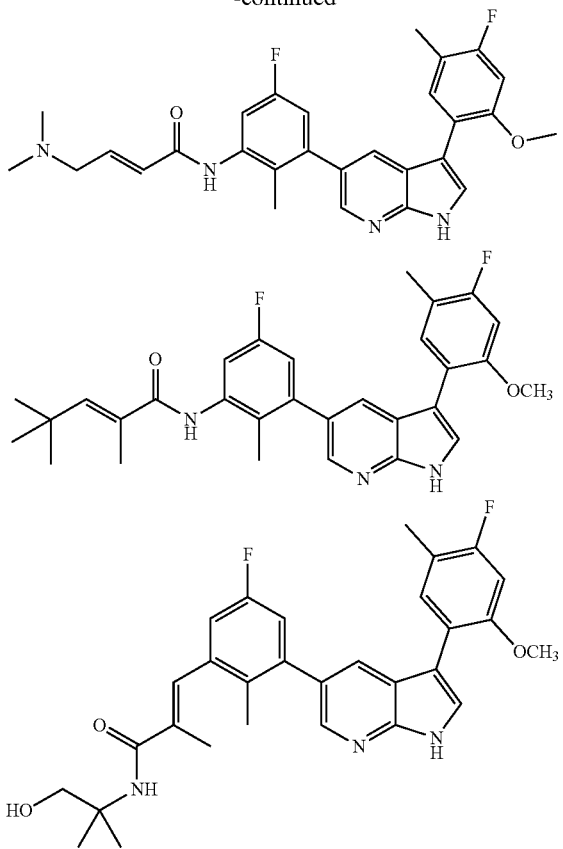

In an aspect of the invention, compounds of the present invention are described by Formula (I) and pharmaceutically acceptable salts thereof, wherein $L^1$ is H, $X^1$ is CH, and $X^2$ is >C=O, and the other variables are as defined above for Formula (I).

In an embodiment of this aspect of the invention, compounds of the present invention are described by Formula (I) and pharmaceutically acceptable salts thereof, wherein $L^1$ is H, $X^1$ is CH, and $X^2$ is >C=O, Z is phenyl, and the other variables are as defined above for Formula (I).

In an embodiment of this aspect of the invention, compounds of the present invention are described by Formula (I) and pharmaceutically acceptable salts thereof, wherein $L^1$ is H, $X^1$ is CH, and $X^2$ is >C=O, Z is phenyl, $L^1$ is H, and the other variables are as defined above for Formula (I).

Compounds of the present invention include the compound:

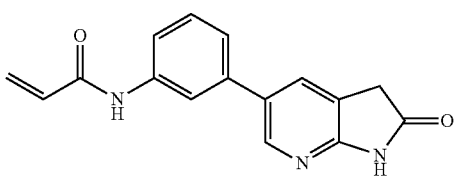 [SMILES: C=CC(=O)Nc1cccc(-c2cnc3c(c2)CC(=O)N3)c1]

The invention will be further understood upon consideration of the following non-limiting Examples. In other aspects or embodiments include any of the compounds in Table 1, that fall within the scope of any of the embodiments described above of the compounds of Formula I, or pharmaceuticals acceptable salts thereof.

Unless otherwise stated the following terms used in the specification and claims have the meanings discussed below:

"Alkyl" refers to a saturated straight or branched hydrocarbon radical of one to six carbon atoms, preferably one to four carbon atoms, e.g., methyl, ethyl, propyl, 2-propyl, n-butyl, iso-butyl, tert-butyl, pentyl, hexyl, and the like, preferably methyl, ethyl, propyl, or 2-propyl. Representative saturated straight chain alkyls include methyl, ethyl, n-propyl, n-butyl, n-pentyl, n-hexyl, and the like; while saturated branched alkyls include isopropyl, sec-butyl, isobutyl, tert-butyl, isopentyl, and the like. Cyclic alkyls are referred to herein as a "cycloalkyl."

Unsaturated alkyls contain at least one double or triple bond between adjacent carbon atoms (referred to as an "alkenyl" or "alkynyl", respectively.) Representative straight chain and branched alkenyls include ethylenyl, propylenyl, 1-butenyl, 2-butenyl, isobutylenyl, 1-pentenyl, 2-pentenyl, 3-methyl-1-butenyl, 2-methyl-2-butenyl, 2,3-dimethyl-2-butenyl, and the like; while representative straight chain and branched alkynyls include acetylenyl, propynyl, 1-butynyl, 2-butynyl, 1-pentynyl, 2-pentynyl, 3-methyl-1-butynyl, and the like.

"$C_{0-4}$alkyl" refers to an alkyl with 0, 1, 2, 3, or 4 carbon atoms. $C_{0-4}$alkyl with 0 carbon atoms is a hydrogen atom when terminal and is a direct bond when linking.

"Alkylene" means a linear saturated divalent hydrocarbon radical of one to six carbon atoms or a branched saturated divalent hydrocarbon radical of three to six carbon atoms, e.g., methylene, ethylene, 2,2-dimethylethylene, propylene, 2-methylpropylene, butylene, pentylene, and the like, preferably methylene, ethylene, or propylene.

"Cycloalkyl" refers to a saturated cyclic hydrocarbon radical of three to eight carbon atoms, e.g., cyclopropyl, cyclobutyl, cyclopentyl or cyclohexyl.

"Alkoxy" means a radical —$OR_a$ where $R_a$ is an alkyl as defined above, e.g., methoxy, ethoxy, propoxy, butoxy and the like.

"Halo" means fluoro, chloro, bromo, or iodo, preferably fluoro and chloro.

"Haloalkyl" means alkyl substituted with one or more, preferably one, two or three, same or different halo atoms, e.g., —$CH_2Cl$, —$CF_3$, —$CH_2CF_3$, —$CH_2CCl_3$, and the like.

"Haloalkoxy" means a radical —$OR_b$ where $R_b$ is an haloalkyl as defined above, e.g., trifluoromethoxy, trichloroethoxy, 2,2-dichloropropoxy, and the like.

"Acyl" means a radical —$C(O)R_c$ where $R_c$ is hydrogen, alkyl, or haloalkyl as defined herein, e.g., formyl, acetyl, trifluoroacetyl, butanoyl, and the like.

"Aryl" refers to an all-carbon monocyclic or fused-ring polycyclic (i.e., rings which share adjacent pairs of carbon atoms) groups of 6 to 12 carbon atoms having a completely conjugated pi-electron system. Examples, without limitation, of aryl groups are phenyl, naphthyl and anthracenyl. The aryl group may be substituted or unsubstituted. Unless specifically stated otherwise, "substituted aryl" refers to the aryl group being substituted with one or more, more preferably one, two or three, even more preferably one or two substituents independently selected from the group consisting of alkyl (wherein the alkyl may be optionally substituted with one or two substituents), haloalkyl, halo, hydroxy, alkoxy, mercapto, alkylthio, cyano, acyl, nitro, phenoxy, heteroaryl, heteroaryloxy, haloalkyl, haloalkoxy, carboxy, alkoxycarbonyl, amino, alkylamino dialkylamino, aryl, heteroaryl, carbocycle or heterocycle (wherein the aryl, heteroaryl, carbocycle or heterocycle may be optionally substituted).

"Heteroaryl" refers to a monocyclic or fused ring (i.e., rings which share an adjacent pair of atoms) group of 5 to 12 ring atoms containing one, two, three or four ring heteroatoms selected from N, O, or S, the remaining ring atoms being C, and, in addition, having a completely conjugated pi-electron system. Examples, without limitation, of unsubstituted heteroaryl groups are pyrrole, furan, thiophene, imidazole, oxazole, thiazole, pyrazole, pyridine, pyrimidine, quinoline, isoquinoline, purine, triazole, tetrazole, triazine, and carbazole. The heteroaryl group may be unsubstituted or substituted, such as, for example, 5-methylthiazolyl. Unless specifically stated otherwise, "substituted heteroaryl" refers to the heteroaryl group being substituted with one or more, more preferably one, two or three, even more preferably one or two substituents independently selected from the group consisting of alkyl (wherein the alkyl may be optionally substituted with one or two substituents), haloalkyl, halo, hydroxy, alkoxy, mercapto, alkylthio, cyano, acyl, nitro, haloalkyl, haloalkoxy, carboxy, alkoxycarbonyl, amino, alkylamino dialkylamino, aryl, heteroaryl, carbocycle or heterocycle (wherein the aryl, heteroaryl, carbocycle or heterocycle may be optionally substituted).

"Carbocycle" refers to a saturated, unsaturated or aromatic ring system having 3 to 14 ring carbon atoms. The term "carbocycle", whether saturated or partially unsaturated, also refers to rings that are optionally substituted. The term "carbocycle" includes aryl. The term "carbocycle" also includes aliphatic rings that are fused to one or more aromatic or nonaromatic rings, such as in a decahydronaphthyl or tetrahydronaphthyl, where the radical or point of attachment is on the aliphatic ring. The carbocycle group may be substituted or unsubstituted. Unless specifically stated otherwise, "substituted carbocyle" refers to the carbocycle group being substituted with one or more, more preferably one, two or three, even more preferably one or two substituents independently selected from the group consisting of alkyl (wherein the alkyl may be optionally substituted with one or two substituents), haloalkyl, halo, hydroxy, alkoxy, mercapto, alkylthio, cyano, acyl, nitro, haloalkyl, haloalkoxy, carboxy, alkoxycarbonyl, amino, alkylamino dialkylamino, aryl, heteroaryl, carbocycle or heterocycle (wherein the aryl, heteroaryl, carbocycle or heterocycle may be optionally substituted).

"Heterocycle" refers to a saturated, unsaturated or aromatic cyclic ring system having 3 to 14 ring atoms in which one, two or three ring atoms are heteroatoms selected from N, O, or $S(O)_m$ (where m is an integer from 0 to 2), the remaining ring atoms being C, where one or two C atoms may optionally be replaced by a carbonyl group. The term "heterocycle" includes heteroaryl. Unless specifically stated otherwise, "substituted heterocyclyl" refers to the heterocyclyl ring being substituted independently with one or more, preferably one, two, or three substituents selected from alkyl (wherein the alkyl may be optionally substituted with one or two substituents), haloalkyl, cycloalkylamino, cycloalkylalkyl, cycloalkylaminoalkyl, cycloalkylalkylaminoalkyl, cyanoalkyl, halo, nitro, cyano, hydroxy, alkoxy, amino, alkylamino, dialkylamino, hydroxyalkyl, carboxyalkyl, aminoalkyl, alkylaminoalkyl, dialkylaminoalkyl, aralkyl, heteroaralkyl, aryl, heteroaryl, carbocycle, heterocycle (wherein the aryl, heteroaryl, carbocycle or heterocycle may be optionally substituted), aralkyl, heteroaralkyl, saturated or unsaturated heterocycloamino, saturated or unsaturated heterocycloaminoalkyl, and $-COR_d$ (where $R_d$ is alkyl). More specifically the term heterocyclyl includes, but is not limited to, tetrahydropyranyl, 2,2-dimethyl-1,3-dioxolane, piperidino, N-methylpiperidin-3-yl, piperazino, N-methylpyrrolidin-3-yl, pyrrolidino, morpholino, 4-cyclopropylmethylpiperazino, thiomorpholino, thiomorpholino-1-oxide, thiomorpholino-1,1-dioxide, 4-ethyloxycarbonylpiperazino, 3-oxopiperazino, 2-imidazolidone, 2-pyrrolidinone, 2-oxohomopiperazino, tetrahydropyrimidin-2-one, and the derivatives thereof, including 2-methyl-4,5,6,7-tetrahydro-1H-pyrrolo[2,3-c]pyridinyl. In certain embodiments, the heterocycle group is optionally substituted with one or two substituents independently selected from halo, alkyl, alkyl substituted with carboxy, ester, hydroxy, alkylamino, saturated or unsaturated heterocycloamino, saturated or unsaturated heterocycloaminoalkyl, or dialkylamino.

"Optional" or "optionally" means that the subsequently described event or circumstance may but need not occur, and that the description includes instances where the event or circumstance occurs and instances in which it does not. For example, "heterocyclic group optionally substituted with an alkyl group" means that the alkyl may but need not be present, and the description includes situations where the heterocycle group is substituted with an alkyl group and situations where the heterocycle group is not substituted with the alkyl group.

Lastly, unless specifically stated otherwise, the term "substituted" as used herein means any of the above groups (e.g., alkyl, aryl, heteroaryl, carbocycle, heterocycle, etc.) wherein at least one hydrogen atom is replaced with a substituent. In the case of an oxo substituent ("=O") two hydrogen atoms are replaced. "Substituents" within the context of this invention, if not specified, include halogen, hydroxy, oxo, cyano, nitro, amino, alkylamino, dialkylamino, alkyl, alkoxy, thioalkyl, haloalkyl (e.g., $-CF_3$), hydroxyalkyl, aryl, substituted aryl, arylalkyl, substituted arylalkyl, heteroaryl, substituted heteroaryl, heteroarylalkyl, substituted heteroarylalkyl, heterocycle, substituted heterocycle, heterocyclealkyl, substituted heterocyclealkyl, $-NR_eR_f$, $-NR_eC(=O)R_f$, $-NR_eC(=O)NR_eR_f$, $-NR_eC(=O)OR_f$, $-NR_eSO_2R_f$, $-OR_e$, $-C(=O)R_e$, $-C(=O)OR_e$, $-C(=O)NR_eR_f$, $-OC(=O)NR_eR_f$, $-SH$, $-SR_e$, $-SOR_e$, $-S(=O)_2R_e$, $-OS(=O)_2R_e$, $-S(=O)_2OR_e$, wherein $R_e$ and $R_f$ are the same or different and independently hydrogen, alkyl, haloalkyl, substituted alkyl, aryl, substituted aryl, arylalkyl, substituted arylalkyl, heteroaryl, substituted heteroaryl, heteroarylalkyl, substituted heteroarylalkyl, heterocycle, substituted heterocycle, heterocyclealkyl or substituted heterocyclealkyl.

Compounds that have the same molecular formula but differ in the nature or sequence of bonding of their atoms or the arrangement of their atoms in space are termed "isomers". Isomers that differ in the arrangement of their atoms in space are termed "stereoisomers". Stereoisomers that are not mirror images of one another are termed "diastereomers" and those that are non-superimposable mirror images of each other are termed "enantiomers". When a compound has an asymmetric center, for example, it is bonded to four different groups; a pair of enantiomers is possible. An enantiomer can be characterized by the absolute configuration of its asymmetric center and is described by the R- and S-sequencing rules of Cahn and Prelog (Cahn, R., Ingold, C., and Prelog, V. Angew. Chem. 78:413-47, 1966; Angew. Chem. Internat. Ed. Eng. 5:385-415, 511, 1966), or by the manner in which the molecule rotates the plane of polarized light and designated as dextrorotatory or levorotatory (i.e., as (+) or (−)-isomers respectively). A chiral compound can exist as either individual enantiomer or as a mixture thereof. A mixture containing equal proportions of the enantiomers is called a "racemic mixture".

The compounds of this invention may possess one or more asymmetric centers; such compounds can therefore be produced as individual (R)- or (S)-stereoisomers or as mixtures thereof. Unless indicated otherwise, the description or naming of a particular compound in the specification and claims is intended to include both individual enantiomers and mixtures, racemic or otherwise, thereof. The methods for the determination of stereochemistry and the separation of stereoisomers are well-known in the art (see discussion in Ch. 4 of ADVANCED ORGANIC CHEMISTRY, 4$^{th}$ edition, March, J., John Wiley and Sons, New York City, 1992).

The compounds of the present invention may exhibit the phenomena of tautomerism and structural isomerism. This invention encompasses any tautomeric or structural isomeric form and mixtures thereof which possess the ability to modulate ITK and JAK3 activity and is not limited to, any one tautomeric or structural isomeric form.

It is contemplated that a compound of the present invention would be metabolized by enzymes in the body of the organism such as human being to generate a metabolite that can modulate the activity of the protein kinases. Such metabolites are within the scope of the present invention.

A compound of the present invention or a pharmaceutically acceptable salt thereof can be administered as such to a human patient or can be administered in pharmaceutical compositions in which the foregoing materials are mixed with suitable carriers or excipient(s). Techniques for formulation and administration of drugs may be found, for example, in REMINGTON'S PHARMACOLOGICAL SCIENCES, Mack Publishing Co., Easton, Pa., latest edition.

A "pharmaceutical composition" refers to a mixture of one or more of the compounds described herein or pharmaceutically acceptable salts or prodrugs thereof, with other chemical components, such as pharmaceutically acceptable excipients. The purpose of a pharmaceutical composition is to facilitate administration of a compound to an organism.

"Pharmaceutically acceptable excipient" refers to an inert substance added to a pharmaceutical composition to further facilitate administration of a compound. Examples, without limitation, of excipients include calcium carbonate, calcium phosphate, various sugars and types of starch, cellulose derivatives, gelatin, vegetable oils and polyethylene glycols.

"Pharmaceutically acceptable salt" refers to those salts which retain the biological effectiveness and properties of the parent compound. Such salts may include: (1) acid addition salt which is obtained by reaction of the free base of the parent compound with inorganic acids such as hydrochloric acid, hydrobromic acid, nitric acid, phosphoric acid, sulfuric acid, and perchloric acid and the like, or with organic acids such as acetic acid, oxalic acid, (D)- or (L)-malic acid, maleic acid, methanesulfonic acid, ethanesulfonic acid, p-toluenesulfonic acid, salicylic acid, tartaric acid, citric acid, succinic acid or malonic acid and the like, preferably hydrochloric acid or (L)-malic acid; or (2) salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, tromethamine, N-methylglucamine, and the like.

The compound of the present invention may also act, or be designed to act, as a prodrug. A "prodrug" refers to an agent, which is converted into the parent drug in vivo. Prodrugs are often useful because, in some situations, they may be easier to administer than the parent drug. They may, for instance, be bioavailable by oral administration whereas the parent drug is not. The prodrug may also have improved solubility in pharmaceutical compositions over the parent drug. An example, without limitation, of a prodrug would be a compound of the present invention, which is, administered as an ester (the "prodrug"), phosphate, amide, carbamate, or urea.

"Therapeutically effective amount" refers to that amount of the compound being administered which will relieve to some extent one or more of the symptoms of the disorder being treated. In reference to the treatment of cancer, a therapeutically effective amount refers to that amount which has the effect of: (1) reducing the size of the tumor; (2) inhibiting tumor metastasis; (3) inhibiting tumor growth; and/or (4) relieving one or more symptoms associated with the cancer. In reference to the treatment of inflammation, a therapeutically effective amount refers to that amount which has the effect of reducing the pain, temperature, and/or swelling symptomatic of inflammation, both locally or generally.

The term "disease", as used herein, means any disease or other deleterious condition in which an ITK or JAK3 is known to play a role. The term "disease" also means those diseases or conditions that are alleviated by treatment with ITK or JAK3 modulators. Such conditions include, without limitation, cancer and other hyperproliferative disorders as well as inflammation. In certain embodiments, the cancer is a cancer of colon, breast, stomach, prostate, pancreas, or ovarian tissue. Such disease includes those associated with abnormal cell growth such as autoimmune, inflammation, rheumatoid arthritis, systemic lupus erythematosus, atherosclerosis, ulcerative colitis, psoriatic arthritis, psoriasis, and Crohn's.

The term "ITK or JAK3 activity-mediated condition" or "disease", as used herein, means any disease or other deleterious condition in which ITK or JAK3 activity is known to play a role. The term "ITK or JAK3 activity-mediated condition" also means those diseases or conditions that are alleviated by treatment with an ITK or JAK3 inhibitor.

As used herein, "administer" or "administration" refers to the delivery of an inventive compound or of a pharmaceutically acceptable salt thereof or of a pharmaceutical composition containing an inventive compound or a pharmaceutically acceptable salt thereof of this invention to an organism for the purpose of prevention or treatment of a protein kinase-related disorder.

Suitable routes of administration may include, without limitation, oral, rectal, transmucosal or intestinal administration or intramuscular, subcutaneous, intramedullary, intrathecal, direct intraventricular, intravenous, intravitreal, intraperitoneal, intranasal, or intraocular injections. In certain embodiments, the preferred routes of administration are oral and intravenous. Alternatively, one may administer the compound in a local rather than systemic manner, for example, via injection of the compound directly into a solid tumor, often in a depot or sustained release formulation. Furthermore, one may administer the drug in a targeted drug delivery system, for example, in a liposome coated with tumor-specific antibody. In this way, the liposomes may be targeted to and taken up selectively by the tumor.

Pharmaceutical compositions of the present invention may be manufactured by processes well known in the art, e.g., by means of conventional mixing, dissolving, granulating, dragee-making, levigating, emulsifying, encapsulating, entrapping or lyophilizing processes.

Pharmaceutical compositions for use in accordance with the present invention may be formulated in any conventional manner using one or more physiologically acceptable carriers comprising excipients and auxiliaries which facilitate processing of the active compounds into preparations which can be used pharmaceutically. Proper formulation is dependent upon the route of administration chosen.

For injection, the compounds of the invention may be formulated in aqueous solutions, preferably in physiologically compatible buffers such as Hanks' solution, Ringer's solution, or physiological saline buffer. For transmucosal administration, penetrants appropriate to the barrier to be permeated are used in the formulation. Such penetrants are generally known in the art.

For oral administration, the compounds can be formulated by combining the active compounds with pharmaceutically acceptable carriers well known in the art. Such carriers enable the compounds of the invention to be formulated as tablets, pills, lozenges, dragees, capsules, liquids, gels, syrups, slurries, suspensions and the like, for oral ingestion by a patient. Pharmaceutical preparations for oral use can be made using a solid excipient, optionally grinding the resulting mixture, and processing the mixture of granules, after adding other suitable auxiliaries if desired, to obtain tablets or dragee cores. Useful excipients are, in particular, fillers such as sugars, including lactose, sucrose, mannitol, or sorbitol, cellulose preparations such as, for example, maize starch, wheat starch, rice starch and potato starch and other materials such as gelatin, gum tragacanth, methyl cellulose, hydroxypropylmethyl-cellulose, sodium carboxymethylcellulose, and/or polyvinyl-pyrrolidone (PVP). If desired, disintegrating agents may be added, such as cross-linked polyvinyl pyrrolidone, agar, or alginic acid. A salt such as sodium alginate may also be used.

Dragee cores are provided with suitable coatings. For this purpose, concentrated sugar solutions may be used which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical compositions which can be used orally include push-fit capsules made of gelatin, as well as soft, sealed capsules made of gelatin and a plasticizer, such as glycerol or sorbitol. The push-fit capsules can contain the active ingredients in admixture with filler such as lactose, a binder such as starch, and/or a lubricant such as talc or magnesium stearate and, optionally, stabilizers. In soft capsules, the active compounds may be dissolved or suspended in suitable liquids, such as fatty oils, liquid paraffin, or liquid polyethylene glycols. Stabilizers may be added in these formulations, also. Pharmaceutical compositions which may also be used include hard gelatin capsules. The capsules or pills may be packaged into brown glass or plastic bottles to protect the active compound from light. The containers containing the active compound capsule formulation are preferably stored at controlled room temperature (15-30° C.).

For administration by inhalation, the compounds for use according to the present invention may be conveniently delivered in the form of an aerosol spray using a pressurized pack or a nebulizer and a suitable propellant, e.g., without limitation, dichlorodifluoromethane, trichlorofluoromethane, dichlorotetra-fluoroethane or carbon dioxide. In the case of a pressurized aerosol, the dosage unit may be controlled by providing a valve to deliver a metered amount. Capsules and cartridges of, for example, gelatin for use in an inhaler or insufflator may be formulated containing a powder mix of the compound and a suitable powder base such as lactose or starch.

The compounds may also be formulated for parenteral administration, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulating materials such as suspending, stabilizing and/or dispersing agents.

Pharmaceutical compositions for parenteral administration include aqueous solutions of a water soluble form, such as, without limitation, a salt, of the active compound. Additionally, suspensions of the active compounds may be prepared in a lipophilic vehicle. Suitable lipophilic vehicles include fatty oils such as sesame oil, synthetic fatty acid esters such as ethyl oleate and triglycerides, or materials such as liposomes. Aqueous injection suspensions may contain substances which increase the viscosity of the suspension, such as sodium carboxymethyl cellulose, sorbitol, or dextran. Optionally, the suspension may also contain suitable stabilizers and/or agents that increase the solubility of the compounds to allow for the preparation of highly concentrated solutions.

Alternatively, the active ingredient may be in powder form for constitution with a suitable vehicle, e.g., sterile, pyrogen-free water, before use.

The compounds may also be formulated in rectal compositions such as suppositories or retention enemas, using, e.g., conventional suppository bases such as cocoa butter or other glycerides.

In addition to the formulations described previously, the compounds may also be formulated as depot preparations. Such long acting formulations may be administered by implantation (for example, subcutaneously or intramuscularly) or by intramuscular injection. A compound of this invention may be formulated for this route of administration with suitable polymeric or hydrophobic materials (for instance, in an emulsion with a pharmacologically acceptable oil), with ion exchange resins, or as a sparingly soluble derivative such as, without limitation, a sparingly soluble salt.

A non-limiting example of a pharmaceutical carrier for the hydrophobic compounds of the invention is a cosolvent system comprising benzyl alcohol, a nonpolar surfactant, a water-miscible organic polymer and an aqueous phase such as the VPD cosolvent system. VPD is a solution of 3% w/v benzyl alcohol, 8% w/v of the nonpolar surfactant polysorbate 80, and 65% w/v polyethylene glycol 300, made up to volume in absolute ethanol. The VPD cosolvent system (VPD: D5W) consists of VPD diluted 1:1 with a 5% dextrose in water solution. This cosolvent system dissolves hydrophobic compounds well, and itself produces low toxicity upon systemic administration. Naturally, the proportions of such a cosolvent system may be varied considerably without destroying its solubility and toxicity characteristics. Furthermore, the identity of the cosolvent components may be varied: for example, other low-toxicity nonpolar surfactants may be used instead of polysorbate 80, the fraction size of polyethylene glycol may be varied, other biocompatible polymers may replace polyethylene glycol, e.g., polyvinyl pyrrolidone, and other sugars or polysaccharides may substitute for dextrose.

Alternatively, other delivery systems for hydrophobic pharmaceutical compounds may be employed. Liposomes and emulsions are well known examples of delivery vehicles or carriers for hydrophobic drugs. In addition, certain organic solvents such as dimethylsulfoxide also may be employed, although often at the cost of greater toxicity.

Additionally, the compounds may be delivered using a sustained-release system, such as semipermeable matrices of solid hydrophobic polymers containing the therapeutic agent. Various sustained-release materials have been established and are well known by those skilled in the art. Sustained-release capsules may, depending on their chemical nature, release the compounds for a few weeks up to over 100 days. Depending on the chemical nature and the biological stability of the therapeutic reagent, additional strategies for protein stabilization may be employed.

The pharmaceutical compositions herein also may comprise suitable solid or gel phase carriers or excipients. Examples of such carriers or excipients include, but are not limited to, calcium carbonate, calcium phosphate, various sugars, starches, cellulose derivatives, gelatin, and polymers such as polyethylene glycols.

Many of the ITK and JAK3-modulating compounds of the invention may be provided as physiologically acceptable salts wherein the claimed compound may form the negatively or the positively charged species. Examples of salts in which the compound forms the positively charged moiety include, without limitation, quaternary ammonium (defined elsewhere herein), salts such as the hydrochloride, sulfate, carbonate, lactate, tartrate, malate, maleate, succinate wherein the nitrogen atom of the quaternary ammonium group is a nitrogen of the selected compound of this invention which has reacted with the appropriate acid. Salts in which a compound of this invention forms the negatively charged species include, without limitation, the sodium, potassium, calcium and magnesium salts formed by the reaction of a carboxylic acid group in the compound with an appropriate base (e.g. sodium hydroxide (NaOH), potassium hydroxide (KOH), calcium hydroxide ($Ca(OH)_2$), etc.).

Pharmaceutical compositions suitable for use in the present invention include compositions wherein the active ingredients are contained in an amount sufficient to achieve the intended purpose, e.g., the modulation of protein kinase activity and/or the treatment or prevention of a protein kinase-related disorder.

More specifically, a therapeutically effective amount means an amount of compound effective to prevent, alleviate or ameliorate symptoms of disease or prolong the survival of the subject being treated.

Determination of a therapeutically effective amount is well within the capability of those skilled in the art, especially in light of the detailed disclosure provided herein.

For any compound used in the methods of the invention, the therapeutically effective amount or dose can be estimated initially from cell culture assays. Then, the dosage can be formulated for use in animal models so as to achieve a circulating concentration range that includes the $IC_{50}$ as determined in cell culture (i.e., the concentration of the test compound which achieves a half-maximal inhibition of the ITK or JAK3, or surrogate marker activity). Such information can then be used to more accurately determine useful doses in humans.

Toxicity and therapeutic efficacy of the compounds described herein can be determined by standard pharmaceutical procedures in cell cultures or experimental animals, e.g., by determining the $IC_{50}$ and the $LD_{50}$ (both of which are discussed elsewhere herein) for a subject compound. The data obtained from these cell culture assays and animal studies can be used in formulating a range of dosage for use in humans. The dosage may vary depending upon the dosage form employed and the route of administration utilized. The exact formulation, route of administration and dosage can be chosen by the individual physician in view of the patient's condition. (See, e.g., GOODMAN & GILMAN'S THE PHARMACOLOGICAL BASIS OF THERAPEUTICS, Ch. 3, $9^{th}$ ed., Ed. by Hardman, J., and Limbard, L., McGraw-Hill, New York City, 1996, p. 46.)

Dosage amount and interval may be adjusted individually to provide plasma levels of the active species which are sufficient to maintain the kinase modulating effects. These plasma levels are referred to as minimal effective concentrations (MECs). The MEC will vary for each compound but can be estimated from in vitro data, e.g., the concentration necessary to achieve 50-90% inhibition of ITK or JAK3, or surrogate marker may be ascertained using the assays described herein. Dosages necessary to achieve the MEC will depend on individual characteristics and route of administration. HPLC assays or bioassays can be used to determine plasma concentrations.

Dosage intervals can also be determined using MEC value. Compounds should be administered using a regimen that maintains plasma levels above the MEC for 10-90% of the time, preferably between 30-90% and most preferably between 50-90%.

At present, the therapeutically effective amounts of compounds of the present invention may range from approximately 2.5 mg/m² to 1500 mg/m² per day. Additional illustrative amounts range from 0.2-1000 mg/qid, 2-500 mg/qid, and 20-250 mg/qid.

In cases of local administration or selective uptake, the effective local concentration of the drug may not be related to plasma concentration, and other procedures known in the art may be employed to determine the correct dosage amount and interval.

The amount of a composition administered will, of course, be dependent on the subject being treated, the severity of the affliction, the manner of administration, the judgment of the prescribing physician, etc.

The compositions may, if desired, be presented in a pack or dispenser device, such as an FDA approved kit, which may contain one or more unit dosage forms containing the active ingredient. The pack may for example comprise metal or plastic foil, such as a blister pack. The pack or dispenser device may be accompanied by instructions for administration. The pack or dispenser may also be accompanied by a notice associated with the container in a form prescribed by a governmental agency regulating the manufacture, use or sale of pharmaceuticals, which notice is reflective of approval by the agency of the form of the compositions or of human or veterinary administration. Such notice, for example, may be of the labeling approved by the U.S. Food and Drug Administration for prescription drugs or of an approved product insert. Compositions comprising a compound of the invention formulated in a compatible pharmaceutical carrier may also be prepared, placed in an appropriate container, and labeled for treatment of an indicated condition. Suitable conditions indicated on the label may include treatment of a tumor, inhibition of angiogenesis, treatment of fibrosis, diabetes, and the like.

As mentioned above, the compounds and compositions of the invention will find utility in a broad range of diseases and conditions mediated by protein kinases, including diseases and conditions mediated by ITK or JAK3 activity. Such diseases may include by way of example and not limitation, cancers such as lung cancer, NSCLC (non small cell lung cancer), oat-cell cancer, bone cancer, pancreatic cancer, skin cancer, dermatofibrosarcoma protuberans, cancer of the head and neck, cutaneous or intraocular melanoma, uterine cancer, ovarian cancer, colo-rectal cancer, cancer of the anal region, stomach cancer, colon cancer, breast cancer, gynecologic tumors (e.g., uterine sarcomas, carcinoma of the fallopian tubes, carcinoma of the endometrium, carcinoma of the cervix, carcinoma of the vagina or carcinoma of the vulva), Hodgkin's Disease, hepatocellular cancer, cancer of the esophagus, cancer of the small intestine, cancer of the endocrine system (e.g., cancer of the thyroid, pancreas, parathyroid or adrenal glands), sarcomas of soft tissues, cancer of the urethra, cancer of the penis, prostate cancer (particularly hormone-refractory), chronic or acute leukemia, solid tumors of childhood, hypereosinophilia, lymphocytic lymphomas, cancer of the bladder, cancer of the kidney or ureter (e.g., renal cell carcinoma, carcinoma of the renal pelvis), pediatric malignancy, neoplasms of the central nervous system (e.g., primary CNS lymphoma, spinal axis tumors, medulloblastoma, brain stem gliomas or pituitary adenomas), Barrett's esophagus (pre-malignant syndrome), neoplastic cutaneous disease, psoriasis, mycoses fungoides, and benign prostatic hypertrophy, diabetes related diseases such as diabetic retinopathy, retinal ischemia, and retinal neovascularization, hepatic cirrhosis, angiogenesis, cardiovascular disease such as atherosclerosis, immunological disease such as autoimmune disease and renal disease.

The inventive compound can be used in combination with one or more other chemotherapeutic agents. The dosage of the inventive compounds may be adjusted for any drug-drug reaction. In one embodiment, the chemotherapeutic agent is selected from the group consisting of mitotic inhibitors, alkylating agents, anti-metabolites, cell cycle inhibitors, enzymes, topoisomerase inhibitors such as CAMPTOSAR (irinotecan), biological response modifiers, anti-hormones, antiangiogenic agents such as MMP-2, MMP-9 and COX-2 inhibitors, anti-androgens, platinum coordination complexes (cisplatin, etc.), substituted ureas such as hydroxyurea; methylhydrazine derivatives, e.g., procarbazine; adrenocortical suppressants, e.g., mitotane, aminoglutethimide, hormone and hormone antagonists such as the adrenocorticosteriods (e.g., prednisone), progestins (e.g., hydroxyprogesterone caproate), estrogens (e.g., diethylstilbesterol), antiestrogens such as tamoxifen, androgens, e.g., testosterone propionate, and aromatase inhibitors, such as anastrozole, and AROMASIN (exemestane).

Examples of alkylating agents that the above method can be carried out in combination with include, without limitation, fluorouracil (5-FU) alone or in further combination with leukovorin; other pyrimidine analogs such as UFT, capecitabine, gemcitabine and cytarabine, the alkyl sulfonates, e.g., busulfan (used in the treatment of chronic granulocytic leukemia), improsulfan and piposulfan; aziridines, e.g., benzodepa, carboquone, meturedepa and uredepa; ethyleneimines and methylmelamines, e.g., altretamine, triethylenemelamine, triethylenephosphoramide, triethylenethiophosphoramide and trimethylolmelamine; and the nitrogen mustards, e.g., chlorambucil (used in the treatment of chronic lymphocytic leukemia, primary macroglobulinemia and non-Hodgkin's lymphoma), cyclophosphamide (used in the treatment of Hodgkin's disease, multiple myeloma, neuroblastoma, breast cancer, ovarian cancer, lung cancer, Wilm's tumor and rhabdomyosarcoma), estramustine, ifosfamide, novembrichin, prednimustine and uracil mustard (used in the treatment of primary thrombocytosis, non-Hodgkin's lymphoma, Hodgkin's disease and ovarian cancer); and triazines, e.g., dacarbazine (used in the treatment of soft tissue sarcoma).

Examples of antimetabolite chemotherapeutic agents that the above method can be carried out in combination with include, without limitation, folic acid analogs, e.g., methotrexate (used in the treatment of acute lymphocytic leukemia, choriocarcinoma, mycosis fungiodes, breast cancer, head and neck cancer and osteogenic sarcoma) and pteropterin; and the purine analogs such as mercaptopurine and thioguanine which find use in the treatment of acute granulocytic, acute lymphocytic and chronic granulocytic leukemias.

Examples of natural product-based chemotherapeutic agents that the above method can be carried out in combination with include, without limitation, the vinca alkaloids, e.g., vinblastine (used in the treatment of breast and testicular cancer), vincristine and vindesine; the epipodophyllotoxins, e.g., etoposide and teniposide, both of which are useful in the treatment of testicular cancer and Kaposi's sarcoma; the antibiotic chemotherapeutic agents, e.g., daunorubicin, doxorubicin, epirubicin, mitomycin (used to treat stomach, cervix, colon, breast, bladder and pancreatic cancer), dactinomycin, temozolomide, plicamycin, bleomycin (used in the treatment of skin, esophagus and genitourinary tract cancer); and the enzymatic chemotherapeutic agents such as L-asparaginase.

An inventive compound can also be used with other signal transduction inhibitors, such as agents that can inhibit EGFR (epidermal growth factor receptor) responses, such as EGFR antibodies, EGF antibodies, and molecules that are EGFR inhibitors; VEGF (vascular endothelial growth factor) inhibitors; and erbB2 receptor inhibitors, such as organic molecules or antibodies that bind to the erbB2 receptor, such as HERCEPTIN (Genentech, Inc., South San Francisco, Calif.). EGFR inhibitors are described in, for example in WO 95/19970, WO 98/14451, WO 98/02434, and U.S. Pat. No. 5,747,498 and such substances can be used in the present invention as described herein.

EGFR-inhibiting agents include, but are not limited to, the monoclonal antibodies C225 and anti-EGFR 22Mab (ImClone Systems, Inc., New York, N.Y.), the compounds erlotinib (OSI Pharmaceuticals, Inc., Melville, N.Y.), ZD-1839 (AstraZeneca), BIBX-1382 (Boehringer Ingelheim), MDX-447 (Medarex Inc., Annandale, N.J.), and OLX-103 (Merck & Co., Whitehouse Station, N.J.), and EGF fusion toxin (Seragen Inc., Hopkinton, Mass.).

These and other EGFR-inhibiting agents can be used in the present invention. VEGF inhibitors, for example SU-5416 and SU-6668 (Sugen Inc., South San Francisco, Calif.), can also be combined with an inventive compound. VEGF inhibitors are described in, for example, WO 01/60814 A3, WO 99/24440, PCT International Application PCT/IB99/00797, WO 95/21613, WO 99/61422, U.S. Pat. No. 5,834,504, WO 01/60814, WO 98/50356, U.S. Pat. Nos. 5,883,113 , 5,886,020 , 5,792,783, WO 99/10349, WO 97/32856, WO 97/22596, WO 98/54093, WO 98/02438, WO 99/16755, and WO 98/02437, all of which are incorporated herein in their entireties by reference. Other examples of some specific VEGF inhibitors useful in the present invention are IM862 (Cytran Inc., Kirkland, Wash.); anti-VEGF monoclonal antibody of Genentech, Inc.; and angiozyme, a synthetic ribozyme from Ribozyme (Boulder, Colo.) and Chiron (Emeryville, Calif.). These and other VEGF inhibitors can be used in the present invention as described herein. Further, pErbB2 receptor inhibitors, such as GW-282974 (Glaxo Wellcome plc), and the monoclonal antibodies AR-209 (Aronex Pharmaceuticals Inc., The Woodlands, Tex.) and 2B-1 (Chiron), can furthermore be combined with an inventive compound, for example, those indicated in WO 98/02434, WO 99/35146, WO 99/35132, WO 98/02437, WO 97/13760, WO 95/19970, U.S. Pat. No. 5,587,458 and U.S. Pat. No. 5,877,305, which are all hereby incorporated herein in their entireties by reference. ErbB2 receptor inhibitors useful in the present invention are also described in U.S. Pat. No. 6,284,764, incorporated in its entirety herein by reference. The erbB2 receptor inhibitor compounds and substance described in the aforementioned PCT applications, U.S. patents, and U.S. provisional applications, as well as other compounds and substances that inhibit the erbB2 receptor, can be used with an inventive compound, in accordance with the present invention.

An inventive compound can also be used with other agents useful in treating cancer, including, but not limited to, agents capable of enhancing antitumor immune responses, such as CTLA4 (cytotoxic lymphocyte antigen 4) antibodies, and other agents capable of blocking CTLA4; and anti-proliferative agents such as other farnesyl protein transferase inhibitors, for example the farnesyl protein transferase inhibitors described in the references cited in the "Background" section, of U.S. Pat. No. 6,258,824 B1.

The above method can also be carried out in combination with radiation therapy, wherein the amount of an inventive compound in combination with the radiation therapy is effective in treating the above diseases. Techniques for administering radiation therapy are known in the art, and these techniques can be used in the combination therapy described herein. The administration of the compound of the invention in this combination therapy can be determined as described herein.

TABLE 1

List of Examples

| Ex. No. | Structure | Name | *Mol. Wt. |
|---|---|---|---|
| 1 | 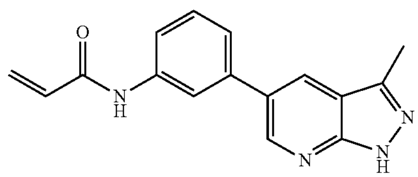 [SMILES: C=CC(=O)Nc1cccc(-c2cnc3[nH]nc(C)c3c2)c1] | N-(3-(3-methyl-1H-pyrazolo[3,4-b]pyridin-5-yl)phenyl)acrylamide | 278.310 |
| 2 | 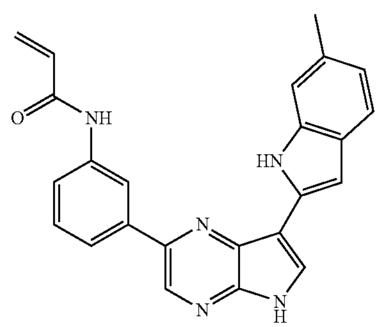 [SMILES: C=CC(=O)Nc1cccc(-c2cnc3[nH]cc(-c4cc5ccc(C)cc5[nH]4)c3n2)c1] | N-(3-(7-(6-methyl-1H-indol-2-yl)-5H-pyrrolo[2,3-b]pyrazin-2-yl)phenyl)acrylamide | 393.441 |
| 3 | 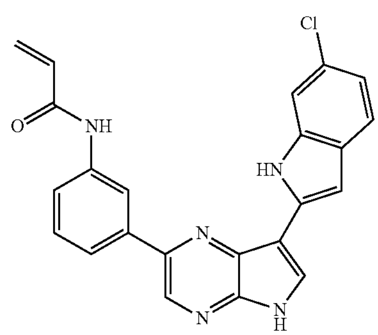 [SMILES: C=CC(=O)Nc1cccc(-c2cnc3[nH]cc(-c4cc5ccc(Cl)cc5[nH]4)c3n2)c1] | N-(3-(7-(6-chloro-1H-indol-2-yl)-5H-pyrrolo[2,3-b]pyrazin-2-yl)phenyl)acrylamide | 413.85 |

TABLE 1-continued

List of Examples

| Ex. No. | Structure | Name | *Mol. Wt. |
|---|---|---|---|
| 4 | 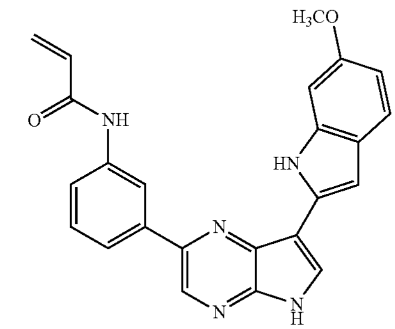 [SMILES: C=CC(=O)Nc1cccc(-c2cnc3[nH]cc(-c4cc5ccc(OC)cc5[nH]4)c3n2)c1] | N-(3-(7-(6-chloro-1H-indol-2-yl)-5H-pyrrolo[2,3-b]pyrazin-2-yl)phenyl)acrylamide | 409.440 |
| 5 | 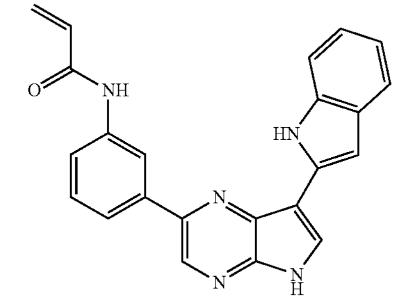 [SMILES: C=CC(=O)Nc1cccc(-c2cnc3[nH]cc(-c4cc5ccccc5[nH]4)c3n2)c1] | N-(3-(7-(1H-indol-2-yl)-5H-pyrrolo[2,3-b]pyrazin-2-yl)phenyl)acrylamide | 379.414 |
| 6 | 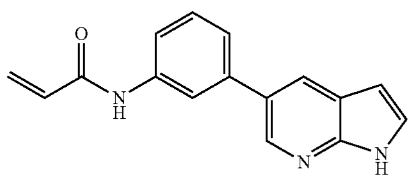 [SMILES: C=CC(=O)Nc1cccc(-c2cnc3[nH]ccc3c2)c1] | N-(3-(1H-pyrrolo[2,3-b]pyridin-5-yl)phenyl)acrylamide | 263.294 |
| 7 | 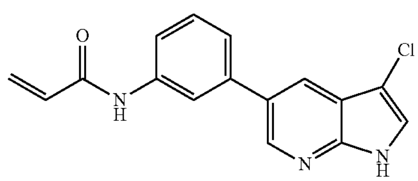 [SMILES: C=CC(=O)Nc1cccc(-c2cnc3[nH]cc(Cl)c3c2)c1] | N-(3-(3-chloro-1H-pyrrolo[2,3-b]pyridin-5-yl)phenyl)acrylamide | 297.739 |
| 8 | 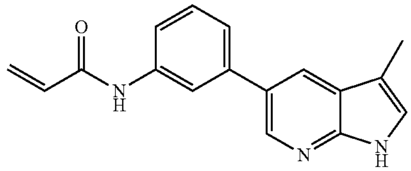 [SMILES: C=CC(=O)Nc1cccc(-c2cnc3[nH]cc(C)c3c2)c1] | N-(3-(3-methyl-1H-pyrrolo[2,3-b]pyridin-5-yl)phenyl)acrylamide | 277.321 |
| 9 | 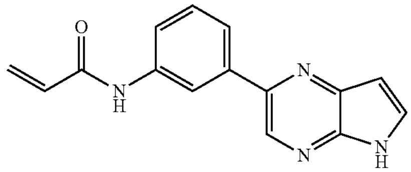 [SMILES: C=CC(=O)Nc1cccc(-c2cnc3[nH]ccc3n2)c1] | N-(3-(5H-pyrrolo[2,3-b]pyrazin-2-yl)phenyl)acrylamide | 264.282 |
| 10 | 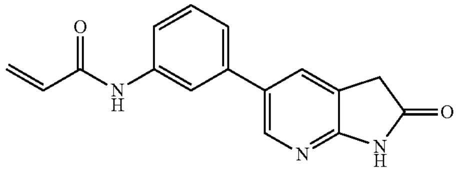 [SMILES: C=CC(=O)Nc1cccc(-c2cnc3c(c2)CC(=O)N3)c1] | N-(3-(2-oxo-2,3-dihydro-1H-pyrrolo[2,3-b]pyridin-5-yl)phenyl)acrylamide | 279.293 |

TABLE 1-continued

List of Examples

| Ex. No. | Structure | Name | *Mol. Wt. |
|---|---|---|---|
| 11 | 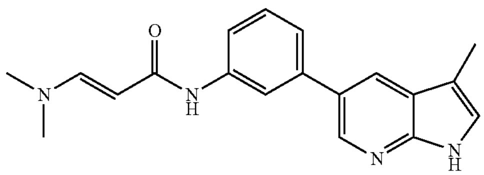 [SMILES: Cc1c[nH]c2ncc(-c3cccc(NC(=O)/C=C/N(C)C)c3)cc12] | (E)-3-(dimethylamino)-N-(3-(3-methyl-1H-pyrrolo[2,3-b]pyridin-5-yl)phenyl)acrylamide | 320.388 |
| 12 | 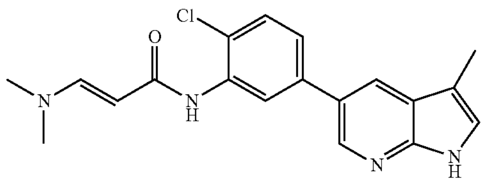 [SMILES: Cc1c[nH]c2ncc(-c3ccc(Cl)c(NC(=O)/C=C/N(C)C)c3)cc12] | (E)-N-(2-chloro-5-(3-methyl-1H-pyrrolo[2,3-b]pyridin-5-yl)phenyl)-3-(dimethylamino)acrylamide | 354.833 |
| 13 | 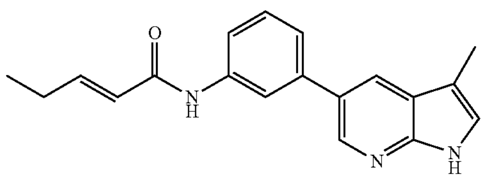 [SMILES: CC/C=C/C(=O)Nc1cccc(-c2cnc3[nH]cc(C)c3c2)c1] | (E)-N-(3-(3-methyl-1H-pyrrolo[2,3-b]pyridin-5-yl)phenyl)pent-2-enamide | 305.374 |
| 14 | 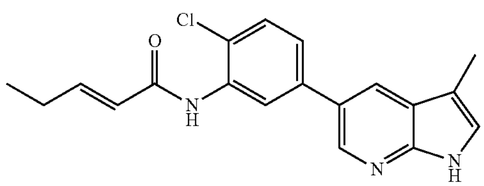 [SMILES: CC/C=C/C(=O)Nc1cc(-c2cnc3[nH]cc(C)c3c2)ccc1Cl] | (E)-N-(2-chloro-5-(3-methyl-1H-pyrrolo[2,3-b]pyridin-5-yl)phenyl)pent-2-enamide | 339.819 |
| 15 | 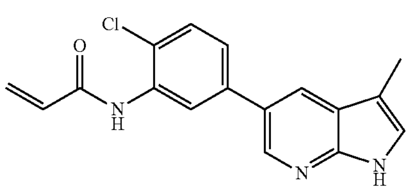 [SMILES: C=CC(=O)Nc1cc(-c2cnc3[nH]cc(C)c3c2)ccc1Cl] | N-(2-chloro-5-(3-methyl-1H-pyrrolo[2,3-b]pyridin-5-yl)phenyl)acrylamide | 311.080 |
| 16 | 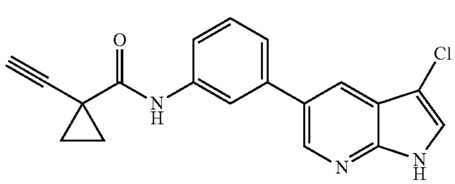 [SMILES: C#CC1(C(=O)Nc2cccc(-c3cnc4[nH]cc(Cl)c4c3)c2)CC1] | N-(3-(3-chloro-1H-pyrrolo[2,3-b]pyridin-5-yl)phenyl)-1-ethynylcyclopropanecarboxamide | 335.787 |
| 17 | 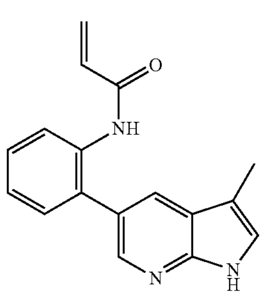 [SMILES: C=CC(=O)Nc1ccccc1-c1cnc2[nH]cc(C)c2c1] | N-(2-(3-methyl-1H-pyrrolo[2,3-b]pyridin-5-yl)phenyl)acrylamide | 277.321 |

TABLE 1-continued

List of Examples

| Ex. No. | Structure | Name | *Mol. Wt. |
|---|---|---|---|
| 18 | 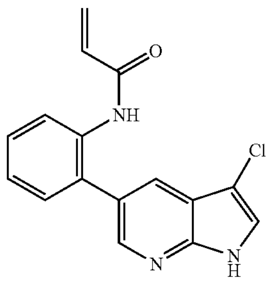 [SMILES: C=CC(=O)Nc1ccccc1-c1cnc2[nH]cc(Cl)c2c1] | N-(2-(3-chloro-1H-pyrrolo[2,3-b]pyridin-5-yl)phenyl)acrylamide | 279.739 |
| 19 | 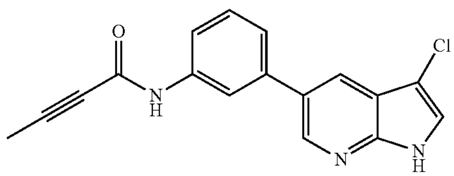 [SMILES: CC#CC(=O)Nc1cccc(-c2cnc3[nH]cc(Cl)c3c2)c1] | N-(3-(3-chloro-1H-pyrrolo[2,3-b]pyridin-5-yl)phenyl)but-2-ynamide | 309.750 |
| 20 | 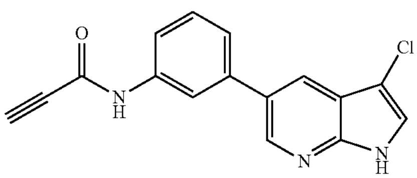 [SMILES: C#CC(=O)Nc1cccc(-c2cnc3[nH]cc(Cl)c3c2)c1] | N-(3-(3-chloro-1H-pyrrolo[2,3-b]pyridin-5-yl)phenyl)propiolamide | 295.732 |
| 21 | 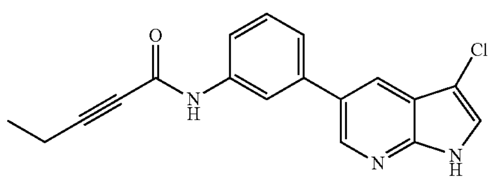 [SMILES: CCC#CC(=O)Nc1cccc(-c2cnc3[nH]cc(Cl)c3c2)c1] | N-(3-(3-chloro-1H-pyrrolo[2,3-b]pyridin-5-yl)phenyl)pent-2-ynamide | 323.776 |
| 22 | 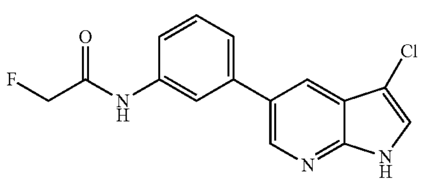 [SMILES: O=C(CF)Nc1cccc(-c2cnc3[nH]cc(Cl)c3c2)c1] | N-(3-(3-chloro-1H-pyrrolo[2,3-b]pyridin-5-yl)phenyl)-2-fluoroacetamide | 303.718 |
| 23 | 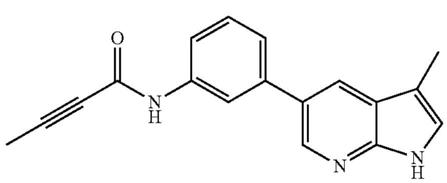 [SMILES: CC#CC(=O)Nc1cccc(-c2cnc3[nH]cc(C)c3c2)c1] | N-(3-(3-methyl-1H-pyrrolo[2,3-b]pyridin-5-yl)phenyl)but-2-ynamide | 289.331 |
| 24 | 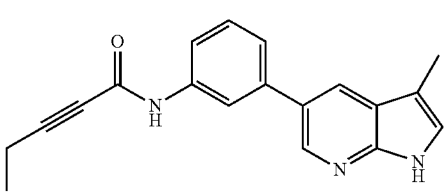 [SMILES: CCC#CC(=O)Nc1cccc(-c2cnc3[nH]cc(C)c3c2)c1] | N-(3-(3-methyl-1H-pyrrolo[2,3-b]pyridin-5-yl)phenyl)pent-2-ynamide | 303.358 |

TABLE 1-continued

List of Examples

| Ex. No. | Structure | Name | *Mol. Wt. |
|---|---|---|---|
| 25 | 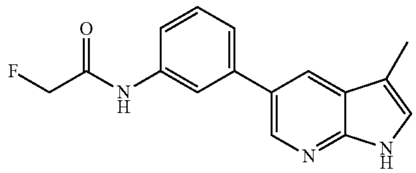 [SMILES: Cc1c[nH]c2ncc(-c3cccc(NC(=O)CF)c3)cc12] | 2-fluoro-N-(3-(3-methyl-1H-pyrrolo[2,3-b]pyridin-5-yl)phenyl)acetamide | 283.300 |
| 26 | 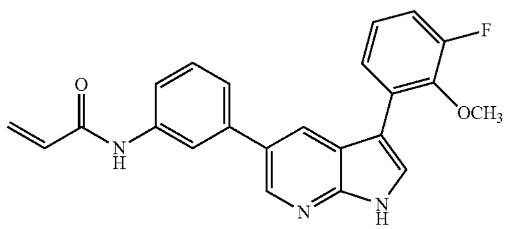 [SMILES: C=CC(=O)Nc1cccc(-c2cnc3[nH]cc(-c4cccc(F)c4OC)c3c2)c1] | N-(3-(3-(3-fluoro-2-methoxyphenyl)-1H-pyrrolo[2,3-b]pyridin-5-yl)phenyl)acrylamide | 387.406 |
| 27 | 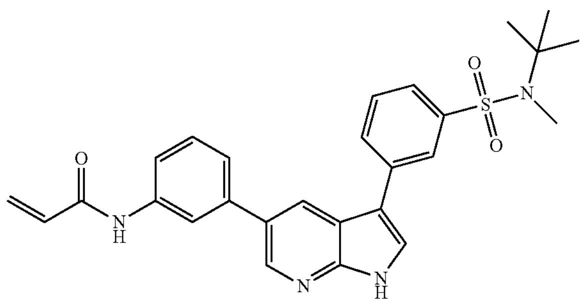 [SMILES: C=CC(=O)Nc1cccc(-c2cnc3[nH]cc(-c4cccc(S(=O)(=O)N(C)C(C)(C)C)c4)c3c2)c1] | N-(3-(3-(3-(N-(tert-butyl)-N-methylsulfamoyl)phenyl)-1H-pyrrolo[2,3-b]pyridin-5-yl)phenyl)acrylamide | 488.601 |
| 28 | 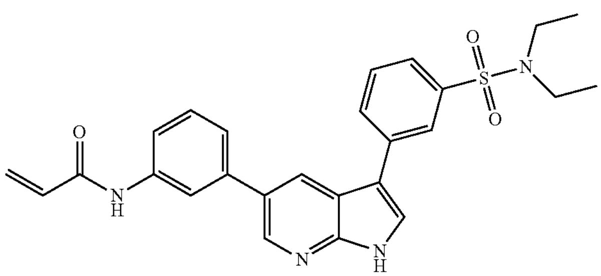 [SMILES: C=CC(=O)Nc1cccc(-c2cnc3[nH]cc(-c4cccc(S(=O)(=O)N(CC)CC)c4)c3c2)c1] | N-(3-(3-(3-(N,N-diethylsulfamoyl)phenyl)-1H-pyrrolo[2,3-b]pyridin-5-yl)phenyl)acrylamide | 474.575 |
| 29 | 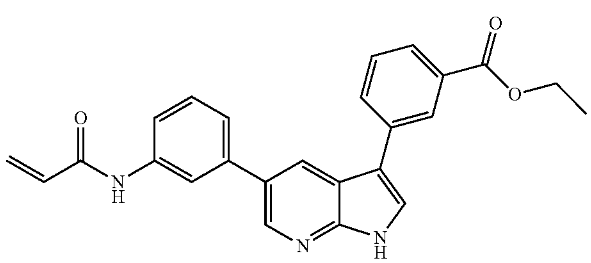 [SMILES: C=CC(=O)Nc1cccc(-c2cnc3[nH]cc(-c4cccc(C(=O)OCC)c4)c3c2)c1] | ethyl 3-(5-(3-acrylamidophenyl)-1H-pyrrolo[2,3-b]pyridin-3-yl)benzoate | 411.450 |
| 30 | 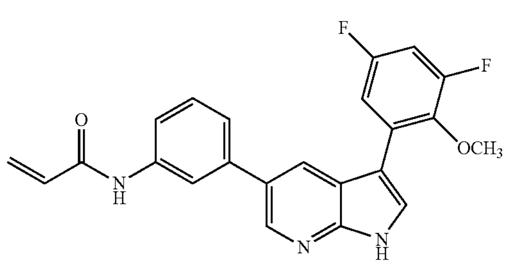 [SMILES: C=CC(=O)Nc1cccc(-c2cnc3[nH]cc(-c4cc(F)cc(F)c4OC)c3c2)c1] | N-(3-(3-(3,5-difluoro-2-methoxyphenyl)-1H-pyrrolo[2,3-b]pyridin-5-yl)phenyl)acrylamide | 405.397 |

TABLE 1-continued

List of Examples

| Ex. No. | Structure | Name | *Mol. Wt. |
|---|---|---|---|
| 31 | 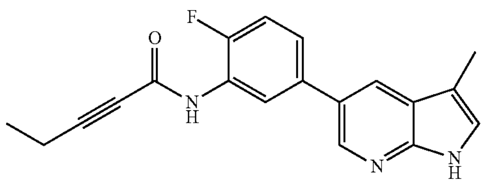 [SMILES: CCC#CC(=O)Nc1cc(-c2cnc3[nH]cc(C)c3c2)ccc1F] | N-(2-fluoro-5-(3-methyl-1H-pyrrolo[2,3-b]pyridin-5-yl)phenyl)propiolamide | 321.348 |
| 32 | 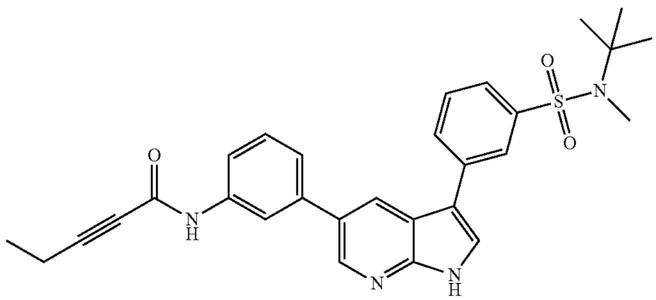 [SMILES: CCC#CC(=O)Nc1cccc(-c2cnc3[nH]cc(-c4cccc(S(=O)(=O)N(C)C(C)(C)C)c4)c3c2)c1] | N-(3-(3-(3-(N-(tert-butyl)-N-methylsulfamoyl)phenyl)-1H-pyrrolo[2,3-b]pyridin-5-yl)phenyl)pent-2-ynamide | 514.639 |
| 33 | 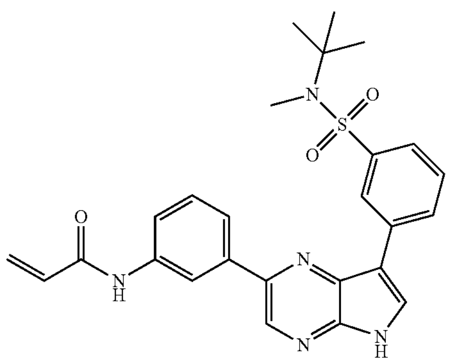 [SMILES: C=CC(=O)Nc1cccc(-c2cnc3[nH]cc(-c4cccc(S(=O)(=O)N(C)C(C)(C)C)c4)c3n2)c1] | N-(3-(7-(3-(N-(tert-butyl)-N-methylsulfamoyl)phenyl)-5H-pyrrolo[2,3-b]pyrazin-2-yl)phenyl)acrylamide | 489.589 |
| 34 | 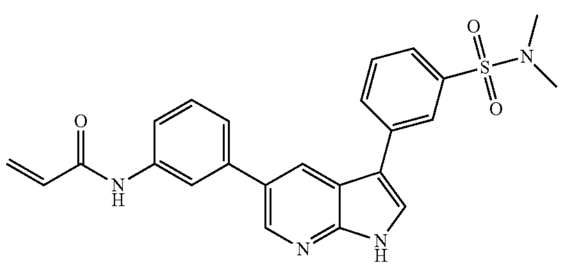 [SMILES: C=CC(=O)Nc1cccc(-c2cnc3[nH]cc(-c4cccc(S(=O)(=O)N(C)C)c4)c3c2)c1] | N-(3-(3-(3-(N,N-dimethylsulfamoyl)phenyl)-1H-pyrrolo[2,3-b]pyridin-5-yl)phenyl)acrylamide | 446.521 |
| 35 | 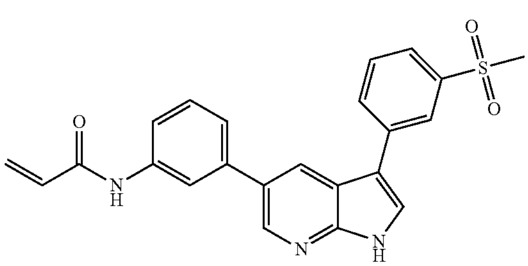 [SMILES: C=CC(=O)Nc1cccc(-c2cnc3[nH]cc(-c4cccc(S(C)(=O)=O)c4)c3c2)c1] | N-(3-(3-(3-(methylsulfonyl)phenyl)-1H-pyrrolo[2,3-b]pyridin-5-yl)phenyl)acrylamide | 417.480 |

TABLE 1-continued

List of Examples

| Ex. No. | Structure | Name | *Mol. Wt. |
|---|---|---|---|
| 36 | 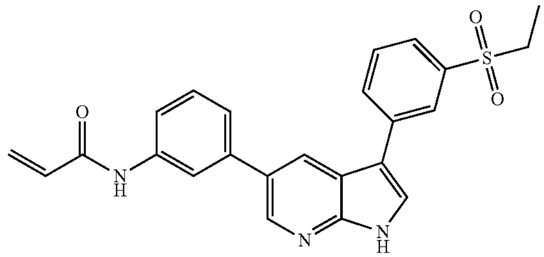 [SMILES: C=CC(=O)Nc1cccc(-c2cnc3[nH]cc(-c4cccc(S(=O)(=O)CC)c4)c3c2)c1] | N-(3-(3-(3-(ethylsulfonyl)phenyl)-1H-pyrrolo[2,3-b]pyridin-5-yl)phenyl)acrylamide | 431.507 |
| 37 | 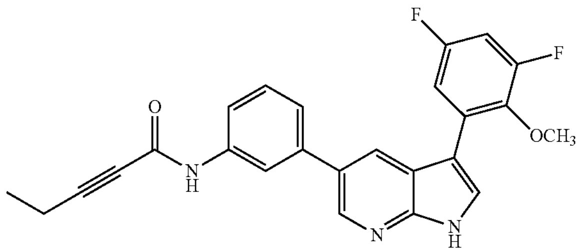 [SMILES: CCC#CC(=O)Nc1cccc(-c2cnc3[nH]cc(-c4cc(F)cc(F)c4OC)c3c2)c1] | N-(3-(3-(3,5-difluoro-2-methoxyphenyl)-1H-pyrrolo[2,3-b]pyridin-5-yl)phenyl)pent-2-ynamide | 431.434 |
| 38 | 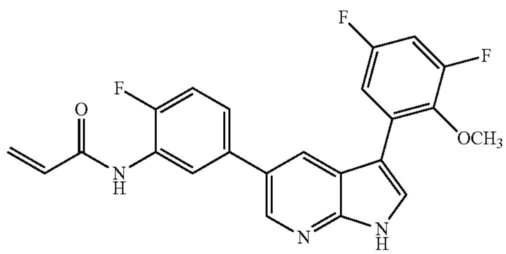 [SMILES: C=CC(=O)Nc1cc(-c2cnc3[nH]cc(-c4cc(F)cc(F)c4OC)c3c2)ccc1F] | N-(5-(3-(3,5-difluoro-2-methoxyphenyl)-1H-pyrrolo[2,3-b]pyridin-5-yl)-2-fluorophenyl)acrylamide | 423.387 |
| 39 | 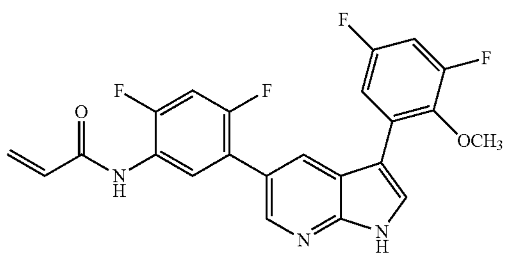 [SMILES: C=CC(=O)Nc1cc(-c2cnc3[nH]cc(-c4cc(F)cc(F)c4OC)c3c2)c(F)cc1F] | N-(5-(3-(3,5-difluoro-2-methoxyphenyl)-1H-pyrrolo[2,3-b]pyridin-5-yl)-2,4-difluorophenyl)acrylamide | 441.378 |
| 40 | 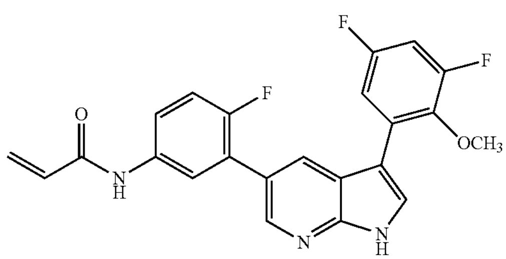 [SMILES: C=CC(=O)Nc1ccc(F)c(-c2cnc3[nH]cc(-c4cc(F)cc(F)c4OC)c3c2)c1] | N-(3-(3-(3,5-difluoro-2-methoxyphenyl)-1H-pyrrolo[2,3-b]pyridin-5-yl)-4-fluorophenyl)acrylamide | 423.387 |
| 41 | 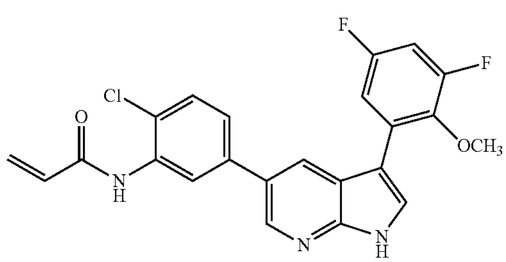 | N-(2-chloro-5-(3-(3,5-difluoro-2-methoxyphenyl)-1H-pyrrolo[2,3-b]pyridin-5-yl)phenyl)acrylamide | 439.842 |

TABLE 1-continued

List of Examples

| Ex. No. | Structure | Name | *Mol. Wt. |
|---|---|---|---|
| 42 | 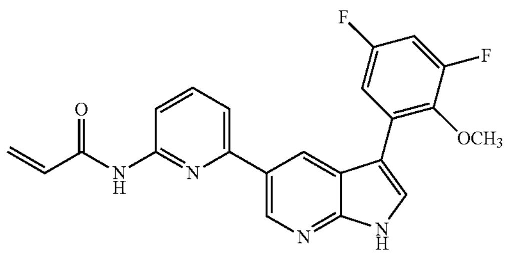 [SMILES: C=CC(=O)Nc1cccc(-c2cnc3[nH]cc(-c4cc(F)cc(F)c4OC)c3c2)n1] | N-(6-(3-(3,5-difluoro-2-methoxyphenyl)-1H-pyrrolo[2,3-b]pyridin-5-yl)pyridin-2-yl)acrylamide | 406.385 |
| 43 | 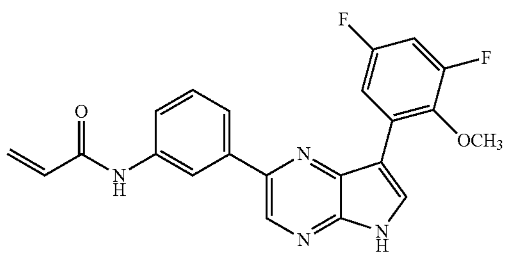 [SMILES: C=CC(=O)Nc1cccc(-c2cnc3[nH]cc(-c4cc(F)cc(F)c4OC)c3n2)c1] | N-(3-(7-(3,5-difluoro-2-methoxyphenyl)-5H-pyrrolo[2,3-b]pyrazin-2-yl)phenyl)acrylamide | 406.385 |
| 44 | 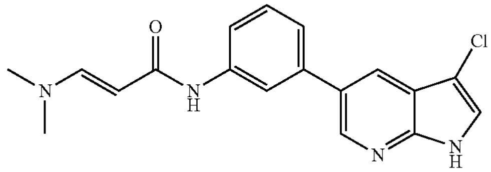 [SMILES: CN(C)/C=C/C(=O)Nc1cccc(-c2cnc3[nH]cc(Cl)c3c2)c1] | (E)-N-(3-(3-chloro-1H-pyrrolo[2,3-b]pyridin-5-yl)phenyl)-3-(dimethylamino)acrylamide | 340.807 |
| 45 | 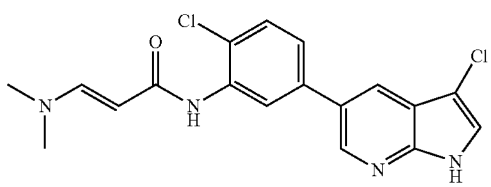 [SMILES: CN(C)/C=C/C(=O)Nc1cc(-c2cnc3[nH]cc(Cl)c3c2)ccc1Cl] | (E)-N-(3-(3-chloro-1H-pyrrolo[2,3-b]pyridin-5-yl)phenyl)-3-(dimethylamino)acrylamide | 375.252 |
| 46 | 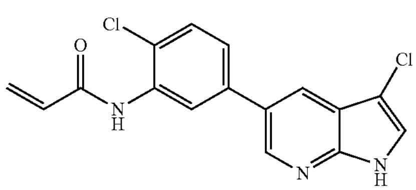 | N-(2-chloro-5-(3-chloro-1H-pyrrolo[2,3-b]pyridin-5-yl)phenyl)acrylamide | 332.184 |
| 47 | 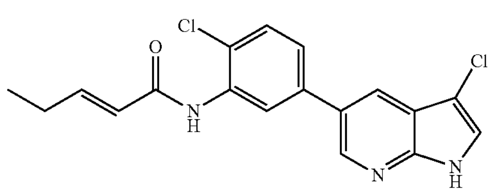 [SMILES: CC/C=C/C(=O)Nc1cc(-c2cnc3[nH]cc(Cl)c3c2)ccc1Cl] | (E)-N-(2-chloro-5-(3-chloro-1H-pyrrolo[2,3-b]pyridin-5-yl)phenyl)pent-2-enamide | 360.237 |
| 48 | 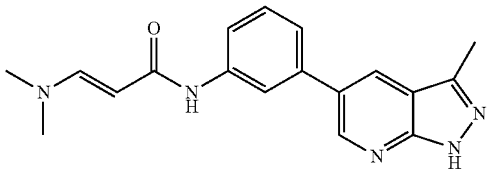 [SMILES: Cc1n[nH]c2ncc(-c3cccc(NC(=O)/C=C/N(C)C)c3)cc12] | (E)-3-(dimethylamino)-N-(3-(3-methyl-1H-pyrazolo[3,4-b]pyridin-5-yl)phenyl)acrylamide | 321.376 |

TABLE 1-continued

List of Examples

| Ex. No. | Structure | Name | *Mol. Wt. |
|---|---|---|---|
| 49 | 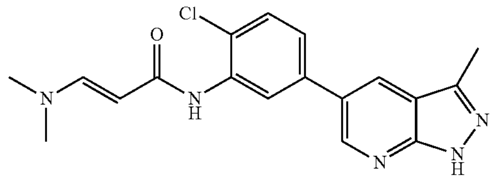 [SMILES: Cc1n[nH]c2ncc(-c3ccc(Cl)c(NC(=O)/C=C/N(C)C)c3)cc12] | (E)-N-(2-chloro-5-(3-methyl-1H-pyrazolo[3,4-b]pyridin-5-yl)phenyl)-3-(dimethylamino)acrylamide | 355.821 |
| 50 | 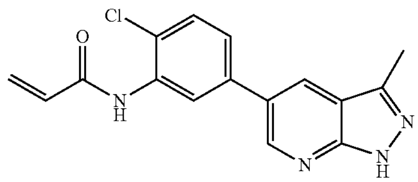 [SMILES: C=CC(=O)Nc1cc(-c2cnc3[nH]nc(C)c3c2)ccc1Cl] | N-(2-chloro-5-(3-methyl-1H-pyrazolo[3,4-b]pyridin-5-yl)phenyl)acrylamide | 312.754 |
| 51 | 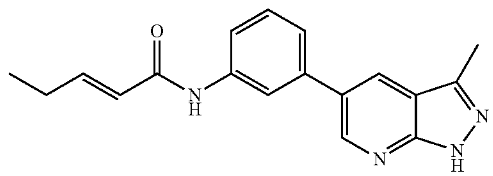 [SMILES: CC/C=C/C(=O)Nc1cccc(-c2cnc3[nH]nc(C)c3c2)c1] | (E)-N-(3-(3-methyl-1H-pyrazolo[3,4-b]pyridin-5-yl)phenyl)pent-2-enamide | 306.362 |
| 52 | 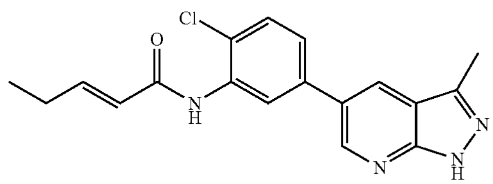 [SMILES: CC/C=C/C(=O)Nc1cc(-c2cnc3[nH]nc(C)c3c2)ccc1Cl] | (E)-N-(2-chloro-5-(3-methyl-1H-pyrazolo[3,4-b]pyridin-5-yl)phenyl)pent-2-enamide | 340.807 |
| 53 | 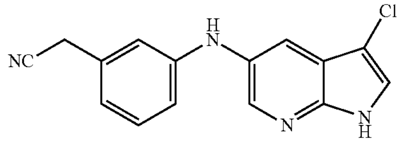 [SMILES: N#CCc1cccc(Nc2cnc3[nH]cc(Cl)c3c2)c1] | 2-(3-((3-chloro-1H-pyrrolo[2,3-b]pyridin-5-yl)amino)phenyl)acetonitrile | 282.728 |
| 54 | 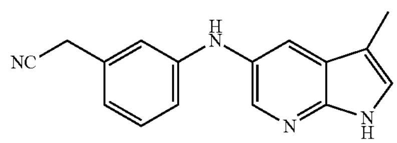 [SMILES: Cc1c[nH]c2ncc(Nc3cccc(CC#N)c3)cc12] | 2-(3-((3-methyl-1H-pyrrolo[2,3-b]pyridin-5-yl)amino)phenyl)acetonitrile | 262.309 |
| 55 | 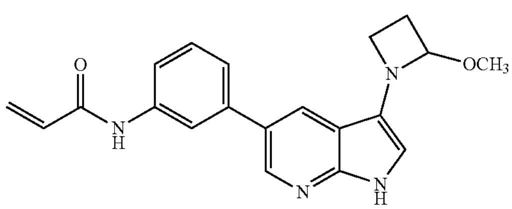 [SMILES: C=CC(=O)Nc1cccc(-c2cnc3[nH]cc(N4CCC4OC)c3c2)c1] | N-(3-(3-(3,3-difluoroazetidin-1-yl)-1H-pyrrolo[2,3-b]pyridin-5-yl)phenyl)acrylamide | 348.398 |
| 56 | 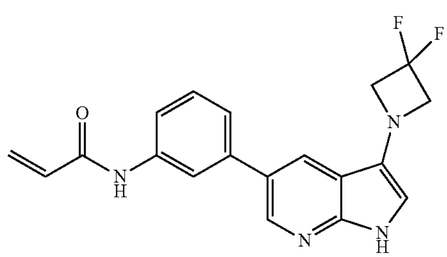 [SMILES: C=CC(=O)Nc1cccc(-c2cnc3[nH]cc(N4CC(F)(F)C4)c3c2)c1] | N-(3-(3-(3,3-difluoroazetidin-1-yl)-1H-pyrrolo[2,3-b]pyridin-5-yl)phenyl)acrylamide | 354.353 |

TABLE 1-continued

List of Examples

| Ex. No. | Structure | Name | *Mol. Wt. |
|---|---|---|---|
| 57 | 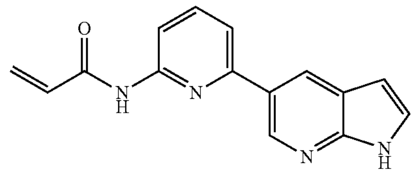 [SMILES: C=CC(=O)Nc1cccc(-c2cnc3[nH]ccc3c2)n1] | N-(6-(1H-pyrrolo[2,3-b]pyridin-5-yl)pyridin-2-yl)acrylamide | 264.280 |
| 58 | 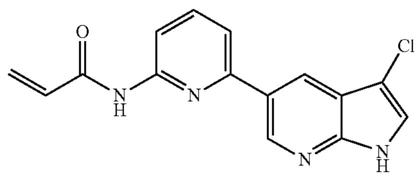 [SMILES: C=CC(=O)Nc1cccc(-c2cnc3[nH]cc(Cl)c3c2)n1] | N-(6-(3-chloro-1H-pyrrolo[2,3-b]pyridin-5-yl)pyridin-2-yl)acrylamide | 298.727 |
| 59 | 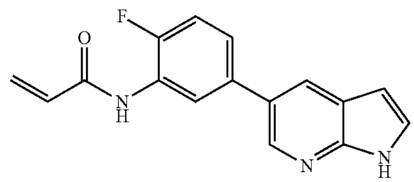 [SMILES: C=CC(=O)Nc1cc(-c2cnc3[nH]ccc3c2)ccc1F] | N-(2-fluoro-5-(1H-pyrrolo[2,3-b]pyridin-5-yl)phenyl)acrylamide | 281.280 |
| 60 | 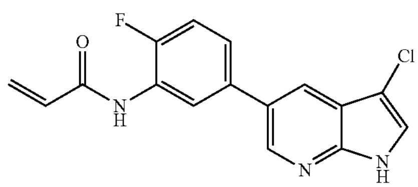 [SMILES: C=CC(=O)Nc1cc(-c2cnc3[nH]cc(Cl)c3c2)ccc1F] | N-(6-(3-chloro-1H-pyrrolo[2,3-b]pyridin-5-yl)-3-fluoropyridin-2-yl)acrylamide | 315.729 |
| 61 | 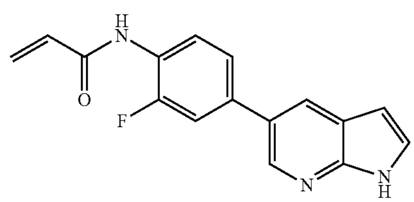 [SMILES: C=CC(=O)Nc1ccc(-c2cnc3[nH]ccc3c2)cc1F] | N-(2-fluoro-4-(1H-pyrrolo[2,3-b]pyridin-5-yl)phenyl)acrylamide | 281.280 |
| 62 | 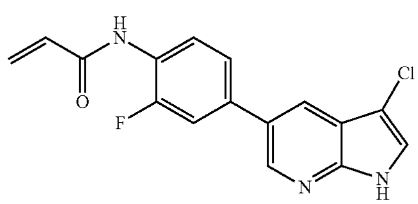 [SMILES: C=CC(=O)Nc1ccc(-c2cnc3[nH]cc(Cl)c3c2)cc1F] | -(4-(3-chloro-1H-pyrrolo[2,3-b]pyridin-5-yl)-2-fluorophenyl)acrylamide | 315.729 |
| 63 | 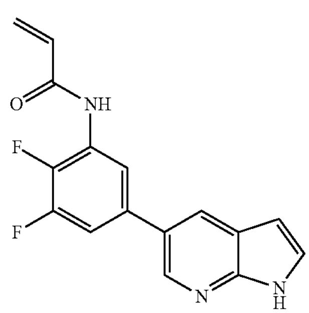 [SMILES: C=CC(=O)Nc1cc(-c2cnc3[nH]ccc3c2)cc(F)c1F] | N-(2,3-difluoro-5-(1H-pyrrolo[2,3-b]pyridin-5-yl)phenyl)acrylamide | 299.270 |

TABLE 1-continued

List of Examples

| Ex. No. | Structure | Name | *Mol. Wt. |
|---|---|---|---|
| 64 | 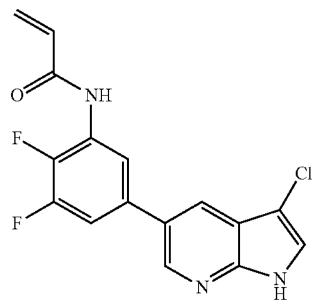 [SMILES: C=CC(=O)Nc1cc(-c2cnc3[nH]cc(Cl)c3c2)cc(F)c1F] | N-(5-(3-chloro-1H-pyrrolo[2,3-b]pyridin-5-yl)-2,3-difluorophenyl)acrylamide | 333.720 |
| 65 | 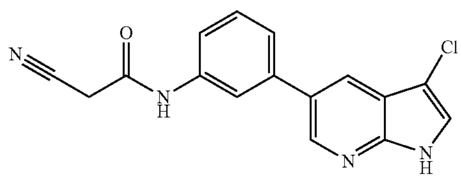 [SMILES: N#CCC(=O)Nc1cccc(-c2cnc3[nH]cc(Cl)c3c2)c1] | N-(3-(3-chloro-1H-pyrrolo[2,3-b]pyridin-5-yl)phenyl)but-3-ynamide | 310.738 |
| 66 | 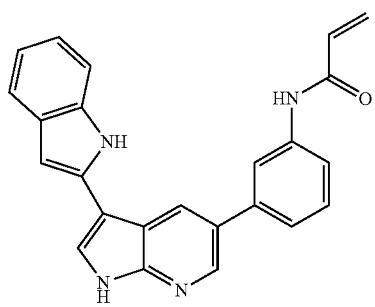 [SMILES: C=CC(=O)Nc1cccc(-c2cnc3[nH]cc(-c4cc5ccccc5[nH]4)c3c2)c1] | N-(3-(3-(1H-indol-2-yl)-1H-pyrrolo[2,3-b]pyridin-5-yl)phenyl)acrylamide | 378.46 |
| 67 | 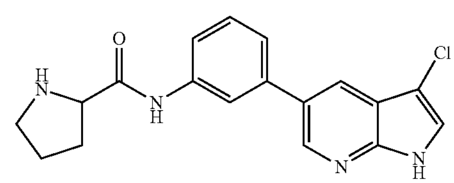 [SMILES: O=C(Nc1cccc(-c2cnc3[nH]cc(Cl)c3c2)c1)C1CCCN1] | N-(3-(3-chloro-1H-pyrrolo[2,3-b]pyridin-5-yl)phenyl)pyrrolidine-2-carboxamide | 340.810 |
| 68 | 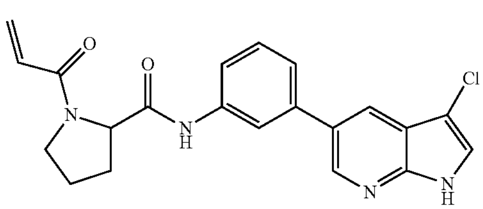 [SMILES: C=CC(=O)N1CCCC1C(=O)Nc1cccc(-c2cnc3[nH]cc(Cl)c3c2)c1] | 1-acryloyl-N-(3-(3-chloro-1H-pyrrolo[2,3-b]pyridin-5-yl)phenyl)pyrrolidine-2-carboxamide | 394.850 |
| 69 | 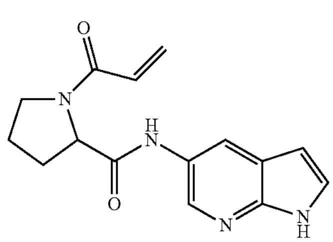 [SMILES: C=CC(=O)N1CCCC1C(=O)Nc1cnc2[nH]ccc2c1] | 1-acryloyl-N-(1H-pyrrolo[2,3-b]pyridin-5-yl)pyrrolidine-2-carboxamide | 284.313 |

TABLE 1-continued

List of Examples

| Ex. No. | Structure | Name | *Mol. Wt. |
|---|---|---|---|
| 70 | 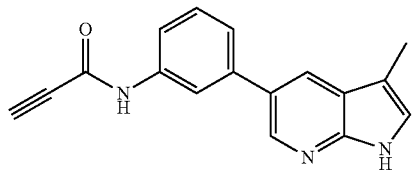 [SMILES: C#CC(=O)Nc1cccc(-c2cnc3[nH]cc(C)c3c2)c1] | N-(3-(3-methyl-1H-pyrrolo[2,3-b]pyridin-5-yl)phenyl)propiolamide | 273.305 |
| 71 | 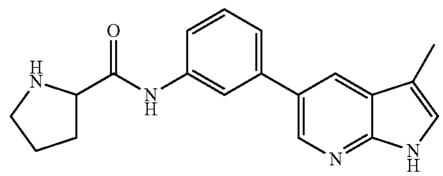 [SMILES: Cc1c[nH]c2ncc(-c3cccc(NC(=O)C4CCCN4)c3)cc12] | N-(3-(3-methyl-1H-pyrrolo[2,3-b]pyridin-5-yl)phenyl)pyrrolidine-2-carboxamide | 320.390 |
| 72 | 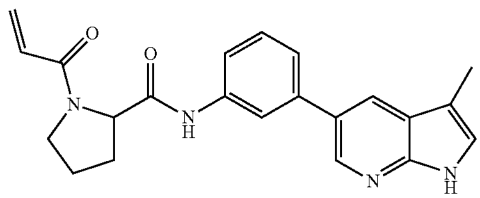 [SMILES: C=CC(=O)N1CCCC1C(=O)Nc1cccc(-c2cnc3[nH]cc(C)c3c2)c1] | 1-acryloyl-N-(3-(3-methyl-1H-pyrrolo[2,3-b]pyridin-5-yl)phenyl)pyrrolidine-2-carboxamide | 374.436 |
| 73 | 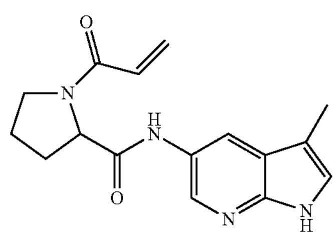 [SMILES: C=CC(=O)N1CCCC1C(=O)Nc1cnc2[nH]cc(C)c2c1] | 1-acryloyl-N-(1H-pyrrolo[2,3-b]pyridin-5-yl)pyrrolidine-2-carboxamide | 284.313 |
| 74 | 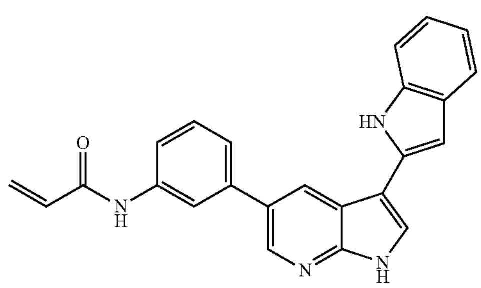 [SMILES: C=CC(=O)Nc1cccc(-c2cnc3[nH]cc(-c4cc5ccccc5[nH]4)c3c2)c1] | N-(3-(3-(1H-indol-2-yl)-1H-pyrrolo[2,3-b]pyridin-5-yl)phenyl)acrylamide | 378.426 |
| 75 | 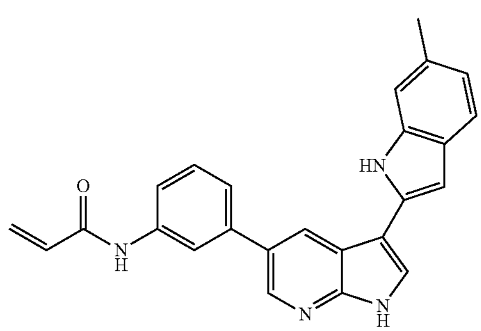 [SMILES: C=CC(=O)Nc1cccc(-c2cnc3[nH]cc(-c4cc5ccc(C)cc5[nH]4)c3c2)c1] | N-(3-(3-(6-methyl-1H-indol-2-yl)-1H-pyrrolo[2,3-b]pyridin-5-yl)phenyl)acrylamide | 392.458 |

TABLE 1-continued

List of Examples

| Ex. No. | Structure | Name | *Mol. Wt. |
|---|---|---|---|
| 76 | 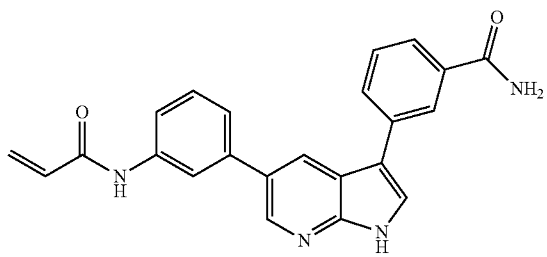 [SMILES: C=CC(=O)Nc1cccc(-c2cnc3[nH]cc(-c4cccc(C(N)=O)c4)c3c2)c1] | 3-(5-(3-acrylamidophenyl)-1H-pyrrolo[2,3-b]pyridin-3-yl)benzamide | 382.410 |
| 77 | 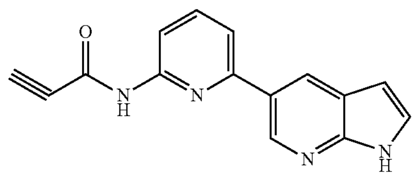 [SMILES: C#CC(=O)Nc1cccc(-c2cnc3[nH]ccc3c2)n1] | N-(6-(1H-pyrrolo[2,3-b]pyridin-5-yl)pyridin-2-yl)propiolamide | 262.270 |
| 78 | 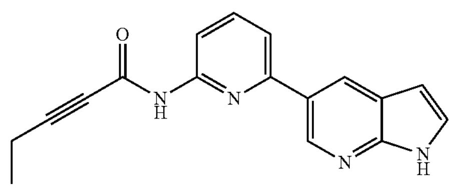 [SMILES: CCC#CC(=O)Nc1cccc(-c2cnc3[nH]ccc3c2)n1] | N-(6-(1H-pyrrolo[2,3-b]pyridin-5-yl)pyridin-2-yl)pent-2-ynamide | 290.320 |
| 79 | 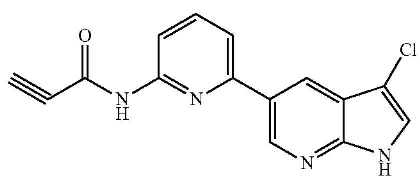 [SMILES: C#CC(=O)Nc1cccc(-c2cnc3[nH]cc(Cl)c3c2)n1] | N-(6-(3-chloro-1H-pyrrolo[2,3-b]pyridin-5-yl)pyridin-2-yl)propiolamide | 296.711 |
| 80 | 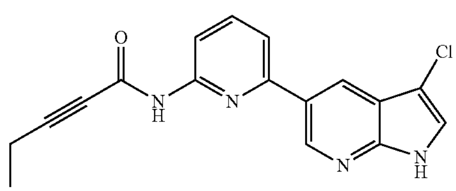 [SMILES: CCC#CC(=O)Nc1cccc(-c2cnc3[nH]cc(Cl)c3c2)n1] | N-(6-(3-chloro-1H-pyrrolo[2,3-b]pyridin-5-yl)pyridin-2-yl)pent-2-ynamide | 324.764 |
| 81 | 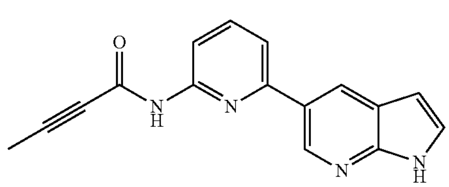 [SMILES: CC#CC(=O)Nc1cccc(-c2cnc3[nH]ccc3c2)n1] | N-(6-(1H-pyrrolo[2,3-b]pyridin-5-yl)pyridin-2-yl)but-2-ynamide | 276.290 |
| 82 | 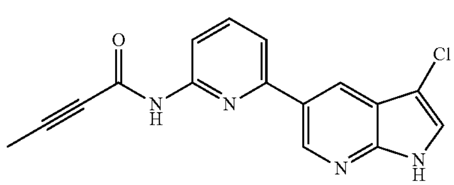 [SMILES: CC#CC(=O)Nc1cccc(-c2cnc3[nH]cc(Cl)c3c2)n1] | N-(6-(3-chloro-1H-pyrrolo[2,3-b]pyridin-5-yl)pyridin-2-yl)but-2-ynamide | 310.738 |

TABLE 1-continued

List of Examples

| Ex. No. | Structure | Name | *Mol. Wt. |
|---|---|---|---|
| 83 | 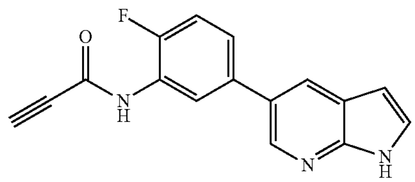 [SMILES: C#CC(=O)Nc1cc(-c2cnc3[nH]ccc3c2)ccc1F] | N-(2-fluoro-5-(1H-pyrrolo[2,3-b]pyridin-5-yl)phenyl)propiolamide | 279.70 |
| 84 | 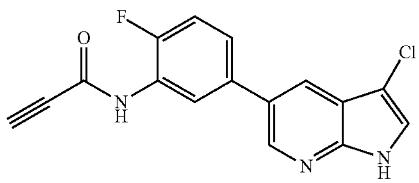 [SMILES: C#CC(=O)Nc1cc(-c2cnc3[nH]cc(Cl)c3c2)ccc1F] | N-(5-(3-chloro-1H-pyrrolo[2,3-b]pyridin-5-yl)-2-fluorophenyl)propiolamide | 313.714 |
| 85 | 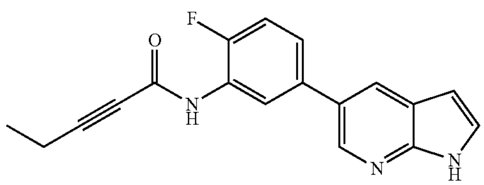 | N-(2-fluoro-5-(1H-pyrrolo[2,3-b]pyridin-5-yl)phenyl)pent-2-ynamide | 307.320 |
| 86 | 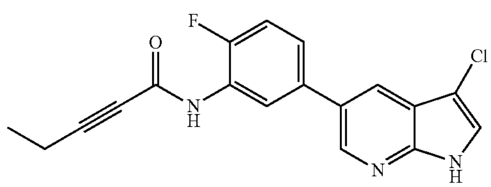 [SMILES: CCC#CC(=O)Nc1cc(-c2cnc3[nH]cc(Cl)c3c2)ccc1F] | N-(5-(3-chloro-1H-pyrrolo[2,3-b]pyridin-5-yl)-2-fluorophenyl)pent-2-ynamide | 341.767 |
| 87 | 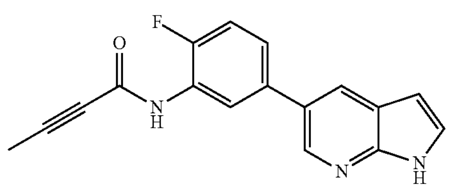 [SMILES: CC#CC(=O)Nc1cc(-c2cnc3[nH]ccc3c2)ccc1F] | N-(2-fluoro-5-(1H-pyrrolo[2,3-b]pyridin-5-yl)phenyl)but-2-ynamide | 293.300 |
| 88 | 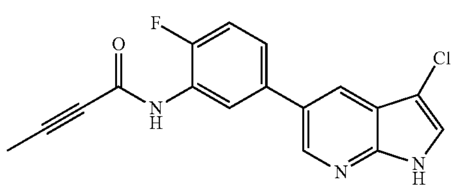 [SMILES: CC#CC(=O)Nc1cc(-c2cnc3[nH]cc(Cl)c3c2)ccc1F] | N-(5-(3-chloro-1H-pyrrolo[2,3-b]pyridin-5-yl)-2-fluorophenyl)but-2-ynamide | 327.740 |
| 89 | 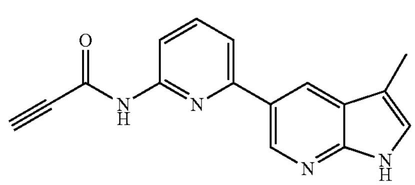 [SMILES: C#CC(=O)Nc1cccc(-c2cnc3[nH]cc(C)c3c2)n1] | N-(5-(3-methyl-1H-pyrrolo[2,3-b]pyridin-5-yl)phenyl)propiolamide | 276.293 |
| 90 | 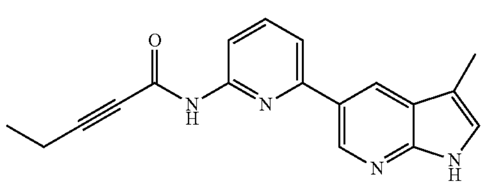 [SMILES: CCC#CC(=O)Nc1cccc(-c2cnc3[nH]cc(C)c3c2)n1] | N-(6-(3-methyl-1H-pyrrolo[2,3-b]pyridin-5-yl)pyridin-2-yl)pent-2-ynamide | 304.350 |

TABLE 1-continued

List of Examples

| Ex. No. | Structure | Name | *Mol. Wt. |
|---|---|---|---|
| 91 | 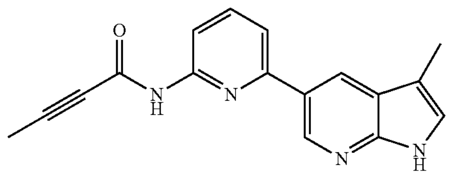 [SMILES: CC#CC(=O)Nc1cccc(-c2cnc3[nH]cc(C)c3c2)n1] | N-(6-(3-methyl-1H-pyrrolo[2,3-b]pyridin-5-yl)pyridin-2-yl)but-2-ynamide | 290.320 |
| 92 | 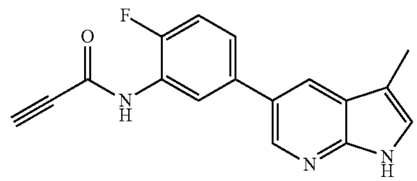 [SMILES: C#CC(=O)Nc1cc(-c2cnc3[nH]cc(C)c3c2)ccc1F] | N-(2-fluoro-5-(3-methyl-1H-pyrrolo[2,3-b]pyridin-5-yl)phenyl)propiolamide | 293.95 |
| 93 | 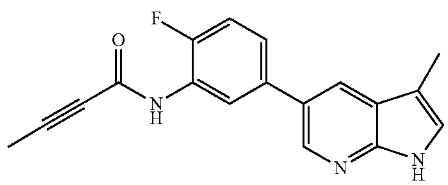 | N-(2-fluoro-5-(3-methyl-1H-pyrrolo[2,3-b]pyridin-5-yl)phenyl)but-2-ynamide | 307.322 |
| 94 | 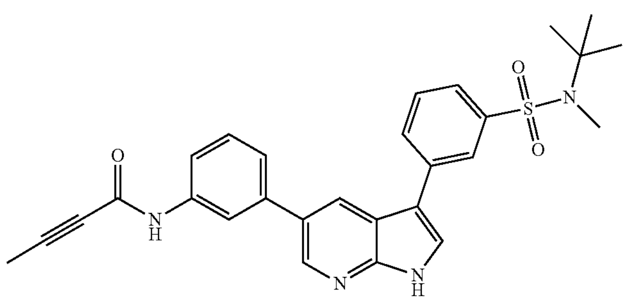 [SMILES: CC#CC(=O)Nc1cccc(-c2cnc3[nH]cc(-c4cccc(S(=O)(=O)N(C)C(C)(C)C)c4)c3c2)c1] | N-(3-(3-(3-(N-(tert-butyl)-N-methylsulfamoyl)phenyl)-1H-pyrrolo[2,3-b]pyridin-5-yl)phenyl)but-2-ynamide | 500.612 |
| 95 | 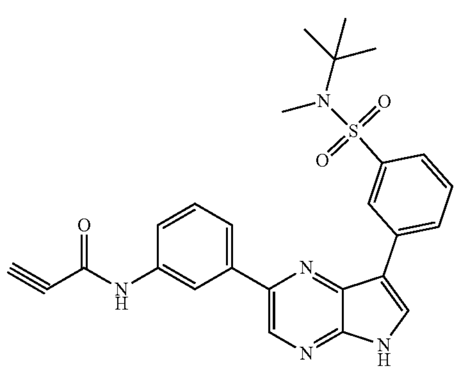 [SMILES: C#CC(=O)Nc1cccc(-c2cnc3[nH]cc(-c4cccc(S(=O)(=O)N(C)C(C)(C)C)c4)c3n2)c1] | N-(3-(7-(3-(N-(tert-butyl)-N-methylsulfamoyl)phenyl)-5H-pyrrolo[2,3-b]pyrazin-2-yl)phenyl)propiolamide | 487.573 |

TABLE 1-continued

List of Examples

| Ex. No. | Structure | Name | *Mol. Wt. |
|---|---|---|---|
| 96 | 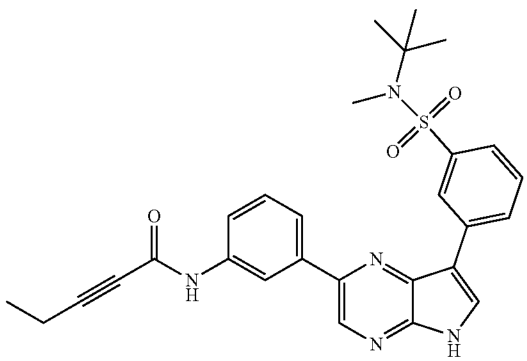 [SMILES: CCC#CC(=O)Nc1cccc(-c2cnc3[nH]cc(-c4cccc(S(=O)(=O)N(C)C(C)(C)C)c4)c3n2)c1] | N-(3-(7-(3-(N-(tert-butyl)-N-methylsulfamoyl)phenyl)-5H-pyrrolo[2,3-b]pyrazin-2-yl)phenyl)pent-2-ynamide | 515.627 |
| 97 | 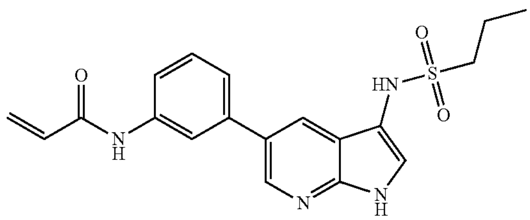 [SMILES: C=CC(=O)Nc1cccc(-c2cnc3[nH]cc(NS(=O)(=O)CCC)c3c2)c1] | N-(3-(3-(propylsulfonamido)-1H-pyrrolo[2,3-b]pyridin-5-yl)phenyl)acrylamide | 384.452 |
| 98 | 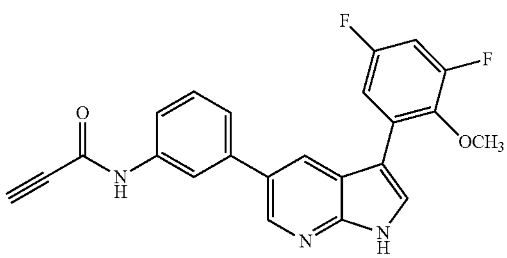 [SMILES: C#CC(=O)Nc1cccc(-c2cnc3[nH]cc(-c4cc(F)cc(F)c4OC)c3c2)c1] | N-(3-(3-(3,5-difluoro-2-methoxyphenyl)-1H-pyrrolo[2,3-b]pyridin-5-yl)phenyl)propiolamide | 403.381 |

TABLE 2

List of abbreviation and meaning used throughout this application

| Abbreviation | Meaning |
|---|---|
| CHCl3 | Chloroform - CHCl₃ |
| CDCl3 | Chloroform deuterated solvent - CDCl₃ |
| DCM | Dichloromethane - CH₂Cl₂ |
| DME | 1,2-Dimethoxyethane |
| DMF | N,N-Dimethylformamide |
| DMSO | Dimethylsulfoxide |
| DMSO-d₆ | Dimethylsulfoxide deuterated solvent |
| Pd₂(dba)3 | Tris(dibenzylideneacetone)dipalladium(0) |
| Pd(PH3)4 | Tetrakis(trifluorophosphine)palladium(0) |
| PTSA | p-Toluene Sulfonic Acid |
| THF | Tetrahydrofuran |
| ±BINAP | rac 2.2'-Bis(diphenylphosphino)-9,9-dimethylxanthene |
| Xantphos | 4,5-Bis(diphenylphosphino)-9,9-dimethylxanthene |
| Pd(dppf)Cl₂•CH₂Cl₂ | [1,1'-bis(diphenylphosphino)ferrocene]-dichloropalladium II DCM |
| Et | Ethyl |
| Me | Methyl |
| MeOH | Methanol |
| EtOH | Ethanol |
| EtOAc | Ethylacetate |
| AcCN/MeCN | Acetonitrile |
| DIPEA | Diisopropylethylamine |
| IP | Isopropanol |
| Na₂CO₃ | Sodium Carbonate |
| K₂CO₃ | Potassium Carbonate |
| Cs₂CO₃ | Cesium Carbonate |
| TFA | Trifluoroacetic acid |
| EDC HCl | N-Ethyl-N'-(3-dimethylaminopropyl)carbodiimide HCl |
| HOBT | 1-Hydroxybenzotriazole hydrate |
| HOAc | Acetic Acid |
| Et | Ethyl |
| TMS | Trimethylsilyl |
| NBS | N-Bromosuccinamide |
| NCS | N-Chlorosuccinamide |
| PG | Protecting Group |
| g, gm | Gram(s) |
| mg | Milligram(s) |
| h, hr | Hour |
| min | Minute(s) |
| M | Molar, molarity |
| mM | Millimolar |
| μM | Micromolar |
| nM | Nanomolar |
| L, l | Liter(s) |
| mL, ml | Milliliter(s) |
| μL | Microliter(s) |
| RM | Reaction Mixture or Reaction Mass |
| SM | Starting Material |

TABLE 2-continued

List of abbreviation and meaning used throughout this application

| Abbreviation | Meaning |
|---|---|
| RT, rt | Room Temperature |
| HPLC | High-Performance Liquid Chromatography |
| LCMS | Liquid Chromatography Mass Spectrometry |
| MS or ms | Mass Spectrometry |
| NMR | Nuclear Magnetic Resonance Spectroscopy |
| TLC | Thin Layer Chromatography |
| UV | Ultra-Violet Spectrometry |
| s | Singlet |
| d, Dt, dt | Doublet, doublet of doublet |
| t, tr | Triplet |
| m | Multiplet |

Methods of Preparation of Compounds

In certain embodiments, the Examples depicted below are compounds prepared according to general procedures given in the following sections. Although the synthetic methods and Schemes depict the syntheses of certain compounds of the present invention, the methods and other methods known to one of ordinary skill in the art can be applied to all the compounds of the genus, the genus sub-class and species of each of these compounds as described herein. All aspects of this invention can be understood from the following Schemes. The following are exemplary and are not intended to limit the scope of the invention.

EXAMPLES

Experimental Details and Examples

Melting points were determined in a MP-96 digital Polmon apparatus. $^1$H NMR and $^{13}$C NMR spectra were recorded at RT in CDCl$_3$ or DMSO-d$_6$ at Jeol 400-MHz NMR spectrophotometer using solvent peaks for CDCl$_3$: 7.27 and DMSO-d$_6$ 2.50 (D) as internal references. The assignment of chemical shifts is based on standard NMR experiments ($^1$H, $^{13}$C). Mass spectra were recorded on a Shimadzu LCMS LC-210EV spectrometer with an API-ES ionization source. Jasco-FTIR-4100 was used to record the IR spectra. TLC analyses were performed on silica F254 and detection by UV light at 254 nm, or by spraying with phosphomolybdic-H$_2$SO$_4$ dyeing reagent, KMNO$_4$ or iodine. Column chromatography were performed on silica Gel 60 (230 mesh). Purifications and separations were performed on a standard silica flash chromatography system. The purity of the samples has been determined by HPLC for the % area peak corresponding to the retention of compound and elemental analysis for C, H, N and O was carried out using Perkin-Elmer 2400 elemental analyser and chloride analysis performed using calorimetric titration at the Intertek USA Inc., QTI.

General Synthetic Methodology

The compounds of this invention are prepared in general by methods such as those depicted in the general Schemes 1 and 2 below, and the preparative examples that follow.

Example 1

N-(3-(3-methyl-1H-pyrazolo[3,4-b]pyridin-5-yl)phenyl)acrylamide (4)

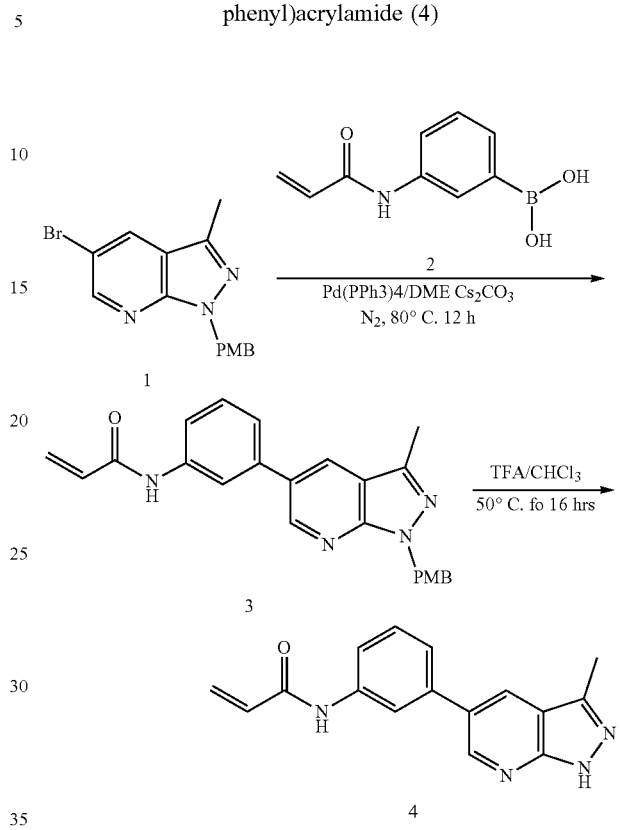

N-(3-(1-(4-methoxybenzyl)-3-methyl-1H-pyrazolo[3,4-b]pyridin-5-yl)phenyl)-acrylamide (Compound 3)

To a stirred solution of 1 (0.134 mg, 0.402 mmol), 2 (0.100 g, 0.366 mmol) in 1,2-dimethoxyethane (10 mL) was added cesium carbonate (233 mg, 0.732 mmol). The reaction was degassed and purged with nitrogen for 15 min. Pd(PPh$_3$)$_4$ (0.126 g, 0.0109 mmol) was added to the reaction, degassed, purged again with nitrogen for another 15 min. The reaction mass was heated to 80° C., stirred overnight under sealed condition. The reaction was cooled to RT and diluted with chloroform. The organic layer was filtered through Celite bed, and concentrated to get the crude, which was passed through 100-200 mesh silica gel where eluting at 40% ethyl acetate in hexane gave Compound 3

N-(3-(3-methyl-1H-pyrazolo[3,4-b]pyridin-5-yl)phenyl)acrylamide (4), EXAMPLE 1

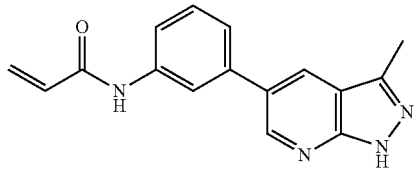

To a stirred solution of Compound 3 (70 mg, 0.175 mmol) in chloroform (15 mL) was added trifluoroacetic acid (3 mL) and heated to 50° C. overnight. The reaction was evaporated and diluted with water; pH was adjusted to 8-10 with sodium carbonate solution. The aqueous phase was extracted with dichloromethane twice (2×25 mL). The organic layer was dried over sodium sulphate and concentrated to get the crude, which was passed through 100-200 mesh silica gel eluting the EXAMPLE 1 at 60% ethyl acetate in hexane as pale yellow colour solid. MS-ES+277.9, $^1$H NMR (400 MHz, DMSO-D6-$D_6$) 4: 13.29 (s, 1H), 10.29 (s, 1H), 8.74 (d, 1H), 8.40 (d, 1H), 8.03 (s, 1H), 7.69 (m, 1H), 7.43 (m, 2H), 6.44 (m, 1H), 6.26 (dd, 1H), 5.78 (dd, 1H), 2.55 (s, 3H).

Example 2

N-(3-(7-(6-methyl-1H-indol-2-yl)-5H-pyrrolo[2,3-b]pyrazin-2 yl)phenyl) acrylamide (10)

Scheme 2

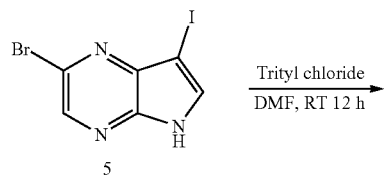

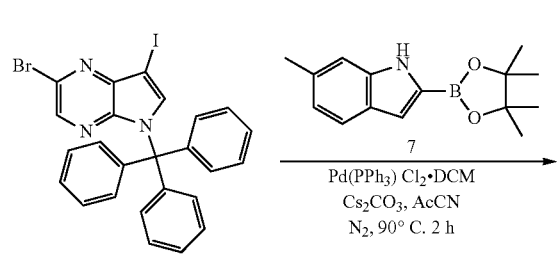

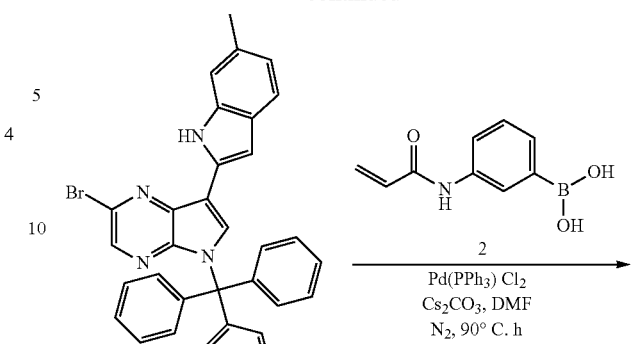

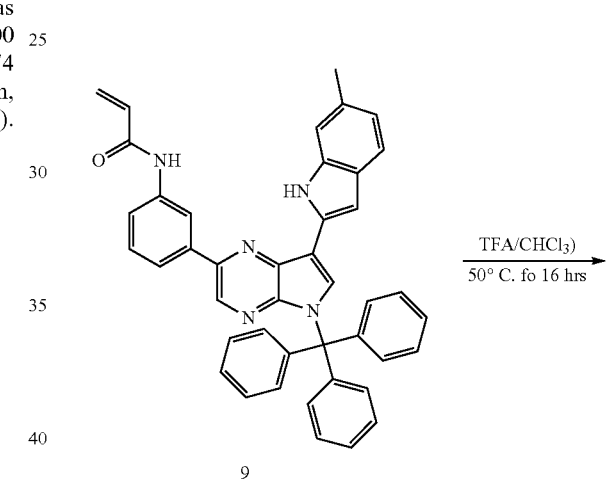

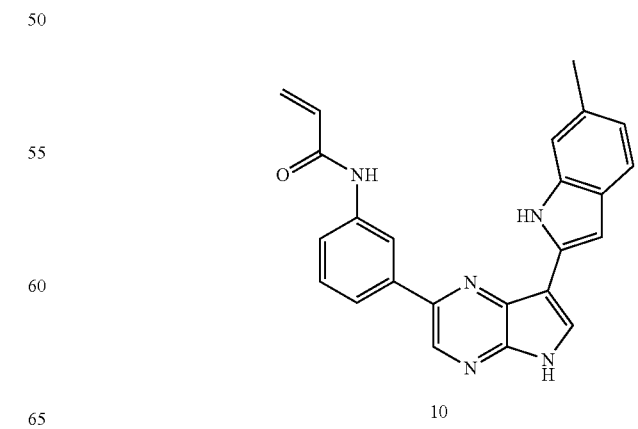

2-bromo-7-(6-methyl-1H-indol-2-yl)-5-trityl-5H-pyrrolo[2,3-b]pyrazine (Compound 8)

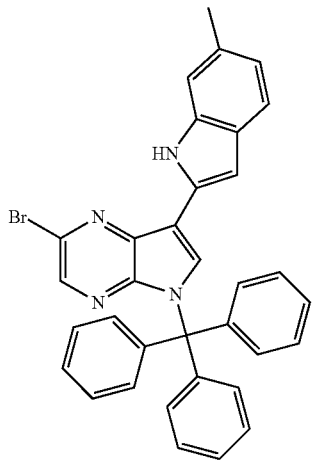

A solution of 2-bromo-7-iodo-5-trityl-5H-pyrrolo[2,3-b]pyrazine (6) (100 mg, 0.1766 mmol), 6-methyl-2-(4,4,5,5-tetramethyl-1,3,2-dioxaborolan-2-yl)-1H-indole (7) (47 mg, 0.1766 mmol) in acetonitrile (5 mL) was added cesium carbonate (115.74 mg, 0.3532 mmol). The resulting reaction mixture was degassed, purged with nitrogen for 10 min followed by the addition of Pd(PPh3) Cl$_2$.DCM (7.06 mg, 0.0088 mmol) to the reaction mixture, which was again degassed, purged with nitrogen for another 15 min. The final reaction mixture was stirred for 2 h at 90° C. in a seal tube. After completion of the reaction, the contents were allowed to cool to RT and was diluted with DCM (25 mL) and filtered through Celite bed. The organic layer was concentrated to get the crude. The resulting oil was purified by flash chromatography by using 100-200 mesh silica gel. The compound was eluted at 27% ethyl acetate in hexane to afford pale yellow solid (30 mg) of compound 2-bromo-7-(6-methyl-1H-indol-2-yl)-5-trityl-5H-pyrrolo[2,3-b]pyrazine (8).

N-(3-(7-(6-methyl-1H-indol-2-yl)-5-trityl-5H-pyrrolo[2,3-b]pyrazin-2-yl)phenyl)acrylamide (9)

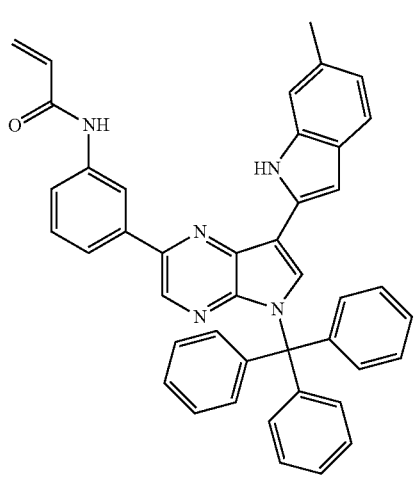

A solution of 2-bromo-7-(6-methyl-1H-indol-2-yl)-5-trityl-5H-pyrrolo[2,3-b]pyrazine 8 (30 mg, 0.0528 mmol) and (3-acrylamidophenyl)boronic acid 2 (10.9 mg, 0.0528 mmol) in DMF was added cesium carbonate (34.74 mg, 0.1056 mmol). The reaction was degassed and purged with nitrogen for 10 min. Pd(PPh3)Cl$_2$ (2.06 mg, 0.00264 mmol) was added to the reaction and again degassed for 15 min. The reaction was stirred for 2 h at 90° C. The reaction mixture was allowed to cool to rt. The reaction was diluted with DCM filtered through Celite. The organic layer was concentrated to get the crude. The resulting oil was purified through flash chromatography by using 100-200 mesh silica gel. The compound was eluted at 40% ethyl acetate in hexane to afford off white colour solid compound N-(3-(7-(6-methyl-1H-indol-2-yl)-5-trityl-5H-pyrrolo[2,3-b]pyrazin-2-yl)phenyl)acrylamide 9.

N-(3-(7-(6-methyl-1H-indol-2-yl)-5H-pyrrolo[2,3-b]pyrazin-2-yl)phenyl)acrylamide (10, Example 2)

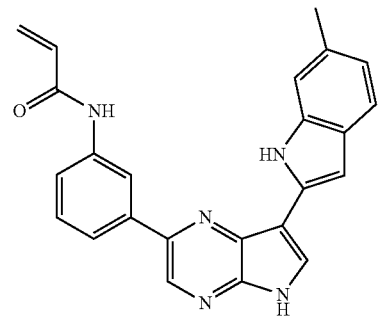

A solution of Compound 9 (20 mg, 0314 mmol) in chloroform was added trifluoro acetic acid. The reaction was stirred overnight at 45° C. The reaction was completely distilled and diluted with water, adjust the pH to 9-10 with 1 molar NaOH solution at 20-25° C. The aqueous layer was extracted with DCM (25 mL) twice. The organic layer was dried over sodium sulphate, filtered and concentrated to get the crude. The resulting oil was purified via silica gel chromatography using gradient of 50% Ethyl acetate: hexane afforded Compound 10. MS-ES+393.16; $^1$H NMR (400 MHz, DMSO-D6-d$_6$) 10: 12.29 (d, 1H), 11.17 (d, 1H), 10.39 (d, 1H), 8.84 (d, 1H), 8.54 (d, 1H), 7.94 (d, 2H), 7.55 (d, 2H), 7.49 (d, 2H), 7.26 (d, 2H), 6.83 (d, 1H), 6.54 (d, 1H), 6.36 (d, 1H) 5.81 (d, 1H), 4.45 (d, 3H).

Example 3

N-(3-(7-(1H-indol-2-yl)-5H-pyrrolo[2,3-b]pyrazin-2-yl)phenyl)acrylamide (14)

2-bromo-7-(1H-indol-2-yl)-5-trityl-5H-pyrrolo[2,3-b]pyrazine (Compound 12)

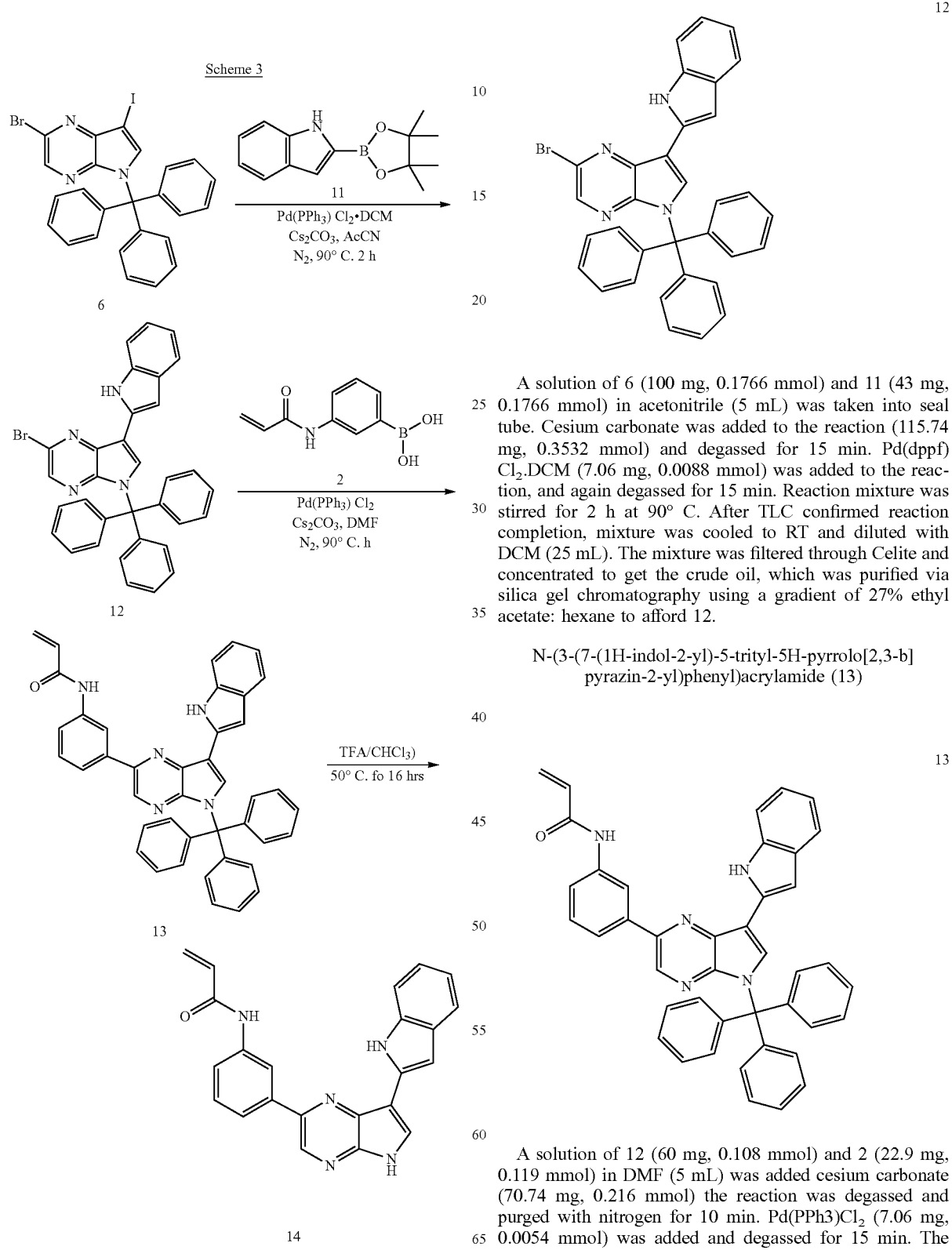

A solution of 6 (100 mg, 0.1766 mmol) and 11 (43 mg, 0.1766 mmol) in acetonitrile (5 mL) was taken into seal tube. Cesium carbonate was added to the reaction (115.74 mg, 0.3532 mmol) and degassed for 15 min. Pd(dppf)Cl$_2$.DCM (7.06 mg, 0.0088 mmol) was added to the reaction, and again degassed for 15 min. Reaction mixture was stirred for 2 h at 90° C. After TLC confirmed reaction completion, mixture was cooled to RT and diluted with DCM (25 mL). The mixture was filtered through Celite and concentrated to get the crude oil, which was purified via silica gel chromatography using a gradient of 27% ethyl acetate: hexane to afford 12.

N-(3-(7-(1H-indol-2-yl)-5-trityl-5H-pyrrolo[2,3-b]pyrazin-2-yl)phenyl)acrylamide (13)

A solution of 12 (60 mg, 0.108 mmol) and 2 (22.9 mg, 0.119 mmol) in DMF (5 mL) was added cesium carbonate (70.74 mg, 0.216 mmol) the reaction was degassed and purged with nitrogen for 10 min. Pd(PPh3)Cl$_2$ (7.06 mg, 0.0054 mmol) was added and degassed for 15 min. The reaction mixture was stirred for 2 h at 90° C. and then allowed to cool to RT, diluted with DCM (25 mL) and filtered through Celite plug. The organic layer was concentrated to get crude material as an oil, which was purified via silica gel chromatography using a gradient of 40% ethyl acetate: hexane to afford compound 13.

N-(3-(7-(1H-indol-2-yl)-5H-pyrrolo[2,3-b]pyrazin-2-yl)phenyl)acrylamide (14)

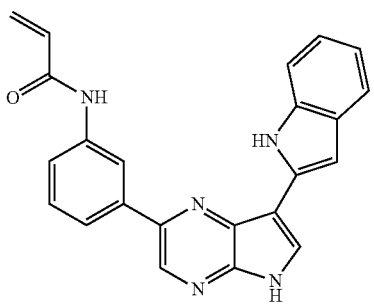

14

A solution of compound 13 (90 mg, 1.449 mmol) in chloroform was added trifluoroacetic acid. The reaction was stirred overnight at 45° C., distilled off TFA and diluted with water and pH was adjusted to 9-10 with 1M NaOH solution at 20-25° C. The aqueous layer was extracted with dichloromethane (25 mL) twice. The organic layer was dried over sodium sulphate, filtered and concentrated to get the crude. The resulting oil was purified via silica gel chromatography using gradient of 50% Ethyl acetate in hexane to afford brown colour solid Compound 14. MS-ES+379.41, $^1$H NMR (400 MHz, DMSO-D6-$d_6$) 14: 11.36 (d, 1H), 10.40 (d, 1H), 8.89 (d, 1H), 8.54 (d, 1H), 8.38 (d, 1H), 7.94 (d, 2H), 7.55 (d, 2H), 7.43 (d, 2H), 7.13 (d, 2H), 6.56 (d, 1H), 6.36 (d, 1H), 5.83 (d, 1H), 5.31 (d, 1H).

Example 4

N-(3-(3-chloro-1H-pyrrolo[2,3-b]pyridin-5-yl)phenyl)acrylamide (16)

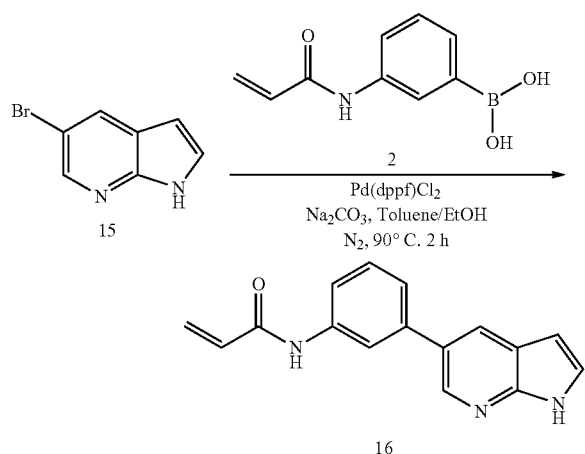

A solution of 15 (100 mg, 0.510 mmol) and 2 (84.2 mg, 0.510 mmol) in toluene/Ethanol (4:1 mL) was added Na$_2$CO$_3$ (111.69 mg, 1.02 mmol) the reaction was degassed and purged with nitrogen for 10 min. Pd(dppf)Cl$_2$ (20.7 mg, 0.025 mmol) was added to the reaction, which was degassed and purged with nitrogen for another 10 min. The reaction was heated to 90° C. under sealed condition overnight. The reaction mixture was allowed to cool to RT and diluted with chloroform. The organic layer was filtered through Celite and concentrated to get the crude, which was purified through flash chromatography by using 100-200 mesh silica gel. The compound 16 was eluted at 1% methanol in chloroform as off-white solid. Ms-ES+ 264.9; $^1$H NMR (400 MHz, DMSO-D$_6$) 16: 9.99 (s, 1H), 9.40 (s, 1H), 7.25 (s, 1H), 7.08 (m, 2H), 6.45 (m, 2H), 6.21 (d, 1H), 5.71 (d, 1H)

Example 5

N-(3-(3-chloro-1H-pyrrolo[2,3-b]pyridin-5-yl)phenyl)acrylamide (18)

Scheme 5

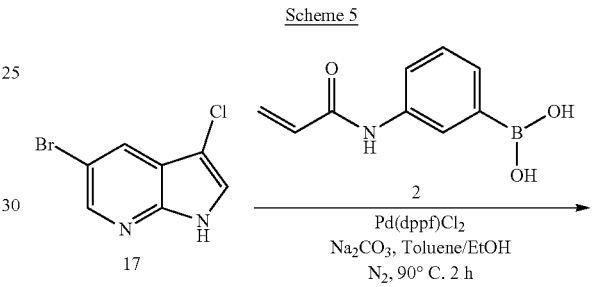

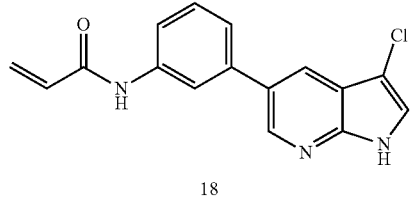

A solution of 17 (0.4 g, 1.73 mmol) and 2 (0.285 g, 1.73 mmol) in ethanol and toluene (4:16 mL) was added sodium carbonate (0.363 g, 3.463 m, eq). The reaction was degassed and purged with nitrogen for 15 min. Pd(dppf)Cl$_2$.DCM (70.58 mg, 0.0865 mmol) was added to the reaction and again degassed it for 15 min. The reaction mixture was stirred for 2 h at 90° C. After 2 h reaction mixture allowed to cool to rt and diluted with dichloromethane. The organic layer was filtered through Celite plug. The organic layer was concentrated to get crude. The resulting oil was purified via silica gel chromatography using a gradient of 30% ethyl acetate: hexane to afford Compound 18 in. MS-ES+298.5; 1H NMR (400 MHz, DMSO-D6) 18:10.26 (d, 1H), 8.58 (d, 1H), 8.07 (d, 1H), 8.03 (d, 1H), 7.75 (d, 2H), 7.46 (d, 2H), 6.46 (d, 1H), 6.43 (d, 1H), 6.31 (d, 1H)

Example 6

N-(3-(3-methyl-1H-pyrrolo[2,3-b]pyridin-5-yl)phenyl)acrylamide (20)

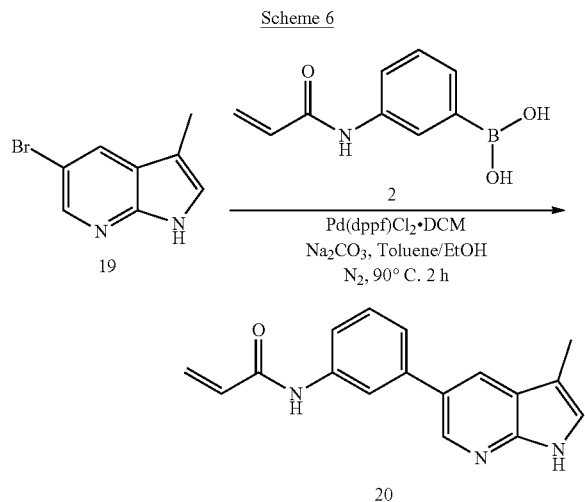

Scheme 6

A solution of 19 (50 mg, 0.2369 mmol) and 2 (50 mg, 0.2369 mmol) in ethanol and toluene (1:4 mL) was added sodium carbonate (49.74 mg, 0.4738 mmol). The reaction was degassed and purged with nitrogen for 15 min. Pd(dppf)Cl$_2$.DCM (9.06 mg, 0.0114 mmol), and again degassed for 15 min. The reaction mixture was stirred for 2 h at 90° C. and the reaction mixture allowed to cool to rt and diluted with DCM (25 mL). The organic layer was filtered through Celite and concentrated to get the crude. The resulting oil was purified via silica gel chromatography using a gradient of 30% ethyl acetate: hexane to afford Compound 20. MS-ES+277 1 H NMR (400 MHz, DMSO-D6) 20: 11.37 (d, 1H), 10.24 (d, 1H), 8.45 (d, 1H), 8.09 (d, 2H), 7.68 (d, 1H), 7.43 (d, 2H), 7.28 (d, 1H), 6.46 (d, 1H), 6.44 (d, 1H), 5.79 (d, 1H), 2.30 (d, 1H).

Example 7

N-(3-(5H-pyrrolo[2,3-b]pyrazin-2-yl)phenyl)acrylamide (22)

Scheme 7

A solution of 21 (100 mg, 0.507 mmol) and 2 (84 mg, 0.507 mmol) in toluene and ethanol (4:1 mL) was added Na$_2$CO$_3$ (111.01 mg, 1.014 mmol). The reaction was degassed and purged with nitrogen for 10 min. Pd(dppf)Cl$_2$ (20.7 mg, 0.025 mmol) was added to the reaction. The reaction was degassed and purged with nitrogen for another 10 min. The reaction was heated to 90° C. under sealed condition overnight, allowed to cool to RT, and diluted with chloroform. The organic layer was filtered through Celite and concentrated to get the crude, which was purified through flash chromatography by using 100-200 mesh silica gel. The compound was eluted in 40% ethyl acetate in hexane as an off-white solid 22. MS-ES+264.8; 1H NMR (400 MHz, DMSO-D$_6$) 22: 9.99 (bs, 1H), 9.40 (bs, 1H), 7.25 (bs, 1H), 7.08 (m, 1H), 7.00 (d, 1H), 6.42 (m, 2H), 6.21 (m, 1H), 5.71 (m, 1H).

Example 8

(E)-N-(3-(3-methyl-1H-pyrrolo[2,3-b]pyridin-5-yl)phenyl)pent-2-enamide (26)

Scheme 8

83

3-(3-methyl-1H-pyrrolo[2,3-b]pyridin-5-yl)aniline (24)

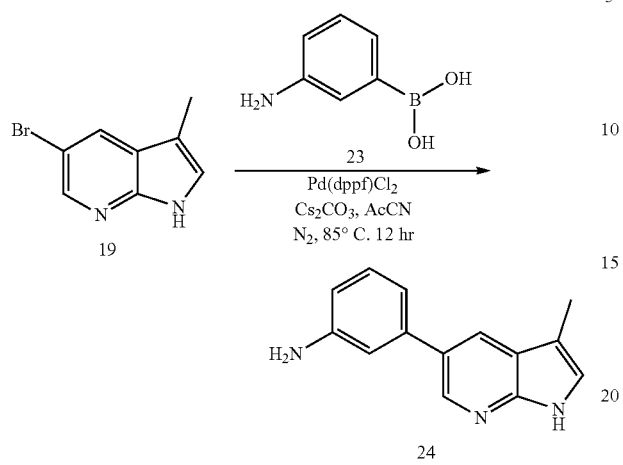

A solution of 19 (100 mg, 0.473 mmol) and 23 (62 mg, 0.4739 mmol) in acetonitrile (5 mL) was added cesium carbonate (310 mg, 0.946 mmol). The reaction was degassed and purged with nitrogen for 15 min. Pd(dppf)Cl$_2$ (25.4 mg, 0.0218 mmol) was added and again degassed and purged with nitrogen for 15 min. The reaction was stirred overnight at 85° C., allowed to cool to rt, then diluted with DCM (25 mL) and filtered through Celite plug and concentrated to get the crude compound. The resulting oil was purified via silica gel chromatography using a gradient of 40% ethyl acetate: hexane to afford compound 24.

(E)-N-(3-(3-methyl-1H-pyrrolo[2,3-b]pyridin-5-yl)phenyl)pent-2-enamide (26)

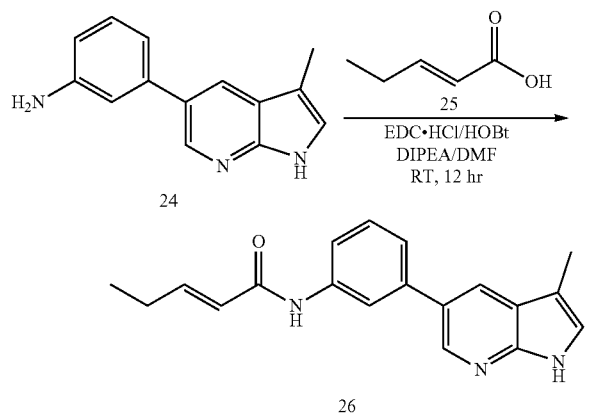

A solution of 24 (50 mg, 0.2242 mmol) and trans-2-pentenoic acid 25 (24.6 mg, 0.246 eq) in DMF was added EDC.HCl (33 mg, 0.2706 mmol) and HOBt (36.5 mg, 0.2706 mmol). DIPEA (57.9 mg, 0.448 eq) was added to the reaction, stirred 12 h at RT and check the TLC for completion of the reaction and quench the reaction mixture with dilute water. The organic layer was treated with ethyl acetate (25 mL) and was washed with brine solution (25 mL) and dried over sodium sulphate, filtered and concentrated to get

84 the crude product. The resulting oil was purified through silica gel chromatography using a gradient of 4% Ethyl acetate: hexane to afford 8 mg of Compound 26. MS-ES+ 305.1 1H NMR (400 MHz, DMSO-D6-d$_6$): 11.45 (s, 1H), 10.08 (s, 1H), 8.40 (s, 1H), 8.17 (s, 1H), 7.85 (d, 1H), 7.61 (m, 1H), 7.36 (m, 2H), 7.30 (d, 1H), 5.62 (m, 1H), 2.35 (s, 3H).

Example 9

(E)-N-(2-chloro-5-(3-methyl-1H-pyrrolo[2,3-b]pyridin-5-yl)phenyl)pent-2-enamide (29)

Scheme 9

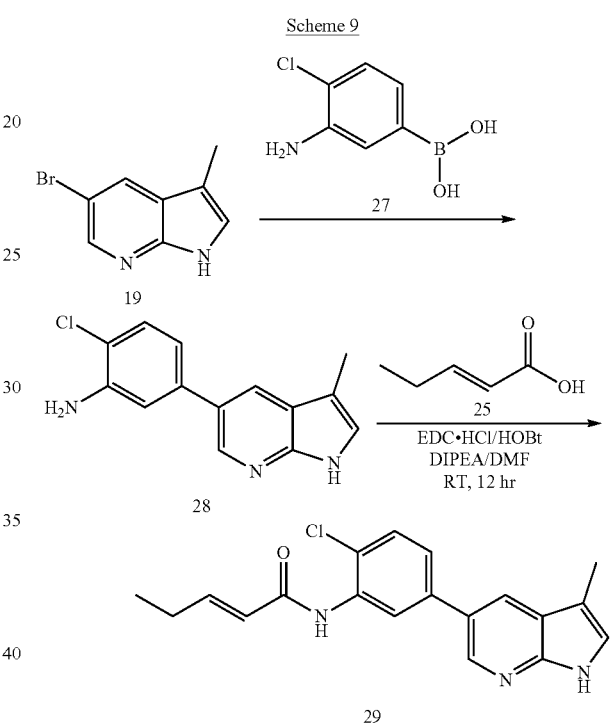

A solution of 19 (200 mg, 0.952 mmol) and 27 (162.8 mg, 0.952 mmol) in acetonitrile was added Na$_2$CO$_3$ (201.6 mg, 1.904 mmol). The reaction was degassed and purged with nitrogen for 10 min. Pd(dppf)Cl$_2$ (38.8 mg, 0.0476 mmol) was added to the reaction. The reaction mass was degassed and purged with nitrogen for another 10 min. The reaction was heated to 90° C. under sealed conditions overnight, then allowed to cool to RT and diluted with chloroform. The organic layer was filtered through Celite and concentrated to get the crude, which was purified through flash chromatography by using 100-200 silica mesh. The compound was eluted at 2% methanol chloroform as off-white colour solid 28.

A solution of 28 (50 mg, 0.194 mmol) and trans-2-pentenoic acid 25 (19.4 mg, 0.194 mmol) in acetonitrile (4 mL) was added triethylamine (39.26 mg, 0.388 mmol). T$_3$P (123.45 mg, 0.388 mmol) was added to the reaction mixture. The reaction was stirred overnight at rt. The reaction was diluted with ethyl acetate (25 mL). The organic layer was washed with water (25 mL) followed by brine solution (25 mL). The organic layer was dried over sodium sulphate, filtered and concentrated to get the crude, which was purified through flash chromatography by using 100-200 mesh silica gel. The compound was eluted at 1.5% methanol in chloroform as pale yellow solid compound 29. MS-ES+339.90; $^1$H NMR (400 MHz, DMSO-D$_6$) 29: 11.40 (s, 1H), 9.53 (d, 1H), 8.45 (s, 1H), 8.12 (m, 2H), 7.57 (d, 2H), 7.28 (s, 1H), 5.63 (m, 2H), 3.15 (m, 2H), 2.30 (m, 5H), 1.68 (d, 3H), 1.23 (bs, 2H).

Example 10

N-(2-chloro-5-(3-chloro-1H-pyrrolo[2,3-b]pyridin-5-yl)phenyl)acrylamide (34)

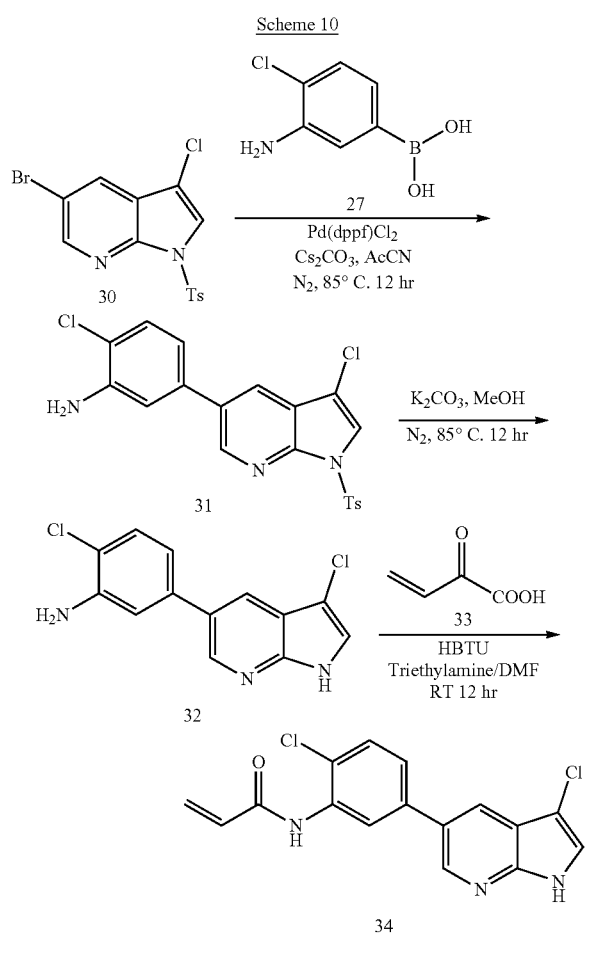

A solution of 30 (100 mg, 0.259 mmol) and 27 (44.5 mg, 0.259 mmol) in acetonitrile was added cesium carbonate (170 mg, 0.5 eq). The reaction was degassed and purged with nitrogen for 15 min. Pd(dppf)Cl$_2$ (25.4 mg, 0.0218 mmol), and again degassed for 15 min and stirred at 85° C. overnight in seal tube. The reaction mixture was allowed to cool to RT and diluted with DCM. The DCM layer was filtered through Celite and concentrated to get the crude. The resulting oil was purified via silica gel chromatography using a gradient of 40% ethyl acetate in hexane to afford 55 mg of compound 31.

A solution of 31 (55 mg, 0.1273 mmol), methanol (8 mL), and water (2 mL) was added potassium carbonate (70 mg, 0.5092 mmol). The reaction was stirred for 12 h at 60° C., then allowed to cool to rt, and methanol distilled off completely. The reaction was diluted with water and extracted with ethyl acetate. The organic layer was dried over sodium sulphate, filtered and concentrated to get the crude. The resulting oil was purified via silica gel chromatography using gradient of 35% ethyl acetate in hexane to afford title compound 32.

A solution of 32 (25 mg, 0.0899 mmol) and acrylic acid 33 (7.0 mg, 0.09892 mmol) in DMF was added HBTU (51 mg, 0.1348 eq). Triethylamine (18 mg, 0.1798 eq) was added to the reaction and stirred for 12 h at RT. The reaction mass was diluted with water, extracted with ethyl acetate and the organic layer washed with brine solution. The organic layer was dried over sodium sulphate, filtered and concentrated to get crude product. The resulting oil was purified via silica gel chromatography using a gradient of 4% Ethyl acetate in hexane to afford the title compound 34. MS-ES+ 332.0, 1H NMR (400 MHz, DMSO-D6-d$_6$) 34: 8.73 (d, 2H), 8.37 (m, 1H), 8.31 (m, 1H), 8.17 (s, 1H), 7.35 (d, 1H), 7.20 (s, 1H), 7.36 (d, 1H), 7.02 (d, 1H), 6.72 (d, 1H), 6.25 (d, 2H).

Example 11

(E)-N-(2-chloro-5-(3-chloro-1H-pyrrolo[2,3-b]pyridin-5-yl)phenyl)pent-2-enamide (35)

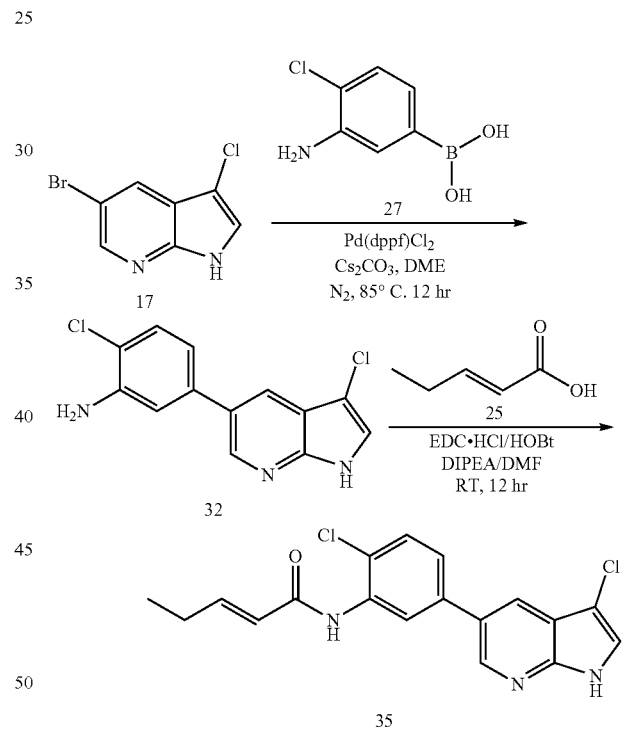

A solution of 17 (100 mg, 0.436 mmol) and 27 (74.5 mg, 0.436 mmol) in DME was added cesium carbonate (286 mg, 0.872 mmol). The reaction was degassed and purged for 15 min. Pd(PPh$_3$)$_4$ (25.4 mg, 0.0218 mmol) was added to the reaction and again degassed, purged with nitrogen for 15 min. reaction was stirred for 12 hrs at 85° C. The reaction mixture was allowing cooling to rt and diluted with DCM (25 mL). The DCM layer was filtered through Celite plug and concentrated to get the crude. The resulting oil was purified via silica gel chromatography using a gradient of 40% ethyl acetate in hexane to afford 55 mg of 32 of off white colour solid.

A solution of above obtained compound 32 (50 mg, 0.1945 mmol) and (E)-pent-2-enoic acid 25 (19.45 mg, 0.1945 mmol) in DMF was added EDC HCl (33.1 mg, 0.2139 mmol) and HOBt (28.8 mg, 0.2139 mmol) and DIPEA (27.5 mg, 0.2139 mmol). The reaction was stirred for 12 h at rt. The reaction mass was diluted with water and extracted with ethyl acetate. The organic layer was washed with water twice, followed by brine solution. The resulting oil was purified via silica gel chromatography using gradient of 20% ethyl acetate in hexane to afford pale yellow colour solid compound 35. MS-ES+359.1, $^1$H NMR (400 MHz, CDCl$_3$) 35: 8.62 (d, 2H), 8.20 (d, 1H), 8.17 (d, 1H), 8.08 (d, 1H), 8.02 (d, 2H), 7.49 (d, 1H), 7.36 (d, 1H), 7.02 (d, 1H), 6.97 (d, 1H), 4.19 (d, 2H), 2.48 (d, 2H), 1.23 (d, 3H).

Example 12

N-(6-(1H-pyrrolo[2,3-b]pyridin-5-yl)pyridin-2-yl)acrylamide (39)

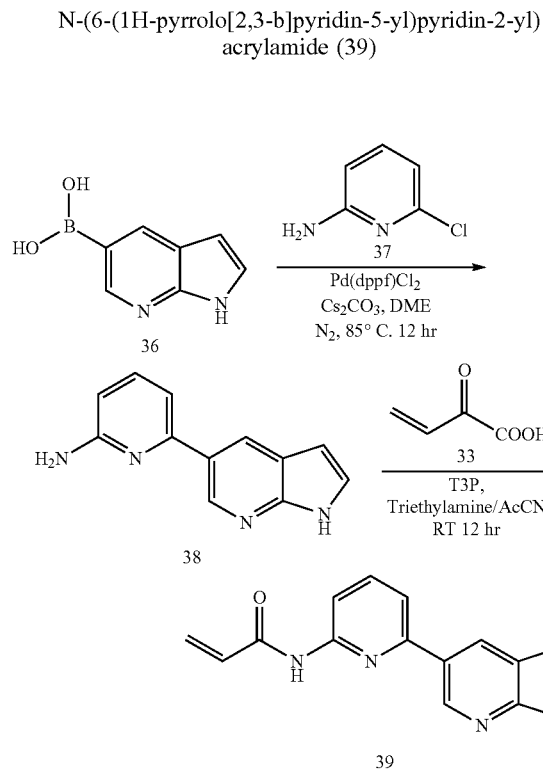

A solution of 36 (200 mg, 0.819 mmol) and 37 (105.3 mg, 0.819 mmol) in DMF was added cesium carbonate (533.6 mg, 1.638 mmol). The reaction was purged and degassed with nitrogen for 10 min. Pd(PPh$_3$)$_2$Cl$_2$ (28.7 mg, 0.0409 mmol) was added to the reaction and again degassed and purged with nitrogen for 10 min. Reaction was sealed and heated to 90° C. overnight. The reaction was allowed to cool to rt and diluted with dichloromethane and filtered through Celite bed. The organic layer was concentrated to get the crude product. The crude was purified through flash chromatography by using 100-200 mesh silica gel. The compound was eluted at 1% methanol in chloroform as pale yellow colour solid 38.

A solution of 38 (50 mg, 0.237 mmol) and acrylic acid 33 (17.14 mg, 0.237 mmol) in acetonitrile was added triethylamine (47.95 mg, 0.474 mmol). T$_3$P (150.8 mg, 0.474 mmol) was added to the reaction mixture. The reaction was stirred overnight at rt. The reaction was diluted with ethyl acetate (25 mL). The organic layer was washed with water (25 mL) followed by brine solution (25 mL). The organic layer was dried over sodium sulphate, filtered and concentrated to get the crude, which was purified through flash chromatography by using 100-200 mesh silica gel. The compound was eluted at 2% methanol in chloroform as off-white solid 39. MS-ES+264.9, 1H NMR (400 MHz, CDCl3): 8.91 (d, 1H), 8.78 (bs, 1H), 8.50 (d, 1H), 8.23 (m, 1H), 8.07 (bs, 1H), 7.80 (t, 1H), 7.53 (m, 1H), 7.35 (m, 1H), 6.59 (m, 1H), 6.49 (m, 1H), 6.29 (m, 1H), 5.84 (m, 1H).

Example 13

N-(2-fluoro-5-(1H-pyrrolo[2,3-b]pyridin-5-yl)phenyl)acrylamide (42)

Scheme 13

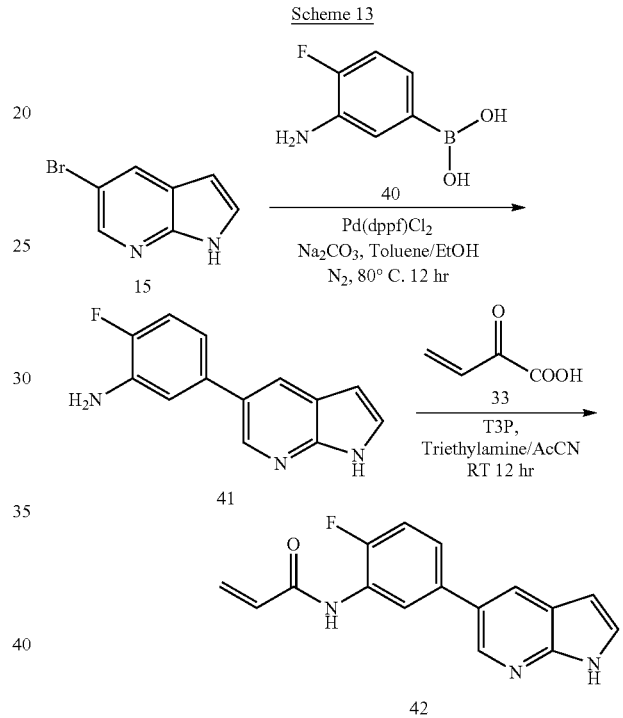

A solution of 15 (100 mg, 0.510 mmol) and 40 (78.6 mg, 0.510 mmol) in toluene/ethanol (4:1) was added sodium carbonate (111.69 mg, 1.02 mmol). The reaction was degassed and purged with nitrogen for 10 min and Pd(dppf)Cl$_2$ (20.8 mg, 0.0255 mmol) added to the reaction. The reaction was again degassed and purged with nitrogen for 10 min. The reaction was heated to 80° C. overnight under sealed condition. The reaction mass was allowed to cool to rt and diluted with chloroform. The organic layer was passed through Celite bed and organic layer was concentrated to get the crude, which was purified through flash chromatography by using 100-200 mesh silica gel. The compound 41 was eluted at 30% ethyl acetate in hexane as off white colour solid.

A solution of 41 (50 mg, 0.219 mmol) and acrylic acid 33 (15.84 mg, 0.219 mmol) in acetonitrile was added triethylamine (44.35 mg, 0.438 mmol). T$_3$P (139.3 mg, 0.438 mmol) was added to the reaction mixture. The reaction was stirred overnight at rt. The reaction was diluted with ethyl acetate (25 mL). The organic layer was washed with water (25 mL) followed by brine solution (25 mL). The organic layer was dried over sodium sulphate, filtered and concentrated to get the crude, which was purified through flash chromatography by using 100-200 mesh silica gel. The compound was eluted at 40% ethyl acetate in hexane as brown colour solid compound 42. MS-ES+281.9, 1H NMR (400 MHz, DMSO-D6): 11.73 (s, 1H), 10.06 (s, 1H), 8.45 (d, 1H), 8.32 (d, 1H), 8.15 (d, 1H), 7.49 (m, 2H), 7.37 (m, 1H), 6.66 (m, 1H), 6.50 (m, 1H), 6.32 (m, 1H), 5.78 (m, 1H).

Example 14

N-(2-fluoro-4-(1H-pyrrolo[2,3-b]pyridin-5-yl)phenyl)acrylamide (45)

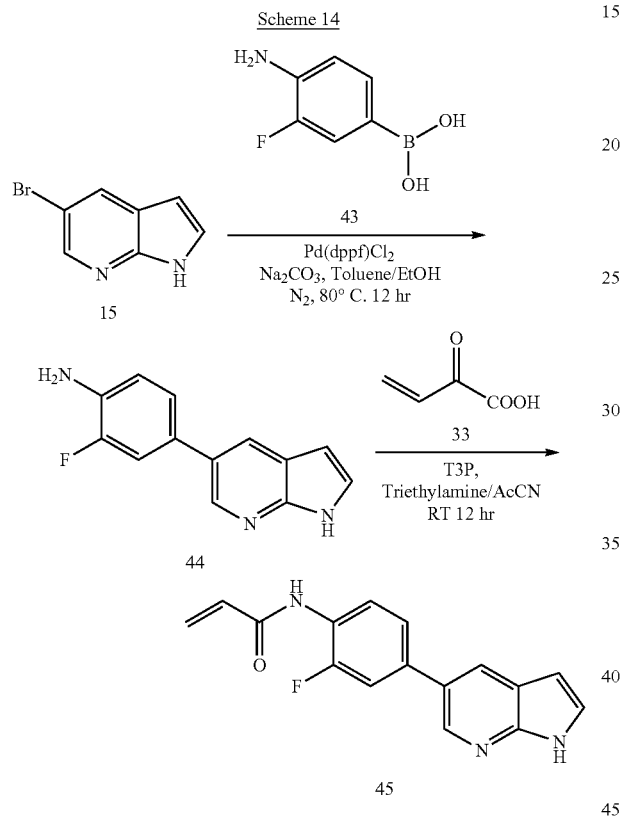

A solution of 15 (100 mg, 0.510 mmol) and 43 (78.6 mg, 0.510 mmol) in toluene/ethanol (4:1) was added sodium carbonate (111.69 mg, 1.02 mmol). The reaction was degassed and purged with nitrogen for 10 min. Pd(dppf)Cl$_2$ (20.8 mg, 0.0255 mmol) was added to the reaction. The reaction was again degassed and purged with nitrogen for 10 min. The reaction was heated to 80° C. overnight under sealed condition. The reaction mass was allowed to cool to rt and diluted with chloroform. The organic layer was passed through Celite bed and organic layer was concentrated to get the crude, which was purified through flash chromatography by using 100-200 mesh silica gel. The compound 44 was eluted at 30% ethyl acetate in hexane as off white colour solid.

A solution of 44 (40 mg, 0.175 mmol) and acrylic acid 33 (12.64 mg, 0.175 mmol) in acetonitrile was added triethylamine (35.41 mg, 0.35 mmol). T$_3$P (111.3 mg, 0.35 mmol) was added to the reaction mixture. The reaction was stirred overnight at rt. The reaction was diluted with ethyl acetate (25 mL). The organic layer was washed with water (25 mL) followed by brine solution (25 mL). The organic layer was dried over sodium sulphate, filtered and concentrated to get the crude, which was purified through flash chromatography by using 100-200 mesh silica gel. The compound was eluted at 40% ethyl acetate in hexane as brown colour solid compound 45. MS-ES+281.9, 1H NMR (400 MHz, DMSO-D6-d$_6$) 45: 11.75 (s, 1H), 10.02 (s, 1H), 8.55 (d, 1H), 8.25 (d, 1H), 8.11 (t, 1H), 7.69 (m, 1H), 7.53 (m, 2H), 6.62 (m, 1H), 6.50 (m, 1H), 6.29 (m, 1H), 5.78 (m, 1H).

Example 15

N-(3-(3-chloro-1H-pyrrolo[2,3-b]pyridin-5-yl)phenyl)-2-cyanoacetamide (48)

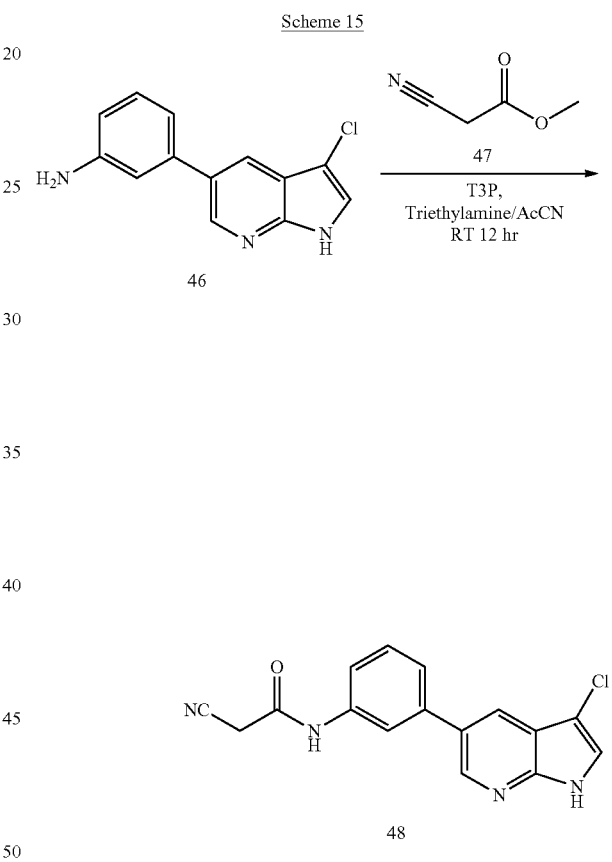

A solution of 46 (50 mg, 0.2057 mmol) and 47 (17.48 mg, 0.2057 mmol) in acetonitrile was added triethyl amine (41.69 mg, 0.4114 mmol). T$_3$P (130.09 mg, 0.4114 mmol) was added to the reaction mixture. The reaction was stirred overnight at rt. The reaction was diluted with ethyl acetate (25 mL). The organic layer was washed with water (25 mL) followed by brine solution (25 mL). The organic layer was dried over sodium sulphate, filtered and concentrated to get the crude, which was purified through flash chromatography by using 100-200 mesh silica gel. The compound was eluted at 1% methanol in chloroform as pale yellow colour solid 48. MS-ES+311.2, 1H NMR (400 MHz, DMSO-D$_6$) 48: 12.09 (bs, 1H), 11.10 (s, 1H), 9.79 (s, 1H), 8.65 (d, 2H), 8.23 (bs, 1H), 8.16 (d, 1H), 7.74 (d, 1H), 7.65 (m, 1H), 7.54 (m, 2H).

Example 16

N-(3-(3-chloro-1H-pyrrolo[2,3-b]pyridin-5-yl)phenyl)-1-cyanocyclopropane-carboxamide (51)

Scheme 16

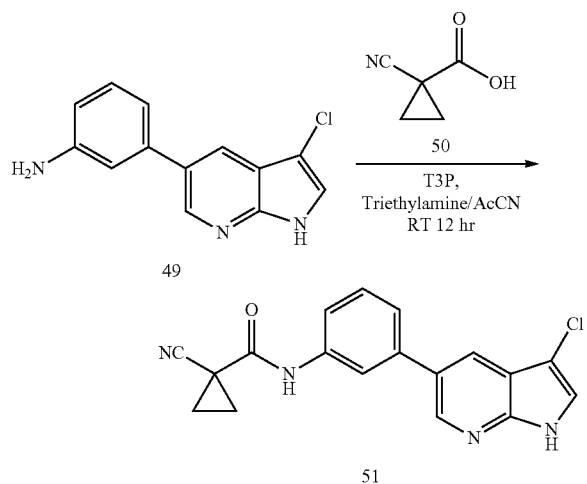

A solution of 49 (50 mg, 0.2057 mmol) and 50 (22.8 mg, 0.2057 mmol) in acetonitrile was added triethylamine (41.69 mg, 0.4114 mmol). T$_3$P (130.09 mg, 0.4114 mmol) was added to the reaction mixture. The reaction was stirred overnight at rt. The reaction was diluted with ethyl acetate (25 mL). The organic layer was washed with water (25 mL) followed by brine solution (25 mL). The organic layer was dried over sodium sulphate, filtered and concentrated to get the crude, which was purified through flash chromatography by using 100-200 mesh silica gel. The compound was eluted at 2% methanol in chloroform as off white colour solid compound 51. MS-ES+334.9; $^1$H NMR (400 MHz, DMSO-D$_6$) 51: 12.08 (s, 1H), 10.07 (s, 1H), 8.58 (s, 1H), 8.06 (s, 1H), 7.94 (s, 1H), 7.73 (d, 1H), 7.50 (m, 1H), 7.43 (m, 2H), 5.55 (m, 4H)

Example 17

N-(2-(3-methyl-1H-pyrrolo[2,3-b]pyridin-5-yl)phenyl)acrylamide (53)

Scheme 17

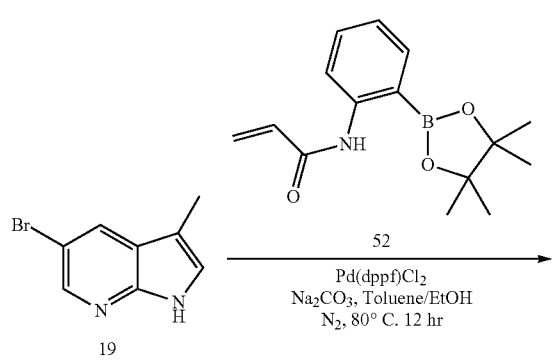

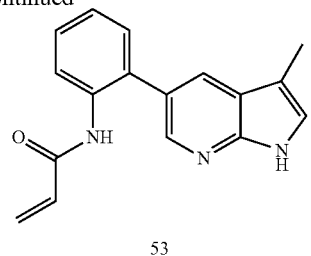

A solution of 19 (100 mg, 0.434 mmol) and 52 (118.2 mg, 0.434 mmol) in toluene/ethanol (4:1) was added sodium carbonate (95.04 mg, 0.868 mmol). The reaction was degassed and purged with nitrogen for 10 min. Pd(dppf)Cl$_2$ (17.72 mg, 0.0217 mmol) was added to the reaction. The reaction mass was degassed and purged with nitrogen for another 10 min. The reaction was heated to 80° C. under sealed condition overnight. The reaction was allowed to cool to rt and diluted with chloroform. The organic layer was filtered through Celite bed and concentrated to get the crude, which was purified through flash chromatography by using 100-200 mesh silica gel. The compound was eluted at 2% methanol in chloroform as off-white colour solid compound 53. MS-ES+277.9; $^1$H NMR (400 MHz, DMSO-D$_6$) 53.: 11.31 (s, 1H), 9.46 (s, 1H), 8.12 (d, 1H), 7.83 (d, 1H), 7.56 (d, 1H), 7.33 (m, 4H), 7.24 (bs, 1H), 6.30 (m, 1H), 6.11 (m, 1H), 5.62 (m, 1H), 2.22 (s, 3H).

Example 18

N-(2-(3-chloro-1H-pyrrolo[2,3-b]pyridin-5-yl)phenyl)acrylamide (54)

Scheme 18

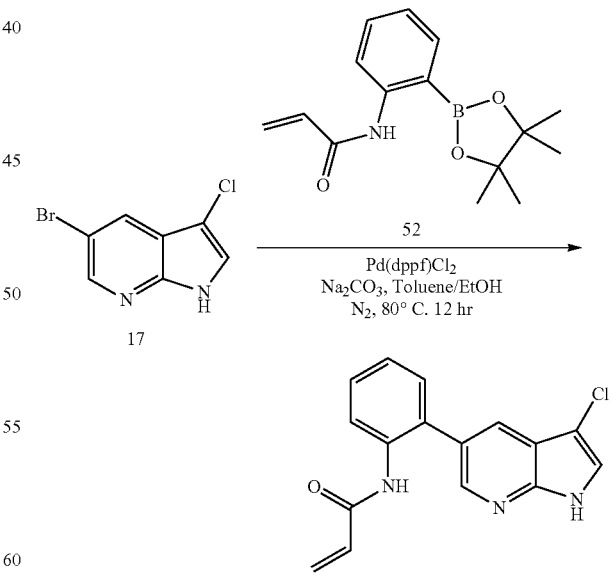

A solution of 17 (100 mg, 0.476 mmol) and 52 (130.01 mg, 0.476 mmol) in toluene/ethanol (4:1) was added sodium carbonate (104.24 mg, 0.952 mmol). The reaction was degassed and purged with nitrogen for 10 min. Pd(dppf)Cl$_2$ (16.72 mg, 0.0238 mmol) was added to the reaction. The reaction mass was degassed and purged with nitrogen for another 10 min. The reaction was heated to 80° C. under sealed condition overnight. The reaction was allowed to cool to rt and diluted with chloroform. The organic layer was filtered through Celite bed and concentrated to get the crude, which was purified through flash chromatography by using 100-200 mesh silica gel. The compound was eluted at 2% methanol in chloroform as off-white colour solid compound 54. MS-ES+297.9; $^1$H NMR (400 MHz, DMSO-D$_6$) 54: 12.05 (s, 1H), 9.55 (s, 1H), 8.24 (d, 1H), 7.83 (d, 1H), 7.72 (d, 1H), 7.57 (d, 1H), 7.41 (m, 3H), 6.30 (m, 1H), 6.12 (d, 1H), 5.63 (d, 1H).

Example 19

N-(3-(3-chloro-1H-pyrrolo[2,3-b]pyridin-5-yl)phenyl)but-2-ynamide (56)

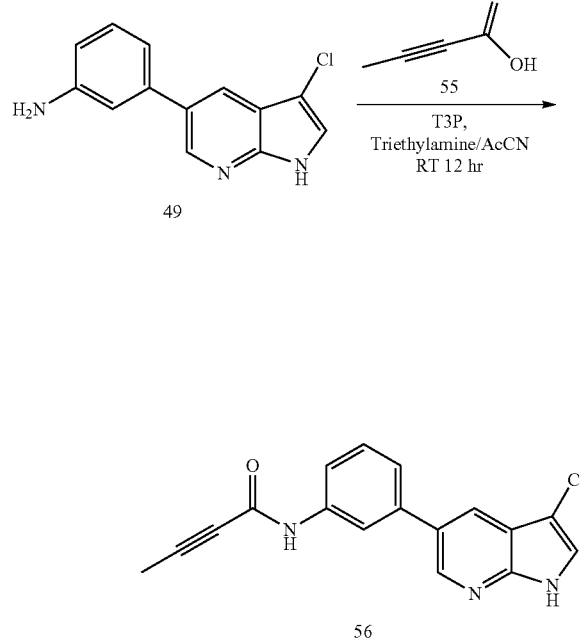

A solution of 49 (25 mg, 0.102 mmol) and 55 (8.6 mg, 0.102 mmol) in acetonitrile (8 ml) was added triethylamine (20.6 mg, 0.204 mmol). T$_3$P (64.90 mg, 0.204 mmol) was added to the reaction mixture. The reaction was stirred overnight at rt. The reaction was diluted with ethyl acetate (25 mL). The organic layer was washed with water (25 mL) followed by brine solution (25 mL). The organic layer was dried over sodium sulphate, filtered and concentrated to get the crude, which was purified through flash chromatography by using 100-200 mesh silica gel. The compound was eluted at 2% methanol in chloroform as pale yellow colour solid compound 56. MS-ES+309.9; $^1$H NMR (400 MHz, DMSO-D$_6$): 12.09 (s, 1H), 10.69 (s, 1H), 8.54 (s, 1H), 8.03 (s, 1H), 7.93 (s, 1H), 7.73 (d, 1H), 7.59 (d, 1H), 7.43 (m, 2H), 2.05 (s, 3H).

Example 20

N-(3-(3-chloro-1H-pyrrolo[2,3-b]pyridin-5-yl)phenyl)propiolamide (58)

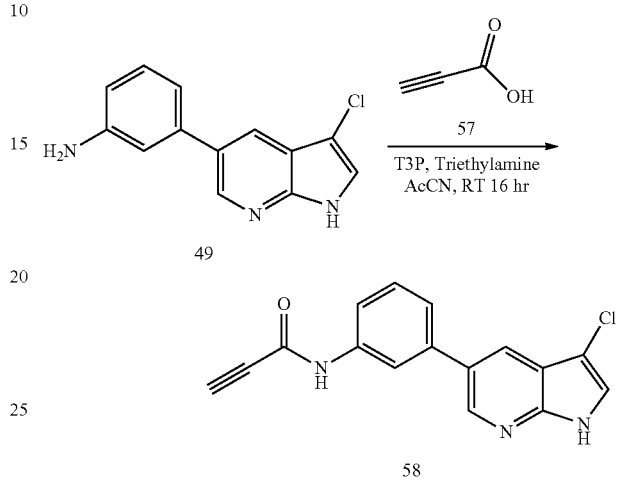

A solution of 49 (25 mg, 0.102 mmol) and 57 (7.14 mg, 0.102 mmol) in acetonitrile (8 mL) was added triethyl amine (20.6 mg, 0.204 mmol). T$_3$P (64.90 mg, 0.204 mmol) was added to the reaction mixture. The reaction was stirred overnight at rt. The reaction was diluted with ethyl acetate (25 mL). The organic layer was washed with water (25 mL) followed by brine solution (25 mL). The organic layer was dried over sodium sulphate, filtered and concentrated to get the crude, which was purified through flash chromatography by using 100-200 mesh silica gel. The compound was eluted at 1% methanol in chloroform as pale yellow colour solid compound 58. MS-ES+295.8, 1H NMR (400 MHz, DMSO-D$_6$) 58: 12.11 (s, 1H), 10.91 (s, 1H), 8.56 (d, 1H), 8.05 (d, 1H) 7.94 (s, 1H), 7.75 (d, 1H), 7.62 (m, 1H), 7.47 (m, 2H), 4.45 (s, 1H)

Example 21

N-(3-(3-chloro-1H-pyrrolo[2,3-b]pyridin-5-yl)phenyl)pent-2-ynamide (60)

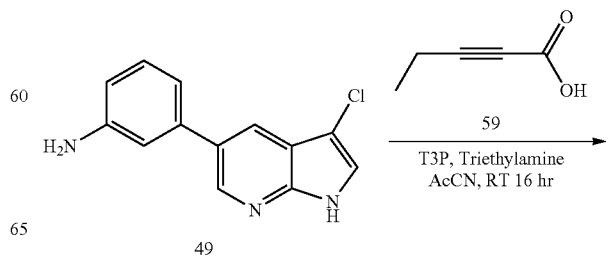

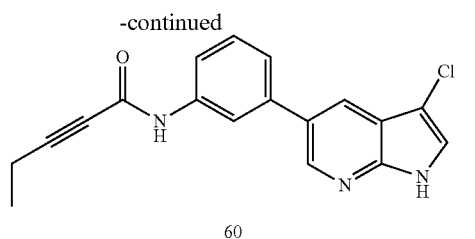

60

A solution of 49 (25 mg, 0.102 mmol) and 59 (9.86 mg, 0.102 mmol) in acetonitrile (4 mL) was added triethylamine (20.6 mg, 0.204 mmol). T$_3$P (64.90 mg, 0.204 mmol) was added to the reaction mixture. The reaction was stirred overnight at rt, then diluted with ethyl acetate (25 mL). The organic layer was washed with water (25 mL) followed by brine solution (25 mL). The organic layer was dried over sodium sulphate, filtered and concentrated to get the crude, which was purified through flash chromatography by using 100-200 mesh silica gel. The compound was eluted at 2% methanol in chloroform as pale yellow colour solid compound 60. MS-ES+323.9, $^1$H NMR (400 MHz, DMSO-D$_6$) 60: 12.10 (s, 1H), 10.68 (s, 1H), 8.55 (d, 1H), 8.04 (d, 1H), 7.93 (bs, 1H), 7.75 (bs, 1H), 7.62 (d, 1H), 7.44 (m, 2H), 2.43 (m, 2H), 1.17 (t, 3H).

Example 22

N-(3-(3-chloro-1H-pyrrolo[2,3-b]pyridin-5-yl)phenyl)-2-fluoroacetamide (62)

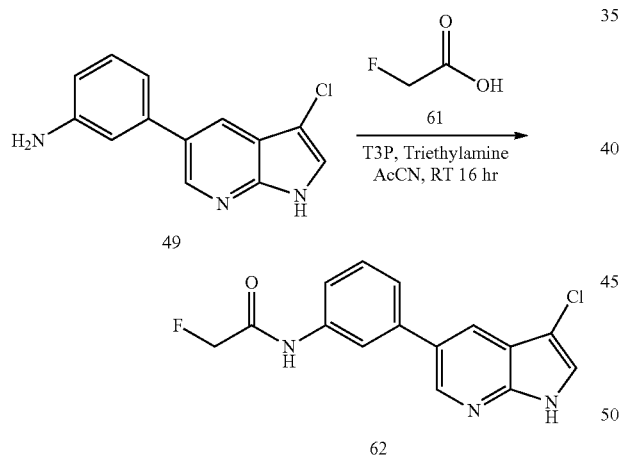

62

A solution of 49 (25 mg, 0.102 mmol) and 61 (7.2 mg, 0.102 mmol) in acetonitrile (4 mL) was added triethylamine (20.6 mg, 0.204 mmol). T$_3$P (64.90 mg, 0.204 mmol) was added to the reaction mixture. The reaction was stirred overnight at rt, then diluted with ethyl acetate (25 mL). The organic layer was washed with water (25 mL) followed by brine solution (25 mL). The organic layer was dried over sodium sulphate, filtered and concentrated to get the crude, which was purified through flash chromatography by using 100-200 mesh silica gel. The compound was eluted at 2% methanol in chloroform as pale yellow colour solid compound 62. MS-ES+303.9; $^1$H NMR (400 MHz, DMSO-D$_6$) 62: 12.09 (s, 1H), 10.18 (s, 1H), 8.58 (d, 1H), 8.06 (m, 2H), 7.71 (m, 2H), 7.47 (m, 2H), 5.08 (s, 1H), 4.96 (s, 1H)

Example 23

N-(3-(3-methyl-1H-pyrrolo[2,3-b]pyridin-5-yl)phenyl)but-2-ynamide (63)

Scheme 23

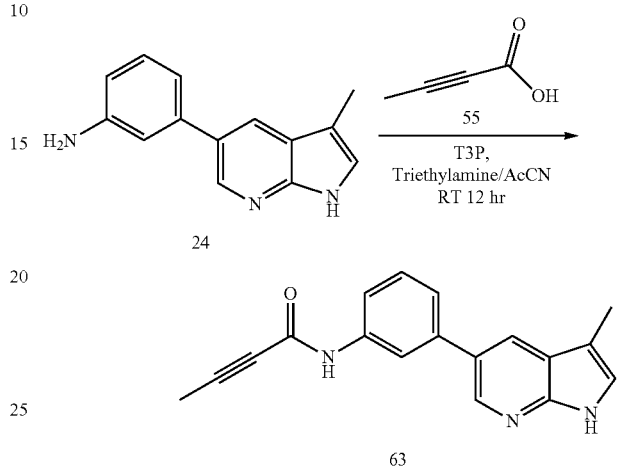

63

A solution of 24 (25 mg, 0.112 mmol) and 55 (9.4 mg, 0.112 mmol) in acetonitrile (4 mL) was added triethylamine (22.6 mg, 0.224 mmol). T$_3$P (71.27 mg, 0.224 mmol) was added to the reaction mixture. The reaction was stirred overnight at rt. The reaction was diluted with ethyl acetate (25 mL). The organic layer was washed with water (25 mL) followed by brine solution (25 mL). The organic layer was dried over sodium sulphate, filtered and concentrated to get the crude, which was purified through flash chromatography by using 100-200 mesh silica gel. The compound was eluted at 1.5% methanol in chloroform as pale yellow colour solid compound 63. MS-ES+289.9; $^1$H NMR (400 MHz, DMSO-D$_6$): 11.38 (s, 1H), 10.68 (s, 1H), 8.41 (s, 1H), 8.07 (s, 1H), 7.91 (s, 1H), 7.58 (m, 1H), 7.40 (m, 2H), 7.28 (s, 1H), 2.30 (s, 3H), 2.06 (s, 3H).

Example 24

N-(3-(3-methyl-1H-pyrrolo[2,3-b]pyridin-5-yl)phenyl)pent-2-ynamide (64)

Scheme 24

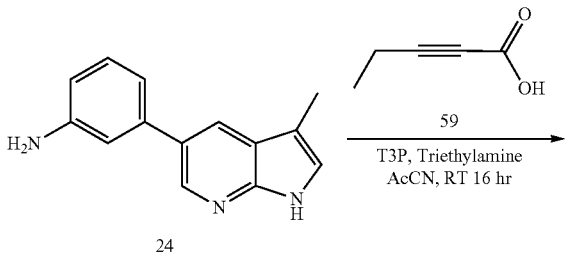

24

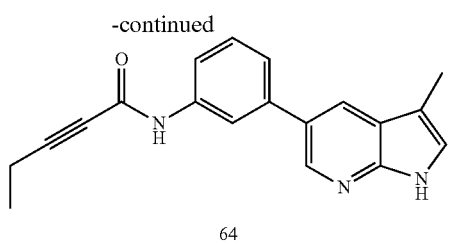
64

A solution of 24 (25 mg, 0.112 mmol) and 59 (9.86 mg, 0.112 mmol) in acetonitrile (4 mL) was added triethylamine (22.6 mg, 0.224 mmol). T$_3$P (71.1 mg, 0.224 mmol) was added to the reaction mixture. The reaction was stirred overnight at rt, then diluted with ethyl acetate (25 mL). The organic layer was washed with water (25 mL) followed by brine solution (25 mL). The organic layer was dried over sodium sulphate, filtered and concentrated to get the crude, which was purified through flash chromatography by using 100-200 mesh silica gel. The compound was eluted at 2% methanol in chloroform as pale yellow colour solid compound 64. MS-ES+303.9; $^1$H NMR (400 MHz, DMSO-D$_6$) 64: 11.37 (s, 1H), 10.65 (s, 1H), 8.41 (d, 1H), 8.06 (d, 1H), 7.90 (bs, 1H), 7.59 (d, 1H), 7.40 (m, 2H), 7.28 (bs, 1H), 2.42 (m, 2H), 2.30 (bs, 3H), 1.17 (t, 3H).

Example 25

2-fluoro-N-(3-(3-methyl-1H-pyrrolo[2,3-b]pyridin-5-yl)phenyl)acetamide (65)

Scheme 25

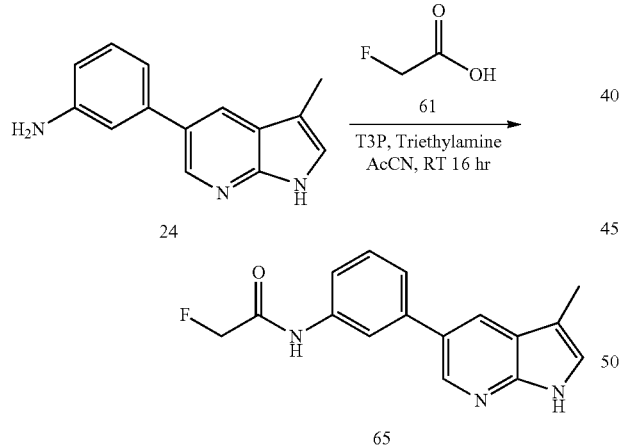

A solution of 24 (25 mg, 0.112 mmol) and 61 (7.91 mg, 0.112 mmol) in acetonitrile (4 mL) was added triethylamine (22.6 mg, 0.224 mmol). T$_3$P (71.1 mg, 0.224 mmol) was added to the reaction mixture. The reaction was stirred overnight at rt, then diluted with ethyl acetate (25 mL). The organic layer was washed with water (25 mL) followed by brine solution (25 mL). The organic layer was dried over sodium sulphate, filtered and concentrated to get the crude, which was purified through flash chromatography by using 100-200 mesh silica gel. The compound was eluted at 1.5% MeOH in chloroform as pale yellow colour solid compound. MS-ES+283.9; $^1$H NMR (400 MHz, DMSO-D$_6$) 65: 11.36 (s, 1H), 10.16 (s, 1H), 8.45 (s, 1H), 8.09 (d, 1H), 7.97 (d, 1H), 7.67 (m, 1H), 7.46 (m, 2H), 7.28 (s, 1H), 5.07 (s, 1H), 4.95 (s, 1H), 2.30 (m, 3H).

Example 26

N-(3-(3-(3-fluoro-2-methoxyphenyl)-1H-pyrrolo[2,3-b]pyridin-5-yl)phenyl) acrylamide (69)

Scheme 26

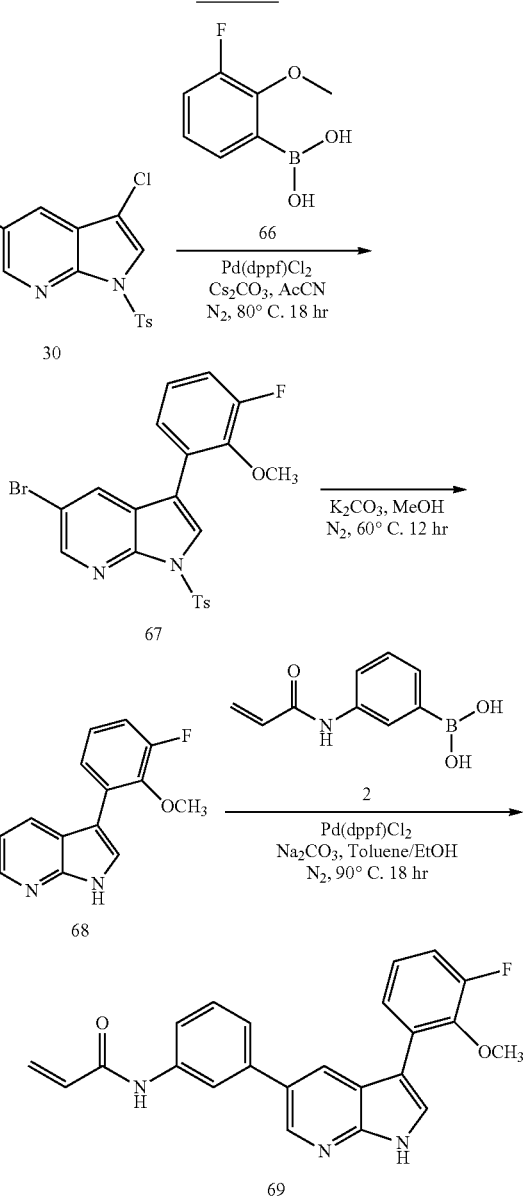

A solution of 30 (200 mg, 0.418 mmol) and 66 (71.01 mg, 0.418 mmol) in acetonitrile was added cesium carbonate (272.36 mg, 0.836 mmol). The reaction was degassed and purged with nitrogen for 10 min. Pd(dppf)Cl$_2$ (17.06 mg, 0.0209 mmol) was added to the reaction. The reaction was degassed and purged with nitrogen for another 10 min. The reaction was heated to 90° C. under sealed condition overnight. The reaction mixture was allowed to cool to rt, and diluted with chloroform. The organic layer was filtered through Celite and concentrated to get the crude, which was purified through flash chromatography by using 100-200 mesh silica gel. The compound was eluted in 3% ethylacetate in hexane as off-white solid 67.

A solution of 67 (150 mg, 0.315 mmol) in methanol (7 mL) and water (3 mL) was added potassium carbonate (86.91 mg, 0.63 mmol). The reaction was heated to 60° C. overnight. The methanol was completely distilled off. Then water was added to the remains of the reaction. The organic phase was extracted with ethyl acetate (50 mL) twice. The organic layer was dried over sodium sulphate and filtered and concentrated to get the crude, which was triturated with hexane to afford the off-white colour solid 68.

A solution of 68 (100 mg, 0.3125 mmol) and 2 (71.01 mg, 0.312 mmol) in toluene and ethanol (4:1 mL) was added $Na_2CO_3$ (68.21 mg, 0.623 mmol). The reaction was degassed and purged with nitrogen for 10 min. Pd(dppf)Cl$_2$ (12.76 mg, 0.0156 mmol) was added to the reaction. The reaction was degassed and purged with nitrogen for another 10 min. The reaction was heated to 90° C. under sealed condition overnight. The reaction mixture was allowed to cool to rt, then diluted with chloroform. The organic layer was filtered through Celite, and concentrated to get the crude, which was purified through flash chromatography by using 100-200 mesh silica gel. The compound was eluted in 2% methanol in dichloromethane as pale yellow colour solid title compound 69. MS-ES+388.0; $^1$H NMR (400 MHz, DMSO-D$_6$) 69: 12.09 (s, 1H), 10.22 (s, 1H), 8.54 (bs, 1H), 8.26 (bs, 1H), 7.95 (d, 1H), 7.83 (d, 1H), 7.71 (m, 1H), 7.43 (m, 2H), 7.20 (m, 2H), 6.44 (m, 1H), 6.25 (m, 1H), 5.75 (m, 1H), 3.66 (s, 3H).

Example 27

N-(3-(3-(3-(N-(tert-butyl)-N-methylsulfamoyl)phenyl)-1H-pyrrolo[2,3-b]pyridin-5-yl)phenyl)acrylamide (73)

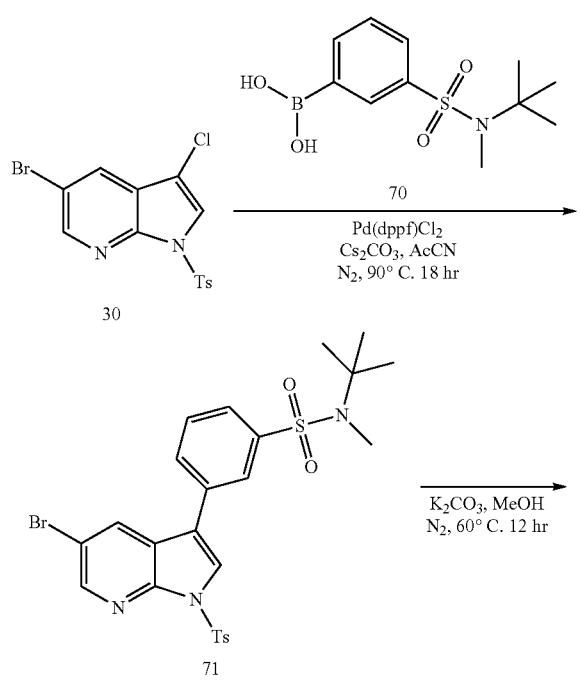

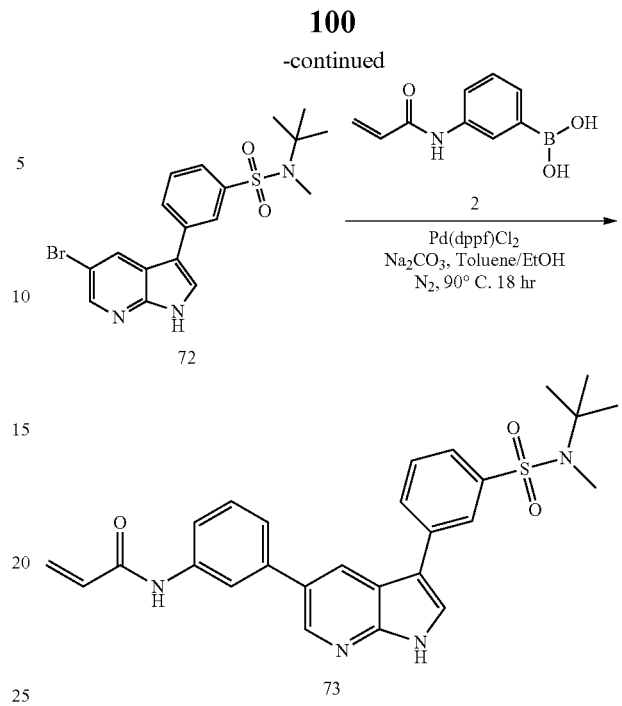

A solution of 30 (150 mg, 0.313 mmol) and 70 (85.70 mg, 0.313 mmol) in acetonitrile was added cesium carbonate (205.36 mg, 0.627 mmol). The reaction was degassed and purged with nitrogen for 10 min. Pd(dppf)Cl$_2$ (12.86 mg, 0.0156 mmol) was added to the reaction. The reaction was degassed and purged with nitrogen for another 10 min. The reaction was heated to 90° C. under sealed condition overnight. The reaction mixture was allowed to cool to rt, then diluted with chloroform. The organic layer was filtered through Celite plug and concentrated to get the crude, which was purified through flash chromatography by using 100-200 mesh silica gel. The compound was eluted in 10% ethyl acetate in hexane as off-white solid 71.

A solution of 71 (100 mg, 0.173 mmol) in methanol (7 mL) and water (3 mL) was added potassium carbonate (47.9 mg, 0.347 mmol). The reaction was heated to 60° C. overnight. The methanol was completely distilled off. Then water was added to the remains of the reaction. The organic phase was extracted with ethyl acetate (50 mL) twice. The organic layer was dried over sodium sulphate and filtered and concentrated to get the crude, which was triturated with hexane to afford the off-white colour solid 72.

A solution of 72 (70 mg, 0.166 mmol) and Compound 64 (27.3 mg, 0.166 mmol) in toluene and ethanol (4:1 mL) was added Na$_2$CO$_3$ (35.02 mg, 0.332 mmol). The reaction was degassed and purged with nitrogen for 10 min. Pd(dppf)Cl$_2$ (6.6 mg, 0.0083 mmol) was added to the reaction. The reaction was degassed and purged with nitrogen for another 10 min. The reaction was heated to 90° C. under sealed condition overnight, allowed to cool to rt, and diluted with chloroform. The organic layer was filtered through Celite bed, concentrated to get the crude, which was purified through flash chromatography by using 100-200 mesh silica gel. The compound was eluted in 2% methanol in dichloromethane as pale yellow colour solid compound 73. MS-ES+487.2, $^1$H NMR (400 MHz, DMSO-D$_6$) 73: 9.12 (bs, 1H), 8.61 (bs, 1H), 8.34 (bs, 1H), 8.10 (bs, 1H), 7.81 (m, 2H), 7.57 (m, 2H), 7.43 (m, 2H), 6.44 (d, 1H), 6.30 (m, 1H), 5.79 (d, 1H), 3.01 (s, 3H), 1.39 (s, 3H).

Example 28

N-(3-(3-(3-(N,N-diethylsulfamoyl)phenyl)-1H-pyrrolo[2,3-b]pyridin-5-yl)-phenyl)acrylamide (77)

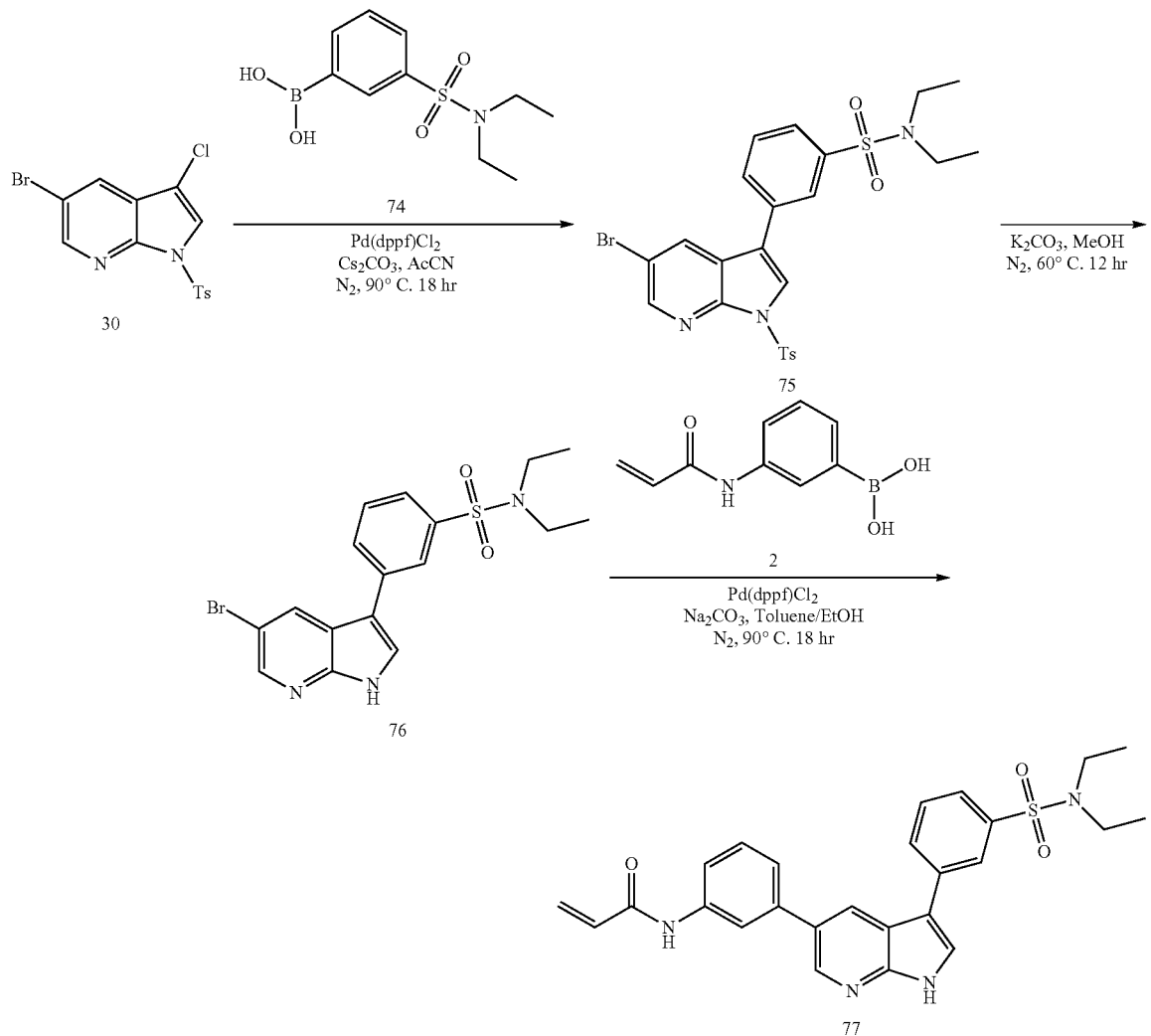

Scheme 28

A solution of 30 (200 mg, 0.418 mmol) and 74 (107.46 mg, 0.418 mmol) in acetonitrile was added cesium carbonate (272.36 mg, 0.836 mmol). The reaction was degassed and purged with nitrogen for 10 min. Pd(dppf)Cl$_2$ (17.06 mg, 0.0209 mmol) was added to the reaction. The reaction was degassed and purged with nitrogen for another 10 min, heated to 90° C. under sealed condition overnight, allowed to cool to rt, and diluted with chloroform. The organic layer was filtered through Celite plug and concentrated to get the crude, which was purified through flash chromatography by using 100-200 mesh silica gel. The compound was eluted in 10% ethyl acetate in hexane as off-white solid 75.

A solution of 75 (150 mg, 0.267 mmol) in methanol (7 mL) and water (3 mL) was added potassium carbonate (73.8 mg, 0.534 mmol). The reaction was heated to 60° C. overnight. The methanol was completely distilled off. Then water was added to the remains of the reaction. The organic phase was extracted with ethyl acetate (50 mL) twice. The organic layer was dried over sodium sulphate and filtered and concentrated to get the crude, which was triturated with hexane to afford the off-white colour solid 76.

A solution of 76 (100 mg, 0.245 mmol) and 2 (40.42 mg, 0.245 mmol) in toluene and ethanol (4:1 mL) was added Na2co3 (53.55 mg, 0.490 mmol). The reaction was degassed and purged with nitrogen for 10 min. Pd(dppf)Cl$_2$ (9.95 mg, 0.0122 mmol) was added to the reaction. The reaction was degassed and purged with nitrogen for another 10 min. The reaction was heated to 90° c. under sealed condition overnight, allowed to cool to rt, and diluted with chloroform. The organic layer was filtered through Celite bed, concentrated to get the crude, which was purified through flash chromatography by using 100-200 mesh silica gel. The compound was eluted in 3% methanol in dichloromethane as pale yellow colour solid compound 77. MS-ES+423.09; 1H NMR (400 MHz, DMSO-D$_6$) 77: 12.23 (s, 1H), 10.26 (s, 1H), 8.56 (d, 1H), 8.35 (s, 1H), 8.04 (m, 4H), 7.68 (m, 3H), 7.45 (m, 2H), 6.43 (m, 2H), 6.30 (m, 1H), 5.77 (m, 1H), 3.24 (m, 4H), 1.06 (m, 6H).

Example 29 ethyl 3-(5-(3-acrylamidophenyl)-1H-pyrrolo[2,3-b]pyridin-3-yl)benzoate (83)

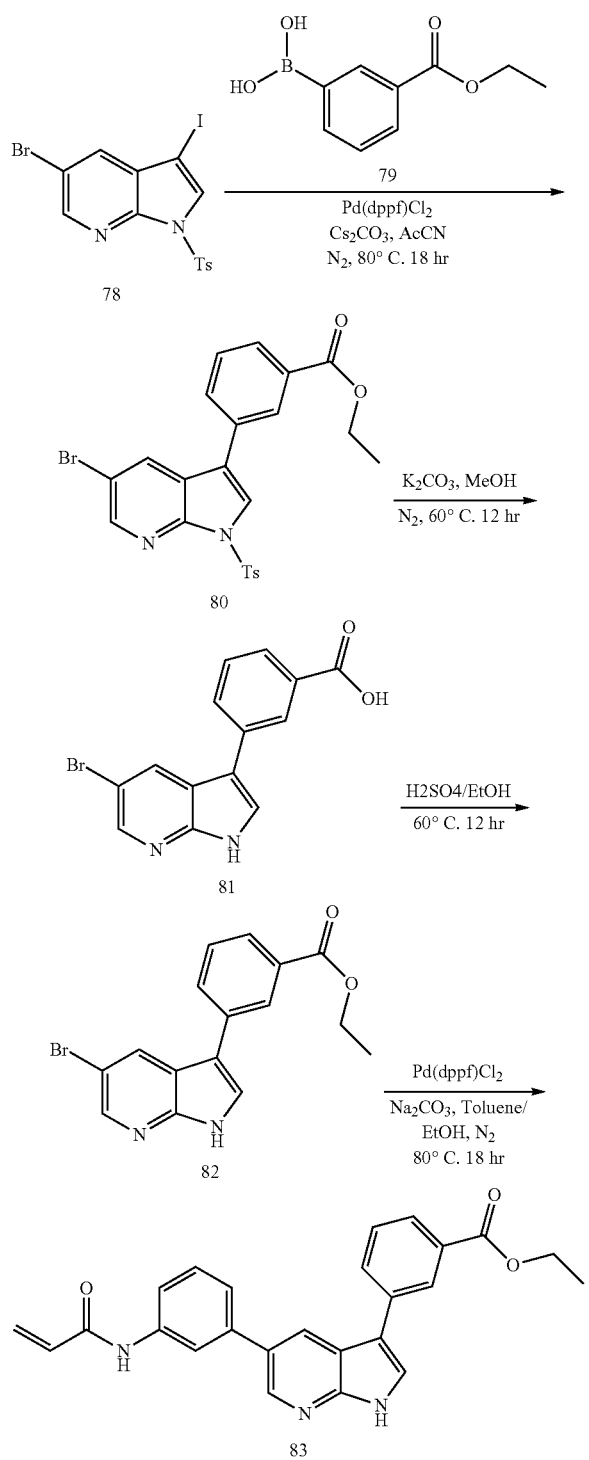

A solution of 78 (200 mg, 0.419 mmol) and 79 (81.3 mg, 0.419 mmol) in acetonitrile was added cesium carbonate (0.838 mmol). The reaction was degassed and purged with nitrogen for 10 min. Pd(dppf)Cl2 (17.0 mg, 0.0209 mmol) was added to the reaction. The reaction was degassed and purged with nitrogen for another 10 min. The reaction was heated to 90° C. under sealed condition overnight, allowed to cool to rt, and diluted with chloroform. The organic layer was filtered through Celite plug and concentrated to get the crude, which was purified through flash chromatography by using 100-200 mesh silica gel. The compound was eluted in 10% ethyl acetate in hexane as off-white solid 80.

A solution of 80 (180 mg, 0.361 mmol) in methanol (7 mL) and water (3 mL) was added potassium carbonate (99.75 mg, 0.722 mmol). The reaction was heated to 60° C. overnight. The methanol was completely distilled off. Then water was added to the remains of the reaction. The organic phase was extracted with ethyl acetate (50 mL) twice. The organic layer was dried over sodium sulphate and filtered and concentrated to get the crude, which was triturated with hexane to afford the off-white colour solid 81.

A solution of 81 (120 mg, 0.379 mmol) was taken in sulfuric acid in ethanol. The reaction mixture was heated to 60° C. overnight, allowed to cool to rt, and diluted with water. The organic phase was extracted with ethyl acetate (50 mL) twice, then dried over sodium sulphate and filtered and concentrated to get the crude, which was triturated with hexane to afford the pale yellow solid 82.

A solution of 82 (100 mg, 0.290 mmol) and 2 (55.5 mg, 0.290 mmol) in toluene and ethanol (4:1 mL) was added Na$_2$CO$_3$ (60.9 mg, 0.580 mmol). The reaction was degassed and purged with nitrogen for 10 min. Pd(dppf)Cl$_2$ (11.8 mg, 0.0145 mmol) was added to the reaction. The reaction was degassed and purged with nitrogen for another 10 min. The reaction was heated to 90° c. under sealed condition overnight. The reaction mixture was allowed to cool to rt, diluted with chloroform. The organic layer was filtered through Celite bed, concentrated to get the crude, which was purified through flash chromatography by using 100-200 mesh silica gel. The compound was eluted in 3% methanol in dichloromethane as pale yellow colour solid compound 83. (Yield: 22 mg, 21%). MS-ES+412.0, $^1$H NMR (400 MHz, DMSO-D6) 83: 12.15 (s, 1H), 10.25 (s, 1H), 8.55 (d, 1H), 8.38 (d, 1H), 8.29 (s, 1H), 8.06 (m, 2H), 8.00 (bs, 1H), 7.85 (d, 1H), 7.71 (m, 1H), 7.62 (t, 1H), 7.45 (m, 2H), 6.47 (m, 1H), 6.30 (m, 1H), 5.77 (m, 1H), 4.35 (m, 2H), 1.35 (m, 3H).

Example 30

N-(3-(3-(3,5-difluoro-2-methoxyphenyl)-1H-pyrrolo[2,3-b]pyridin-5-yl)phenyl) acrylamide (87)

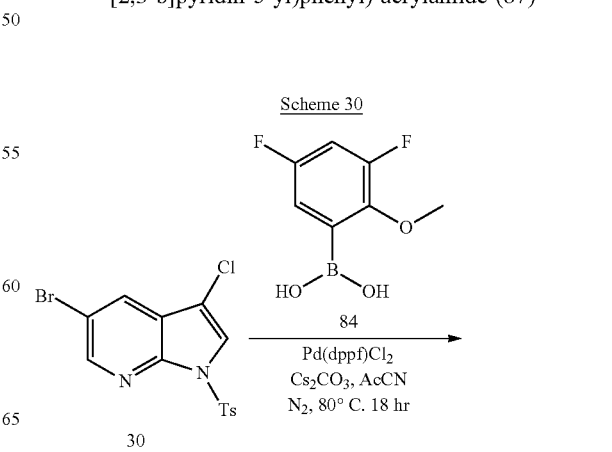

Scheme 30 using 100-200 mesh silica gel. The compound was eluted in 1% methanol in dichloromethane as pale yellow colour solid compound 87. MS-ES+406.1; $^1$H NMR (400 MHz, DMSO-D$_6$) 87: 12.21 (s, 1H), 10.24 (bs, 1H), 8.54 (d, 1H), 8.20 (d, 1H), 7.90 (m, 2H), 7.83 (bs, 1H), 7.43 (d, 2H), 7.22 (m, 2H), 6.42 (m, 1H), 6.25 (d, 1H), 5.75 (d, 1H), 3.60 (s, 3H).

Example 31

N-(2-fluoro-5-(3-methyl-1H-pyrrolo[2,3-b]pyridin-5-yl)phenyl)pent-2-ynamide (89)

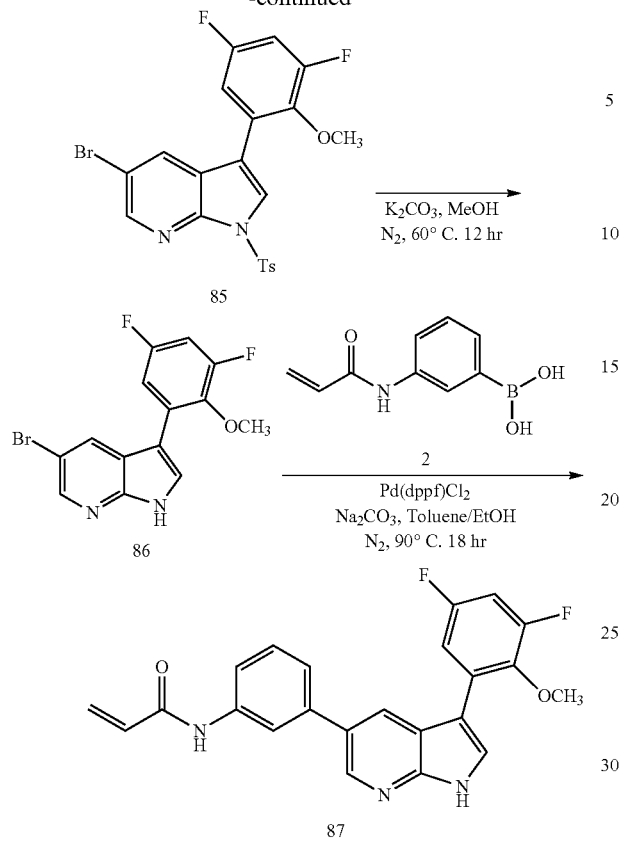

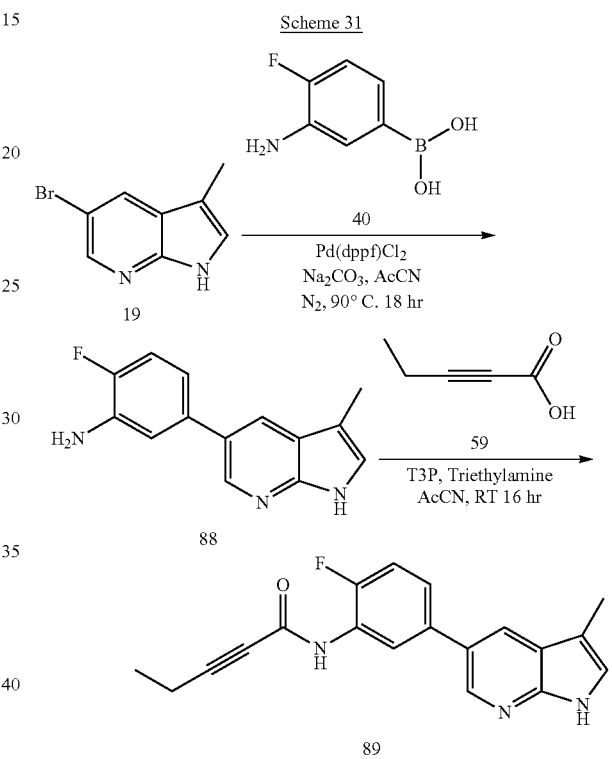

A solution of 30 (200 mg, 0.418 mmol) and 84 (78.60 mg, 0.418 mmol) in acetonitrile was added cesium carbonate (272.36 mg, 0.836 mmol). The reaction was degassed and purged with nitrogen for 10 min. Pd(dppf)Cl$_2$ (17.06 mg, 0.0209 mmol) was added to the reaction. The reaction was degassed and purged with nitrogen for another 10 min, heated to 90° C. under sealed condition overnight, then allowed to cool to rt, and diluted with chloroform. The organic layer was filtered through Celite plug and concentrated to get the crude, which was purified through flash chromatography by using 100-200 mesh silica gel. The compound was eluted in 5% ethyl acetate in hexane as off-white solid compound 85.

A solution of 85 (150 mg, 0.304 mmol) in methanol (7 mL) and water (3 mL) was added potassium carbonate (83.9 mg, 0.608 mmol). The reaction was heated to 60° C. overnight. The methanol was completely distilled off. Then water was added to the remains of the reaction. The organic phase was extracted with ethyl acetate (50 mL) twice. The organic layer was dried over sodium sulphate and filtered and concentrated to get the crude, which was triturated with hexane to afford the off-white colour solid compound 86.

A solution of 86 (80 mg, 0.236 mmol) and 2 (38.9 mg, 0.236 mmol) in toluene and ethanol (4:1 mL) was added Na$_2$CO$_3$ (51.79 mg, 0.473 mmol). The reaction was degassed and purged with nitrogen for 10 min. Pd(dppf)Cl$_2$ (9.6 mg, 0.0118) was added to the reaction. The reaction was degassed and purged with nitrogen for another 10 min, heated to 90° C. under sealed condition overnight, allowed to cool to rt, and diluted with chloroform. The organic layer was filtered through Celite bed, concentrated to get the crude, which was purified through flash chromatography by A solution of 19 (205.4 mg, 0.909 mmol) and 40 (150 mg, 0.909 mmol) in toluene/ethanol (4 mL:1 mL) was added sodium carbonate (190.8 mg, 1.818 mmol). The reaction was degassed and purged with nitrogen for 10 min. Pd(dppf)Cl2 (37.1 mg, 0.0454 mmol) was added to the reaction, which was degassed and purged with nitrogen for another 10 min, heated to 90° C. under sealed condition overnight, then allowed to cool to rt, and diluted with chloroform. The organic layer was filtered through Celite plug and concentrated to get the crude, which was purified through flash chromatography by using 100-200 mesh silica gel. The compound was eluted in 50% ethyl acetate in hexane as off-white solid 88.

A solution of 88 (50 mg, 0.207 mmol) and 59 (20.03 mg, 0.207 mmol) in acetonitrile (4 mL) was added triethylamine (41.9 mg, 0.414 mmol). T$_3$P (131.7 mg, 0.414 mmol) was added to the reaction mixture. The reaction was stirred overnight at rt and diluted with ethyl acetate (25 mL). The organic layer was washed with water (25 mL) followed by brine solution (25 mL). The organic layer was dried over sodium sulphate, filtered and concentrated to get the crude, which was purified through flash chromatography by using 100-200 mesh silica gel. The compound was eluted at 1.5% methanol in chloroform as pale yellow colour solid compound 89. MS-ES+321.9; 1H NMR (400 MHz, DMSO-D6) 89: 8.58 (s, 1H), 8.44 (d, 2H), 8.01 (d, 1H), 7.64 (bs, 1H), 7.28 (m, 1H), 7.18 (m, 1H), 7.09 (bs, 1H), 2.43 (m, 2H), 2.35 (s, 3H), 1.25 (m, 2H).

Example 32

N-(3-(3-(3-(N-(tert-butyl)-N-methylsulfamoyl)phenyl)-1H-pyrrolo[2,3-b]pyridin-5-yl)phenyl)pent-2-ynamide (92)

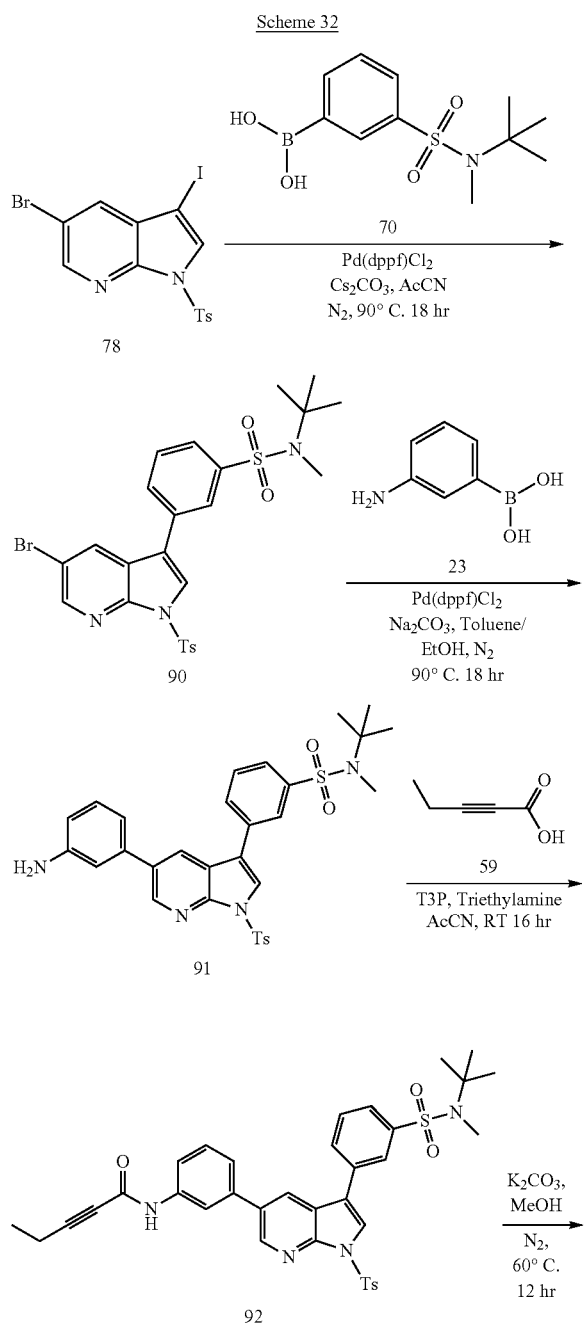

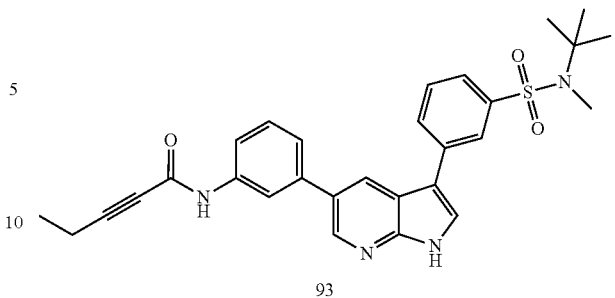

A solution of 78 (150 mg, 0.313 mmol) and 70 (85.70 mg, 0.313 mmol) in acetonitrile was added cesium carbonate (205.36 mg, 0.627 mmol). The reaction was degassed and purged with nitrogen for 10 min. Pd(dppf)Cl$_2$ (12.86 mg, 0.0156 mmol) was added to the reaction. The reaction was degassed and purged with nitrogen for another 10 min, heated to 90° C. under sealed condition overnight, allowed to cool to rt, and diluted with chloroform. The organic layer was filtered through Celite plug and concentrated to get the crude, which was purified through flash chromatography by using 100-200 mesh silica gel. The compound was eluted in 10% ethyl acetate in hexane as off-white solid 90.

A solution of 90 (150 mg, 0.260 mmol) and 23 (44.4 mg, 0.260 mmol) in toluene and ethanol (4:1 mL) was added Na2CO3 (54.6 mg, 0.520 mmol). The reaction was degassed and purged with nitrogen for 10 min. Pd(dppf)Cl2 (10.6 mg, 0.013 mmol) was added to the reaction. The reaction was degassed and purged with nitrogen for another 10 min, heated to 90° C. under sealed condition overnight, allowed to cool to rt, and diluted with chloroform. The organic layer was filtered through Celite bed, concentrated to get the crude, which was purified through flash chromatography by using 100-200 mesh silica gel. The compound was eluted in 3% methanol in dichloromethane as pale yellow colour solid 91.

A solution of 91 (70 mg, 0.119 mmol) and 59 (13.9 mg, 0.142 mmol) in acetonitrile (4 mL) was added triethylamine (24.9 mg, 0.238 mmol). T$_3$P (78.0 mg, 0.238 mmol) was added to the reaction mixture. The reaction was stirred overnight at rt, then diluted with ethyl acetate (25 mL). The organic layer was washed with water (25 mL) followed by brine solution (25 mL). The organic layer was dried over sodium sulphate, filtered and concentrated to get the crude, which was purified through flash chromatography by using 100-200 mesh silica gel. The compound was eluted at 1.5% methanol in chloroform as pale yellow colour solid 92.

A solution of 92 (60 mg, 0.089 mmol) in methanol (7 mL) and water (3 mL) was added potassium carbonate (24.5 mg, 0.178 mmol). The reaction was heated to 60° C. overnight. The methanol was completely distilled off. Then water was added to the remains of the reaction. The organic phase was extracted with ethyl acetate (50 mL) twice. The organic layer was dried over sodium sulphate and filtered and concentrated to get the crude, which was triturated with hexane to afford the off-white colour solid 93. MS-ES+515.1; $^1$H NMR (400 MHz, DMSO-D$_6$): 9.26 (bs, 1H), 8.64 (bs, 1H), 8.33 (bs, 1H), 8.11 (bs, 1H), 7.81 (d, 1H), 7.74 (m, 2H), 7.57 (m, 4H), 7.40 (m, 2H), 3.01 (s, 3H), 2.37 (m, 2H), 1.39 (s, 9H), 1.22 (m, 3H).

Example 33

N-(3-(7-(3-(N-(tert-butyl)-N-methylsulfamoyl)phenyl)-5H-pyrrolo[2,3-b]pyrazine-2-yl)phenyl)acrylamide (97)

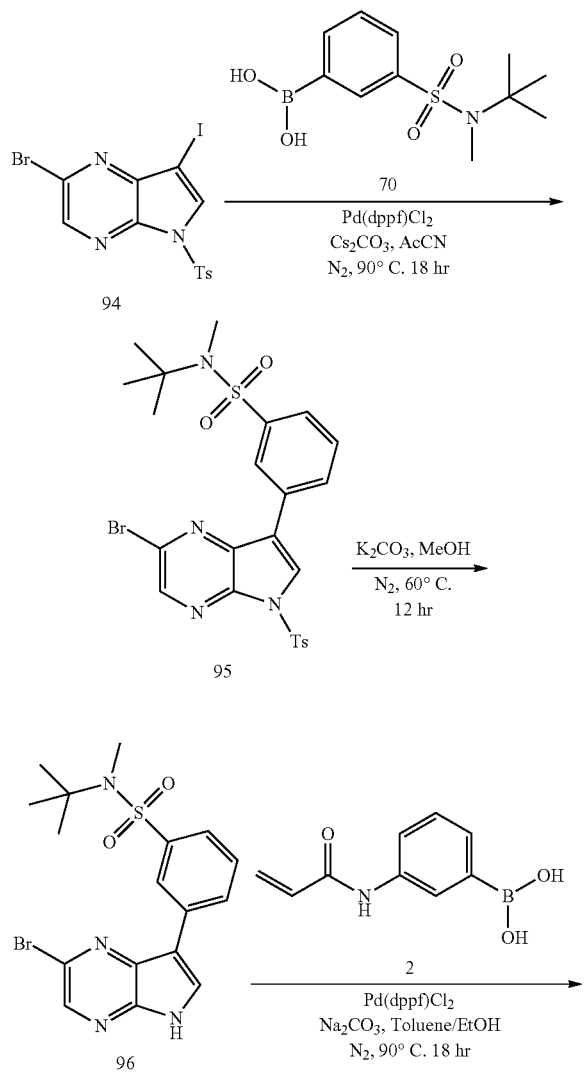

A solution of 94 (200 mg, 0.419 mmol) and 70 (113.5 mg, 0.419 mmol) in acetonitrile was added cesium carbonate (274.8 mg, 0.838 mmol). The reaction was degassed and purged with nitrogen for 10 min. Pd(dppf)Cl2 (17.1 mg, 0.020 mmol) was added to the reaction. The reaction was degassed and purged with nitrogen for another 10 min, heated to 90° C. under sealed condition overnight, allowed to cool to rt, and diluted with chloroform. The organic layer was filtered through Celite plug and concentrated to get the crude, which was purified through flash chromatography by using 100-200 mesh silica gel. The compound was eluted in 10% ethyl acetate in hexane as off-white solid 95.

A solution of 95 (140 mg, 0.243 mmol) in methanol (7 mL) and water (3 mL) was added potassium carbonate (67.068 mg, 0.486 mmol). The reaction was heated to 60° C. overnight. The methanol was completely distilled off. Then water was added to the remains of the reaction. The organic phase was extracted with ethyl acetate (50 mL) twice. The organic layer was dried over sodium sulphate and filtered and concentrated to get the crude, which was triturated with hexane to afford the off-white colour solid 96.

A solution of 96 (80 mg, 0.189 mmol) and 2 (36.2 mg, 0.189 mmol) in toluene and ethanol (4:1 mL) was added $Na_2CO_3$ (39.6 mg, 0.378 mmol). The reaction was degassed and purged with nitrogen for 10 min. Pd(dppf)Cl$_2$ (7.7 mg, 0.009 mmol) was added to the reaction. The reaction was degassed and purged with nitrogen for another 10 min. The reaction was heated to 90° C. under sealed condition overnight, allowed to cool to rt, and diluted with chloroform. The organic layer was filtered through Celite bed concentrated to get the crude, which was purified through flash chromatography by using 100-200 mesh silica gel. The compound was eluted in 3% methanol in dichloromethane as pale yellow colour solid 97. MS-ES+488.2; $^1$H NMR (400 MHz, DMSO-D$_6$) 97: 12.54 (bs, 1H), 10.27 (bs, 1H), 8.90 (bs, 1H), 8.81 (bs, 1H), 8.64 (bs, 1H), 8.44 (m, 1H), 8.38 (bs, 1H), 7.89 (d, 1H), 7.75 (d, 1H), 7.65 (d, 2H), 7.50 (t, 1H), 6.47 (m, 1H), 6.28 (dd, 1H), 5.78 (dd, 1H), 2.98 (s, 3H), 1.29 (s, 1H).

Example 34

N-(3-(3-(3-(N,N-dimethylsulfamoyl)phenyl)-1H-pyrrolo[2,3-b]pyridin-5-yl)phenyl)acrylamide (97)

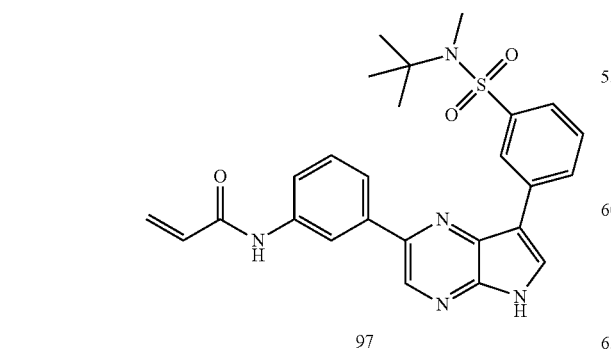

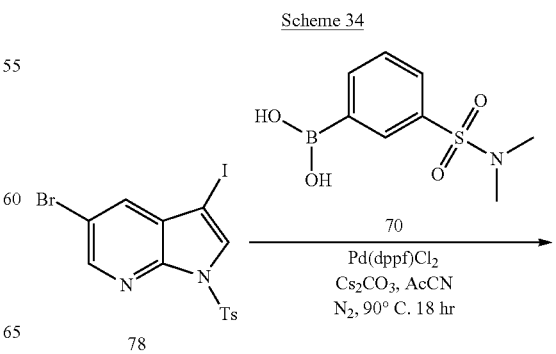

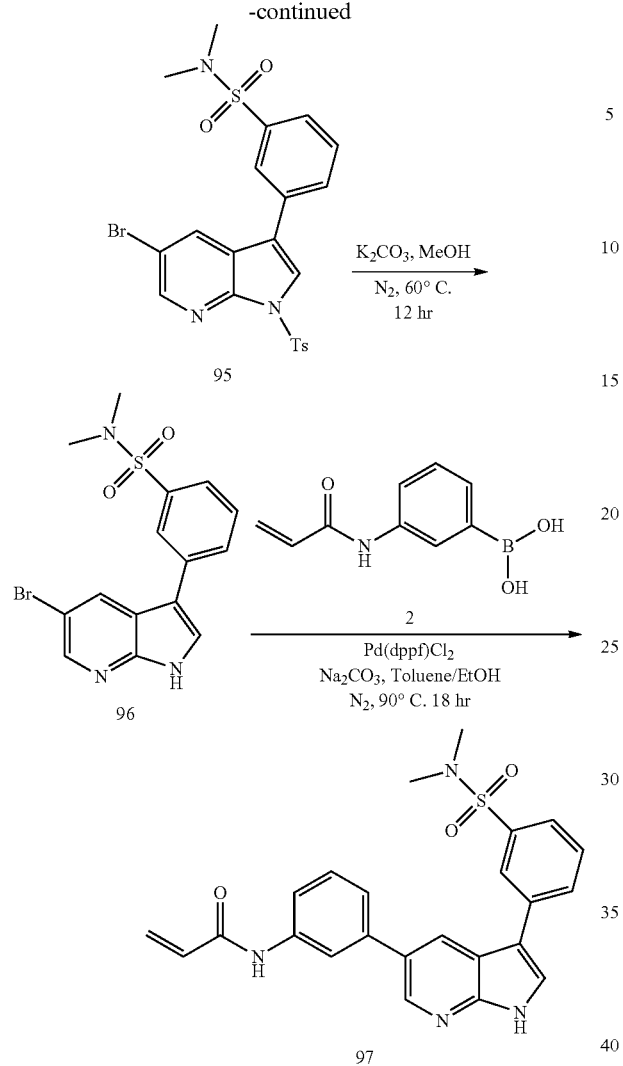

A solution of 78 (200 mg, 0.419 mmol) and 70 (96.05 mg, 0.419 mmol) in acetonitrile was added cesium carbonate (274.8 mg, 0.838 mmol). The reaction was degassed and purged with nitrogen for 10 min. Pd(dppf)Cl$_2$ (17.1 mg, 0.0201 mmol) was added to the reaction. The reaction was degassed and purged with nitrogen for another 10 min. The reaction was heated to 90° C. under sealed condition overnight, allowed to cool to rt, and diluted with chloroform. The organic layer was filtered through Celite plug and concentrated to get the crude, which was purified through flash chromatography by using 100-200 mesh silica gel. The compound was eluted in 10% ethyl acetate in hexane as off-white solid 95.

A solution of 95 (180 mg, 0.337 mmol) in methanol (7 mL) and water (3 mL) was added potassium carbonate (93.0 mg, 0.674 mmol). The reaction was heated to 60° C. overnight. The methanol was completely distilled off. Then water was added to the remains of the reaction. The organic phase was extracted with ethyl acetate (50 mL) twice. The organic layer was dried over sodium sulphate and filtered and concentrated to get the crude, which was triturated with hexane to afford the off-white colour solid 96.

A solution of 96 (100 mg, 0.263 mmol) and 2 (50.3 mg, 0.263 mmol) in toluene and ethanol (4:1 mL) was added Na$_2$CO$_3$ (55.2 mg, 0.526 mmol). The reaction was degassed and purged with nitrogen for 10 min. Pd(dppf)Cl$_2$ (10.7 mg, 0.0132 mmol) was added to the reaction. The reaction was degassed and purged with nitrogen for another 10 min. The reaction was heated to 90° C. under sealed condition overnight, allowed to cool to rt, and diluted with chloroform. The organic layer was filtered through Celite bed, concentrated to get the crude, which was purified through flash chromatography by using 100-200 mesh silica gel. The compound was eluted in 3% methanol in dichloromethane as pale yellow colour solid 97. MS-ES+445.01; $^1$H NMR (400 MHz, DMSO-D$_6$) 97: 12.24 (s, 1H), 10.26 (s, 1H), 8.56 (d, 1H), 8.37 (d, 1H), 8.14 (m, 2H), 8.00 (m, 2H), 7.69 (m, 2H), 7.62 (d, 1H), 7.45 (d, 2H), 6.46 (m, 1H), 6.26 (dd, 1H), 5.77 (dd, 1H), 2.68 (s, 6H).

Example 35

N-(3-(3-(3-(methylsulfonyl)phenyl)-1H-pyrrolo[2,3-b]pyridin-5-yl)phenyl) acrylamide (101)

Scheme 35

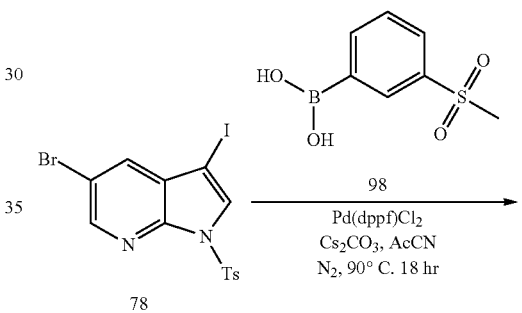

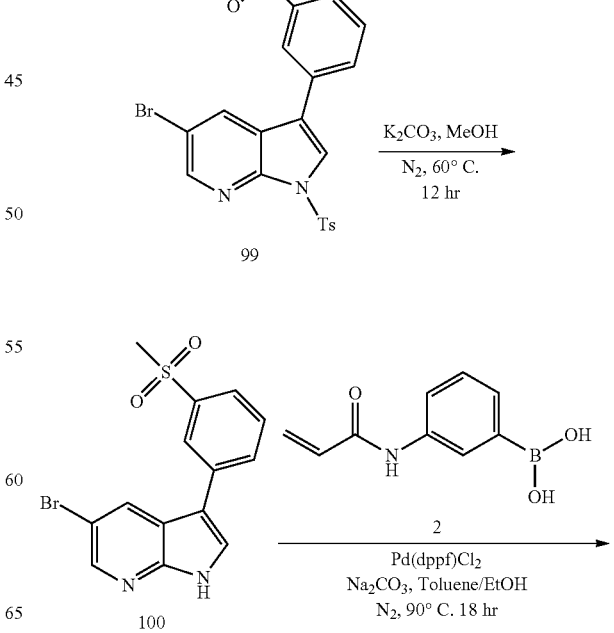

113

-continued

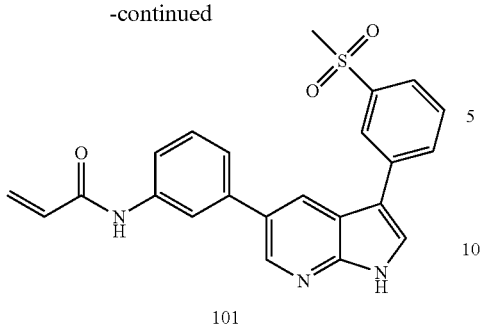

101

A solution of 78 (200 mg, 0.419 mmol) and 98 (83.8 mg, 0.419 mmol) in acetonitrile (10 mL) was added cesium carbonate (275.0 mg, 0.8396 mmol). The reaction was degassed and purged with nitrogen for 10 min. Pd(dppf)Cl$_2$ (17.1 mg, 0.0209 mmol) was added to the reaction. The reaction was degassed and purged with nitrogen for another 10 min, heated to 90° c. under sealed condition overnight, allowed to cool to rt, and diluted with chloroform. The organic layer was filtered through Celite plug and concentrated to get the crude, which was purified through flash chromatography by using 100-200 mesh silica gel. The compound was eluted in 5% ethyl acetate in hexane as off-white solid 99.

A solution of 99 (190 mg, 0.3759 mmol) in methanol (7 mL) and water (3 mL) was added potassium carbonate (155.8 mg, 1.127 mmol). The reaction was heated to 60° C. overnight. The methanol was completely distilled off. Then water was added to the remains of the reaction. The organic phase was extracted with ethyl acetate (50 mL) twice. The organic layer was dried over sodium sulphate and filtered and concentrated to get the crud. The crude was triturated with hexane to afford the off-white colour solid 100.

A solution of 100 (100 mg, 0.2849 mmol) and 2 (54.4 mg, 0.2849 mmol) in toluene and ethanol (4:1 ml) was added Na$_2$CO$_3$ (60.3 mg, 0.5698 mmol). The reaction was degassed and purged with nitrogen for 10 min. Pd(dppf)Cl$_2$ (11.6 mg, 0.01424 mmol) was added to the reaction. The reaction was degassed and purged with nitrogen for another 10 min. The reaction was heated to 90° C. under sealed condition overnight, allowed to cool to rt, and diluted with chloroform. The organic layer was filtered through Celite bed, concentrated to get the crude, which was purified through flash chromatography by using 100-200 mesh silica gel. The compound was eluted in 3% methanol in dichloromethane as pale yellow colour solid 101. MS-ES+417.1; $^1$H NMR (400 MHz, DMSO-D$_6$): 12.26 (s, 1H), 10.25 (s, 1H), 8.54 (s, 1H), 8.40 (s, 1H), 8.21 (s, 1H), 8.14 (d, 2H), 7.98 (d, 1H), 7.78 (m, 1H), 7.70 (m, 2H), 7.46 (m, 2H), 6.44 (m, 1H), 6.25 (dd, 1H), 5.75 (dd, 1H).

114

Example 36

N-(3-(3-(3-(ethylsulfonyl)phenyl)-1H-pyrrolo[2,3-b]pyridin-5-yl)phenyl) acrylamide (105)

Scheme 36

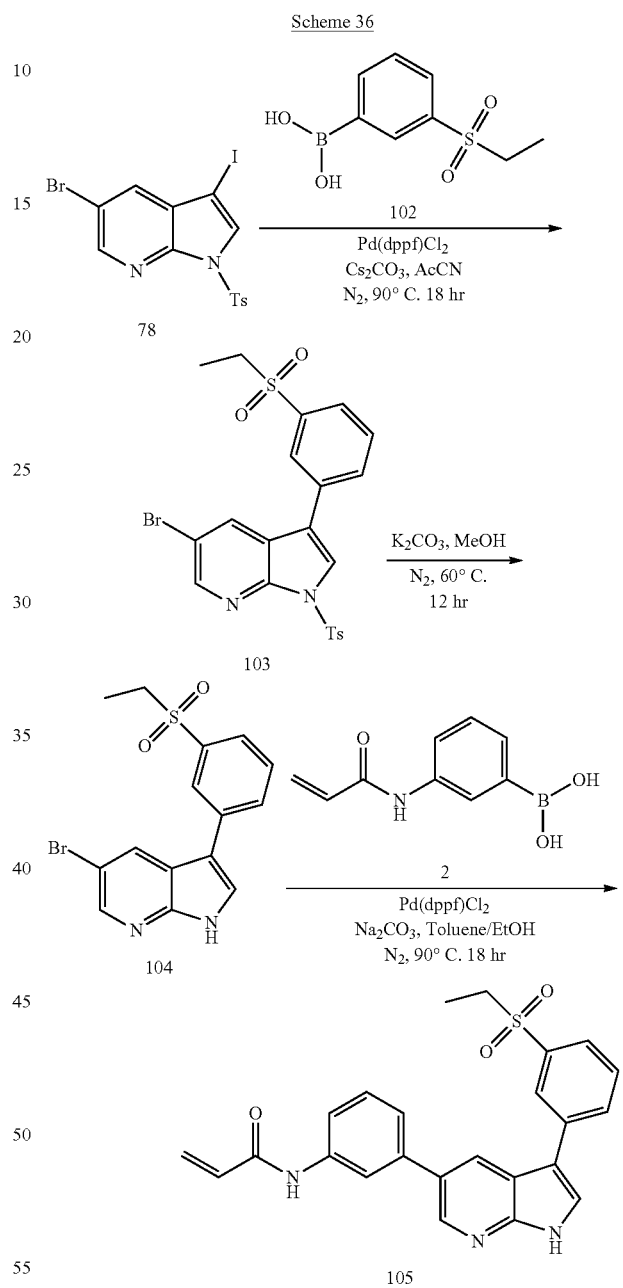

A solution of 78 (200 mg, 0.4192 mmol) and 102 (89.7 mg, 0.4192 mmol) in acetonitrile was added cesium carbonate (274, 9 mg, 0.8384 mmol). The reaction was degassed and purged with nitrogen for 10 min. Pd(dppf)Cl$_2$ (17.1 mg, 0.0209 mmol) was added to the reaction. The reaction was degassed and purged with nitrogen for another 10 min, heated to 90° C. under sealed condition overnight, allowed to cool to rt, and diluted with chloroform. The organic layer was filtered through Celite plug and concentrated to get the crude, which was purified through flash chromatography by using 100-200 mesh silica gel. The compound was eluted in 5% ethyl acetate in hexane as off-white solid 103.

A solution of 103 (170 mg, 0.3273 mmol) in methanol (7 mL) and water (3 mL) was added potassium carbonate (135.7 mg, 0.9819 mmol). The reaction was heated to 60° C. overnight. The methanol was completely distilled off. Then water was added to the remains of the reaction. The organic phase was extracted with ethyl acetate (50 mL) twice. The organic layer was dried over sodium sulphate and filtered and concentrated to get the crude, which was triturated with hexane to afford the off-white colour solid 104.

A solution of 104 (100 mg, 0.2737 mmol) and 2 (52.2 mg, 0.2737 mmol) in toluene and ethanol (4:1 mL) was added $Na_2CO_3$ (58.0 mg, 0.5474 mmol). The reaction was degassed and purged with nitrogen for 10 min. $Pd(dppf)Cl_2$ (11.1 mg, 0.0136 mmol) was added to the reaction. The reaction was degassed and purged with nitrogen for another 10 min, heated to 90° C. under sealed condition overnight, allowed to cool to rt, and diluted with chloroform. The organic layer was filtered through Celite bed, concentrated to get the crude, which was purified through flash chromatography by using 100-200 mesh silica gel. The compound was eluted in 3% methanol in dichloromethane as pale yellow colour solid 105. MS-ES+432.0; $^1$H NMR (400 MHz, DMSO-$D_6$): 12.22 (s, 1H), 10.25 (s, 1H), 8.54 (d, 1H), 8.39 (d, 1H), 8.14 (m, 3H), 7.98 (s, 1H), 7.73 (m, 3H), 7.44 (d, 2H), 6.44 (m, 1H), 6.25 (dd, 1H), 5.75 (m, 1H), 3.35 (m, 2H), 1.14 (m 3H).

Example 37

N-(3-(3-(3,5-difluoro-2-methoxyphenyl)-1H-pyrrolo[2,3-b]pyridin-5-yl)phenyl) pent-2-ynamide (108)

Scheme 37

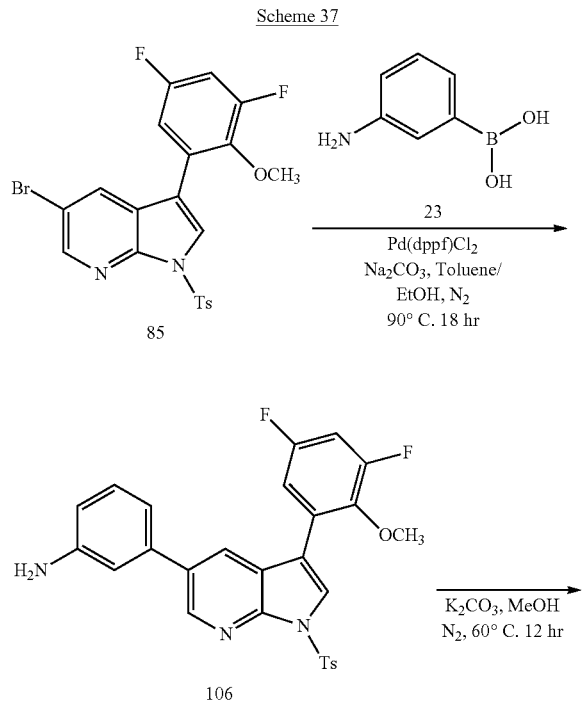

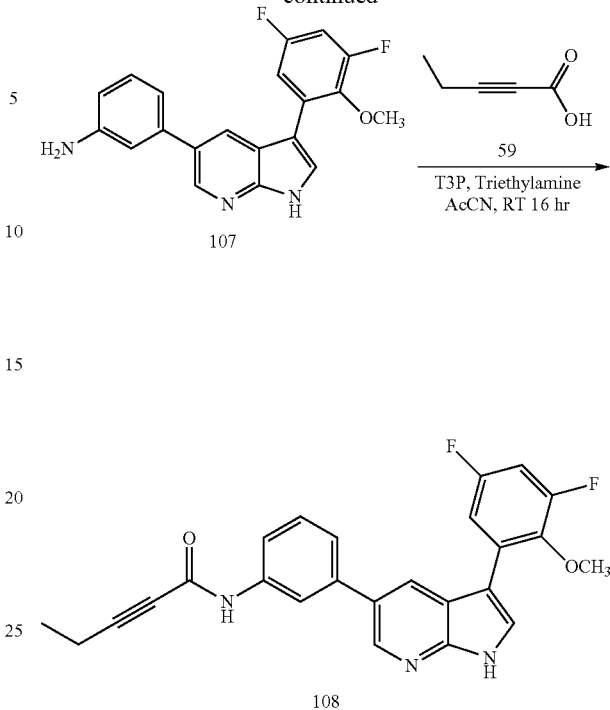

A solution of 85 (400 mg, 0.813 mmol) and 23 (140.6 mg, 0813 mmol) in acetonitrile was added cesium carbonate (274.9 mg, 0.8384 mmol). The reaction was degassed and purged with nitrogen for 10 min. $Pd(dppf)Cl_2$ (33.1 mg, 0.040 mmol) was added to the reaction. The reaction was degassed and purged with nitrogen for another 10 min, heated to 90° C. under sealed condition overnight, allowed to cool to rt, and diluted with chloroform. The organic layer was filtered through Celite plug and concentrated to get the crude, which was purified through flash chromatography by using 100-200 mesh silica gel. The compound was eluted in 5% ethyl acetate in hexane as off-white solid 106.

A solution of 106 (250 mg, 0.594 mmol) in methanol (7 mL) and water (3 mL) was added potassium carbonate (162.84 mg, 1.18 mmol). The reaction was heated to 60° C. overnight. The methanol was completely distilled off. Then water was added to the remains of the reaction. The organic phase was extracted with ethyl acetate (50 mL) twice. The organic layer was dried over sodium sulphate and filtered and concentrated to get the crude, which was titrated with hexane to afford the off-white colour solid 107.

A solution of 107 (100 mg, 0.284 mmol) and 59 (26.7 mg, 0.284 mmol) in acetonitrile (4 mL) was added triethylamine (57 mg, 0.568 mmol). $T_3P$ (186.3 mg, 0.568 mmol) was added to the reaction mixture. The reaction was stirred overnight at rt, and diluted with ethyl acetate (25 mL). The organic layer was washed with water (25 mL) followed by brine solution (25 mL). The organic layer was dried over sodium sulphate, filtered and concentrated to get the crude, which was purified through flash chromatography by using 100-200 mesh silica gel. The compound was eluted at 1.5% methanol in chloroform as pale yellow colour solid 108. MS-ES+432.0; $^1$H NMR (400 MHz, DMSO-$D_6$): 12.12 (s, 1H), 10.66 (s, 1H), 8.51 (d, 1H), 8.20 (d, 1H), 7.87 (d, 2H), 7.62 (d, 1H), 7.39 (m 2H), 7.24 (m, 2H), 3.60 (s, 3H), 3.28 (m, 2H), 2.41 (m, 2H), 1.21 (m, 3H), 1.14 (m, 3H).

Example 38

N-(5-(3-(3,5-difluoro-2-methoxyphenyl)-1H-pyrrolo[2,3-b]pyridin-5-yl)-2-fluorophenyl)acrylamide (111)

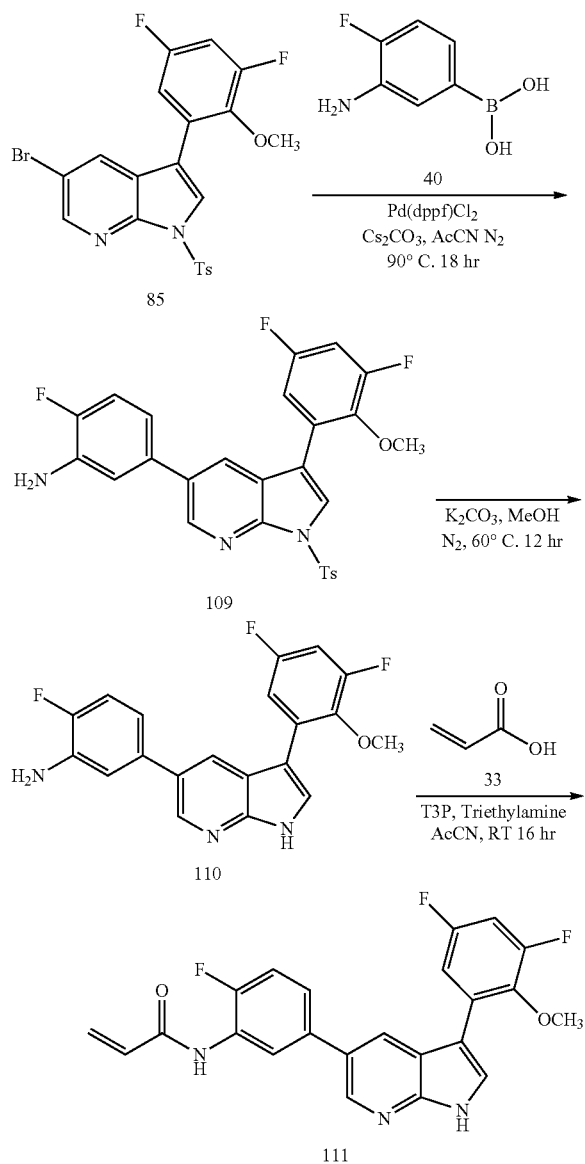

A solution of 85 (150 mg, 0.306 mmol) and 40 (47 mg, 0.306 mmol) in acetonitrile was added cesium carbonate (200 mg, 0.612 mmol). The reaction was degassed and purged with nitrogen for 10 min. Pd(dppf)Cl$_2$ (12 mg, 0.0153 mmol) was added to the reaction. The reaction was degassed and purged with nitrogen for another 10 min, heated to 90° C. under sealed condition overnight, allowed to cool to rt, then diluted with chloroform. The organic layer was filtered through Celite plug and concentrated to get the crude, which was purified through flash chromatography by using 100-200 mesh silica gel. The compound was eluted in 5% ethyl acetate in hexane as off-white solid 109.

A solution of 109 (120 mg, 0.229 mmol) in methanol (7 mL) and water (3 mL) was added potassium carbonate (62 mg, 0.458 mmol). The reaction was heated to 60° C. overnight. The methanol was completely distilled off. Then water was added to the remains of the reaction. The organic phase was extracted with ethyl acetate (50 mL) twice. The organic layer was dried over sodium sulphate and filtered and concentrated to get the crude, which was triturated with hexane to afford the off-white colour solid 110.

A solution of 110 (80 mg, 0.216 mmol) and acrylic acid 33 (15.3 mg, 0.216 mmol) in acetonitrile (4 mL) was added triethylamine (45.79 mg, 0.432 mmol). T$_3$P (141.6 mg, 0.432 mmol) was added to the reaction mixture. The reaction was stirred overnight at rt, and diluted with ethyl acetate (25 mL). The organic layer was washed with water (25 mL) followed by brine solution (25 mL). The organic layer was dried over sodium sulphate, filtered and concentrated to get the crude, which was purified through flash chromatography by using 100-200 mesh silica gel. The compound was eluted at 1.5% methanol in chloroform as pale yellow colour solid 111. MS-ES+424.0; $^1$H NMR (400 MHz, DMSO-D$_6$): 12.22 (s, 1H), 10.07 (s, 1H), 8.52 (d, 1H), 8.31 (d, 1H), 8.22 (d, 1H), 7.91 (d, 1H), 7.53 (m, 1H), 7.36 (m, 1H), 7.24 (m, 1H), 6.63 (m, 1H), 6.27 (dd, 1H), 5.78 (dd, 1H), 3.61 (s, 3H).

Example 39

N-(5-(3-(3,5-difluoro-2-methoxyphenyl)-1H-pyrrolo[2,3-b]pyridin-5-yl)-2,4-difluorophenyl)acrylamide (115)

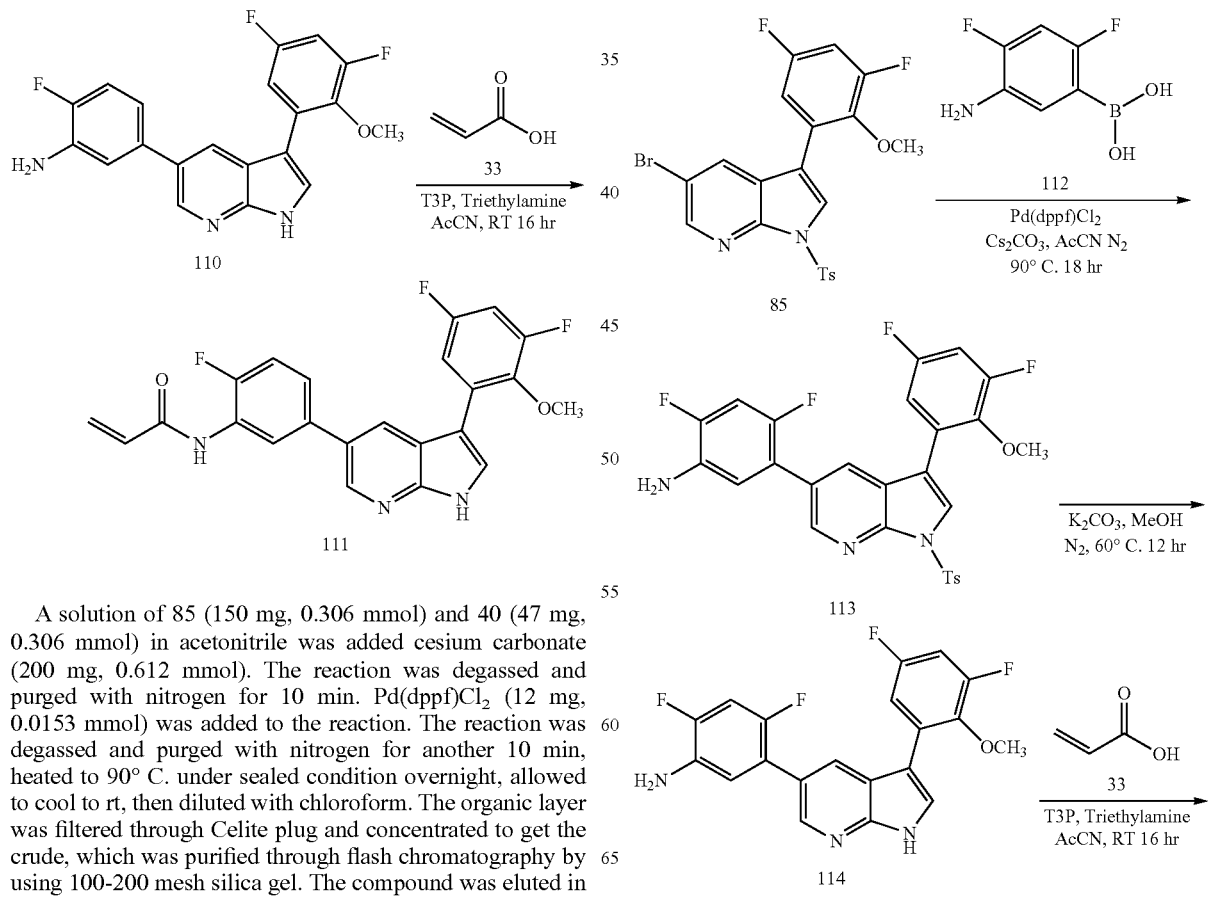

119
-continued

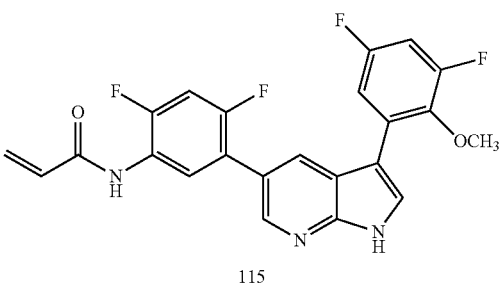

115

A solution of 85 (150 mg, 0.306 mmol) and 112 (64 mg, 0.306 mmol) in acetonitrile was added cesium carbonate (200 mg, 0.612 mmol). The reaction was degassed and purged with nitrogen for 10 min. Pd(dppf)Cl$_2$ (12 mg, 0.0153 mmol) was added to the reaction. The reaction was degassed and purged with nitrogen for another 10 min, heated to 90° C. under sealed condition overnight, allowed to cool to rt, and diluted with chloroform. The organic layer was filtered through Celite plug and concentrated to get the crude, which was purified through flash chromatography by using 100-200 mesh silica gel. The compound was eluted in 5% ethyl acetate in hexane as off-white solid 113.

A solution of 113 (130 mg, 0.240 mmol) in methanol (7 mL) and water (3 mL) was added potassium carbonate (65 mg, 0.48 mmol). The reaction was heated to 60° C. overnight. The methanol was completely distilled off. Then water was added to the remains of the reaction. The organic phase was extracted with ethyl acetate (50 mL) twice. The organic layer was dried over sodium sulphate and filtered and concentrated to get the crude, which was triturated with hexane to afford the off white colour solid 114.

A solution of 114 (80 mg, 0.2066 mmol) and acrylic acid 33 (20 mg, 0.289 mmol) in acetonitrile (4 mL) was added triethylamine (41 mg, 0.4132 mmol). T$_3$P (131 mg, 0.4132 mmol) was added to the reaction mixture. The reaction was stirred overnight at rt, and diluted with ethyl acetate (25 mL). The organic layer was washed with water (25 mL) followed by brine solution (25 mL). The organic layer was dried over sodium sulphate, filtered and concentrated to get the crude, which was purified through flash chromatography by using 100-200 mesh silica gel. The compound was eluted at 1.5% methanol in chloroform as pale yellow colour solid 115. MS-ES+442.0; 1H NMR (400 MHz, DMSO-D$_6$): 12.28 (s, 1H), 10.07 (s, 1H), 8.41 (s, 1H), 8.20 (s, 1H), 8.14 (t, 1H), 7.94 (d, 1H), 7.48 (t, 1H), 7.26 (m, 2H), 6.58 (m, 1H), 6.29 (dd, 1H), 5.77 (dd, 1H), 3.61 (s, 3H).

120

Example 40

N-(3-(3-(3,5-difluoro-2-methoxyphenyl)-1H-pyrrolo[2,3-b]pyridin-5-yl)-4-fluorophenyl)acrylamide (119)

Scheme 40

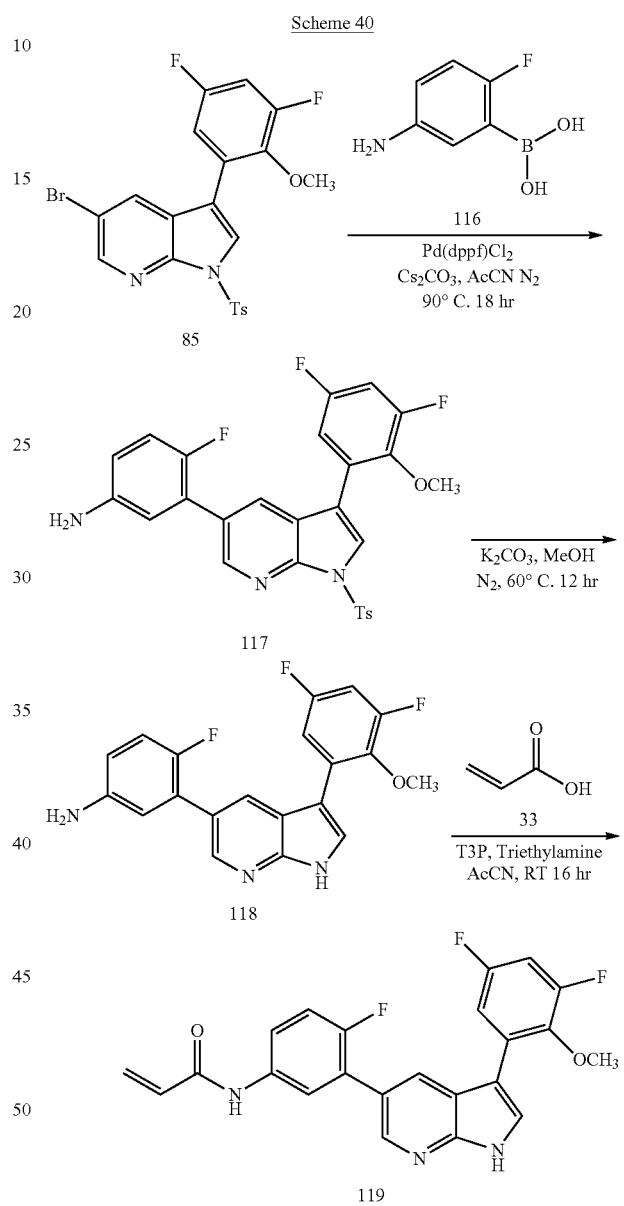

A solution of 85 (150 mg, 0.3060 mmol) and 116 (0.306 mmol) in acetonitrile was added cesium carbonate (200 mg, 0.612 mmol). The reaction was degassed and purged with nitrogen for 10 min. Pd(dppf)Cl$_2$ (12 mg, 0.0153 mmol) was added to the reaction. The reaction was degassed and purged with nitrogen for another 10 min, heated to 90° C. under sealed condition overnight, allowed to cool to rt, and diluted with chloroform. The organic layer was filtered through Celite plug and concentrated to get the crude, which was purified through flash chromatography by using 100-200 mesh silica gel. The compound was eluted in 5% ethyl acetate in hexane as off-white solid 117.

A solution of 117 (125 mg, 0.229 mmol) in methanol (7 mL) and water (3 mL) was added potassium carbonate (62 mg, 0.428 mmol). The reaction was heated to 60° C. overnight. The methanol was completely distilled off. Then water was added to the remains of the reaction. The organic phase was extracted with ethyl acetate (50 mL) twice. The organic layer was dried over sodium sulphate and filtered and concentrated to get the crude, which was triturated with hexane to afford the off-white colour solid 118.

A solution of 118 (80 mg, 0.216 mmol) and Acrylic acid 33 (21 mg, 0.302 mmol) in acetonitrile (4 mL) was added triethylamine (43 mg, 0.432 mmol). $T_3P$ (131 mg, 0.432 mmol) was added to the reaction mixture. The reaction was stirred overnight at rt, and diluted with ethyl acetate (25 mL). The organic layer was washed with water (25 mL) followed by brine solution (25 mL). The organic layer was dried over sodium sulphate, filtered and concentrated to get the crude, which was purified through flash chromatography by using 100-200 mesh silica gel. The compound was eluted at 1.5% methanol in chloroform as pale yellow colour solid 119. MS-ES+424.0; $^1$H NMR (400 MHz, DMSO-$D_6$): 12.28 (s, 1H), 10.28 (s, 1H), 8.44 (s, 1H), 8.21 (s, 1H), 7.94 (d, 1H), 7.86 (m, 1H), 7.71 (m, 1H), 7.26 (m, 3H), 6.41 (m, 1H), 6.29 (dd, 1H), 5.76 (dd, 1H), 3.61 (s, 3H).

Example 41

N-(2-chloro-5-(3-(3,5-difluoro-2-methoxyphenyl)-1H-pyrrolo[2,3-b]pyridin-5-yl)phenyl)acrylamide (122)

Scheme 41

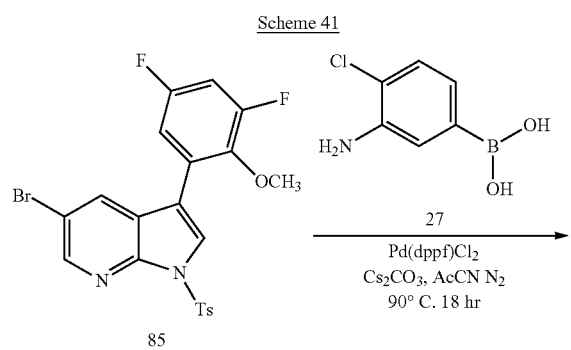

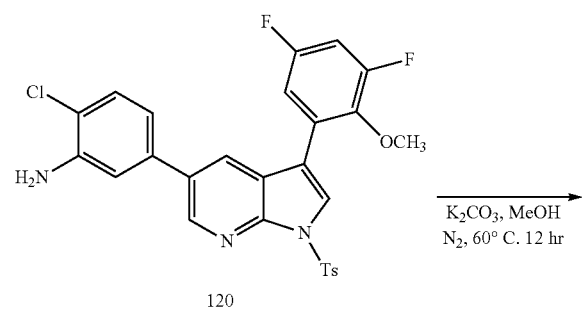

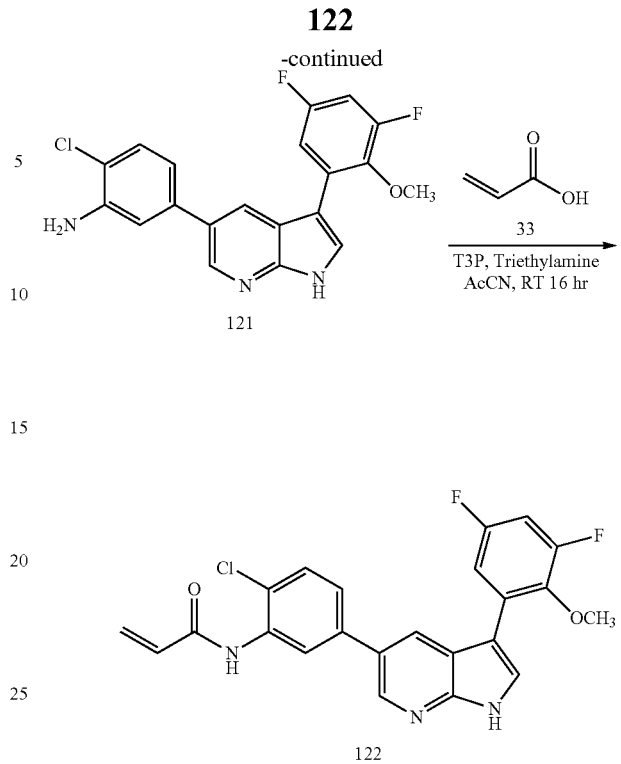

A solution of 85 (150 mg, 0.306 mmol) and 27 (52 mg, 0.306 mmol) in acetonitrile was added cesium carbonate (200 mg, 0.612 mmol). The reaction was degassed and purged with nitrogen for 10 min. Pd(dppf)Cl$_2$ (12 mg, 0.0153 mmol) was added to the reaction. The reaction was degassed and purged with nitrogen for another 10 min and heated to 90° C. under sealed condition overnight. The reaction mixture was allowed to cool to rt, and diluted with chloroform. The organic layer was filtered through Celite plug and concentrated to get the crude, which was purified through flash chromatography by using 100-200 mesh silica gel. The compound was eluted in 5% ethyl acetate in hexane as off-white solid 120.

A solution of 120 (120 mg. 0.222 mmol) in methanol (7 mL) and water (3 mL) was added potassium carbonate (60 mg, 0.444 mmol). The reaction was heated to 60° C. overnight. The methanol was completely distilled off. Then water was added to the remains of the reaction. The organic phase was extracted with ethyl acetate (50 mL) twice. The organic layer was dried over sodium sulphate and filtered and concentrated to get the crude, which was triturated with hexane to afford the off-white colour solid 121.

A solution of 121 (80 mg, 0.207 mmol) and acrylic acid 33 (17.7 mg, 0.249 mmol) in acetonitrile (4 mL) was added triethylamine (43.8 mg, 0.414 mmol). $T_3P$ (135.7 mg, 0.414 mmol) was added to the reaction mixture. The reaction was stirred overnight at rt, and diluted with ethyl acetate (25 mL). The organic layer was washed with water (25 mL) followed by brine solution (25 mL). The organic layer was dried over sodium sulphate, filtered and concentrated to get the crude, which was purified through flash chromatography by using 100-200 mesh silica gel. The compound was eluted at 1.5% methanol in chloroform as pale yellow colour solid 122. MS-ES+440.1; $_1$H NMR (400 MHz, DMSO-$D_6$): 12.24 (s, 1H), 9.85 (s, 1H), 8.56 (d, 1H), 8.27 (s, 1H), 8.13 (s, 1H), 7.92 (d, 1H), 7.61 (s, 2H), 7.29 (m, 2H), 6.64 (m, 1H), 6.27 (dd, 1H), 5.79 (dd, 1H), 3.60 (s, 3H).

Example 42

N-(6-(3-(3,5-difluoro-2-methoxyphenyl)-1H-pyrrolo[2,3-b]pyridin-5-yl)pyridin-2-yl)acrylamide (126)

Scheme 42

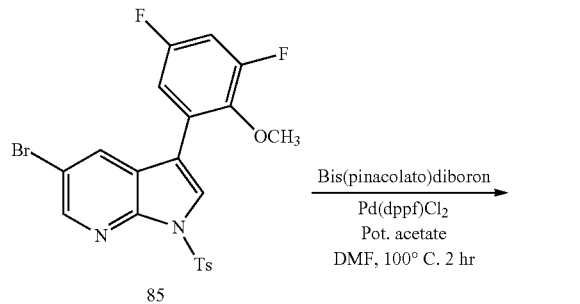

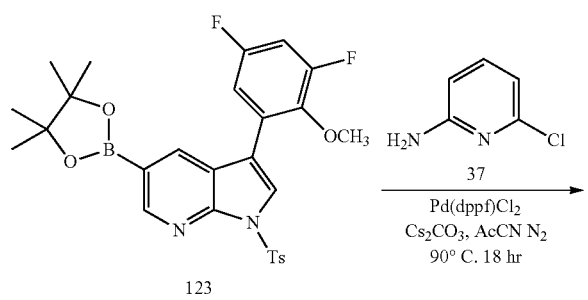

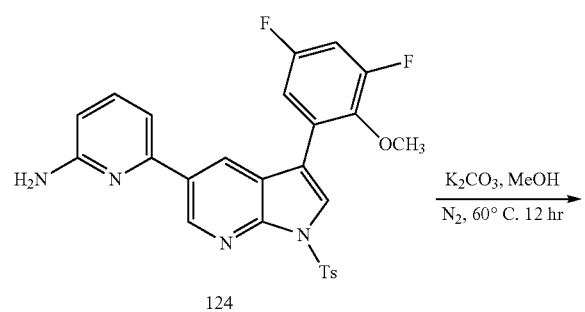

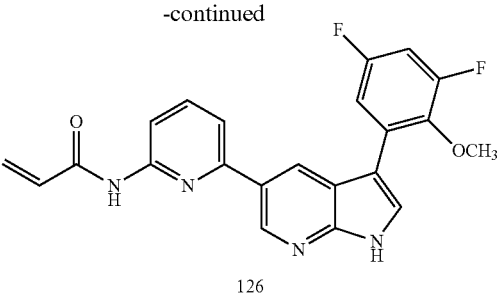

126

To a stirred solution of 85 (250 mg, 0.508 mmol) in DMF was added bis(pinacolato)diboron (257.9 mg, 1.016 mmol). Potassium acetate (99.6 mg, 1.016 mmol) was added and the reaction was degassed and purged with nitrogen for 10 min. Pd(PPh3)2Cl2 (17.8 mg, 0.023 mmol) was added and again degassed and purged with nitrogen for another 10 min. The reaction was sealed and heated to 100° C. for 2 h. After completion of the reaction the reaction was cooled and diluted with chloroform, filtered through Celite bed. The organic layer was washed with cold water (2×50 mL) followed by brine solution (50 mL). The organic layer was dried over sodium sulphate and concentrated to get the crude, which was triturated with hexane to afford black colour solid 123. The solid was preceded for further step without purification.

A solution of 123 (250 mg, 0.46 mmol) and 37 (65 mg, 0.509 mmol) in acetonitrile was added cesium carbonate (301.1 mg, 0.92 mmol). The reaction was degassed and purged with nitrogen for 10 min. Pd(dppf)Cl$_2$ (18 mg, 0.023 mmol) was added to the reaction. The reaction was degassed and purged with nitrogen for another 10 min, heated to 90° C. under sealed condition overnight, allowed to cool to rt, and diluted with chloroform. The organic layer was filtered through Celite plug and concentrated to get the crude, which was purified through flash chromatography by using 100-200 mesh silica gel. The compound was eluted in 5% ethyl acetate in hexane as off-white solid 124.

A solution of 124 (100 mg, 0.198 mmol) was taken in methanol (7 mL) and water (3 mL) was added potassium carbonate (54.7 mg, 0.396 mmol). The reaction was heated to 60° C. overnight. The methanol was completely distilled off. Then water was added to the remains of the reaction. The organic phase was extracted with ethyl acetate (50 mL) twice. The organic layer was dried over sodium sulphate and filtered and concentrated to get the crude, which was triturated with hexane to afford the off-white colour solid 125.

A solution of 125 (60 mg, 0.142 mmol) and acrylic acid 33 (14.1 mg) in acetonitrile (4 mL) was added triethylamine (30.38 mg, 0.284 mmol). T$_3$P (93.102 mg, 0.284 mmol) was added to the reaction mixture. The reaction was stirred overnight at rt, diluted with ethyl acetate (25 mL) and the organic layer was washed with water (25 mL) followed by brine solution (25 mL). The organic layer was dried over sodium sulphate, filtered and concentrated to get the crude, which was purified through flash chromatography by using 100-200 mesh silica gel. The compound was eluted at 1.5% methanol in chloroform as pale yellow colour solid 126. MS-ES+407.0; $^1$H NMR (400 MHz, DMSO-D$_6$) 126: 12.24 (s, 1H), 10.70 (s, 1H), 9.00 (s, 1H), 8.67 (s, 1H), 8.14 (d, 1H), 7.88 (m, 2H), 7.78 (d, 1H), 7.30 (m, 2H), 6.66 (m, 1H), 6.31 (dd, 1H), 5.78 (dd, 1H0, 3.60 (s, 3H).

Example 43

N-(3-(7-(3,5-difluoro-2-methoxyphenyl)-5H-pyrrolo[2,3-b]pyrazin-2-yl)-phenyl)acrylamide (130)

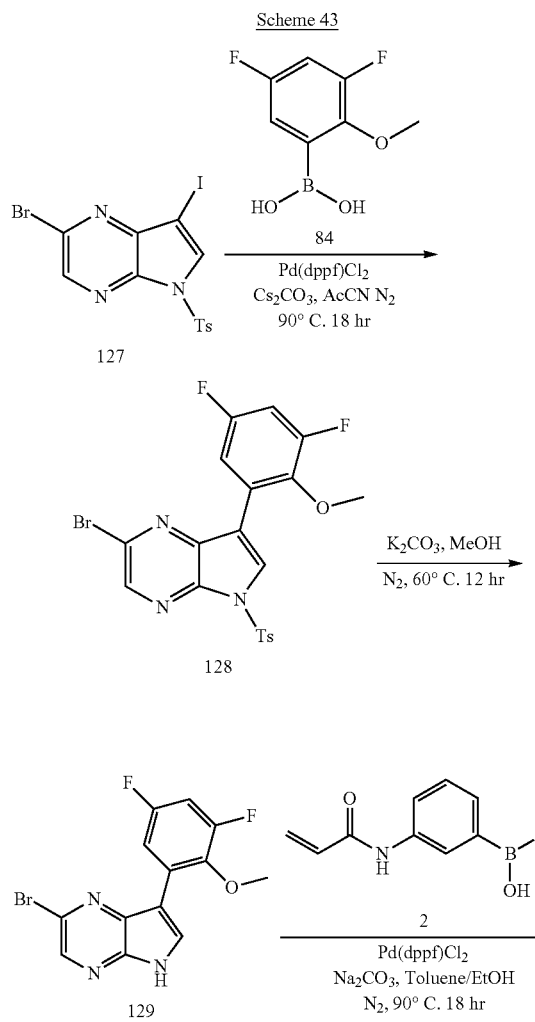

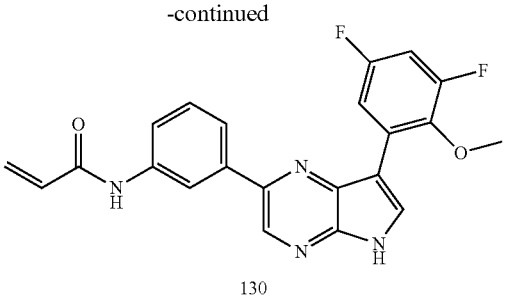

A solution of 127 (200 mg, 0.4184 mmol) and 84 (78.6 mg, 0.4184 mmol) in acetonitrile was added cesium carbonate (274.4 mg, 0.8363 mmol). The reaction was degassed and purged with nitrogen for 10 min. Pd(dppf)Cl$_2$ (17.0 mg, 0.02092 mmol) was added to the reaction. The reaction was degassed and purged with nitrogen for another 10 min, heated to 90° C. under sealed condition overnight, allowed to cool to rt, and diluted with chloroform. The organic layer was filtered through Celite plug and concentrated to get the crude, which was purified through flash chromatography by using 100-200 mesh silica gel. The compound was eluted in 5% ethyl acetate in hexane as off-white solid 128.

A solution of 128 (100 mg, 0.294 mmol) in methanol (7 mL) and water (3 mL) was added potassium carbonate (81.1 mg, 0.588 mmol). The reaction was heated to 60° C. overnight. The methanol was completely distilled off. Then water was added to the remains of the reaction. The organic phase was extracted with ethyl acetate (50 mL) twice. The organic layer was dried over sodium sulphate and filtered and concentrated to get the crude, which was triturated with hexane to afford the off-white colour solid 129.

A solution of 129 (60 mg, 0.235 mmol) and 2 (33.7 mg, 0.235 mmol) in toluene and ethanol (4:1 ml) was added Na$_2$CO$_3$ (50.29 mg, 0.47 mmol). The reaction was degassed and purged with nitrogen for 10 min. Pd(dppf)Cl$_2$ (9.5 mg, 0.01175 mmol) was added to the reaction. The reaction was degassed and purged with nitrogen for another 10 min, heated to 90° C. under sealed condition overnight, allowed to cool to rt, then diluted with chloroform. The organic layer was filtered through Celite bed, concentrated to get the crude, which was purified through flash chromatography by using 100-200 mesh silica gel. The compound was eluted in 3% methanol in dichloromethane as pale yellow colour solid 130. MS-ES+; $^1$H NMR (400 MHz, DMSO-D$_6$) 130: 12.60 (s, 1H), 10.33 (s, 1H), 8.49 (m, 2H), 8.43 (s, 1H), 7.81 (m, 2H), 7.52 (t, 1H), 7.23 (m, 1H), 6.48 (m, 1H), 6.28 (dd, 1H), 5.78 (dd, 1H), 3.88 (s, 3H)

TABLE 1B

List of Examples

| Ex. No. | Structure | Name | *Mol. Wt. |
|---|---|---|---|
| 133 | ![structure] | (E)-N-(3-(3-(3,5-difluoro-2-methoxyphenyl)-1H-pyrrolo[2,3-b]pyridin-5-yl)-4-fluorophenyl)-4-(dimethylamino)but-2-enamide | 481.20 |

TABLE 1B-continued

List of Examples

| Ex. No. | Structure | Name | *Mol. Wt. |
|---|---|---|---|
| 138 | 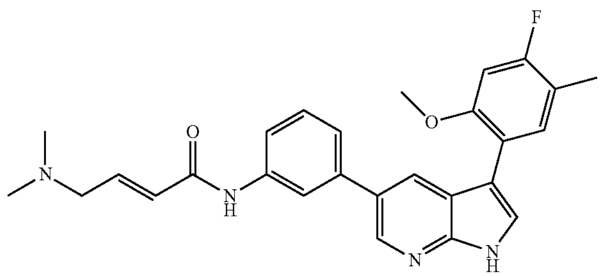 | (E)-4-(dimethylamino)-N-(3-(3-(4-fluoro-2-methoxy-5-methylphenyl)-1H-pyrrolo[2,3-b]pyridin-5-yl)phenyl)but-2-enamide | 458.3 |
| 140 | 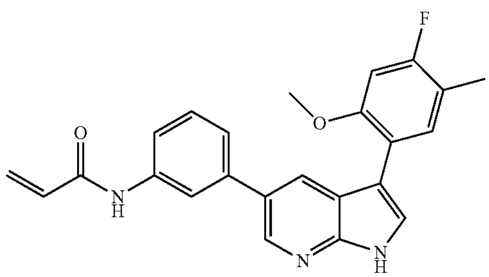 [SMILES: C=CC(=O)Nc1cccc(-c2cnc3[nH]cc(-c4cc(C)c(F)cc4OC)c3c2)c1] | N-(3-(3-(4-fluoro-2-methoxy-5-methylphenyl)-1H-pyrrolo[2,3-b]pyridin-5-yl)phenyl)acrylamide | 402.1 |
| 145 | 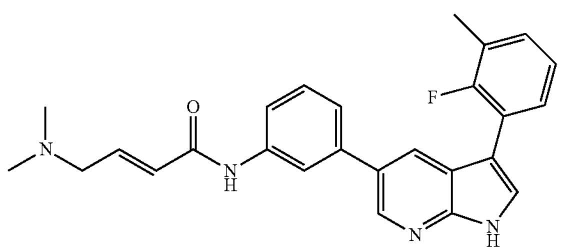 [SMILES: Cc1cccc(-c2c[nH]c3ncc(-c4cccc(NC(=O)/C=C/CN(C)C)c4)cc23)c1F] | (E)-4-(dimethylamino)-N-(3-(3-(2-fluoro-3-methylphenyl)-1H-pyrrolo[2,3-b]pyridin-5-yl)phenyl)but-2-enamide | 428.1 |
| 148 | 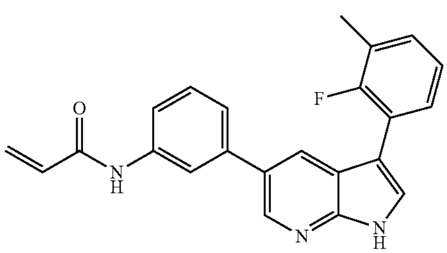 [SMILES: C=CC(=O)Nc1cccc(-c2cnc3[nH]cc(-c4cccc(C)c4F)c3c2)c1] | N-(3-(3-(2-fluoro-3-methylphenyl)-1H-pyrrolo[2,3-b]pyridin-5-yl)phenyl)acrylamide | 372.1 |
| 150 | 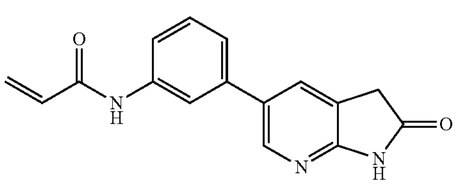 [SMILES: C=CC(=O)Nc1cccc(-c2cnc3c(c2)CC(=O)N3)c1] | N-(3-(2-oxo-2,3-dihydro-1H-pyrrolo[2,3-b]pyridin-5-yl)phenyl)acrylamide | 279.29 |
| 152 | 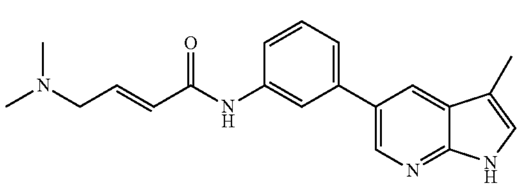 [SMILES: Cc1c[nH]c2ncc(-c3cccc(NC(=O)/C=C/CN(C)C)c3)cc12] | (E)-4-(dimethylamino)-N-(3-(3-methyl-1H-pyrrolo[2,3-b]pyridin-5-yl)phenyl)but-2-enamide | 334.9 |

TABLE 1B-continued

List of Examples

| Ex. No. | Structure | Name | *Mol. Wt. |
|---|---|---|---|
| 153 | 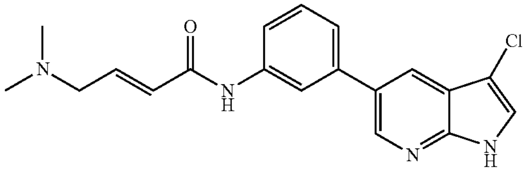 [SMILES: CN(C)C/C=C/C(=O)Nc1cccc(-c2cnc3[nH]cc(Cl)c3c2)c1] | (E)-N-(3-(3-chloro-1H-pyrrolo[2,3-b]pyridin-5-yl)phenyl)-4-(dimethylamino)but-2-enamide | 354.8 |
| 155 | 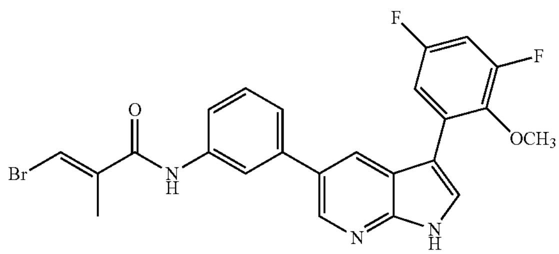 [SMILES: COc1c(F)cc(F)cc1-c1c[nH]c2ncc(-c3cccc(NC(=O)/C(C)=C/Br)c3)cc12] | (E)-3-bromo-N-(3-(3-(3,5-difluoro-2-methoxyphenyl)-1H-pyrrolo[2,3-b]pyridin-5-yl)phenyl)-2-methylacrylamide | 498.20 |
| 156 | 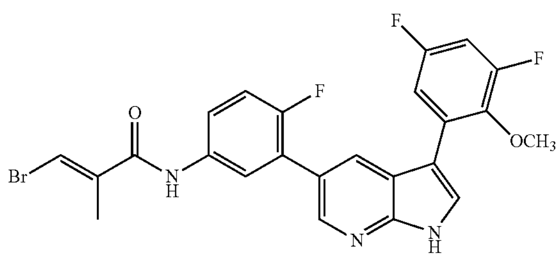 [SMILES: COc1c(F)cc(F)cc1-c1c[nH]c2ncc(-c3cc(NC(=O)/C(C)=C/Br)ccc3F)cc12] | (E)-3-bromo-N-(3-(3-(3,5-difluoro-2-methoxyphenyl)-1H-pyrrolo[2,3-b]pyridin-5-yl)-4-fluorophenyl)-2-methylacrylamide | 515.20 |
| 158 | 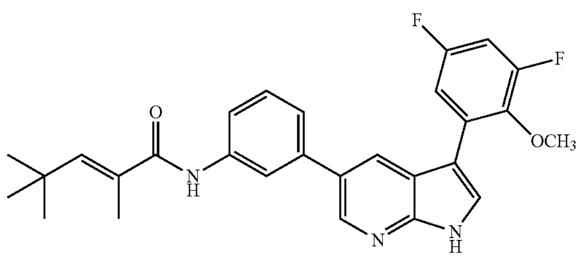 [SMILES: COc1c(F)cc(F)cc1-c1c[nH]c2ncc(-c3cccc(NC(=O)/C(C)=C/C(C)(C)C)c3)cc12] | (E)-N-(3-(3-(3,5-difluoro-2-methoxyphenyl)-1H-pyrrolo[2,3-b]pyridin-5-yl)phenyl)-2,4,4-trimethylpent-2-enamide | 486.19 |
| 159 | 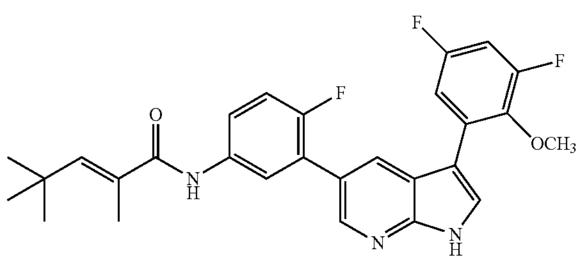 [SMILES: COc1c(F)cc(F)cc1-c1c[nH]c2ncc(-c3cc(NC(=O)/C(C)=C/C(C)(C)C)ccc3F)cc12] | (E)-N-(3-(3-(3,5-difluoro-2-methoxyphenyl)-1H-pyrrolo[2,3-b]pyridin-5-yl)-4-fluorophenyl)-2,4,4-trimethylpent-2-enamide | 504.18 |
| 164 | 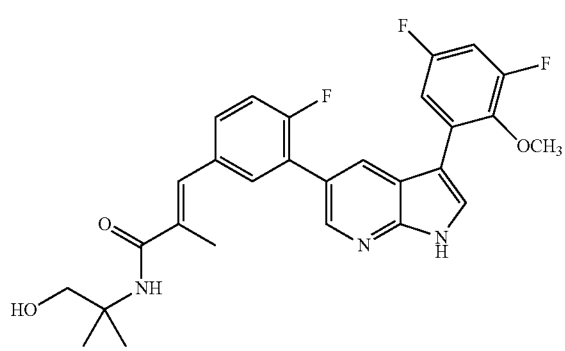 [SMILES: COc1c(F)cc(F)cc1-c1c[nH]c2ncc(-c3cc(/C=C(\C)C(=O)NC(C)(C)CO)ccc3F)cc12] | (E)-3-(3-(3-(3,5-difluoro-2-methoxyphenyl)-1H-pyrrolo[2,3-b]pyridin-5-yl)-4-fluorophenyl)-N-(1-hydroxy-2-methylpropan-2-yl)-2-methylacrylamide | 486.19 |

TABLE 1B-continued

List of Examples

| Ex. No. | Structure | Name | *Mol. Wt. |
|---|---|---|---|
| 168 | 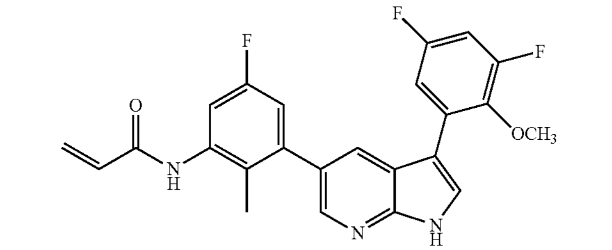 [SMILES: C=CC(=O)Nc1cc(F)cc(-c2cnc3[nH]cc(-c4cc(F)cc(F)c4OC)c3c2)c1C] | N-(3-(3-(3,5-difluoro-2-methoxyphenyl)-1H-pyrrolo[2,3-b]pyridin-5-yl)-5-fluoro-2-methylphenyl)acrylamide | 436.0 |
| 169 | 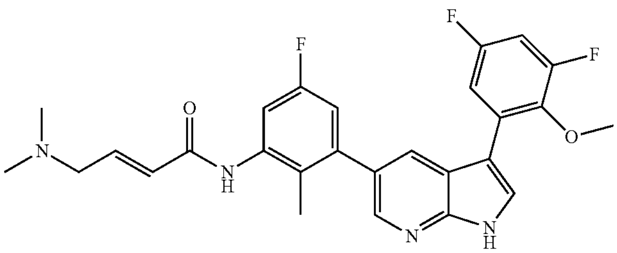 | (E)-N-(3-(3-(3,5-difluoro-2-methoxyphenyl)-1H-pyrrolo[2,3-b]pyridin-5-yl)-5-fluoro-2-methylphenyl)-4-(dimethylamino)but-2-enamide | 494.19 |
| 170 | 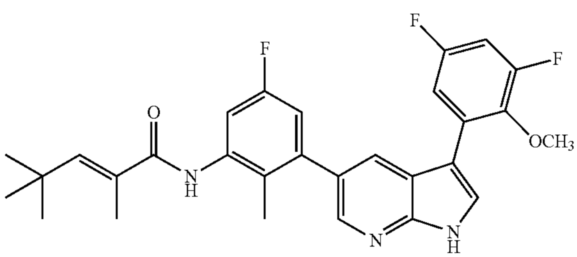 [SMILES: COc1c(F)cc(F)cc1-c1c[nH]c2ncc(-c3cc(F)cc(NC(=O)/C(C)=C/C(C)(C)C)c3C)cc12] | (E)-N-(3-(3-(3,5-difluoro-2-methoxyphenyl)-1H-pyrrolo[2,3-b]pyridin-5-yl)-5-fluoro-2-methylphenyl)-2,4,4-trimethylpent-2-enamide | 507.55 |
| 171 | 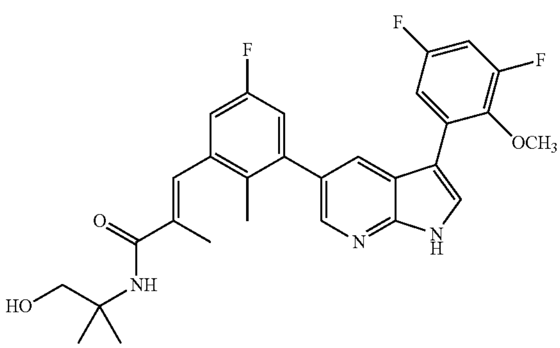 [SMILES: COc1c(F)cc(F)cc1-c1c[nH]c2ncc(-c3cc(F)cc(/C=C(\C)C(=O)NC(C)(C)CO)c3C)cc12] | (E)-3-(3-(3-(3,5-difluoro-2-methoxyphenyl)-1H-pyrrolo[2,3-b]pyridin-5-yl)-5-fluoro-2-methylphenyl)-N-(1-hydroxy-2-methylpropan-2-yl)-2-methylacrylamide | 523.55 |
| 172 | 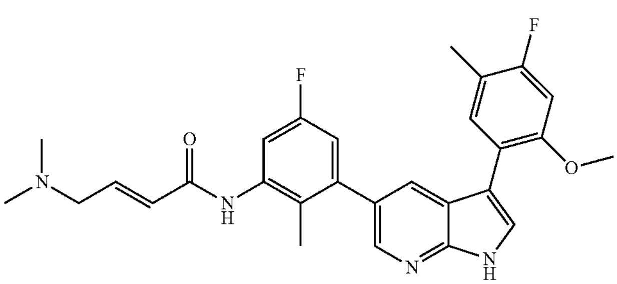 | (E)-4-(dimethylamino)-N-(5-fluoro-3-(3-(4-fluoro-2-methoxy-5-methylphenyl)-1H-pyrrolo[2,3-b]pyridin-5-yl)-2-methylphenyl)but-2-enamide | 490.54 |

TABLE 1B-continued

List of Examples

| Ex. No. | Structure | Name | *Mol. Wt. |
|---|---|---|---|
| 173 | 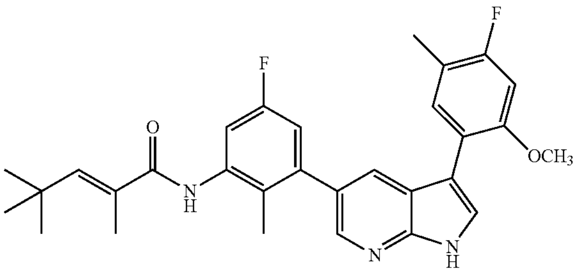 [SMILES: COc1cc(F)c(C)cc1-c1c[nH]c2ncc(-c3cc(F)cc(NC(=O)/C(C)=C/C(C)(C)C)c3C)cc12] | (E)-N-(5-fluoro-3-(3-(4-fluoro-2-methoxy-5-methylphenyl)-1H-pyrrolo[2,3-b]pyridin-5-yl)-2-methylphenyl)-2,4,4-trimethylpent-2-enamide | 503.58 |
| 174 | 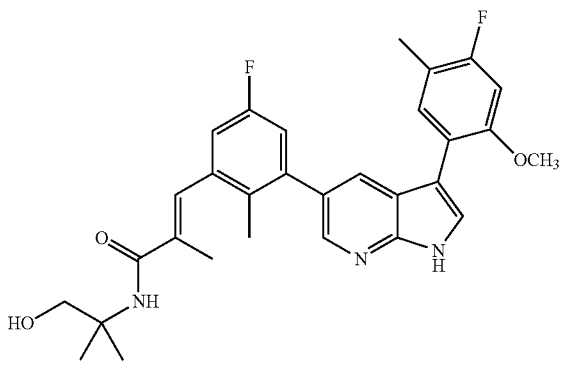 [SMILES: COc1cc(F)c(C)cc1-c1c[nH]c2ncc(-c3cc(F)cc(/C=C(\C)C(=O)NC(C)(C)CO)c3C)cc12] | (E)-3-(5-fluoro-3-(3-(4-fluoro-2-methoxy-5-methylphenyl)-1H-pyrrolo[2,3-b]pyridin-5-yl)-2-methylphenyl)-N-(1-hydroxy-2-methylpropan-2-yl)-2-methylacrylamide | 519.58 |

Example 133

(E)-N-(3-(3-(3,5-difluoro-2-methoxyphenyl)-1H-pyrrolo[2,3-b]pyridin-5-yl)-4-fluorophenyl)-4-(dimethylamino)but-2-enamide (133)

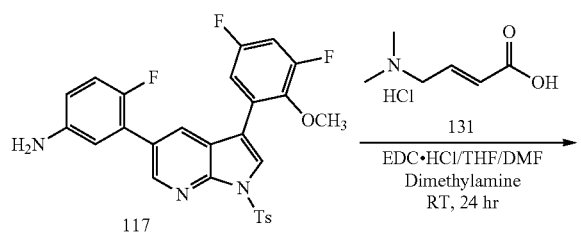

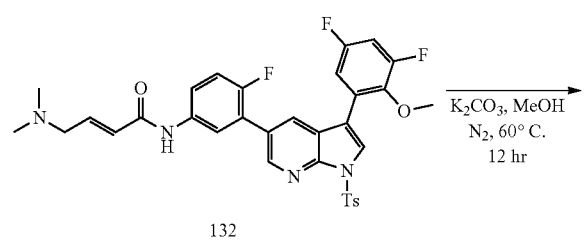

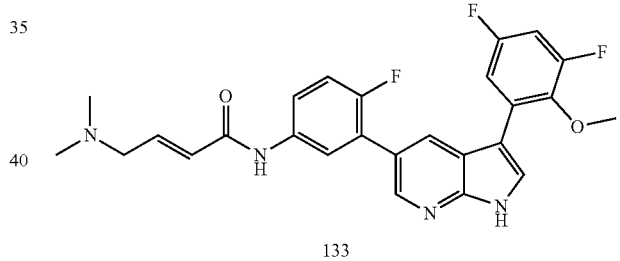

A solution of 117 (100 mg, 0.194 mmol) was dissolved in THF/DMF was added dimethyl amine (31.2 mg, 0.3885 mmol), EDC.HCl (0.3883 mmol) and (E)-4-(dimethylamino)but-2-enoic acid hydrochloride 131 (64.07 mg, 0.3883 mmol) was added to the reaction and stirred at RT for overnight. After completion of the reaction was diluted with water and the aqueous was extracted with 10% methanol in chloroform for two times. The organic layer was dried over sodium sulphate and concentrated to get the crude compound 132. The crude 132 was purified through neutral alumina and the compound was eluted at 2% methanol in chloroform as half white colour solid.

A solution of compound 132 (90 mg, 0.246 mmol) was taken in methanol (7 mL) and water (3 mL) was added potassium carbonate (68.05 mg, 0.493 mmol). The reaction was heated to 60° C. for overnight. The methanol was completely distilled and diluted with water. The organic phase was extracted with ethyl acetate (50 mL) twice. The organic layer was dried over sodium sulphate and filtered and concentrated to get the crude. The crude was purified through flash chromatography by using neutral alumina. The compound was eluted in 2% methanol in chloroform as half white solid (E)-N-(3-(3-(3,5-difluoro-2-methoxyphenyl)-1H-pyrrolo[2,3-b]pyridin-5-yl)-4-fluorophenyl)-4-(dimethylamino)but-2-enamide 133. MS-ES+481.20, ¹HNMR (400 MHz, DMSO) 133: 12.29 (s, 1H), 10.44 (s, 2H), 8.43 (d, 1H), 8.20 (s, 1H), 7.88 (m, 2H), 7.72 (m, 1H), 7.26 (m, 3H), 3.90 (m, 2H), 3.60 (s, 3H), 2.74 (m, 6H).

Example 138

(E)-4-(dimethylamino)-N-(3-(3-(4-fluoro-2-methoxy-5-methylphenyl)-1H-pyrrolo[2,3-b]pyridin-5-yl)phenyl)but-2-enamide (138)

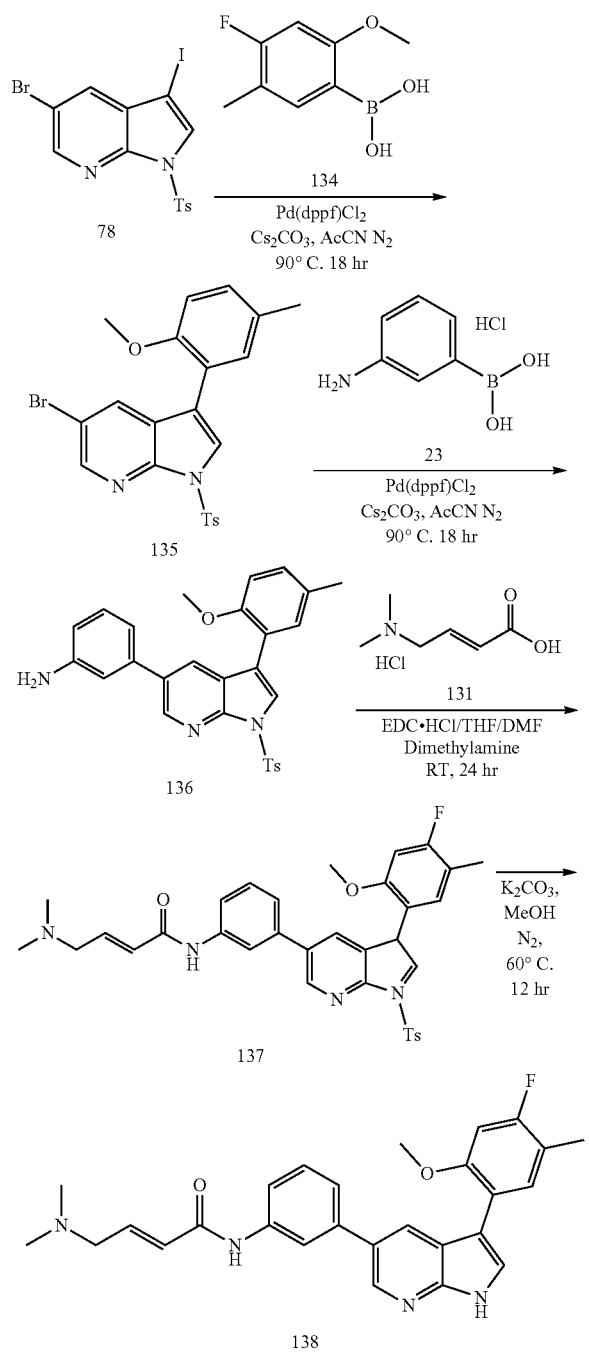

A solution of (4-fluoro-2-methoxy-5-methylphenyl)boronic acid (100 mg, 0.5434 mmol) 134 and 5-bromo-3-iodo-1-tosyl-1H-pyrrolo[2,3-b]pyridine 78 (259.23 mg, 0.5434 mmol) in acetonitrile was added cesium carbonate (356.4 mg, 1.86 mmol). The reaction was degassed and purged with nitrogen for 10 min and Pd(dppf)Cl2 (22.17 mg, 0.0217 mmol) was added to the reaction. The reaction was degassed and purged with nitrogen for another 10 min. The reaction was heated to 90° C. under sealed condition for overnight. The reaction mixture was allowed to cool to room temperature, diluted with chloroform. The organic layer was filtered through celite plug and concentrated to get the crude compound 135. The crude was purified through flash chromatography by using 100-200 mesh silica gel. The compound was eluted in 5% ethyl acetate in hexane as half white solid 5-bromo-3-(4-fluoro-2-methoxy-5-methylphenyl)-1-tosyl-1H-pyrrolo[2,3-b]pyridine 135.

A solution of 5-bromo-3-(4-fluoro-2-methoxy-5-methylphenyl)-1-tosyl-1H-pyrrolo[2,3-b]pyridine 135 (250 mg, 0.5122 mmol) and 23 (145.9 mg, 0.655 mmol) in acetonitrile was added cesium carbonate (336.03 mg, 1.024 mmol). The reaction was degassed and purged with nitrogen for 10 min and Pd(dppf)Cl2 (20.8 mg, 0.02561 mmol) was added to the reaction. The reaction was degassed and purged with nitrogen for another 10 min. The reaction was heated to 90° C. under sealed condition for overnight. The reaction mixture was allowed to cool to room temperature, diluted with chloroform. The organic layer was filtered through celite plug and concentrated to get the crude compound 136. The crude was purified through flash chromatography by using 100-200 mesh silica gel. The compound was eluted in 5% ethyl acetate in hexane as half white solid 3-(3-(4-fluoro-2-methoxy-5-methylphenyl)-1-tosyl-1H-pyrrolo[2,3-b]pyridin-5-yl)aniline 136.

A solution of 136 (100 mg, 0.198 mmol) was dissolved in THF/DMF was added diethyl amine (31.7 mg, 0.396 mmol). EDC.HCl (61.5 mg, 0.396 mmol) and (E)-4-(dimethylamino)but-2-enoic acid hydrochloride 131 (65.34 mg, 0.396 mmol) was added to the reaction and stirred at RT for overnight. After completion the reaction was diluted with water and the aqueous was extracted with 10% methanol in chloroform for two times. The organic layer was dried over sodium sulphate and concentrated to get the crude. The crude was purified through neutral alumina, and the compound was eluted at 2% methanol in chloroform as half white colour solid (E)-4-(dimethylamino)-N-(3-(3-(4-fluoro-2-methoxy-5-methylphenyl)-1-tosyl-1H-pyrrolo[2,3-b]pyridin-5-yl)phenyl)but-2-enamide 137.

A solution of (E)-4-(dimethylamino)-N-(3-(3-(4-fluoro-2-methoxy-5-methylphenyl)-1-tosyl-1H-pyrrolo[2,3-b]pyridin-5-yl)phenyl)but-2-enamide 137 (60 mg, 0.098 mmol) was taken in methanol (7 mL) and water (3 mL) was added potassium carbonate (54.10 mg, 0.392 mmol). The reaction was heated to 60° C. for overnight. The methanol was completely distilled and diluted with water. The organic phase was extracted with ethyl acetate (50 mL) twice. The organic layer was dried over sodium sulphate and filtered and concentrated to get the crude. The crude was purified through flash chromatography by using neutral alumina. The compound was eluted in 2% methanol in chloroform as half white solid (E)-4-(dimethylamino)-N-(3-(3-(4-fluoro-2-methoxy-5-methylphenyl)-1H-pyrrolo[2,3-b]pyridin-5-yl)phenyl)but-2-enamide 138. MS-ES+458.3, ¹H NMR (400 MHz, DMSO): 11.89 (s, 1H), 10.14 (s, 1H), 8.48 (d, 1H), 8.05 (d, 2H), 7.63 (m, 2H), 7.40 (m, 3H), 6.98 (d, 1H), 6.73 (m, 1H), 6.26 (d, 1H), 3.80 (s, 3H), 3.06 (s, 3H), 2.23 (d, 3H), 2.18 (s, 6H).

Example 140

N-(3-(3-(4-fluoro-2-methoxy-5-methylphenyl)-1H-pyrrolo[2,3-b]pyridin-5-yl)phenyl)acrylamide (140)

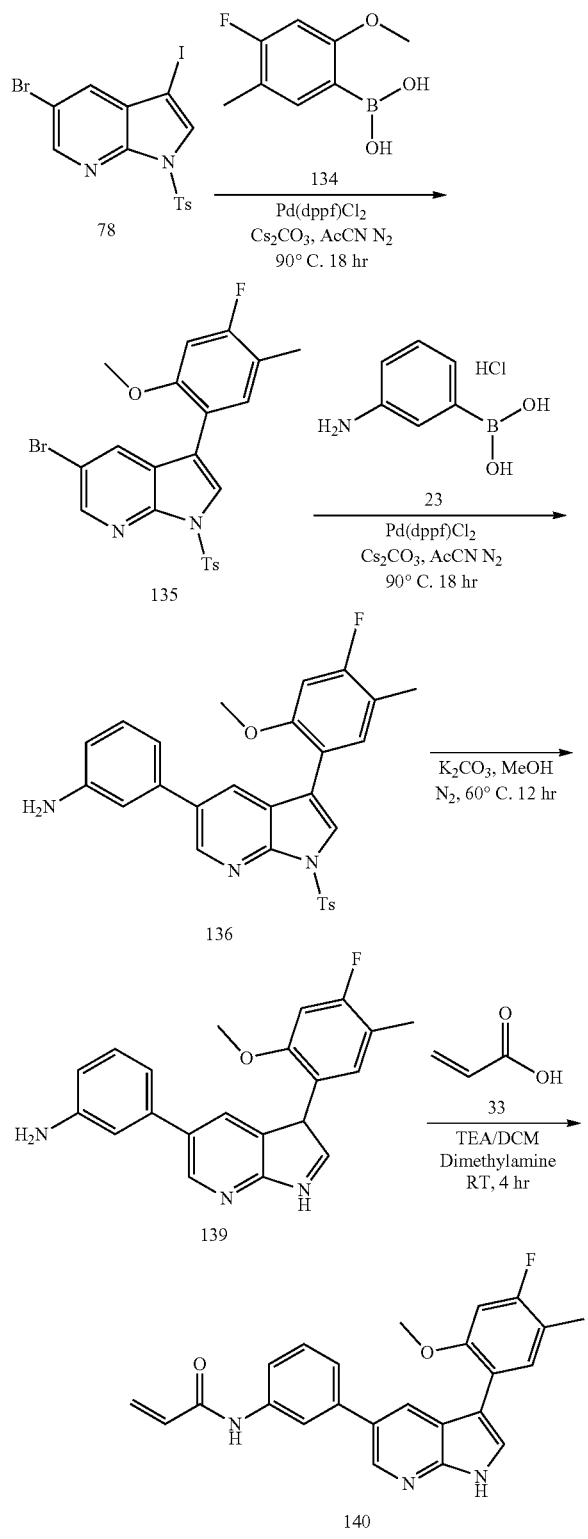

A solution of 134 (100 mg, 0.5434 mmol) and 78 (259.23 mg, 0.5434 mmol) in acetonitrile was added cesium carbonate (356.4 mg, 1.86 mmol). The reaction was degassed and purged with nitrogen for 10 min. Pd(dppf)cl2 (22.17 mg, 0.0217 mmol) was added to the reaction. The reaction was degassed and purged with nitrogen for another 10 min. The reaction was heated to 90° C. under sealed condition for overnight. The reaction mixture was allowed to cool to room temperature, diluted with chloroform. The organic layer was filtered through celite plug and concentrated to get the crude compound. The crude was purified through flash chromatography by using 100-200 mesh silica gel. The compound was eluted in 5% ethyl acetate in hexane as half white solid 135.

A solution of 135 (250 mg, 0.5122 mmol) and 23 (145.9 mg, 0.655 mmol) in acetonitrile was added cesium carbonate (336.03 mg, 1.024 mmol). The reaction was degassed and purged with nitrogen for 10 min. Pd(dppf)Cl$_2$ (20.8 mg, 0.02561 mmol) was added to the reaction. The reaction was degassed and purged with nitrogen for another 10 min. The reaction was heated to 90° C. under sealed condition for overnight. The reaction mixture was allowed to cool to room temperature, diluted with chloroform. The organic layer was filtered through celite plug and concentrated to get the crude. The crude was purified through flash chromatography by using 100-200 mesh silica gel. The compound was eluted in 5% ethyl acetate in hexane as half white solid 136.

A solution of 136 (120 mg) was taken in methanol (7 ml) and water (3 mL) was added potassium carbonate (80 mg). The reaction was heated to 60° C. for overnight. The methanol was completely distilled and diluted with water. The organic phase was extracted with ethyl acetate (50 mL) twice. The organic layer was dried over sodium sulphate and filtered and concentrated to get the crude. The crude was purified through flash chromatography by using neutral alumina. The compound was eluted in 2% methanol in chloroform as half white solid N-(3-(3-(4-fluoro-2-methoxy-5-methylphenyl)-1H-pyrrolo[2,3-b]pyridin-5-yl)phenyl)acrylamide 139.

A solution of 139 (60 mg, 0.17 mmol) was dissolved in dichloromethane (5 ml) and was cooled to 0° C. Triethyl amine (24.03 mg, 0.238 mmol) was added to the reaction mass and kept for stirring. Acrolyl chloride (22.1 mg, 0.221 mmol) was added drop wise to the reaction mass and kept stirring for 4 hr. After completion reaction was quenched with water and the organic layer was separated and aqueous phase was again extracted with DCM. The combined organic layer was washed with brine solution. The organic layer was dried over sodium sulphate and concentrated to get the crude. The crude was purified through 100-200 mesh silica gel eluting the compound at 2% methanol in chloroform as white colour solid N-(3-(3-(4-fluoro-2-methoxy-5-methylphenyl)-1H-pyrrolo[2,3-b]pyridin-5-yl)phenyl)acrylamide 140. MS-ES+402.1, 1H NMR (400 MHz, DMSO) 140: 11.89 (s, 1H), 10.22 (s, 1H), 8.49 (d, 1H), 8.00 (d, 2H), 7.64 (m, 2H), 7.42 (m, 3H), 6.98 (d, 1H), 6.42 (m, 1H), 6.25 (m, 1H), 5.76 (dd, 1H), 3.80 (s, 3H), 2.23 (s, 3H).

Example 145

N-(3-(3-(4-fluoro-2-methoxy-5-methylphenyl)-1H-pyrrolo[2,3-b]pyridin-5-yl)phenyl)acrylamide (145)

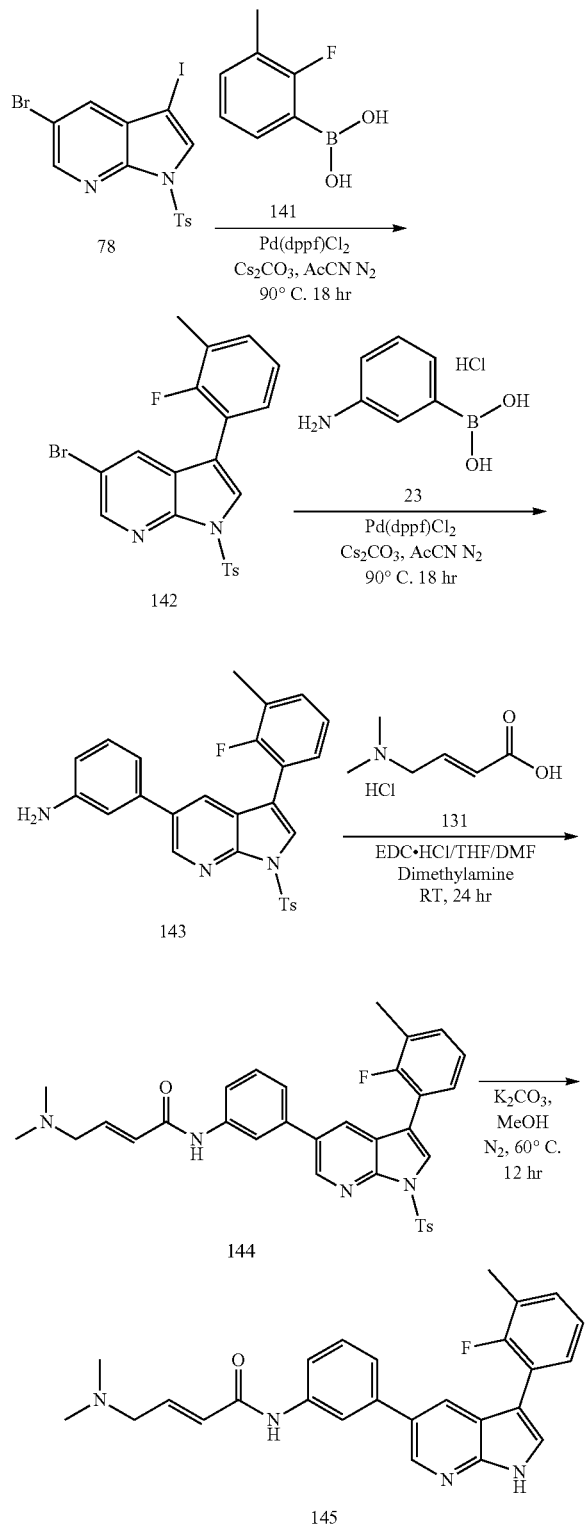

A solution of 78 (500 mg, 1.048 mmol) and (2-fluoro-3-methylphenyl)boronic acid 141 (0.163 mg, 1.048 mmol) in acetonitrile was added cesium carbonate (687.4 mg, 2.096 mmol). The reaction was degassed and purged with nitrogen for 10 min. Pd(dppf)Cl$_2$ (42.7 mg, 0.0524 mmol) was added to the reaction. The reaction was degassed and purged with nitrogen for another 10 min. The reaction was heated to 90° C. under sealed condition for overnight. The reaction mixture was allowed to cool to room temperature, diluted with chloroform. The organic layer was filtered through celite plug and concentrated to get the crude. The crude was purified through flash chromatography by using 100-200 mesh silica gel. The compound was eluted in 5% ethyl acetate in hexane as half white solid compound 142.

A solution of 142 (500 mg, 1.091 mmol) and 23 (310.9 mg, 1.419 mmol) in acetonitrile was added cesium carbonate (715.04 mg, 2.18 mmol). The reaction was degassed and purged with nitrogen for 10 min. Pd(dppf)Cl$_2$ (44.5 mg, 0.0545 mmol) was added to the reaction. The reaction was degassed and purged with nitrogen for another 10 min. The reaction was heated to 90° C. under sealed condition for overnight. The reaction mixture was allowed to cool to room temperature, diluted with chloroform. The organic layer was filtered through celite plug and concentrated to get the crude. The crude was purified through flash chromatography by using 100-200 mesh silica gel. The compound was eluted in 5% ethyl acetate in hexane as half white solid 143.

A solution of 143 (200 mg, 0.424 mmol) was dissolved in THF/DMF was added diethyl amine (67.8 mg, 0.848 mmol). EDC.HCl (131.44 mg, 0.848 mmol) and 131 (139.9 mg, 0.848 mmol) was added to the reaction and stirred at RT for overnight. After completion, the reaction was diluted with water and the aqueous was extracted with 10% methanol in chloroform for two times. The organic layer was dried over sodium sulphate and concentrated to get the crude. The crude was purified through neutral alumina, and the compound was eluted at 2% methanol in chloroform as half white colour compound 144.

A solution of 144 (100 mg, 0.171 mmol) was taken in methanol (7 ml) and water (3 mL) was added potassium carbonate (47.4 mg, 0.343 mmol). The reaction was heated to 60° C. for overnight. The methanol was completely distilled and diluted with water. The organic phase was extracted with ethyl acetate (50 mL) twice. The organic layer was dried over sodium sulphate and filtered and concentrated to get the crude. The crude was purified through flash chromatography by using neutral alumina. The compound was eluted in 2% methanol in chloroform as half white solid (E)-4-(dimethylamino)-N-(3-(3-(2-fluoro-3-methylphenyl)-1H-pyrrolo[2,3-b]pyridin-5yl)phenyl)but-2-enamide 145. MS-ES+428.1, $^1$H NMR (400 MHz, DMSO): 12.14 (s, 1H), 10.31 (s, 1H), 8.54 (d, 1H), 8.18 (s, 1H), 7.94 (s, 1H), 7.81 (s, 1H), 7.75 (m, 1H), 7.58 (t, 1H), 7.44 (m, 2H), 7.17 (m, 2H) 7.08 (m, 1H), 6.35 (d, 1H), 4.40 (m, 1H), 3.99 (d, 2H), 3.03 (s, 3H), 2.33 (s, 6H).

Example 148

N-(3-(3-(2-fluoro-3-methylphenyl)-1H-pyrrolo[2,3-b]pyridin-5-yl)phenyl)acrylamide (148)

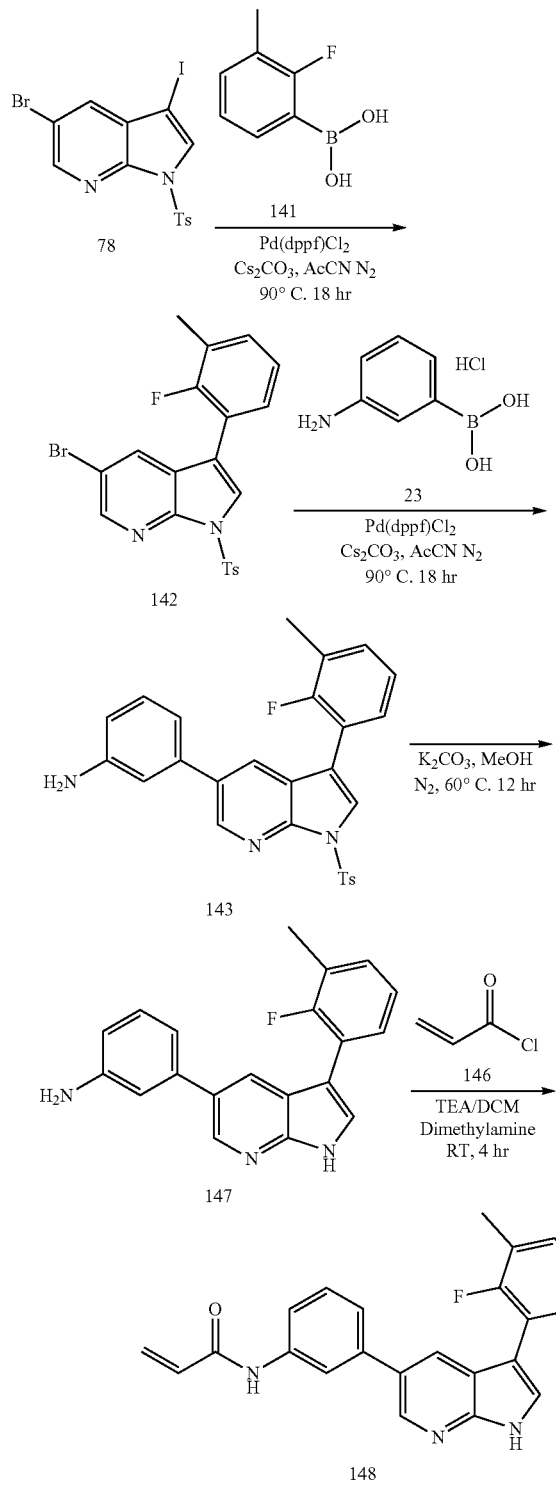

A solution of 78 (500 mg, 1.048 mmol) and 141 (0.163 mg, 1.048 mmol) in acetonitrile was added cesium carbonate (687.4 mg, 2.096 mmol). The reaction was degassed and purged with nitrogen for 10 min. Pd(dppf)Cl$_2$ (42.7 mg, 0.0524 mmol) was added to the reaction. The reaction was degassed and purged with nitrogen for another 10 min. The reaction was heated to 90° C. under sealed condition for overnight. The reaction mixture was allowed to cool to room temperature, diluted with chloroform. The organic layer was filtered through celite plug and concentrated to get the crude. The crude was purified through flash chromatography by using 100-200 mesh silica gel. The compound was eluted in 5% ethyl acetate in hexane as half white solid 143.

A solution of 142 (500 mg, 1.091 mmol) and 23 (310.9 mg, 1.419 mmol) in acetonitrile was added cesium carbonate (715.04 mg, 2.18 mmol). The reaction was degassed and purged with nitrogen for 10 min. Pd(dppf)Cl$_2$ (44.5 mg, 0.05455 mmol) was added to the reaction. The reaction was degassed and purged with nitrogen for another 10 min. The reaction was heated to 90° C. under sealed condition for overnight. The reaction mixture was allowed to cool to room temperature, diluted with chloroform. The organic layer was filtered through celite plug and concentrated to get the crude. The crude was purified through flash chromatography by using 100-200 mesh silica gel. The compound was eluted in 5% ethyl acetate in hexane as half white solid 143.

A solution of 143 (200 mg) was taken in methanol (7 mL) and water (3 mL) was added potassium carbonate (100 mg). The reaction was heated to 60° C. for overnight. The methanol was completely distilled and diluted with water. The organic phase was extracted with ethyl acetate (50 ml) twice. The organic layer was dried over sodium sulphate and filtered and concentrated to get the crude. The crude was triturated with hexane to afford the half white colour solid 147.

A solution of compound 147 (100 mg, 0.3153 mmol) was dissolved in dichloromethane (20 mL) and was cooled to 0° C. Triethyl amine (44.9 mg, 0.4414 mmol) was added to the reaction mass and kept for stirring. Acrolyl chloride (40.9 mg, 0.4099 mmol) was added drop wise to the reaction mass and kept stirring for 4 hr. After completion reaction was quenched with water and the organic layer was separated and aqueous phase was again extracted with DCM. The combined organic layer was washed with brine solution. The organic layer was dried over sodium sulphate and concentrated to get the crude. The crude was purified through 100-200 mesh silica gel eluting the compound at 2% methanol in chloroform as white colour solid N-(3-(3-(2-fluoro-3-methylphenyl)-1H-pyrrolo[2,3-b]pyridin-5-yl)phenyl)acrylamide 148. MS-ES+280, 1H NMR (400 MHz, DMSO): 12.12 (s, 1H), 10.24 (s, 1H), 8.54 (d, 1H), 8.18 (s, 1H), 7.94 (s, 1H), 7.82 (s, 1H), 7.73 (m, 1H), 7.56 (m, 1H), 7.43 (d, 2H), 7.19 (m, 2H), 6.45 (m, 1H), 6.26 (dd, 1H), 5.76 (dd, 1H), 2.33 (s, 3H).

Example 150

N-(3-(2-oxo-2,3-dihydro-1H-pyrrolo[2,3-b]pyridin-5-yl)phenyl)acrylamide (150)

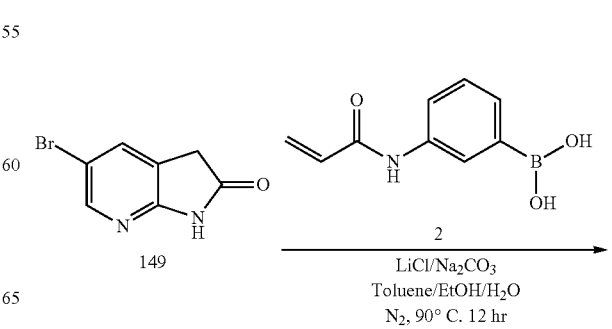

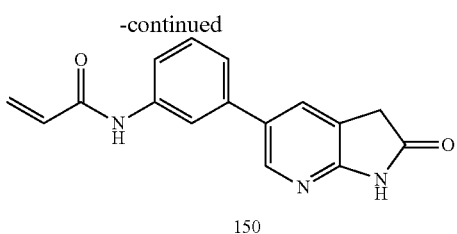

150

A solution of 5-bromo-1H-pyrrolo[2,3-b]pyridin-2(3H)-one 149 (100 mg, 0.4673 mmol) and (3-acrylamidophenyl)boronic acid 64 (98.55 mg, 0.514 mmol) in toluene/ethanol/water was added sodium carbonate (198 mg, 1.8692 mmol). Lithium chloride (59.3 mg, 1.40 mmol) was added to the reaction. The reaction was degassed and purged nitrogen for 10 min. Pd(dppf)Cl$_2$ (19.03 mg, 0.0233 mmol) was added to the reaction. The reaction was degassed and purged with nitrogen for another 10 min. The reaction was heated to 90° C. under sealed condition for overnight. The reaction mixture was allowed to cool to room temperature, diluted with chloroform. The organic layer was filtered through celite plug and concentrated to get the crude. The crude was purified through flash chromatography by using 100-200 mesh silica gel. The compound was eluted in ethyl acetate in hexane as half white solid N-(3-(2-oxo-2,3-dihydro-1H-pyrrolo[2,3-b]pyridin-5-yl)phenyl)acrylamide 150. MS-ES+ 338.9, $^1$H NMR (400 MHz, DMSO): 11.09 (s, 1H), 10.24 (s, 1H), 8.30 (s, 1H), 7.97 (s, 1H), 7.61 (d, 1H), 7.35 (m, 2H), 6.44 (m, 1H), 6.25 (d, 1H), 5.76 (d, 1H), 3.63 (s, 2H).

Example 152

(E)-4-(dimethylamino)-N-(3-(3-methyl-1H-pyrrolo[2,3-b]pyridin-5-yl)phenyl)but-2-enamide (152)

mmol) in acetonitrile was added cesium carbonate (310.1 mg, 0.9478 mmol). The reaction was degassed and purged with nitrogen for 10 min. Pd(dppf)Cl$_2$ (16.88 mg, 0.0206 mmol) was added to the reaction. The reaction was degassed and purged with nitrogen for another 10 min. The reaction was heated to 90° C. under sealed condition for overnight. The reaction mixture was allowed to cool to room temperature, diluted with chloroform. The organic layer was filtered through celite plug and concentrated to get the crude. The crude was purified through flash chromatography by using 100-200 mesh silica gel. The compound was eluted in ethyl acetate in hexane as half white solid 3-(3-methyl-1H-pyrrolo[2,3-b]pyridin-5-yl)aniline 24.

A solution of 3-(3-methyl-1H-pyrrolo[2,3-b]pyridin-5-yl)aniline 24 (100 mg 0.449 mmol) was dissolved in THF/DMF was added diethyl amine (71.46 mg, 0.89 mmol). EDC.HCl (139.19 mg, 0.89 mmol) was added to the reaction then (E)-4-(dimethylamino)but-2-enoic acid 131 (103.8 mg, 0.6292 mmol) was added to the reaction and stirred at RT for overnight. After completion the reaction was diluted with water and the aqueous was extracted with 10% methanol in chloroform for two times. The organic layer was dried over sodium sulphate and concentrated to get the crude. The crude was purified through flash chromatography by using neutral alumina. The compound was eluted in 2% methanol in chloroform as half white solid (E)-4-(dimethylamino)-N-(3-(3-methyl-1H-pyrrolo[2,3-b]pyridin-5-yl) phenyl)but-2-enamide 152. MS-ES+334.9, $^1$H NMR (400 MHz, DMSO): 11.35 (s, 1H), 10.14 (s, 1H), 8.42 (d, 1H), 8.07 (d, 1H), 7.98 (s, 1H), 7.63 (m, 1H), 7.39 (d, 1H), 7.27 (s, 1H), 6.73 (m, 1H), 6.29, (d, 1H), 3.27 (m, 1H), 3.05 (d, 2H), 2.29 (s, 3H), 2.17 (s, 6H).

Example 51

(E)-N-(3-(3-chloro-1H-pyrrolo[2,3-b]pyridin-5-yl)phenyl)-4-(dimethylamino)but-2-enamide (153)

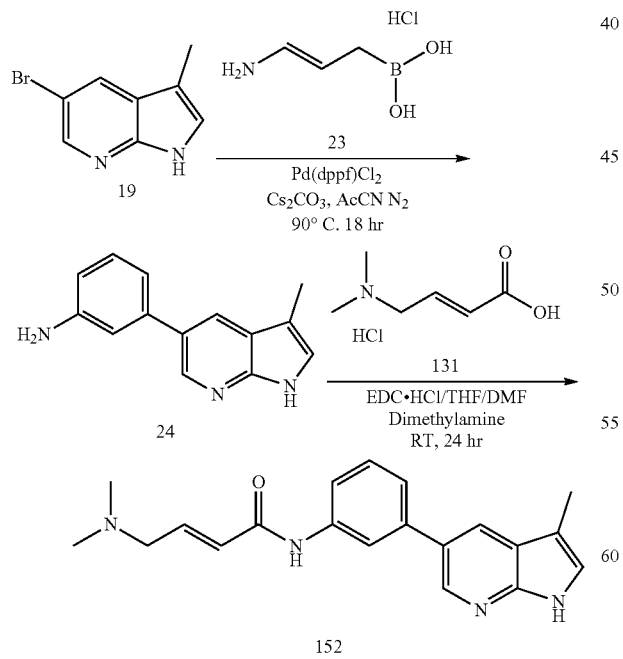

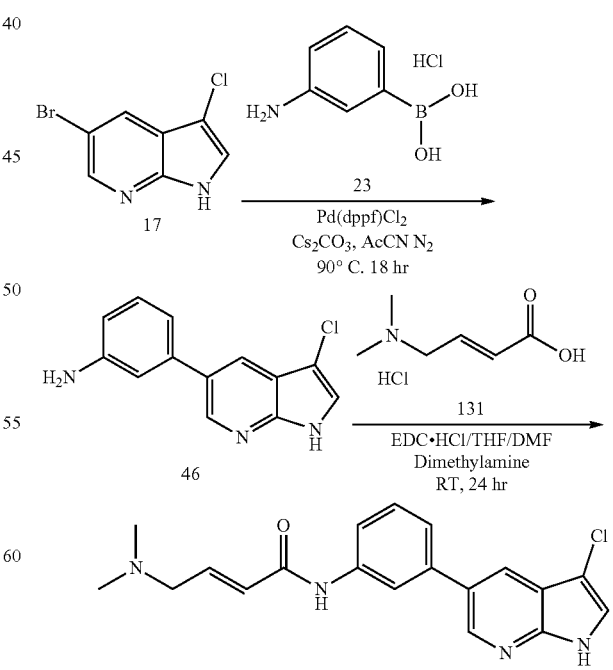

A solution of 5-bromo-3-methyl-1H-pyrrolo[2,3-b]pyridine 19 (100 mg, 0.4139 mmol) and 23 (124.5 mg, 0.5687

A solution of 17 (100 mg, 0.436 mmol) and 23 (114.7 mg, 0.524 mmol) in acetonitrile was added cesium carbonate (286.01 mg, 0.872 mmol). The reaction was degassed and purged with nitrogen for 10 min. Pd(Dppf)Cl$_2$ (17.7 mg 0.0218 mmol) was added to the reaction. The reaction was degassed and purged with nitrogen for another 10 min. The reaction was heated to 90° C. under sealed condition for overnight. The reaction mixture was allowed to cool to room temperature, diluted with chloroform. The organic layer was filtered through celite plug and concentrated to get the crude. The crude was purified through flash chromatography by using 100-200 mesh silica gel. The compound was eluted in ethyl acetate in hexane as half white solid 46.

A solution of 46 (100 mg, 0.4142 mmol) was dissolved in THF/DMF was added diethyl amine (66.2 mg, 0.8284 mmol). EDC.HCl (128.45 mg, 0.8284 mmol) was added to the reaction then AS-2143 (95.07 mg, 0.5759 mmol) was added to the reaction and stirred at RT for overnight. After completion, the reaction was diluted with water and the aqueous was extracted with 10% methanol in chloroform for two times. The organic layer was dried over sodium sulphate and concentrated to get the crude. The crude was purified through flash chromatography by using neutral alumina. The compound was eluted in 2% methanol in chloroform as half white solid (E)-N-(3-(3-chloro-1H-pyrrolo[2,3-b]pyridin-5-yl)phenyl)-4-(dimethylamino)but-2-enamid 153. MS-ES+ 354.8, 1H NMR (400 MHz, DMSO): 12.08 (s, 1H), 10.16 (s, 1H), 8.56 (d, 1H), 8.02 (m, 2H), 7.73 (d, 1H), 7.65 (m, 1H), 7.41 (m, 2H), 6.73 (m, 1H), 6.26 (m, 1H), 3.06 (d, 2H), 2.18 (s, 6H).

Example 155

(E)-3-bromo-N-(3-(3-(3,5-difluoro-2-methoxyphenyl)-1H-pyrrolo[2,3-b]pyridin-5-yl)phenyl)-2-methylacrylamide (155)

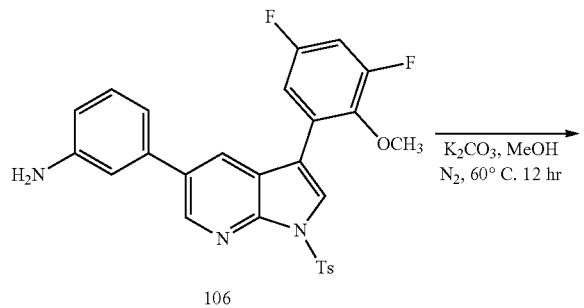

106

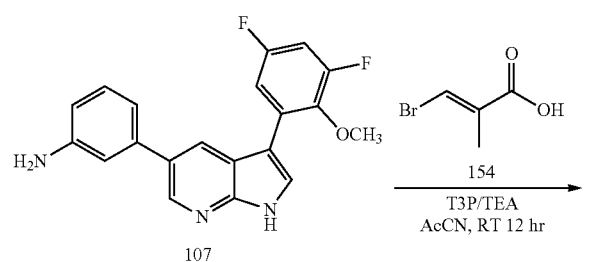

107

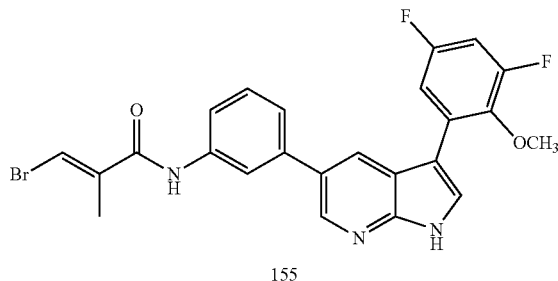

155

A solution of 106 (200 mg) was taken in methanol (7 mL) and water (3 mL) was added potassium carbonate (100 mg). The reaction was heated to 60° C. for overnight. The methanol was completely distilled and diluted with water. The organic phase was extracted with ethyl acetate (50 mL) twice. The organic layer was dried over sodium sulphate and filtered and concentrated to get the crude. The crude was triturated with hexane to afford the half white colour solid 107.

A solution of 107 (100 mg, 0.569 mmol) and 154 (8.6 mg, 1.139 mmol) in acetonitrile (8 mL) was added Triethyl amine (120.7 mg, 1.139 mmol) and T3P (373.5 mg, 1.139 mmol) was added to the reaction mixture. The reaction was stirred for overnight at room temperature. The reaction was diluted with ethyl acetate (25 ml). The organic layer was washed with water (25 mL) followed by brine solution (25 mL). The organic layer was dried over sodium sulphate, filtered and concentrated to get the crude. The crude was purified through flash chromatography by using 100-200 mesh silica gel. The compound was eluted at 2% methanol in chloroform as pale yellow color solid (E)-3-bromo-N-(3-(3-(3,5-difluoro-2-methoxyphenyl)-1H-pyrrolo[2,3-b]pyridin-5-yl)phenyl)-2-methylacrylamide 155. MS-ES+498.20, 1H NMR (400 MHz, DMSO): 12.2 (s, 1H), 10.01 (s, 1H), 8.55 (d, 1H), 8.20 (s, 1d), 7.94 (s, 1H), 7.92 (d, 1H), 7.71 (m, 1H), 7.6 (m, 3H), 7.3 (m, 2H), 3.6 (s, 3H), 2.0 (s, 3H).

Example 156

(E)-3-bromo-N-(3-(3-(3,5-difluoro-2-methoxyphenyl)-1H-pyrrolo[2,3-b]pyridin-5-yl)-4-fluorophenyl)-2-methylacrylamide (156)

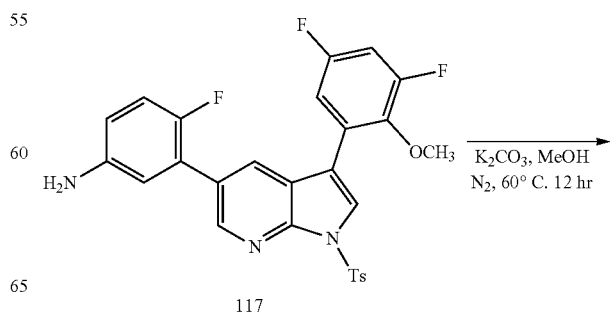

117

148

Example 54

(E)-N-(3-(3-(3,5-difluoro-2-methoxyphenyl)-1H-pyrrolo[2,3-b]pyridin-5-yl)phenyl)-2,4,4-trimethyl-pent-2-enamide (158)

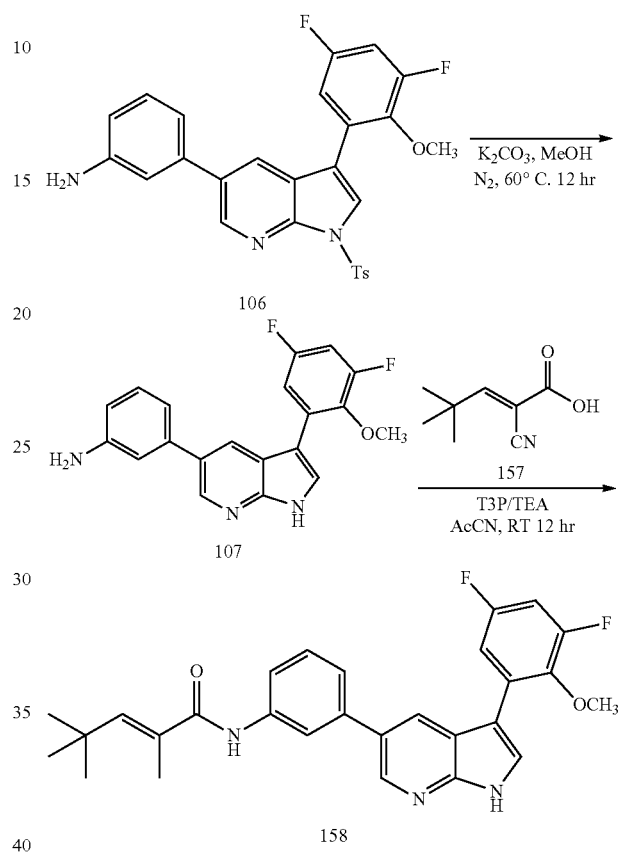

A solution of 117 (200 mg) was taken in methanol (7 mL) and water (3 mL) was added potassium carbonate (100 mg). The reaction was heated to 60° C. for overnight. The methanol was completely distilled and diluted with water. The organic phase was extracted with ethyl acetate (50 mL) twice. The organic layer was dried over sodium sulphate and filtered and concentrated to get the crude. The crude was triturated with hexane to afford the half white colour solid 118.

A solution of 118 (100 mg, 0.277 mmol) and 154 (90.3 mg, 0.554 mmol) in acetonitrile (8 mL) was added Triethyl amine (58.7 mg, 0.554 mmol) and T3P (181.7 mg, 0.554 mmol) was added to the reaction mixture. The reaction was stirred for overnight at room temperature. The reaction was diluted with ethyl acetate (25 ml). The organic layer was washed with water (25 mL) followed by brine solution (25 mL). The organic layer was dried over sodium sulphate, filtered and concentrated to get the crude. The crude was purified through flash chromatography by using 100-200 mesh silica gel. The compound was eluted at 2% methanol in chloroform as pale yellow colour solid (E)-3-bromo-N-(3-(3-(3,5-difluoro-2-methoxyphenyl)-1H-pyrrolo[2,3-b]pyridin-5-yl)-4-fluorophenyl)-2-methylacrylamide 156. MS-ES+515.20, 1H NMR (400 MHz, CDCl3) 8.55 (s, 1H), 8.29 (s, 1H), 7.7 (s, 1H), 7.65 (m, 1H), 7.55 (m, 1H), 7.45 (s, 1H), 7.29 (s, 2H), 7.2 (m, 1H), 7.11 (m, 1H), 6.8 (m, 1H), 3.7 (s, 3H), 2.1 (s, 3H).

A solution of 106 (200 mg) was taken in methanol (7 mL) and water (3 mL) was added potassium carbonate (100 mg). The reaction was heated to 60° C. for overnight. The methanol was completely distilled and diluted with water. The organic phase was extracted with ethyl acetate (50 ml) twice. The organic layer was dried over sodium sulphate and filtered and concentrated to get the crude. The crude was triturated with hexane to afford the half white colour solid 107.

A solution of 107 (100 mg, 0.284 mmol) and (E)-2-cyano-4,4-dimethylpent-2-enoic acid 157 (52.3 mg, 0.341 mmol) in acetonitrile (8 ml) was added Triethyl amine (60.2 mg, 0.568 mmol). T3P (186.3 mg, 0.568 mmol) was added to the reaction mixture. The reaction was stirred for overnight at room temperature. The reaction was diluted with ethyl acetate (25 mL). The organic layer was washed with water (25 mL) followed by brine solution (25 mL). The organic layer was dried over sodium sulphate, filtered and concentrated to get the crude. The crude was purified through flash chromatography by using 100-200 mesh silicagel. The compound was eluted at 30% Ethyl acetate in hexane as pale yellow colour solid (E)-N-(3-(3-(3,5-difluoro-2-methoxyphenyl)-1H-pyrrolo[2,3-b]pyridin-5-yl)phenyl)-2,4,4-trimethylpent-2-enamide 158. MS-ES+486.19, $^1$H NMR (400 MHz, CDCl3): 8.6 (s, 1H), 8.31 (s, 1H), 8.05 (s, 1H), 7.8 (d,

147

-continued

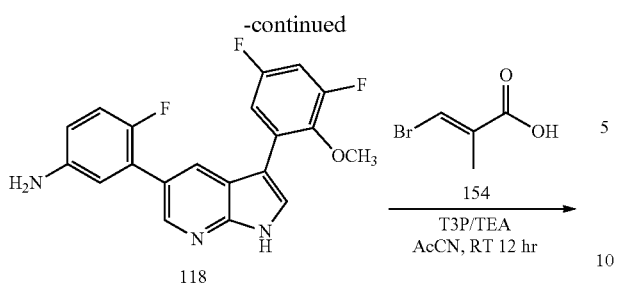

1H), 7.71 (s, 1H), 7.5 (d, 1H), 7.41 (m, 2H), 7.12 (d, 1H), 6.8 (m, 1H), 3.74 (s, 3H), 1.3 (s, 9H).

Example 159

(E)-N-(3-(3-(3,5-difluoro-2-methoxyphenyl)-1H-pyrrolo[2,3-b]pyridin-5-yl)-4-fluorophenyl)-2,4,4-trimethylpent-2-enamide (159)

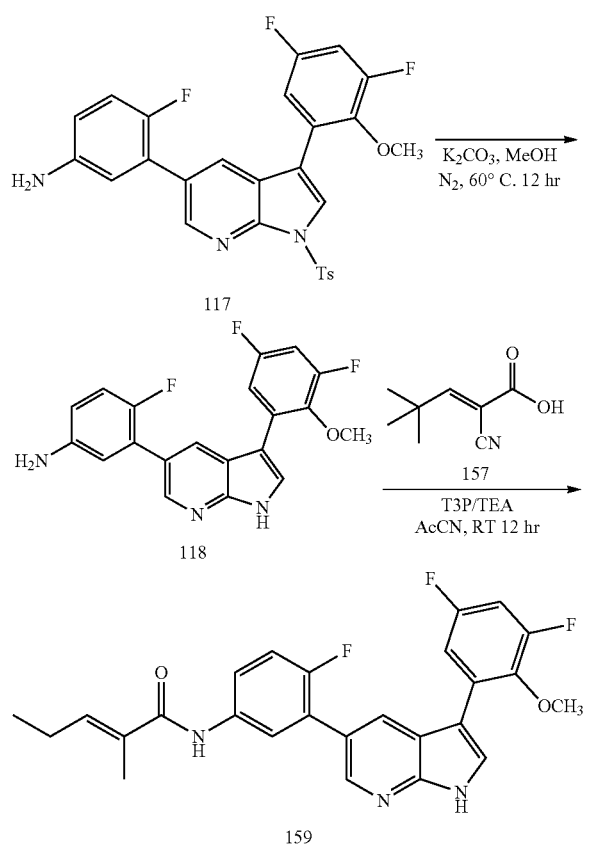

A solution of 117 (200 mg) was taken in methanol (7 mL) and water (3 mL) was added potassium carbonate (100 mg). The reaction was heated to 60° C. for overnight. The methanol was completely distilled and diluted with water. The organic phase was extracted with ethyl acetate (50 mL) twice. The organic layer was dried over sodium sulphate and filtered and concentrated to get the crude. The crude was triturated with hexane to afford the half white colour solid 118.

A solution of 118 (100 mg, 0.27 mmol) and (E)-2-cyano-4,4-dimethylpent-2-enoic acid 157 (50.1 mg, 0.324 mmol) in acetonitrile (8 mL) was added Triethyl amine (55.8 mg, 0.54 mmol) and T3P (178.2 mg, 0.54 mmol) was added to the reaction mixture. The reaction was stirred for overnight at room temperature. The reaction was diluted with ethyl acetate (25 ml). The organic layer was washed with water (25 mL) followed by brine solution (25 ml). The organic layer was dried over sodium sulphate, filtered and concentrated to get the crude. The crude was purified through flash chromatography by using 100-200 mesh silicagel. The compound was eluted at 2% methanol in chloroform as pale yellow colour solid (E)-N-(3-(3-(3,5-difluoro-2-methoxyphenyl)-1H-pyrrolo[2,3-b]pyridin-5-yl)-4-fluorophenyl)-2,4,4-trimethylpent-2-enamide 159. MS-ES+504.18, 1H NMR (400 MHz, CDCl3): 8.547 (s, 1H), 8.31 (s, 1H), 8.001 (s, 1H), 7.8 (s, 1H), 7.75 (s, 1H), 7.71 (m, 1H), 7.57 (m, 1H), 7.2 (s, 1H), 7.11 (m, 1H), 6.8 (m, 1H), 3.74 (s, 3H), 1.3 (s, 9H).

Example 164

(E)-3-(3-(3-(3,5-difluoro-2-methoxyphenyl)-1H-pyrrolo[2,3-b]pyridin-5-yl)-4-fluorophenyl)-N-(1-hydroxy-2-methylpropan-2-yl)-2-methylacrylamide (164)

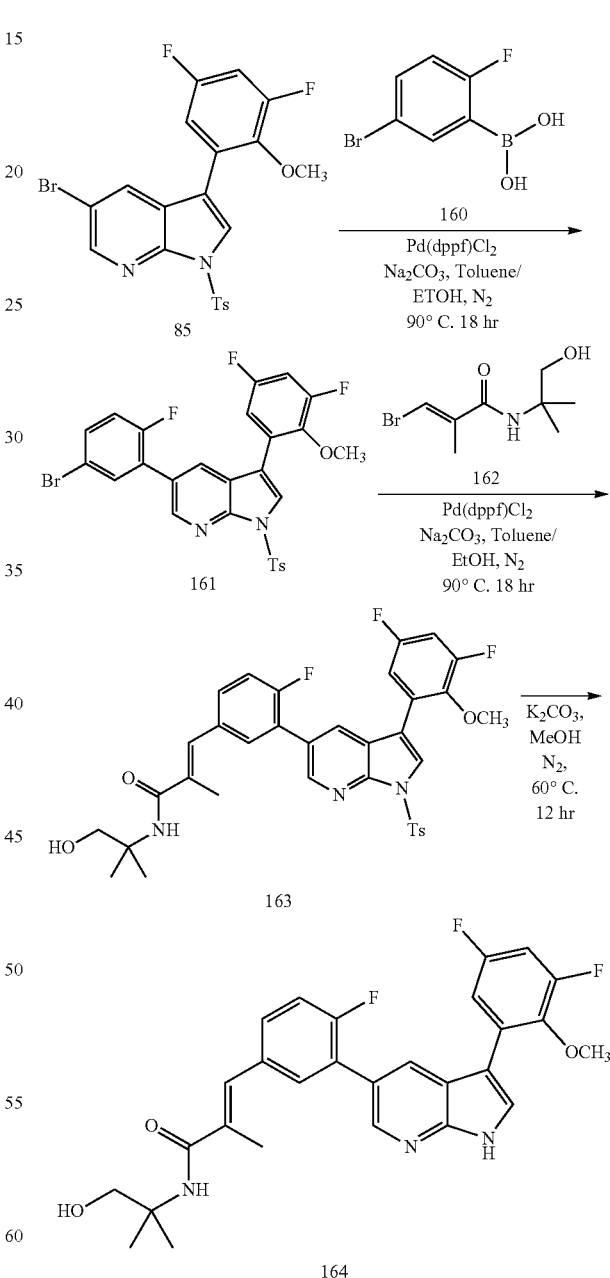

A solution of 85 (250 mg, 0.508 mmol) and 160 (167.6 mg, 0.558 mmol) in acetonitrile was added cesium carbonate (333.2 mg, 1.016 mmol). The reaction was degassed and purged with nitrogen for 10 min. Pd(dppf)$_{Cl2}$ (20.7 mg, 0.0254 mmol) was added to the reaction. The reaction was degassed and purged with nitrogen for another 10 min. The reaction was heated to 90° C. under sealed condition for overnight. The reaction mixture was allowed to cool to room temperature, diluted with chloroform. The organic layer was filtered through celite plug and concentrated to get the crude. The crude was purified through flash chromatography by using 100-200 mesh silica gel. The compound was eluted in ethyl acetate in hexane as half white 161 solid.

A solution of 161 (200 mg, 0.314 mmol) and (E)-3-bromo-N-(1-hydroxy-2-methylpropan-2-yl)-2-methylacrylamide 162 (110.2 mg, 0.628 mmol) in acetonitrile (8 ml) was added $Cs_2CO_3$ (20.6 mg, 0.628 mmol). The reaction was degassed and purged with nitrogen for 10 min. Pd(dppf)Cl$_2$ (12.7 mg, 0.0157 mmol) was added to the reaction. The reaction was degassed and purged with nitrogen for another 10 min. The reaction was heated to 90° C. under sealed condition for overnight. The reaction mixture was allowed to cool to room temperature, diluted with chloroform. The organic layer was filtered through celite plug and concentrated to get the crude. The crude was purified through flash chromatography by using 100-200 mesh silica gel. The compound was eluted in ethyl acetate in hexane as half white solid (E)-3-(3-(3-(3,5-difluoro-2-methoxyphenyl)-1-tosyl-1H-pyrrolo[2,3-b]pyridin-5-yl)-4-fluorophenyl)-N-(1-hydroxy-2-methylpropan-2-yl)-2-methylacrylamide 163.

A solution of 163 (40 mg) was taken in methanol (7 mL) and water (3 mL) was added potassium carbonate (20 mg). The reaction was heated to 60° C. for overnight. The methanol was completely distilled and diluted with water. The organic phase was extracted with ethyl acetate (50 ml) twice. The organic layer was dried over sodium sulphate and filtered and concentrated to get the crude. The crude was triturated with hexane to afford the half white colour solid (E)-3-(3-(3-(3,5-difluoro-2-methoxyphenyl)-1H-pyrrolo[2,3-b]pyridin-5-yl)-4-fluorophenyl)-N-(1-hydroxy-2-methylpropan-2-yl)-2-methylacrylamide 164. MS-ES+486.19, $^1$H NMR (400 MHz, CDCl$_3$): 9.6 (s, 1H), 8.31 (s, 1H), 8.05 (s, 1H), 7.52 (s, 1H) 7.44 (s, 3H), 7.22 (m, 1H), 7.1 (d, 1H), 6.8 (m, 1H), 5.91 (s, 1H), 3.74 (s, 3H), 2.116 (s, 3H), 1.41 (s, 9H).

Example 168

N-(3-(3-(3,5-difluoro-2-methoxyphenyl)-1H-pyrrolo[2,3-b]pyridin-5-yl)-5-fluoro-2-methylphenyl)acrylamide (168)

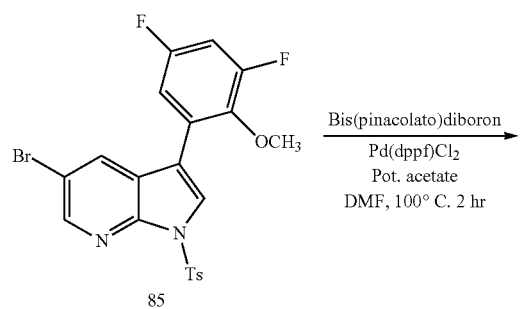

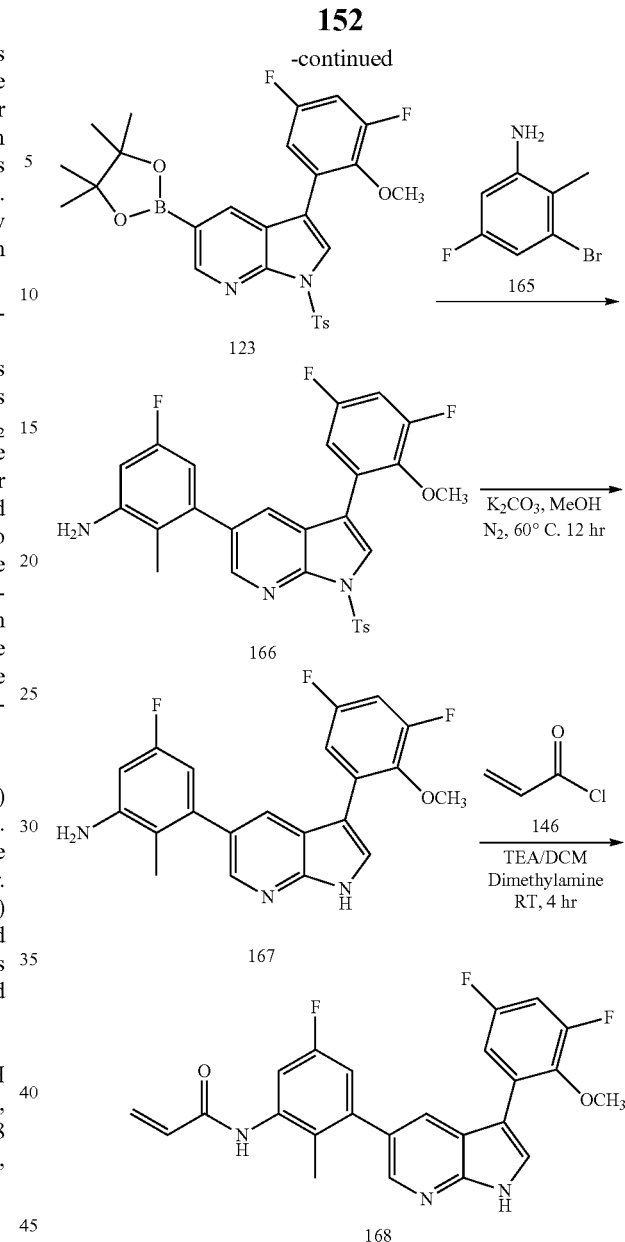

To a stirred solution of 85 (250 mg, 0.508 mmol) in DMF was added bispinacalato diborane (257.9 mg, 1.016 mmol) potassium acetate (99.6 mg, 1.016 mmol) was added and the reaction was degassed and purged with nitrogen for 10 min. Pd(pph$_3$)$_2$Cl$_2$ (17.8 mg, 0.023 mmol) was added and again degassed and purged with nitrogen for another 10 Min. The reaction was sealed and heated to 100 for 2 hr. After completion of the reaction the reaction was cooled and diluted with chloroform, filtered through celite bed. The organic layer was washed with cold water (2×50 ml) followed by brine solution (50 ml). The organic layer was dried over sodium sulphate and concentrated to get the crude. The crude was triturated with hexane to afford black colour solid 123. The solid was proceeded for further step without purification.

A solution of 123 (250 mg, 0.46 mmol) and 3-bromo-5-fluoro-2-methylaniline 165 (112 mg, 0.55 mmol) in acetonitrile was added cesium carbonate (307 mg, 0.936 mmol). The reaction was degassed and purged with nitrogen for 10 min. Pd(dppf)Cl$_2$ (16 mg, 0.0234 mmol) was added to the reaction. The reaction was degassed and purged with nitrogen for another 10 min. The reaction was heated to 90° C. under sealed condition for overnight. The reaction mixture was allowed to cool to room temperature, diluted with chloroform. The organic layer was filtered through celite plug and concentrated to get the crude. The crude was purified through flash chromatography by using 100-200 mesh silica gel. The compound was eluted in 12% ethyl acetate in hexane as half white solid 166.

A solution of 166 (100 mg, 0.186 mmol) was taken in methanol (7 mL) and water (3 ml) was added potassium carbonate (63.3 mg, 0.465 mmol). The reaction was heated to 60° C. for overnight. The methanol was completely distilled and diluted with water. The organic phase was extracted with ethyl acetate (50 mL) twice. The organic layer was dried over sodium sulphate and filtered and concentrated to get the crude. The crude was triturated with hexane to afford the half white colour solid 167.

A solution of 167 (50 mg, 0.130 mmol) was dissolved in dichloromethane (10 mL) and was cooled to 0° C. Triethyl amine (19.7 mg, 0.195 mmol) was added to the reaction mass and kept for stirring. Acrolyl chloride 146 (14 mg, 0.156 mmol) was added drop wise to the reaction mass and kept stirring for 4 hr. After completion reaction was quenched with water and the organic layer was separated and aqueous phase was again extracted with DCM. The combined organic layer was washed with brine solution. The organic layer was dried over sodium sulphate and concentrated to get the crude. The crude was purified through 100-200 mesh silica gel eluting the compound at 2% methanol in chloroform as white colour solid N-(3-(3-(3,5-difluoro-2-methoxyphenyl)-1H-pyrrolo[2,3-b]pyridin-5-yl)-5-fluoro-2-methylphenyl)acrylamide 168. MS-ES-436, 1H NMR (400 MHz, DMSO): 8.46 (d, 2H), 7.91 (m, 2H), 7.52 (s, 1H), 6.93 (m, 3H), 6.45 (m, 1H), 5.86 (m, 1H), 5.50 (m, 1H), 3.67 (m, 3H), 2.09 (m, 3H).

Additional Examples

In Vitro Inhibition Assay

ITK and JAK3 Kinase assay procedures:Enzyme was incubated with substrate peptide in reaction buffer in the presence and absence of test compounds or Staurosporine. All additions were done on ice, followed by the addition of ATP mix. Wells were uniformly mixed using an Eppendorff plate shaker and incubated at 30° C. for 20 min, and stopped by the addition of 5 µL of 3% phosphoric acid. Volume was increased to 100 µL by adding 0.8% phosphoric acid which was then transferred to PC filter mats (Millipore), pre-equilibrated with 70% ethanol and water. Plates were washed thrice with 100 µL 0.8% phosphoric acid and dried for an hour at 60° C. 100 µL scintillation fluid was added into each well and reading taken in Perkin Elmer TOP-COUNT beta counter. The data analysis was performed by averaging the duplicate top count readings for each standard, negative, positive control (enzyme control) and samples and subtracting the average negative control from each reading which results in corrected values. A validation $EC_{50}$ curve was generated by plotting CPM for each Staurosporine concentration on y-axis against the Log concentration of Staurosporine (nM) on the x-axis followed by a best fit curve through the points.

% Inhibition=((Enzyme Control−Compound Treated)/Enzyme Control)×100

Coefficient of Variance ("% CV") between replicates: The % CV values between the replicates were mostly within the acceptable limits of a radiometric experiment. Z' factor evaluation: The value of Z' factor was found to be 0.8 for ITK and 0.9 was derived for others.

All the compounds were tested in 10-dose IC50 mode with 3 fold serial dilution starting at 100 µM. The control compound Staurosporine was tested in 10 dose $IC_{50}$ with 3 fold serial dilution starting at 20 µM. The reactions were carried out at 10 µM ATP for ITK, JAK3 and other TEC and Janus family of kinase. The results for ITK inhibition and JAK3 inhibition of certain EXAMPLES of the present invention are shown in Table 3 below.

TABLE 3

List of Compounds and Corresponding ITK and JAK3 kinases tested*

| Example ID | ITK | JAK3 |
|---|---|---|
| 1 | * | * |
| 2 | ** | ** |
| 3 | ** | ** |
| 4 | ** | ** |
| 5 | *** | *** |
| 6 | * | * |
| 7 | *** | *** |
| 8 | *** | *** |
| 9 | * | * |
| 10 | NA | NA |
| 11 | * | * |
| 12 | * | * |
| 13 | * | * |
| 14 | ** | ** |
| 15 | ** | ** |
| 16 | * | *** |
| 17 | * | * |
| 18 | * | * |
| 19 | *** | *** |
| 20 | *** | *** |
| 21 | *** | *** |
| 22 | * | *** |
| 23 | *** | *** |
| 24 | ** | *** |
| 25 | * | *** |
| 26 | *** | *** |
| 27 | *** | *** |
| 28 | *** | *** |
| 29 | *** | *** |
| 30 | *** | *** |
| 31 | *** | *** |
| 32 | ** | *** |
| 33 | *** | *** |
| 34 | ** | ** |
| 35 | ** | ** |
| 36 | ** | ** |
| 37 | ** | ** |
| 38 | ** | ** |
| 39 | ** | ** |
| 40 | ** | ** |
| 41 | ** | ** |
| 42 | ** | ** |
| 43 | ** | ** |
| 44 | * | * |
| 45 | * | * |
| 46 | * | * |
| 47 | * | * |
| 48 | ** | ** |
| 49 | ** | ** |
| 50 | ** | ** |
| 51 | ** | ** |
| 52 | * | * |
| 53 | * | * |
| 54 | * | * |
| 55 | NA | NA |
| 56 | NA | NA |
| 57 | ** | *** |
| 58 | ** | *** |
| 59 | *** | *** |
| 60 | ** | *** |
| 61 | * | ** |

TABLE 3-continued

List of Compounds and Corresponding ITK and JAK3 kinases tested*

| Example ID | ITK | JAK3 |
|---|---|---|
| 62 | * | ** |
| 63 | * | ** |
| 64 | * | ** |
| 65 | * | ** |
| 66 | *** | *** |
| 67 | ** | ** |
| 68 | ** | ** |
| 69 | ** | ** |
| 70 | ** | *** |
| 71 | ** | ** |
| 72 | ** | ** |
| 73 | ** | ** |
| 74 | * | ** |
| 75 | * | *** |
| 76 | ** | ** |
| 77 | *** | *** |
| 78 | *** | *** |
| 79 | *** | *** |
| 80 | *** | *** |
| 81 | *** | *** |
| 82 | *** | *** |
| 83 | * | *** |
| 84 | * | *** |
| 85 | * | *** |
| 86 | ** | *** |
| 87 | ** | *** |
| 88 | ** | *** |
| 89 | ** | *** |
| 90 | *** | *** |
| 91 | *** | *** |
| 92 | *** | *** |
| 93 | ** | ** |
| 94 | ** | ** |
| 95 | ** | ** |
| 96 | ** | ** |
| 97 | ** | ** |
| 98 | ** | ** |
| 133 | ** | ** |
| 138 | ** | ** |
| 140 | * | ** |
| 145 | ** | ** |
| 148 | *** | *** |
| 150 | ** | ** |
| 152 | ** | ** |
| 153 | ** | *** |
| 155 | NA | NA |
| 156 | NA | NA |
| 158 | *** | *** |
| 159 | *** | *** |
| 164 | NA | NA |
| 168 | *** | *** |
| 169 | *** | *** |
| 170 | *** | *** |
| 171 | NA | NA |
| 172 | *** | *** |
| 173 | *** | *** |
| 174 | NA | NA |

*Kinase Inhibition Result for Selected Compounds
*** <0.1 μM,
** >0.1 μM,
* >1 μM
ND = Not Determined
NA = Not Available Protein Kinase Selectivity Profiler Selected compounds were tested against 442 protein kinases in single dose duplicate mode at a concentration of 0.5 to 1 μM). A control compound was tested in 10-dose $IC_{50}$ mode with 3-fold serial dilution starting at 20 μM. Reactions were carried out at 10 μM ATP. Data pages include raw data, % Enzyme activity (relative to DMSO controls), and curve fits.

In Vivo Models Experiment

Pharmacokinetics

The bio-availability and pharmacokinetics of some compounds of the present invention were examined in male Sprague Dawley rats. A total of 6 male rats were used in the study. The study was performed using parallel design (n=3) with serial sampling.

Dose formulations were prepared on the day of doing. Blood samples were collected at 0.083 (only IV), 0.25, 0.5, 1, 2, 4, 8 and 24 h post-dose. At each time point, approximately 0.2 mL of blood was withdrawn from each cannulated rat through jugular vein and transferred to a pre-labeled microfuge tube containing 204 of 200 mm $K_2EDTA$ permL of blood. Following collection of blood sample, equal volume of heparinized saline was flushed into jugular vein of rat. The blood samples were centrifuged at 5000 g for 5 min at 4±2° C. The plasma was separated within 30 min of scheduled time and stored below −60° C. until bio-analysis. The plasma samples were analyzed for selected test EXAMPLES using a fixxxt-for purpose liquid chromatographic tandem mass spectrometric detection (LC-MS/MS) method with a lower limit of quantification of 2.2 ng/mL. The pharmacokinetic parameters for select EXAMPLES were calculated using the non-compartmental analysis tool of validated WinNonlin® software (Version 5.2).

Pharmacokinetic parameters (mean±SD; n=3) of 7 following intravenous bolus and oral gavage administration of 7 solution in male Sprague Dawley rats are shown in Table 4 below:

TABLE 4

| Formulation | Route/Dose (mg/kg) | $T_{max}$ (h) | $C_{max}$ (ng/mL) | $AUC_{last}$ (ng · h/mL) | $AUC_{inf}$ (ng · h/mL) | CL (mL/min/kg) | $V_{ss}$ (L/kg) | $T_{1/2}$ (h) | F [a] |
|---|---|---|---|---|---|---|---|---|---|
| Solution | IV (5) | NA | 3849.91 [b] ± 710.44 | 2599.10 ± 636.93 | 2617.38 ± 647.47 | 33.42 ± 9.57 | 1.61 ± 0.28 | 0.54 ± 0.05 | — |
| | PO (20) | 0.25 [c] (0.25-0.50) | 852.56 ± 83.61 | 1583.84 ± 179.45 | 1599.77 ± 182.86 | NA | NA | NA | 15 |

[a] $AUC_{inf}$ and nominal doses were used for bioavailability (% F) calculation;
[b] back extrapolated concentration at time zero;
[c] $T_{max}$ is represented as median (range);
NA: not applicable Design Strategy and Structural Modeling of JAK3 and ITK 1H-pyrrolo[2,3-b]pyridine, 1H-pyrazolo[3,4-b]pyridine and 5H-pyrrolo[2,3-b]pyrazine series of compounds its analogs series were designed using X-ray crystal structural models of JAK3 and ITK. Based on the 3-D profile scoring, the structural template was chosen from PDB database JAK3 (3ZEP) and ITK (3MJ2). Several models were built and refined to check the 3D profile and implemented the FIELDS technology lead to the successful discovery and claim of 1H-pyrrolo[2,3-b]pyridine series of compounds.

Biochemical Inhibition of JAK3, ITK 1H-pyrrolo[2,3-b]pyridine series of compounds and analogues in Table 3B were synthesized and tested in 10-dose $IC_{50}$ mode with 3 fold serial dilutions starting at 100 μM. The reactions were carried out at 10 μM ATP for JAK3 and ITK. The compounds 5, 7, 8, 16, 19-33, 48-51, 57-60, 66, 75, 77-92 and 133-153 exhibited biochemical $IC_{50}$=between 0.1 to 1 μM against JAK3 and ITK respectively. $IC_{50}$ data for selected analogues were given in Table 5 (empty cells indicate no inhibition).

TABLE 5

$IC_{50}$ nM of Example compounds

| Kinases | EX. 5, 7, 8, 16, 19-33, 48-51, 57-60, 66, 75, 77-92 (from Table 1) | 133-153 (from Table 1B) | Staurosporine |
|---|---|---|---|
| JAK1 | | | <1.00 |
| JAK2 | | | <1.00 |
| JAK3 | 0.1 to 1 μM | 0.1 to 1 μM | <1.00 |
| ITK | 0.1 to 1 μM | 0.1 to 1 μM | 4.02 |

Competition Binding Assay for JAK3

Binding constants (Kds) were calculated (1H-pyrrolo[2,3-b]pyridine series: Table 5) with a standard dose-response curve using the Hill equation: Response=Background+Signal−Background 1+($Kd^{Hill\ Slope}$/$Dose^{Hill\ Slope}$). The Hill Slope was set to −1 and the curves were fitted using a non-linear least square fit with the Levenberg-Marquardt algorithm. 1H-pyrrolo[2,3-b]pyridine series

TABLE 6

$IC_{50}$ nM:

| | Target | | | |
|---|---|---|---|---|
| | Arm A | Arm B | Arm C | Arm D |
| | Gene Symbol | | | |
| | Kd (nM) | Kd (nM) | Kd (nM) | Kd (nM) |
| JAK3(JH1domain) | 2.5 | 7 | 23 | 70 |

Protein Kinase Selectivity Profiler

Selectivity of 1H-pyrrolo[2,3-b]pyridine, 1H-pyrazolo[3,4-b]pyridine and 5H-pyrrolo[2,3-b]pyrazine series of compounds: In vitro profiling was performed at DiscoveRx using the "The KINOMEscan™ screening platform employs an active site-directed competition binding assay to quantitatively measure interactions between selected few inhibitors and 456 human kinases. Kinome tree representations were prepared using TREEspot interaction map and inhibitor 1H-pyrrolo[2,3-b]pyridine was tested in single dose duplicate mode at a concentration of 0.5 μM. Reactions were carried out at 10 μM ATP. Data pages include raw data, % Enzyme activity (relative to DMSO controls) and curve fits. The inhibitor found to be highly selective JAK3 inhibitor, selectivity profile consistent with the target profile. $IC_{50}$ of ZAK (an upstream of the MAPK cascade) CDK11 and CDK8 kinases labelled on Kinome map tree had activity of >0.5 to 1 μM inhibition.

Janus and TEC Kinase Selectivity 1H-pyrrolo[2,3-b]pyridine, 1H-pyrazolo[3,4-b]pyridine and 5H-pyrrolo[2,3-b]pyrazine series of compounds exhibited over >100 fold selective against Janus and TEC family of kinases except for the BMX and TXK it had activity of 30 and 45 nM respectively. The data summarized in Table 7 for 1H-pyrrolo[2,3-b]pyridine class of compounds. (Empty cells indicate no inhibition).

TABLE 7

1H-pyrrolo[2,3-b]pyridine class of Janus and TEC Kinase Selectivity.

| | Example Compound $IC_{50*}$ (nM) | | |
|---|---|---|---|
| Kinase | 133-153 | 5, 7, 8, 16, 19-33, 48-51, 57-60, 66, 75, 77-92 | $IC_{50}$ (nM) Staurosporine* |
| BMX/ETK | 153.7 | 30 | 12.02 |
| BTK | 7558 | 739 | 22.07 |
| ITK | 72.4 | 35 | 12.81 |
| JAK1 | | | 1.01 |
| JAK2 | >100000 | | <1.00 |
| JAK3 | <5.00 | <5 | <1.00 |

Cellular Profiling

SelectScreen® (10-point titration inhibition results) cell-based pathway profiling further supports the biochemical potencies, 1H-pyrrolo[2,3-b]pyridine and CP-690550/Tofacitinib ((Table 8) potently inhibited IL-4 stimulated STAT6 phosphorylation with an $IC_{50}$ of 77 & 61 nM. Low mM inhibition of 1H-pyrrolo[2,3-b]pyridine in IL-6, IFN-g, and EPO assays is an indication of JAK3 selectivity over other Janus where are NFAT/T-cell receptor activity is directly related to ITK inhibition. Additionally 1H-pyrrolo[2,3-b]pyridine activity on IL-2 and IL-6 release from CD4+ T cells using HTRF was performed. 1H-pyrrolo[2,3-b]pyridine series exhibited similar or low μM inhibition of IL-2 and IL-6 release from CD4+ T cells (0.6 and 2.80 μM) when compared with the standard BMS509744 (0.35 μM) whereas tofacitinib had 1.2 μM IL-2 inhibition activity. These results further supports the 1H-pyrrolo[2,3-b]pyridine series cellular activity on ITK inhibition.

TABLE 8

| Cmpd ID | Pathway | Cell Line Tested | Stim | $IC_{50}$ (nM) | Control | Control $IC_{50}$ (nM) |
|---|---|---|---|---|---|---|
| 19-33, 133-153 | IL-4/ STAT6 | STAT6-bla RA1 | IL-4 | 77 | JAK Inhibitor I | 14.5 |
| 19-33, 133-153 | JAK/ STAT | SIE-bla HEK 293T | IFN-gamma | 3100 | JAK Inhibitor I | 83.5 |
| 19-33, 133-153 | JAK/ STAT | SIE-bla HEK 293T | IL-6 | 1990 | JAK Inhibitor I | 22 |
| 19-33, 133-153 | JAK2/ STAT5 | irf1-bla TF1 | EPO | 4650 | JAK Inhibitor I | 6.92 |
| 19-33, 133-153 | T cell receptor | NFAT-bla Jurkat | anti-CD3:CD28 | 176 | Ro-31-8220 | 615 |

PLC-γ1 Inhibition—Calcium Efflux (FLIPER) Assay: To determine the pharmacodynamics effect of covalent ITK inhibition, T cells were stimulated at various times following ITK inhibition and the phosphorylation of PLCγ1 was measured. 1H-pyrrolo[2,3-b]pyridine series of compounds found to be inhibitors of PLCγ1 mediated calcium release from CD4+ T cells via TCR engagement (cellular ITK inhibition). This was corroborated by the IC$_{50}$'s, with 1H-pyrrolo[2,3-b]pyridine series of compounds and found to be 630 nM ITK: The T Cell Receptor (TCR) pathway is significantly effected when NFAT cellular profiling assay was performed where 1H-pyrrolo[2,3-b]pyridine series is inhibited with an IC$_{50}$ of 176 nM and Tofacitinib (CP-690550) had >10 uM. This data is a direct read out for ITK inhibition mechanism for 1H-pyrrolo[2,3-b]pyridine series. Additionally PLCγ phosphorylation data further supports the ITK pharmacology.

Efficacy of 1H-pyrrolo[2,3-b]pyridine Series of Compounds on Inhibition of Anti-CD3e Antibody Induced CD4$^+$ T Cell Cytokine-IL-2, IL-4 and IFN-γ Production in Male BALB/c Mice 1H-pyrrolo[2,3-b]pyridine series of compounds Mice IL-2, IL-4 and IFN-g: 60 mg/Kg is highly efficacious. There is a significant increase in serum IL-2, IL-4 and IFN-gamma (P<0.001) of Positive Control animals compared to negative control animals. 1H-pyrrolo[2,3-b]pyridine series of compounds are not significantly decreased serum IL-2, IL-4 and IFN-gamma at doses used when compared to Positive control. However, at 60 mg/Kg dose 1H-pyrrolo[2,3-b]pyridine series of compounds significantly reduced IFN-g production. Reference compound CP-690550 has shown significant decrease in serum IL-2, IL-4 and IFN-gamma at 1.5 hrs post-antibody treatment. Dexamethasone has shown significant decrease in serum IL-2, IL-4 and IFN-gamma at 1.5 hrs post-antibody treatment.

Effects of 1H-pyrrolo[2,3-b]pyridine series of compounds Administered PO, BID in 11 Day DBA/1OlaHsd Mouse Established Type II Collagen Arthritis 1H-pyrrolo[2,3-b]pyridine series of compounds was dosed in BID study due to its 4 times higher solubility over non-salt form. 1H-pyrrolo[2,3-b]pyridine series of compounds at dose 100 mg/Kg is well tolerated with no clinical signs. Tofacitinib at 60 mg/Kg had body weight change from day 1 and this is the highest dose recommended for Tofacitinib and cannot be dosed over 60 mg due to solubility issues. The body weight is generally a direct reflection of efficacy, the more efficacious the treatment the less body weight (bw) loss. This does not hold true in instances of overt toxicity. So, the bw increase in the 100 mg/kg group of 1H-pyrrolo[2,3-b]pyridine series of compounds is a reflection of increased efficacy (animals are able to move better, and have a more normal appetite, more normal water consumption during the schedule), 1H-pyrrolo[2,3-b]pyridine series of compounds efficacy by attenuating paw arthritis scores (swelling, edema and paw volumes). The collagen-induced arthritis in mice demonstrated that the suppression of the inflammatory response did not require continuous exposure to 1H-pyrrolo[2,3-b]pyridine series of compounds for effectiveness (84%) In the case of Tofacitinib had 97% is significant but clearly >90% majorly due to immunosuppression was confirmed since Tofacitinib treated mice had fever in all the in vivo studies and such symptoms were not observed with 1H-pyrrolo[2,3-b]pyridine series of compounds.

The CIS study is an established/chronic CIA model study we conducted where 1H-pyrrolo[2,3-b]pyridine series of compounds highly efficacious similar or higher over Tofacitinib and no infections were seen.

We claim:
1. A compound according to Formula (I):

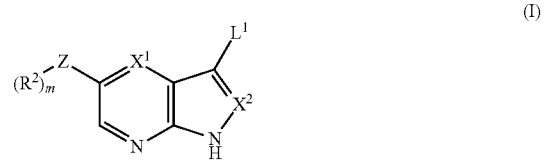

or a pharmaceutically acceptable salt thereof, wherein:
$X^1$ is N and $X^2$ is CH;
$L^1$ is

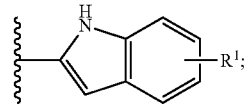

$R^1$ is independently H, halo, $C_{1-4}$alkyl, or $C_{1-4}$alkoxy;
Z is

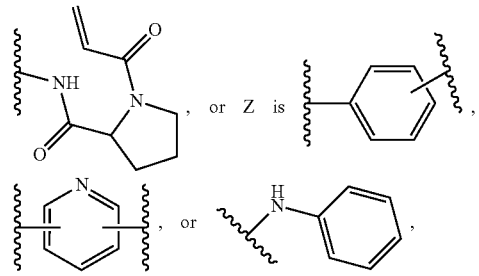

optionally substituted with 1-3 independent halo or $C_{1-4}$alkyl substituents;
$R^2$ is independently H, halo, $C_{1-4}$alkyl, cyano-$C_{1-4}$alkyl,

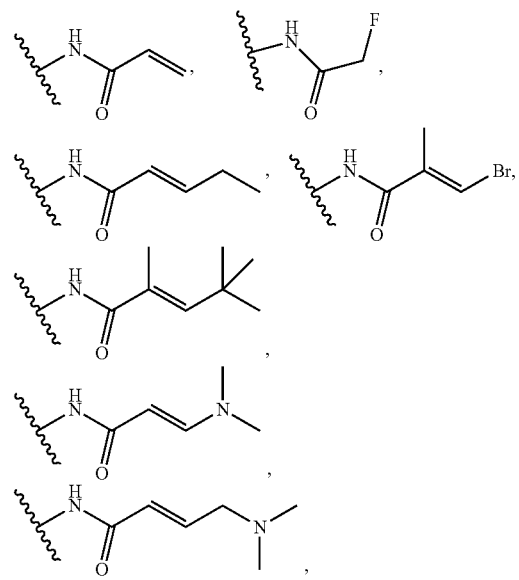

-continued

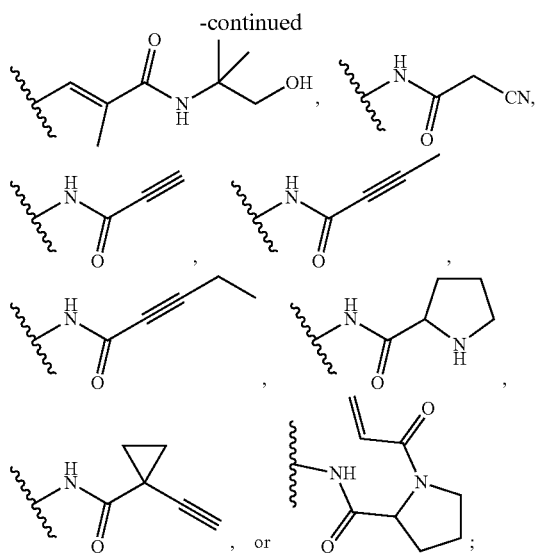

and m is 0, 1, 2 or 3.

2. The compound according to claim 1, or a pharmaceutically acceptable salt thereof, wherein Z is phenyl.

3. The compound according to claim 1, wherein $R^2$ is independently cyano-$C_{1-4}$alkyl,

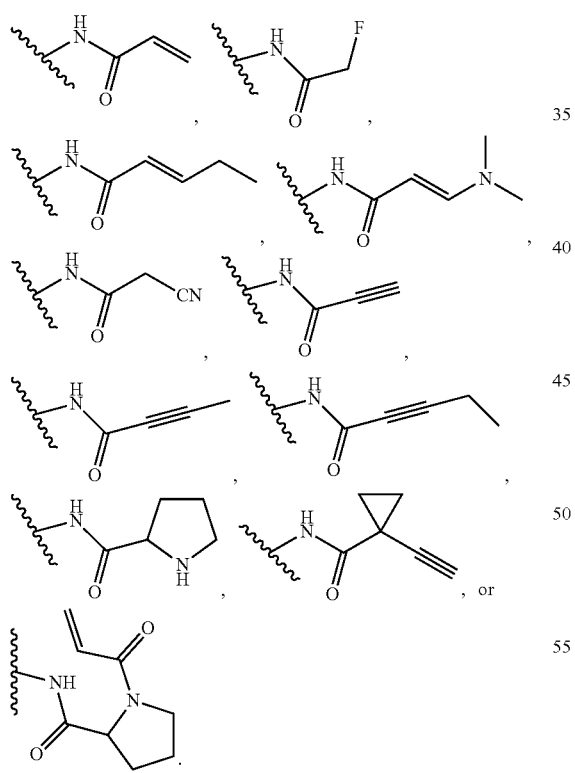

4. A method of modulating Janus kinase activity and/or interleukin-2-inducible T-cell kinase activity in a mammal, comprising administering to said mammal an effective amount of a compound according to claim 1.

5. The method according to claim 4, wherein said mammal suffers from a disease selected from rheumatoid arthritis, psoriasis, lupus erythematosus, systemic lupus erythematosus, idiopathic thrombocytopenia purpura, restenosis, angioplasty, tumor, atherosclerosis, chronic allograft rejection, acute allograft rejection, chronic graft versus host disease, asthma, allergic acute rhinitis, psoriatic arthritis, systemic sclerosis, atopical dermatitis, erythemas, alopecia, or multiple sclerosis.

6. The method according to claim 4, wherein said mammal suffers from an immunodeficiency disorder.

7. The method according to claim 4, wherein said mammal suffers from a myeloproliferative disorder, cancer, acute leukemia, or gain of function mutations associated with inherited polycythemia.

8. The method according to claim 4, wherein said mammal suffers from psoriasis, psoriatic arthritis, or atopical dermatitis.

9. A compound selected from the group consisting of

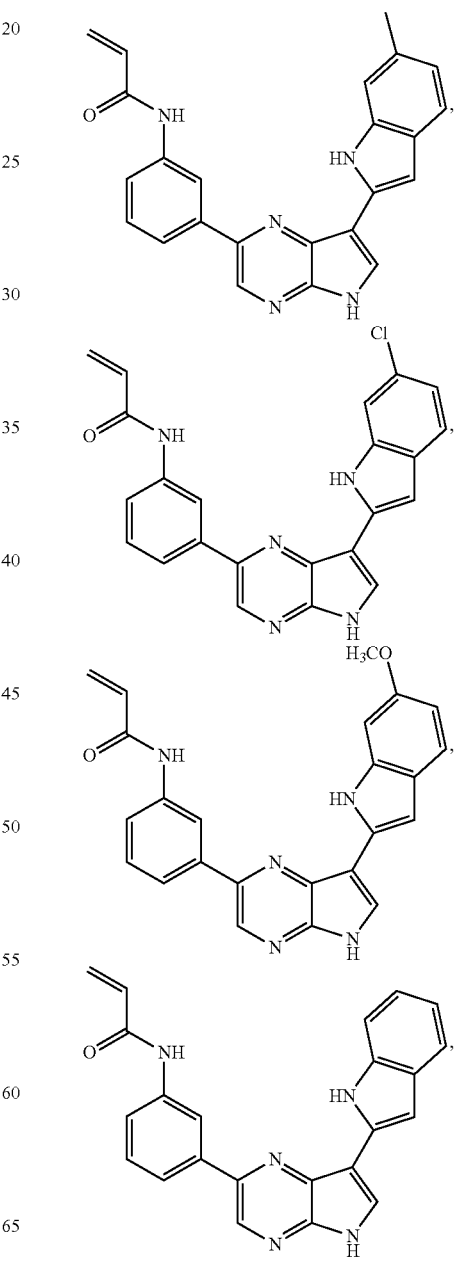

-continued

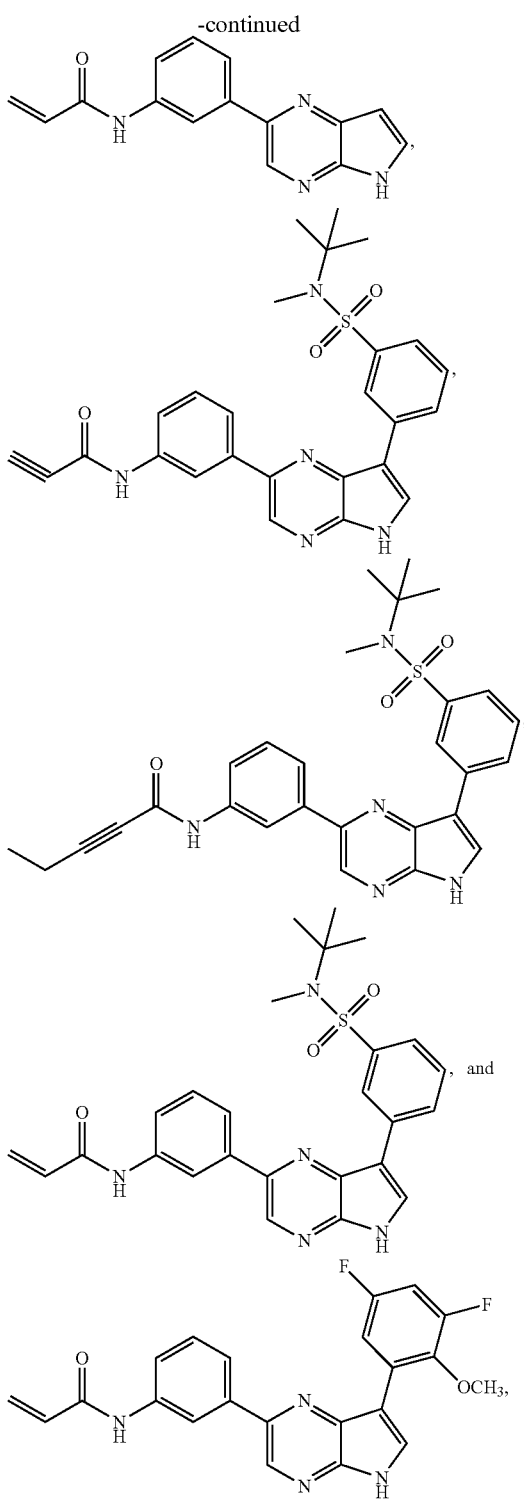

and pharmaceutically acceptable salts thereof.

10. A method of modulating Janus kinase activity and/or interleukin-2-inducible T-cell kinase activity in a mammal, comprising administering to said mammal an effective amount of a compound according to claim 9.

11. The method according to claim 10, wherein said mammal suffers from a disease selected from rheumatoid arthritis, psoriasis, lupus erythematosus, systemic lupus erythematosus, idiopathic thrombocytopenia purpura, restenosis, angioplasty, tumor, atherosclerosis, chronic allograft rejection, acute allograft rejection, chronic graft versus host disease, asthma, allergic acute rhinitis, psoriatic arthritis, systemic sclerosis, atopical dermatitis, erythemas, alopecia, or multiple sclerosis.

12. The method according to claim 10, wherein said mammal suffers from an immunodeficiency disorder.

13. The method according to claim 10, wherein said mammal suffers from a myeloproliferative disorder, cancer, acute leukemia, or gain of function mutations associated with inherited polycythemia.

14. The method according to claim 10, wherein said mammal suffers from psoriasis, psoriatic arthritis, or atopical dermatitis.

15. A compound selected from the group consisting of

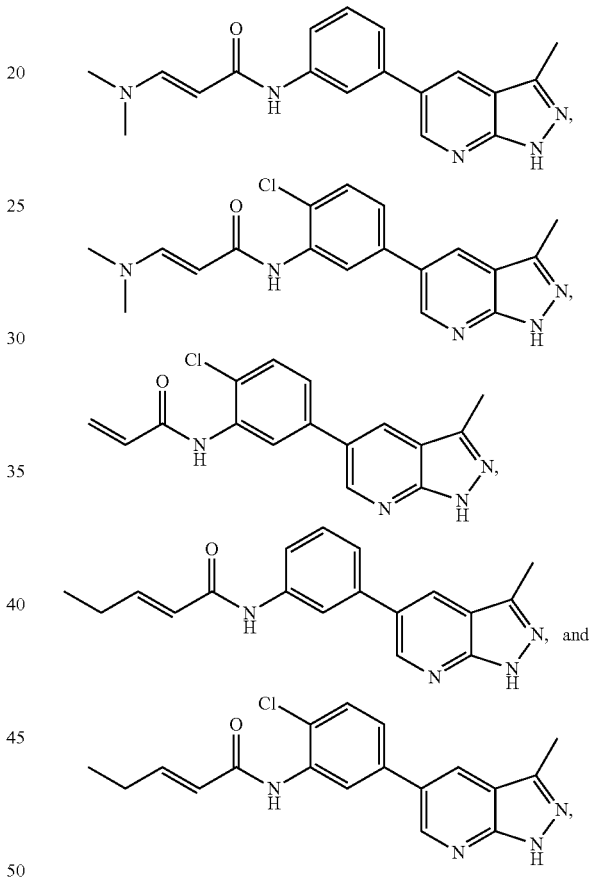

and pharmaceutically acceptable salts thereof.

16. A method of modulating Janus kinase activity and/or interleukin-2-inducible T-cell kinase activity in a mammal, comprising administering to said mammal an effective amount of a compound according to claim 15.

17. The method according to claim 16, wherein said mammal suffers from a disease selected from rheumatoid arthritis, psoriasis, lupus erythematosus, systemic lupus erythematosus, idiopathic thrombocytopenia purpura, restenosis, angioplasty, tumor, atherosclerosis, chronic allograft rejection, acute allograft rejection, chronic graft versus host disease, asthma, allergic acute rhinitis, psoriatic arthritis, systemic sclerosis, atopical dermatitis, erythemas, alopecia, or multiple sclerosis.

18. The method according to claim 16, wherein said mammal suffers from an immunodeficiency disorder.

19. The method according to claim 16, wherein said mammal suffers from a myeloproliferative disorder, cancer, acute leukemia, or gain of function mutations associated with inherited polycythemia.

20. The method according to claim 16, wherein said mammal suffers from psoriasis, psoriatic arthritis, or atopical dermatitis.

* * * * *